(12) United States Patent
Bollag et al.

(10) Patent No.: US 9,730,918 B2
(45) Date of Patent: Aug. 15, 2017

(54) KINASE MODULATION, AND INDICATIONS THEREFOR

(71) Applicant: Plexxikon Inc., Berkeley, CA (US)

(72) Inventors: Gideon Bollag, Hercules, CA (US); Klaus-Peter Hirth, San Francisco, CA (US); Prabha N. Ibrahim, Mountain View, CA (US); Paul Lin, Oakland, CA (US); Brian West, San Francisco, CA (US)

(73) Assignee: Plexxikon Inc., Berkeley, CA (US)

( * ) Notice: Subject to any disclaimer, the term of this patent is extended or adjusted under 35 U.S.C. 154(b) by 0 days.

(21) Appl. No.: 15/147,781

(22) Filed: May 5, 2016

(65) Prior Publication Data

US 2016/0243092 A1    Aug. 25, 2016

Related U.S. Application Data

(63) Continuation of application No. 13/802,106, filed on Mar. 13, 2013, now Pat. No. 9,358,235.

(60) Provisional application No. 61/754,318, filed on Jan. 18, 2013, provisional application No. 61/612,912, filed on Mar. 19, 2012.

(51) Int. Cl.
| | | |
|---|---|---|
| *A61K 31/444* | (2006.01) | |
| *A61K 31/357* | (2006.01) | |
| *A61K 31/436* | (2006.01) | |
| *A61K 45/06* | (2006.01) | |
| *A61K 31/437* | (2006.01) | |
| *A61K 31/4545* | (2006.01) | |
| *A61K 31/506* | (2006.01) | |
| *A61K 31/5377* | (2006.01) | |
| *C07D 471/04* | (2006.01) | |
| *A61K 9/00* | (2006.01) | |

(52) U.S. Cl.
CPC .......... *A61K 31/444* (2013.01); *A61K 9/0053* (2013.01); *A61K 31/357* (2013.01); *A61K 31/436* (2013.01); *A61K 31/437* (2013.01); *A61K 31/4545* (2013.01); *A61K 31/506* (2013.01); *A61K 31/5377* (2013.01); *A61K 45/06* (2013.01); *C07D 471/04* (2013.01)

(58) Field of Classification Search
CPC .............. A61K 2300/00; A61K 31/436; A61K 31/437; A61K 31/4545; A61K 31/506; A61K 31/357; A61K 31/444; A61K 31/5377; A61K 45/06; A61K 9/0053; C07D 471/04

See application file for complete search history.

(56) References Cited

U.S. PATENT DOCUMENTS

| | | |
|---|---|---|
| 7,202,266 B2 | 4/2007 | Arnold et al. |
| 7,348,338 B2 | 3/2008 | Arnold et al. |
| 7,476,746 B2 | 1/2009 | Artis et al. |
| 7,491,831 B2 | 2/2009 | Artis et al. |
| 7,498,342 B2 | 3/2009 | Ibrahim et al. |
| 7,504,509 B2 | 3/2009 | Ibrahim et al. |
| 7,517,970 B2 | 4/2009 | West et al. |
| 7,531,568 B2 | 5/2009 | Lin et al. |
| 7,572,806 B2 | 8/2009 | Arnold et al. |
| 7,585,859 B2 | 9/2009 | Ibrahim et al. |
| 7,605,168 B2 | 10/2009 | Ibrahim et al. |
| 7,723,374 B2 | 5/2010 | Artis et al. |
| 7,863,288 B2 | 1/2011 | Ibrahim et al. |
| 7,863,289 B2 | 1/2011 | Spevak et al. |
| 7,872,018 B2 | 1/2011 | Ibrahim et al. |
| 7,893,075 B2 | 2/2011 | Zhang et al. |
| 7,947,708 B2 | 5/2011 | Ibrahim et al. |
| 8,053,463 B2 | 11/2011 | Lin et al. |
| 8,067,434 B2 | 11/2011 | Ibrahim et al. |
| 8,110,576 B2 | 2/2012 | Ibrahim et al. |
| 8,119,637 B2 | 2/2012 | Ibrahim et al. |
| 8,129,404 B2 | 3/2012 | Ibrahim et al. |
| 8,143,271 B2 | 3/2012 | Ibrahim et al. |
| 8,153,641 B2 | 4/2012 | Ibrahim et al. |
| 8,158,636 B2 | 4/2012 | Ibrahim et al. |
| 8,198,273 B2 | 6/2012 | Ibrahim et al. |
| 8,268,858 B2 | 9/2012 | Wu et al. |
| 8,367,828 B2 | 2/2013 | Arnold et al. |
| 8,404,700 B2 | 3/2013 | Zhang et al. |
| 8,415,469 B2 | 4/2013 | Ibrahim et al. |
| 8,461,169 B2 | 6/2013 | Zhang et al. |
| 8,470,818 B2 | 6/2013 | Ibrahim et al. |
| 8,642,606 B2 | 2/2014 | Ibrahim et al. |
| 8,673,928 B2 | 3/2014 | Ibrahim et al. |

(Continued)

FOREIGN PATENT DOCUMENTS

| | | |
|---|---|---|
| CN | 102993199 | 3/2013 |
| WO | WO-97/49703 | 12/1997 |

(Continued)

OTHER PUBLICATIONS

Eisai Co. Ltd (News Release, No. 10-64) 2010.*
Mertens (Atlas of Genetics and Cytogenetics in Oncology and Heematology, 2001).*
U.S. Appl. No. 14/798,167, filed Jul. 13, 2015, Ibrahim et al.
U.S. Appl. No. 14/602,119, filed Jan. 21, 2015, Ibrahim et al.
U.S. Appl. No. 14/637,303, filed Mar. 3, 2015, Lin et al.
U.S. Appl. No. 14/733,830, filed Jun. 8, 2015, Zhang et al.
U.S. Appl. No. 14/839,668, filed Aug. 28, 2015, Ibrahim.
U.S. Appl. No. 14/846,545, filed Sep. 4, 2015, Zhang et al.

(Continued)

*Primary Examiner* — Uma Ramachandran
(74) *Attorney, Agent, or Firm* — Sheppard Mullin Richter & Hampton LLP

(57) ABSTRACT

The present disclosure provides methods of using protein kinase inhibitors for treating diseases and conditions, including diseases and conditions associated with activity of any protein kinase selected from Fms protein kinase including any mutations thereof, Kit protein kinase any mutations thereof, Flt-3 protein kinase any mutations thereof and combinations thereof.

3 Claims, 19 Drawing Sheets

(56) References Cited

U.S. PATENT DOCUMENTS

| | | | |
|---|---|---|---|
| 8,722,702 B2 | 5/2014 | Zhang et al. | |
| 8,865,735 B2 | 10/2014 | Ibrahim et al. | |
| 8,901,301 B2 | 12/2014 | Ibrahim et al. | |
| 8,912,204 B2 | 12/2014 | Ibrahim et al. | |
| 2004/0142864 A1 | 7/2004 | Bremer et al. | |
| 2004/0171062 A1 | 9/2004 | Hirth et al. | |
| 2005/0048573 A1 | 3/2005 | Artis et al. | |
| 2005/0079548 A1 | 4/2005 | Artis et al. | |
| 2005/0164300 A1 | 7/2005 | Artis et al. | |
| 2005/0170431 A1 | 8/2005 | Ibrahim et al. | |
| 2006/0058339 A1 | 3/2006 | Ibrahim et al. | |
| 2006/0135540 A1 | 6/2006 | Lin et al. | |
| 2006/0160135 A1 | 7/2006 | Wang et al. | |
| 2006/0160837 A1* | 7/2006 | Cichowski | A61K 31/4745 514/291 |
| 2007/0032519 A1 | 2/2007 | Zhang et al. | |
| 2007/0054928 A1* | 3/2007 | Bannen | A61K 31/47 514/266.2 |
| 2007/0066641 A1 | 3/2007 | Ibrahim et al. | |
| 2007/0072904 A1 | 3/2007 | Lin et al. | |
| 2008/0221127 A1 | 9/2008 | Lin et al. | |
| 2008/0234349 A1 | 9/2008 | Lin et al. | |
| 2008/0249137 A1 | 10/2008 | Lin et al. | |
| 2009/0076046 A1 | 3/2009 | Zhang et al. | |
| 2010/0190777 A1 | 7/2010 | Wu et al. | |
| 2010/0310659 A1 | 12/2010 | Desai et al. | |
| 2011/0092538 A1 | 4/2011 | Spevak et al. | |
| 2011/0112127 A1 | 5/2011 | Zhang et al. | |
| 2011/0166174 A1 | 7/2011 | Ibrahim et al. | |
| 2011/0183988 A1 | 7/2011 | Ibrahim et al. | |
| 2011/0230482 A1 | 9/2011 | Zhang et al. | |
| 2011/0263595 A1 | 10/2011 | Zhang et al. | |
| 2012/0015966 A1 | 1/2012 | Lin et al. | |
| 2012/0053177 A1 | 3/2012 | Ibrahim et al. | |
| 2012/0122860 A1 | 5/2012 | Visor et al. | |
| 2012/0165366 A1 | 6/2012 | Ibrahim et al. | |
| 2012/0245174 A1 | 9/2012 | Ibrahim et al. | |
| 2013/0237531 A1 | 9/2013 | Wu et al. | |
| 2013/0261117 A1 | 10/2013 | Ibrahim et al. | |
| 2013/0274259 A1 | 10/2013 | Zhang et al. | |
| 2013/0303534 A1 | 11/2013 | Ibrahim et al. | |
| 2014/0038948 A1 | 2/2014 | Wu et al. | |
| 2014/0045840 A1 | 2/2014 | Zhang et al. | |
| 2014/0094611 A1 | 4/2014 | Ibrahim et al. | |
| 2014/0128373 A1 | 5/2014 | Ibrahim et al. | |
| 2014/0128390 A1 | 5/2014 | Lin et al. | |
| 2014/0213554 A1 | 7/2014 | Wu et al. | |
| 2014/0243365 A1 | 8/2014 | Zhang et al. | |
| 2014/0288070 A1 | 9/2014 | Ibrahim et al. | |
| 2014/0303121 A1 | 10/2014 | Zhang et al. | |
| 2014/0303187 A1 | 10/2014 | Wu et al. | |
| 2014/0357612 A1 | 12/2014 | Zhang et al. | |
| 2015/0080372 A1 | 3/2015 | Ibrahim et al. | |
| 2015/0133400 A1 | 5/2015 | Zhang et al. | |
| 2015/0166547 A1 | 6/2015 | Ibrahim et al. | |
| 2015/0183793 A1 | 7/2015 | Zhang et al. | |

FOREIGN PATENT DOCUMENTS

| | | | |
|---|---|---|---|
| WO | WO-2005/062795 | 7/2005 | |
| WO | WO-2006/009755 | 1/2006 | |
| WO | WO-2006/009797 | 1/2006 | |
| WO | WO-2006/015123 | 2/2006 | |
| WO | WO 2007/002325 | 1/2007 | |
| WO | WO-2007/002433 | 1/2007 | |
| WO | WO-2007/013896 | 2/2007 | |
| WO | WO-2007/106236 | 9/2007 | |
| WO | WO 2008/063888 | * 5/2008 | |
| WO | WO-2008/063888 | 5/2008 | |
| WO | WO-2008/064255 | 5/2008 | |
| WO | WO-2008/064265 | 5/2008 | |
| WO | WO 2008/080001 | 7/2008 | |
| WO | WO 2010/111527 | 9/2010 | |
| WO | WO 2010/129467 | 11/2010 | |
| WO | WO-2011/057022 | 5/2011 | |
| WO | WO-2011/133637 | 10/2011 | |
| WO | WO-2012/158957 | 11/2012 | |

OTHER PUBLICATIONS

Benjamin, et al., "Management of gastrointestinal stromal tumors in the imatinib era: selected case studies," The Oncologist (2006), 11(1):9-20.

Calabresi, et al., "Section IX: Chemotherapy of neoplastic diseases," *Goodman & Gilman's The Pharmacological Basis of Therapeutics*, Tenth Edition, McGraw-Hill Medical Publishing Division, (2001), pp. 1381, 1383-1385 and 1388.

Cassier, et al., "Efficacy of imatinib mesylate for the treatment of locally advanced and/or metastatic tenosynovial giant cell tumor/pigmented villonodular synovitis," Cancer (2012), 118(6);1649-1655.

Cecil Textbook of Medicine, Part XIV: Oncology, 1996, 1004-1010.

Denardo, et al., "Leukocyte complexity predicts breast cancer survival and functionally regulates response to chemotherapy," Cancer Discovery, 1(1), 34 pages (e-published Apr. 3, 2011 as doi:10.1158/2159-8274).

Fan et al., "Ester Prodrugs of Ampicillin Tailored for Intracellular Accumulation," *Bioorganix & Medinical Chem. Letters*, (1997), 7(24):3107-3112.

Gura, "Cancer models: Systems for identifying new drugs are often faulty," Science (1997), 278(5340):1041-1042.

He, et al., "Gamma-secretase activating protein, a therapeutic target for Alzheimer's disease," *Nature*, (2010), 467(7311):95-98.

Holmes, et al., "Long-term effects of Aβ42 immunisation in Alzheimer's disease: follow-up of a randomised, placebo-controlled phase I trail," *Lancet* (2008) 372:216-233.

International Preliminary Report on Patentability for PCT/US2013/032835 dated Sep. 23, 2014 (8 pages).

Johnson, et al., "Relationships between drug activity in NCI preclinical in vitro and in vivo models and early clinical trials," British J. of Cancer (2001), 84(10, 1424-1431.

Larson, "CML: Live long and prosper," Blood (2011), 118(17):4499-4500.

Natali, et al., "Breast cancer is associated with loss of the c-kit oncogene product," *Int. J. Cancer*, (1992) 52:713-717.

Nelson, "Novel agent shows 'dramatic' responses in PVNS," Medscape, May 15, 2014, available at http://www.medscape.com/viewarticle/825217.

Patwardhan, et al., "Sustained Inhibition of receptor tyrosine kinases and macrophage depletion by PLX3397 and rapamycin as a potential new approach for the treatment of MPNSTs," Clin. Cancer Res. (2014), 20(12); 1-13.

PLX3397 Phase 3 study for pigmented villonodular synovitis (PVNS) or giant cell tumor of the tendon sheath (GCT-TS) (ENLIVEN), 2015, available at https://clinicaltrials.gov/ct2/show/NCT02371369.

Pearce, Center Drug Design and Discovery Neidle, Stephen, ed. (Elsevier/Academic Press, 2008).

Prada, et al., "Neurofibroma-associated macrophages play roles in tumor growth and response to pharmacological inhibition," Acta Neuropathol. (2013), 125:159-168.

Ravi, et al., "Treatment of tenosynovial giant cell tumor and pigmented villonodular synovitis," Curr. Opin. Oncol. (2011), 23(4):361-366.

Robertson, et al., "Imatinib mesylate for plexiform neurofibromas in patients with neurofibromatosis type 1: a phase 2 trial," Lancet Oncol. (2012), 13(12):1218-1224.

Search report from PCT/US2013/032835 dated May 7, 2013.

Sikora, et al., "Cancer Drug Development in the Post-Genomic Age," *Current Science*, (2001), 81(5):549-554.

Tap, et al., "A pilot study of PLX3397, a selective colony-stimulating factor 1 receptor (CSF1R) kinase inhibitor, in pigmented villonodular synovitis (PVNS)," J. Clin. Oncol. (2014), 32:5s.

Verspoor, et al., "Pigmented villonodular synovitis: current concepts about diagnosis and management," Future Oncol. (2013), 9(10): 1515-1531.

(56) References Cited

OTHER PUBLICATIONS

Zips, et al., "New Anticancer Agents In Vitro and In Vivo Evaluation," InVivo, (2005):19:1-8.
Chiryougaku (Therapeutics), 2010, 44(12), p. 1405-1408 (14 pages).
DeNardo et al, "Leukocyte Complexity Predicts Breast Cancer Survival and Functionally Regulates Response to Chemotherapy," Cancer Discovery, vol. 54 Jun. 2011 pp. 54-67.
Havalen (eribulin mesylate) injection for intravenous adminitration Reference ID: 3078607 Feb. 2012 (16 pages).
Murphey et al., "Pigmented Villonodular Synovitis: Radiologic-Pathologic Correlation," 2008, RadioGraphics, vol. 28, No. 5, (1493-1519 pages).
Shirasawa et al., "Malignant Transformatioin of Pigmented Villonodular Synovitis a Case Report," (Seikei-Geka to Saigai-Geka vol. 33 No. 1984).
West et al., "Cancer Research", AACR 101$^{st}$ annual meeting 2010 abstract, 2010, Abstract 3850 (2 pages).

\* cited by examiner

KINASE MODULATION, AND INDICATIONS THEREFOR

CROSS REFERENCE TO RELATED APPLICATIONS

This application is a continuation of U.S. application Ser. No. 13/802,106, filed on Mar. 13, 2013, which claims the benefit under 35 U.S.C. §119(e) of U.S. Provisional Application No. 61/612,912 filed Mar. 19, 2012 and 61/754,318, filed Jan. 18, 2013, which are both incorporated by reference in their entirety.

FIELD

This disclosure relates to methods for the use of protein kinase inhibitors in treating diseases and conditions associated with modulation of the activity of protein kinases.

SUMMARY

The present disclosure provides methods for the use of a compound or a composition as described herein, or a salt, a solvate, a hydrate, a prodrug, a tautomer or an isomer thereof in treating diseases and conditions associated with regulation or modulation of the activity of one or more of any of Fms protein kinase, Kit protein kinase, Flt-3 protein kinase and combinations thereof, including any mutations of these kinases.

In one aspect, the present disclosure provides a method for treating a subject suffering from a disease or condition mediated by a protein kinase selected from c-fms, c-kit, flt3 or combinations thereof and/or infiltration or activation of macrophages or microglia. The method includes administering to the subject an effective amount of a compound of Formula I':

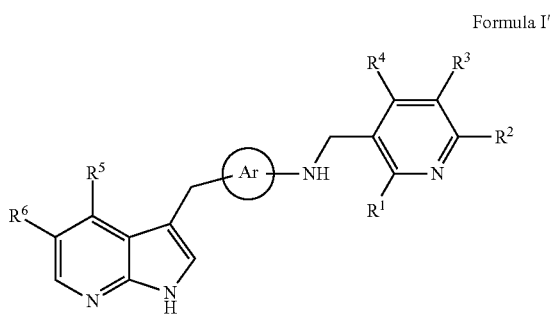

Formula I' or a pharmaceutically acceptable salt, a prodrug, a tautomer or a stereoisomer thereof, wherein:

Ar is selected from the group consisting of:

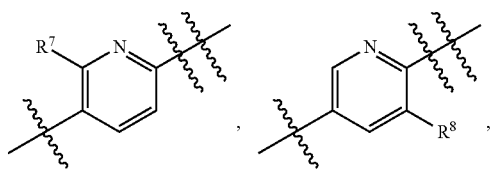

-continued

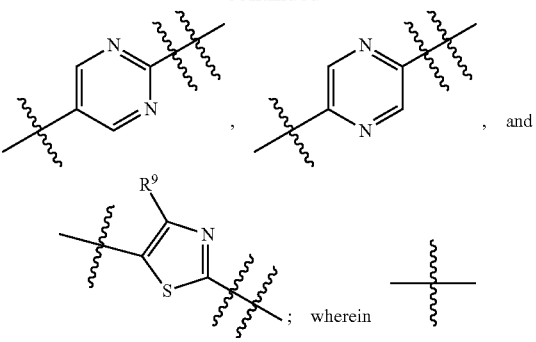

; wherein indicates the point of attachment of Ar to —CH$_2$— of Formula I and wherein

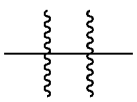 [SMILES: **]

indicates the point of attachment of Ar to —NH— of Formula I';

$R^1$, $R^2$, $R^3$ and $R^4$ are each independently selected from the group consisting of —H, halogen, lower alkyl, halogen substituted lower alkyl, halogen substituted lower alkoxy, alkoxy substituted lower alkyl, cycloalkylamino, —CN, —O—$R^{40}$, —S(O)$_2$—$R^{41}$, —S(O)$_2$—N(H)—$R^{42}$, —N(H)—$R^{42}$, —N($R^{42}$)$_2$, and —N(H)—S(O)$_2$—$R^{43}$, provided that at least two of $R^1$, $R^2$, $R^3$ and $R^4$ are —H and one of $R^1$, $R^2$, $R^3$ and $R^4$ is other than hydrogen, wherein:
  $R^{40}$ is lower alkyl, fluoro substituted lower alkyl, methoxy substituted lower alkyl, or cycloalkyl;
  $R^{41}$, $R^{42}$ and $R^{43}$ are lower alkyl;
$R^5$ is selected from the group consisting of —H, —F, —Cl, —Br, lower alkyl, halogen substituted alkyl, lower alkenyl, lower alkynyl, cycloalkyl, phenyl, pyrazolyl, —CN, —O—$R^{10}$, —C(O)—N(H)—$R^{11}$, —C(O)—O—$R^{11}$, —S(O)$_2$—$R^{12}$, —S(O)$_2$—N(H)—$R^{11}$, —N(H)—C(O)—$R^{12}$, and —N(H)—S(O)$_2$—$R^{12}$, wherein pyrazolyl is optionally substituted with lower alkyl or heterocycloalkyl;
$R^6$ is selected from the group consisting of H, halogen, lower alkyl, halogen substituted alkyl, lower alkenyl, lower alkynyl, cycloalkyl, phenyl, pyrazolyl, —CN, —O—$R^{13}$, —C(O)—N(H)—$R^{14}$, —C(O)—O—$R^{14}$, —S(O)$_2$—$R^{15}$, —S(O)$_2$—N(H)—$R^{14}$, —N(H)—C(O)—$R^{15}$, and —N(H)—S(O)$_2$—$R^{15}$, wherein pyrazolyl is optionally substituted with lower alkyl or heterocycloalkyl;
$R^7$ is H, halogen or lower alkyl;
$R^8$ is H, halogen or lower alkoxy; p
$R^9$ is H or halogen;
$R^{10}$ and $R^{13}$ are independently —H, lower alkyl, lower alkyl substituted with —O—CH$_3$, lower alkyl substituted with di-alklylamine, or lower alkyl substituted with heterocycloalkyl;
$R^{11}$ and $R^{14}$ are independently hydrogen or lower alkyl; and
$R^{12}$ and $R^{15}$ are each independently lower alkyl,
wherein the disease or condition is selected from stem cell ablation and myelopreparation for stem cell transplant, primary progressive multiple sclerosis, complex regional pain syndrome, reflex sympathetic dystrophy, muscular dystrophy, duchenne muscular dystrophy, causalgia, neuro-inflammation, neuroinflammatory disorders, benign forgetfulness, HIV, binswager type dementia, dementia with lewy bodie, prosencephaly, microencepahy, cerebral palsy, congenital hydrocephalus, abdominal dropsy, progressive supranuclear palsy, glaucoma, addiction disorders, dependencies, alcoholism, tremors, Wilson's disease, vascular dementias, multi infarct dementia, frontotemporal dementia, pseudo-dementia, bladder cancer, basal cell carcinoma, cholangiocarcinoma, colon cancer, endometrial cancer, esophageal cancer, Ewing's sarcoma, gastric cancer, glioma, hepatocellular carcinoma, Hodgkin lymphoma, laryngeal carcinoma, leukemia, liver cancer, lung cancer, melanoma, mesothelioma, pancreatic cancer, rectal cancer, renal cancer, squamous cell carcinoma, t cell lymphoma, thyroid cancer, monocytic leukemia, pheochromocytoma, malignant peripheral nerve cell tumors, malignant peripheral nerve sheath tumors (MPNST), cutaneous and plexiform neurofibromas, leiomyoadenomatoid tumor, fibroids, uterine fibroids, leiomyosarcoma, papillary thyroid cancer, anaplastic thyroid cancer, medullary thyroid cancer, follicular thyroid cancer, hurthle cell carcinoma, thyroid cancer, ascites, malignant ascites, mesothelioma, salivary gland tumors, mucoepidermoid carcinoma of the salivary gland, acinic cell carcinoma of the salivary gland, gastrointestinal stromal tumors (GIST), tumors that cause effusions in potential spaces of the body, pleural effusions, pericardial effusions, peritoneal effusions aka ascites, giant cell tumors (GCT), GCT of bone, pigmented villonodular synovitis (PVNS), tenosynovial giant cell tumor (TGCT), TCGT of tendon sheath (TGCT-TS), and other sarcomas; tumor angiogenesis and paracrine tumor growth and tumors that express aberrantly or otherwise Fms, CSF1R, CSF1 or IL-34, or activating mutations or translocations of any of the foregoing. In some embodiments, the macrophages are tumor-associated macrophages.

In another aspect, the disclosure provides a method for treating a subject suffering from a disease or condition mediated by a protein kinase selected from c-fms, c-kit, flt3 or combinations thereof and/or infiltration or activation of macrophages, CD14+CD16++ monocytes, microglia, osteoclasts or combinations thereof. The method includes administering to the subject an effective amount of a compound of Formula IV:

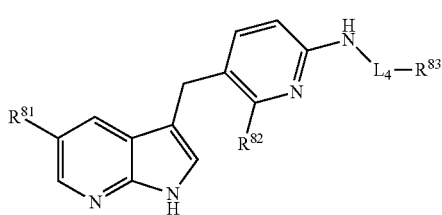

IV or a pharmaceutically acceptable salt, a prodrug, a tautomer or an isomer thereof,
wherein:
$L_4$ is —$CH_2$—, —$CH_2CH_2$—, —$CH(R^{40})$—, —C(O)— or —C(O)NH—;
$R^{81}$ is selected from the group consisting of hydrogen, —$OR^{41}$, —CN, fluoro, chloro, lower alkyl, fluoro substituted lower alkyl, cycloalkyl, heterocycloalkyl, aryl and heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{41}$, —$NR^{41}R^{41}$, —$OR^{41}$ and —$S(O)_2R^{41}$;

$R^{82}$ is selected from the group consisting of hydrogen, fluoro, $C_{1-3}$ alkyl, fluoro substituted $C_{2-3}$ alkyl, OH, $C_{1-3}$ alkoxy, and fluoro substituted $C_{1-3}$ alkoxy;
$R^{83}$ is heterocycloalkyl, heteroaryl, or

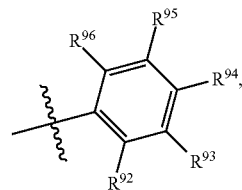

in which

indicates the attachment point of $R^{83}$ to $L_4$ of Formula III, wherein heterocycloalkyl or heteroaryl are optionally substituted with one or more substituents selected from the group consisting of halogen, lower alkyl, fluoro substituted lower alkyl, cycloalkylamino, —$NHR^{41}$, —$NR^{41}R^{41}$, —$OR^{41}$ and —$S(O)_2R^{41}$;
$R^{92}$, $R^{93}$, $R^{94}$, $R^{95}$, and $R^{96}$ are independently selected from the group consisting of hydrogen, halogen, lower alkyl, fluoro substituted lower alkyl, cycloalkylamino, —NHS$(O)_2R^{41}$, —$NHC(O)R^{41}$, —$NHR^{41}$, —$NR^{41}R^{41}$, —$OR^{41}$ and —$S(O)_2R^{41}$;
$R^{40}$ is selected from the group consisting of lower alkyl, and fluoro substituted lower alkyl;
$R^{41}$ at each occurrence is independently selected from the group consisting of lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, and heteroaryl as $R^{41}$ or as substituents of lower alkyl are optionally substituted with one or more substituents selected from the group consisting of —OH, —$NH_2$, —CN, —$NO_2$, —$S(O)_2NH_2$, —$C(O)NH_2$, —$OR^{42}$, —$SR^{42}$, —$NHR^{42}$, —$NR^{42}R^{42}$, —$NR^{39}C(O)R^{42}$, —$NR^{39}S(O)_2R^{42}$, —$S(O)_2R^{42}$, halogen, lower alkyl, fluoro substituted lower alkyl, and cycloalkylamino; and
$R^{42}$ at each occurrence is independently selected from the group consisting of lower alkyl, heterocycloalkyl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, and wherein heterocycloalkyl and heteroaryl are optionally substituted with one or more substituents selected from the group consisting of halogen, —CN, lower alkyl, fluoro substituted lower alkyl, lower alkoxy and fluoro substituted lower alkoxy; provided, however, that the compound is other than those set forth in Table 2, wherein the disease or condition is selected from stem cell ablation and myelopreparation for stem cell transplant, primary progressive multiple sclerosis, complex regional pain syndrome, reflex sympathetic dystrophy, muscular dystrophy, duchenne muscular dystrophy, causalgia, neuro-inflammation, neuroinflammatory disorders, benign forgetfulness, HIV, binswager type dementia, dementia with lewy bodie, prosencephaly, microencepahy, cerebral palsy, congenital hydrocephalus, abdominal dropsy, progressive supranuclear palsy, glaucoma, addiction disorders, dependencies, alcoholism, tremors, Wilson's disease, vascular dementias, multi infarct dementia, frontotemporal dementia, pseudo-dementia, bladder cancer, basal cell carcinoma, cholangiocarcinoma, colon cancer, endometrial cancer, esophageal cancer, Ewing's sarcoma, gastric cancer, glioma, hepatocellular carcinoma, Hodgkin lymphoma, laryngeal carcinoma, leukemia, liver cancer, lung cancer, melanoma, mesothelioma, pancreatic cancer, rectal cancer, renal cancer, squamous cell carcinoma, t cell lymphoma, thyroid cancer, monocytic leukemia, pheochromocytoma, malignant peripheral nerve cell tumors, malignant peripheral nerve sheath tumors (MPNST), cutaneous and plexiform neurofibromas, leiomyoadenomatoid tumor, fibroids, uterine fibroids, leiomyosarcoma, papillary thyroid cancer, anaplastic thyroid cancer, medullary thyroid cancer, follicular thyroid cancer, hurthle cell carcinoma, thyroid cancer, ascites, malignant ascites, mesothelioma, salivary gland tumors, mucoepidermoid carcinoma of the salivary gland, acinic cell carcinoma of the salivary gland, gastrointestinal stromal tumors (GIST), tumors that cause effusions in potential spaces of the body, pleural effusions, pericardial effusions, peritoneal effusions aka ascites, giant cell tumors (GCT), GCT of bone, pigmented villonodular synovitis (PVNS), tenosynovial giant cell tumor (TGCT), TCGT of tendon sheath (TGCT-TS), and other sarcomas; tumor angiogenesis and paracrine tumor growth and tumors that express aberrantly or otherwise Fms, CSF1R, CSF1 or IL-34, or activating mutations or translocations of any of the foregoing.

In yet another aspect, the present disclosure provides a method for treating a disease or condition as described herein using a compound as described herein in combination with an agent as described herein or a suitable therapy or medical procedure as described herein.

Additional aspects and embodiments will be apparent from the following Drawings and Detailed Description and from the claims.

BRIEF DESCRIPTION OF THE DRAWINGS

FIG. 7B: Reduced CFU-M. FIG. 7C: reduced osteoclast formation. FIG. 7D: reduced osteoclast migration. FIG. 7E: a c-kit/c-fms inhibitors blocks osteoclast resorption in normal and NF1 cells.

FIG. 7F: bone mineral density. FIG. 7G: bone volume. WT=wild type; NF1=neurofibromatosis-1; S=Sham O/C=ovariectomized control; O/D=ovariectomized plus compound A.

DETAILED DESCRIPTION

I. Definitions

Figure 1:
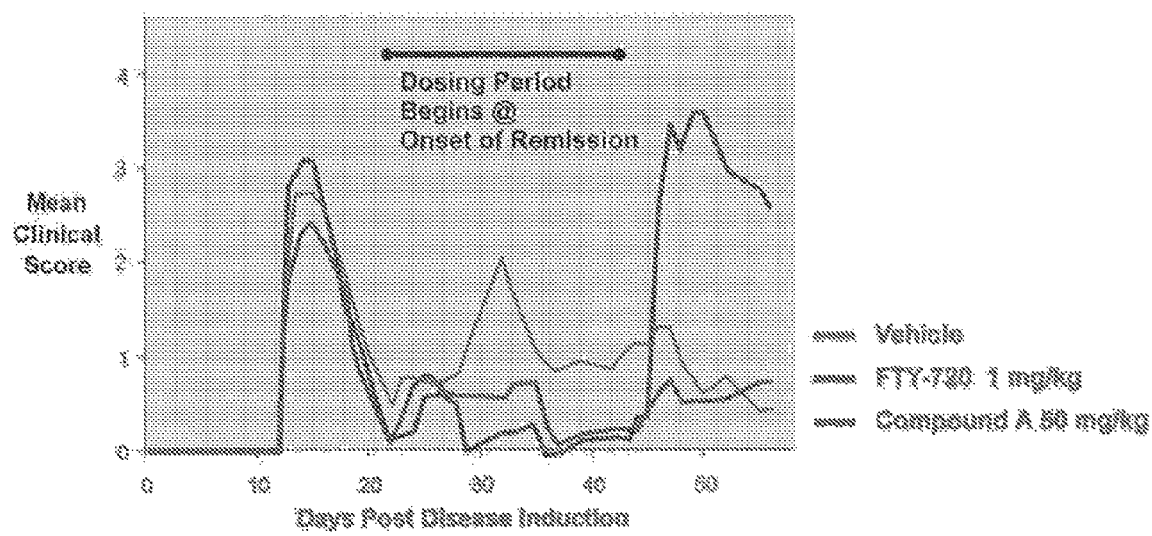
FIG. 1 shows efficacy of a compound as described herein to decrease the severity of PLP139-151-induced relapsing-remitting EAE in specialized mice.

As used herein the following definitions apply unless clearly indicated otherwise:

All atoms designated within a Formula described herein, either within a structure provided, or within the definitions of variables related to the structure, is intended to include any isotope thereof, unless clearly indicated to the contrary. It is understood that for any given atom, the isotopes may be present essentially in ratios according to their natural occurrence, or one or more particular atoms may be enhanced with respect to one or more isotopes using synthetic methods known to one skilled in the art. Thus, hydrogen includes for example $^{1}H$, $^{2}H$, $^{3}H$; carbon includes for example $^{11}C$, $^{12}C$, $^{13}C$, $^{14}C$; oxygen includes for example $^{16}O$, $^{17}O$, $^{18}O$; nitrogen includes for example $^{13}N$, $^{14}N$, $^{15}N$; sulfur includes for example $^{32}S$, $^{33}S$, $^{34}S$, $^{35}S$, $^{36}S$, $^{37}S$, $^{38}S$; fluoro includes for example $^{17}F$, $^{18}F$, $^{19}F$; chloro includes for example $^{35}Cl$, $^{36}Cl$, $^{37}Cl$, $^{38}Cl$, $^{39}Cl$; and the like.

"Halogen" or "Halo" refers to all halogens, that is, chloro (Cl), fluoro (F), bromo (Br), or iodo (I).

"Lower alkyl" alone or in combination means an alkane-derived radical containing from 1 to 6 carbon atoms (unless specifically defined) that includes a straight chain alkyl or branched alkyl. In many embodiments, a lower alkyl is a straight or branched alkyl group containing from 1-6, 1-4, or 1-2, carbon atoms, such as methyl, ethyl, propyl, isopropyl, butyl, t-butyl, and the like. A lower alkyl may be independently substituted as described herein, unless indicated otherwise, with one or more, preferably 1, 2, 3, 4 or 5, also 1, 2, or 3 substituents, wherein the substituents are as indicated. Furthermore, possible substitutions are attached at any available atom to produce a stable compound. For example "halo substituted lower alkyl" denotes a lower alkyl group substituted with one or more halogen atoms, where preferably the lower alkyl is substituted with 1, 2, 3, 4 or 5 halogen atoms, also 1, 2, or 3 halogen atoms. Furthermore, possible substitutions are attached at any available atom to produce a stable compound. For example "fluoro substituted lower alkyl" denotes a lower alkyl group substituted with one or more fluoro atoms, such as perfluoroalkyl, where preferably the lower alkyl is substituted with 1, 2, 3, 4 or 5 fluoro atoms, also 1, 2, or 3 fluoro atoms. Exemplary fluoro substituted lower alkyl includes, but is not limited to, $CF_3$, $CF_2CF_3$, $CH_2CF_3$, and the like. It is understood that substitutions are chemically feasible and attached at any available atom to provide a stable compound.

"Lower alkoxy" refers to those lower alkyl groups as defined herein attached to the remainder of the molecule via an oxygen atom. Representative alkoxy groups include methoxy, ethoxy, n-propoxy, i-propoxy, n-butoxy, n-pentoxy, n-heptoxy, and the like, as well as isomers thereof.

"Lower alkenyl" alone or in combination means a straight or branched hydrocarbon containing 2-6 carbon atoms (unless specifically defined) and at least one, preferably 1-3, more preferably 1-2, most preferably one, carbon to carbon double bond. Carbon to carbon double bonds may be either contained within a straight chain or branched portion. The straight chain or branched lower alkenyl group is chemically feasible and attached at any available point to provide a stable compound. Examples of lower alkenyl groups include ethenyl, propenyl, isopropenyl, butenyl, and the like.

"Lower alkynyl" alone or in combination means a straight or branched hydrocarbon containing 2-6 carbon atoms (unless specifically defined) containing at least one, preferably one, carbon to carbon triple bond. The straight chain or branched lower alkynyl group is chemically feasible and attached at any available point to provide a stable compound. Examples of alkynyl groups include ethynyl, propynyl, butynyl, and the like.

"Cycloalkyl" refers to saturated or unsaturated, non-aromatic monocyclic, bicyclic or tricyclic carbon ring systems of 3-10, also 3-8, more preferably 3-6, ring members per ring, such as cyclopropyl, cyclopentyl, cyclohexyl, adamantyl, and the like.

"Heterocycloalkyl" refers to a saturated or unsaturated non-aromatic cycloalkyl group having from 5 to 10 atoms in which from 1 to 3 carbon atoms in the ring are replaced by heteroatoms of O, S or N, and are optionally fused with benzo or heteroaryl of 5-6 ring members. Heterocycloalkyl is also intended to include oxidized S or N, such as sulfinyl, sulfonyl and N-oxide of a tertiary ring nitrogen. Heterocycloalkyl is also intended to include compounds in which a ring carbon may be oxo substituted, i.e. the ring carbon is a carbonyl group, such as lactones and lactams. The point of attachment of the heterocycloalkyl ring is at a carbon or nitrogen atom such that a stable ring is retained. Examples of heterocycloalkyl groups include, but are not limited to, morpholino, tetrahydrofuranyl, dihydropyridinyl, piperidinyl, pyrrolidinyl, pyrrolidonyl, piperazinyl, dihydrobenzofuryl, and dihydroindolyl.

"Cycloalkylamino" denotes the group —$NR^aR^b$, where $R^a$ and $R^b$ combine with the nitrogen to form a 5-7 membered heterocycloalkyl, where the heterocycloalkyl may contain an additional heteroatom within the ring, such as O, N, or S, and may also be further substituted with lower alkyl. Examples of 5-7 membered heterocycloalkyl include, but are not limited to, piperidine, piperazine, 4-methylpiperazine, morpholine, and thiomorpholine. It is understood that when cycloalkylamino is a substituent on other moieties, these are chemically feasible and attached at any available atom to provide a stable compound.

"Aryl" alone or in combination refers to a monocyclic or bicyclic ring system containing aromatic hydrocarbons such as phenyl or naphthyl, which may be optionally fused with a cycloalkyl of preferably 5-7, more preferably 5-6, ring members. A "substituted aryl" is an aryl that is independently substituted, with one or more, preferably 1, 2, 3, 4 or 5, also 1, 2, or 3 substituents, attached at any available atom to produce a stable compound.

"Heteroaryl" alone or in combination refers to a monocyclic aromatic ring structure containing 5 or 6 ring atoms, or a bicyclic aromatic group having 8 to 10 atoms, containing one or more, preferably 1-4, more preferably 1-3, even more preferably 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable compound is produced. Examples of heteroaryl groups include, but are not limited to, pyridinyl, pyridazinyl, pyrazinyl, quinoaxalyl, indolizinyl, benzo[b]thienyl, quinazolinyl, purinyl, indolyl, quinolinyl, pyrimidinyl, pyrrolyl, oxazolyl, thiazolyl, thienyl, isoxazolyl, oxathiadiazolyl, isothiazolyl, tetrazolyl, imidazolyl, triazinyl, furanyl, benzofuryl, and indolyl. "Nitrogen containing heteroaryl" refers to heteroaryl wherein any heteroatoms are N. A "substituted heteroaryl" is a heteroaryl that is independently substituted, with one or more, preferably 1, 2, 3, 4 or 5, also 1, 2, or 3 substituents, attached at any available atom to produce a stable compound.

"Mono-alkylamino" denotes the group —$NHR^{bb}$ where $R^{bb}$ is lower alkyl. "Di-alkylamino" denotes the group —$NR^{bb}R^{cc}$, where $R^{bb}$ and $R^{cc}$ are independently lower alkyl. While it is understood that when mono-alkylamino, di-alkylamino, or cycloalkylamino are substituents on other moieties that are attached at any available atom to produce a stable compound, the nitrogen of mono-alkylamino, di-alkylamino, or cycloalkylamino as substituents is not bound to a carbon atom that is bound to an —O—, —S—, or —N— of the other moiety.

"Lower alkylthio" refers to those lower alkyl groups as defined herein attached to the remainder of the molecule via an sulfur atom. Representative alkylthio groups include methylthio, ethylthio, n-propylthio, i-propylthio, n-butylthio, n-pentylthio, n-heptylthio, and the like, as well as isomers thereof.

As used herein, the terms "treat", "treating", "therapy", "therapies", and like terms refer to the administration of material, e.g., any one or more compound(s) as described herein in an amount effective to prevent, alleviate, or ameliorate one or more symptoms of a disease or condition, i.e., indication, and/or to prolong the survival of the subject being treated.

As used herein, the term "Fms and/or Kit and/or Flt3 protein kinase mediated disease or condition" refers to a disease or condition in which the biological function of a Fms protein kinase, including any mutation thereof, a Kit protein kinase, including any mutation thereof, a Flt3 protein kinase, including any mutation thereof or both a Fms and Kit protein kinase, including any mutations thereof, affects the development, course, and/or symptoms of the disease or condition, and/or in which modulation of the Fms and/or Kit and/r flt3 protein kinase alters the development, course, and/or symptoms of the disease or condition. A Fms and/or Kit and/or Flt3 protein kinase mediated disease or condition includes a disease or condition for which modulation provides a therapeutic benefit, e.g. wherein treatment with Fms and/or Kit and/or Flt3 protein kinase inhibitor(s), including one or more compound(s) described herein, provides a therapeutic benefit to the subject suffering from or at risk of the disease or condition.

As used herein, the terms "Fms protein kinase mediated disease or condition," "c-fms mediated disease or condition," and the like refer to a disease or condition in which the biological function of a Fms protein kinase, including any mutations thereof, affects the development, course, and/or symptoms of the disease or condition, and/or in which modulation of the Fms protein kinase alters the development, course, and/or symptoms of the disease or condition. The Fms protein kinase mediated disease or condition includes a disease or condition for which Fms inhibition provides a therapeutic benefit, e.g. wherein treatment with Fms inhibitor(s), including one or more compound(s) described herein, provides a therapeutic benefit to the subject suffering from or at risk of the disease or condition.

As used herein, the terms "Kit protein kinase mediated disease or condition," "c-kit mediated disease or condition," and the like refer to a disease or condition in which the biological function of a Kit protein kinase, including any mutations thereof, affects the development, course, and/or symptoms of the disease or condition, and/or in which modulation of the Kit protein kinase alters the development, course, and/or symptoms of the disease or condition. The Kit protein kinase mediated disease or condition includes a disease or condition for which Kit inhibition provides a therapeutic benefit, e.g. wherein treatment with Kit inhibitor(s), including one or more compound(s) described herein, provides a therapeutic benefit to the subject suffering from or at risk of the disease or condition.

As used herein, the term "dual Fms/Kit inhibitor" refers to a compound that inhibits both Fms and Kit protein kinases, i.e. a compound having an $IC_{50}$ of less than 500 nm, less than 100 nM, less than 50 nM, less than 20 nM, less than 10 nM, less than 5 nM, or less than 1 nM as determined in a generally accepted Fms kinase activity assay and having an $IC_{50}$ of less than 500 nm, less than 100 nM, less than 50 nM, less than 20 nM, less than 10 nM, less than 5 nM, or less than 1 nM as determined in a comparable generally accepted Kit kinase activity assay, wherein the activity is approximately equipotent on each. Compounds are considered approximately equipotent if the ratio of $IC_{50}$ for Kit kinase activity divided by the $IC_{50}$ for Fms kinase activity is in the range of 20 to 0.05, also 10 to 0.1, also 5 to 0.2. Such compounds are effective in treating a disease or condition that is either or both of a Fms protein kinase mediated and Kit protein kinase mediated disease or condition. Such compounds are preferably, but not necessarily, selective with respect to other protein kinases, i.e. when compared to another protein kinase, the $IC_{50}$ for the other kinase divided by the $IC_{50}$ for Fms kinase is >20, also >30, also >40, also >50, also >60, also >70, also >80, also >90, also >100. Preferably, the compounds are selective relative to other protein kinases including, but not limited to, CSK, Insulin receptor kinase, AMPK, PDGFR or VEGFR. While it is understood that a dual Fms/Kit inhibitor may be used to treat any Fms protein kinase mediated disease or condition, the dual inhibition of Fms and Kit provides beneficial effects in treating certain diseases or conditions, including, but not limited to, metastatic breast cancer, prostate cancer, multiple myeloma, melanoma, acute myeloid leukemia, brain metastases, neurofibromatosis, gastrointestinal stromal tumors, rheumatoid arthritis, or multiple sclerosis.

As used herein, the term "dual Fms/Flt-3 inhibitor" refers to a compound that inhibits both Fms and Flt-3 protein kinases, i.e. a compound having an $IC_{50}$ of less than 500 nm, less than 100 nM, less than 50 nM, less than 20 nM, less than 10 nM, less than 5 nM, or less than 1 nM as determined in a generally accepted Fms kinase activity assay and having an $IC_{50}$ of less than 500 nm, less than 100 nM, less than 50 nM, less than 20 nM, less than 10 nM, less than 5 nM, or less than 1 nM as determined in a comparable generally accepted Flt-3 kinase activity assay, wherein the activity is approximately equipotent on each. Compounds are considered approximately equipotent if the ratio of $IC_{50}$ for Flt-3 kinase activity divided by the $IC_{50}$ for Fms kinase activity is in the range of 20 to 0.05, also 10 to 0.1, also 5 to 0.2. Such compounds are effective in treating a disease or condition that is either or both of a Fms protein kinase mediated and Flt-3 protein kinase mediated disease or condition. Such compounds are preferably, but not necessarily, selective with respect to other protein kinases, i.e. when compared to another protein kinase, the $IC_{50}$ for the other kinase divided by the $IC_{50}$ for Fms kinase is >20, also >30, also >40, also >50, also >60, also >70, also >80, also >90, also >100. Preferably, the compounds are selective relative to other protein kinases including, but not limited to, CSK, Insulin receptor kinase, AMPK, PDGFR or VEGFR. While it is understood that a dual Fms/Flt-3 inhibitor may be used to treat any Fms protein kinase mediated disease or condition, the dual inhibition of Fms and Flt-3 provides beneficial effects in treating certain diseases or conditions, including, but not limited to, acute myeloid leukemia.

As used herein, the term "Fms selective inhibitor" refers to a compound that selectively inhibits Fms kinase relative to Kit kinase, i.e. a compound having an $IC_{50}$ of less than 500 nm, less than 100 nM, less than 50 nM, less than 20 nM, less than 10 nM, less than 5 nM, or less than 1 nM as determined in a generally accepted Fms kinase activity assay and when determined in a comparable generally accepted Kit kinase activity assay will have a ratio of $IC_{50}$ for Kit kinase divided by the $IC_{50}$ for Fms kinase of >20, also >30, also >40, also >50, also >60, also >70, also >80, also >90, also >100. Such compounds are effective in treating a disease or condition that is Fms protein kinase mediated, without effecting Kit protein kinase. Such compounds are preferably, but not necessarily, selective with respect to other protein kinases, i.e. when compared to another protein kinase, the $IC_{50}$ for the other kinase divided by the $IC_{50}$ for Fms kinase is >20, also >30, also >40, also >50, also >60, also >70, also >80, also >90, also >100. Preferably, the compounds are selective relative to other protein kinases including, but not limited to, CSK, Insulin receptor kinase, AMPK, PDGFR or VEGFR. While it is understood that a Fms selective inhibitor may be used to treat any Fms protein kinase mediated disease or condition, the Fms selectivity provides beneficial effects in treating certain diseases or conditions, including, but not limited to, rheumatoid arthritis, Alzheimer's disease, Parkinson's disease, osteoarthritis, nephritis, diabetic nephropathy, or renal hypertrophy.

As used herein, the term "blood brain barrier" refers to the physical barrier in the circulation system that prevents many substances, including certain small molecule drugs, from entering into the central nervous system (CNS). Drugs which are intended to interact with molecular targets in the CNS must cross the blood brain barrier to reach their intended targets. Conversely, peripherally acting agents should not cross the blood brain barrier so as to avoid any CNS related side effects. The ability of a compound to penetrate the blood brain barrier is expressed as the blood brain barrier permeability or the ratio of the steady-state concentrations of the compound in the brain and in the blood. The experimental blood brain barrier permeability can be measured by in vivo methods. Various methods can be employed for measuring the fraction of compound transported from the blood to brain tissue, including brain blood partitioning, brain perfusion, brain uptake index, and intracerebral microdialysis. However, these in vivo methods are laborious and low-throughput in nature. In practice, in silico computational methods are often used to predict the blood brain barrier permeability prior to in vivo confirmation. Most of the blood brain barrier models that have been built so far are based on the assumption that the majority of the compounds are transported across the blood brain barrier by passive diffusion. Of all the physicochemical properties, polar surface area (PSA) shows the best correlation with the blood brain barrier permeability for passively diffused compounds. Empirical evidence suggests that compounds having a polar surface area of 100 or greater typically have a low probability of crossing the blood brain barrier. Polar surface area is readily calculated from the compound structure using a published algorithm (Ertl et al., J. Med. Chem. 2000, 43:3714-3717). While it is understood that a Fms selective inhibitor may be used to treat any Fms protein kinase mediated disease or condition, compounds that effectively cross the blood brain barrier provide beneficial effects in treating certain diseases or conditions, including, but not limited to, multiple sclerosis, glioblastoma, Alzheimer's disease, and Parkinson's disease, while compounds that do not effectively cross the blood brain barrier provide beneficial effects in treating certain diseases or conditions, including, but not limited to, rheumatoid arthritis, osteoarthritis, atherosclerosis, systemic lupus erythematosus, glomerulonephritis, interstitial nephritis, Lupus nephritis, tubular necrosis, diabetic nephropathy, or renal hypertrophy.

As used herein, the term "solid form" refers to a solid preparation (i.e. a preparation that is neither gas nor liquid) of a pharmaceutically active compound that is suitable for administration to an intended animal subject for therapeutic purposes. The solid form includes any complex, such as a salt, co-crystal or an amorphous complex, as well as any polymorph of the compound. The solid form may be substantially crystalline, semi-crystalline or substantially amorphous. The solid form may be administered directly or used in the preparation of a suitable composition having improved pharmaceutical properties. For example, the solid form may be used in a formulation comprising at least one pharmaceutically acceptable carrier or excipient.

As used herein, the term "semi-crystalline" material embraces material which is greater than 10% crystallinity, but no greater than 90% crystallinity; preferably "semi-crystalline" material embraces material which is greater than 20% crystallinity, but no greater than 80% crystallinity. In one aspect of the present disclosure, a mixture of solid forms of a compound may be prepared, for example, a mixture of amorphous and crystalline solid forms, e.g. to provide a "semi-crystalline" solid form. Such a "semi-crystalline" solid form may be prepared by methods known in the art, for example by mixing an amorphous solid form with a crystalline solid form in the desired ratio. In some instances, a compound mixed with acid or base forms an amorphous complex; a semi-crystalline solid can be prepared employing an amount of compound component in excess of the stoichiometry of the compound and acid or base in the amorphous complex, thereby resulting in an amount of the amorphous complex that is based on the stoichiometry thereof, with excess compound in a crystalline form. The amount of excess compound used in the preparation of the complex can be adjusted to provide the desired ratio of amorphous complex to crystalline compound in the resulting mixture of solid forms. For example, where the amorphous complex of acid or base and compound has a 1:1 stoichiometry, preparing said complex with a 2:1 mole ratio of compound to acid or base will result in a solid form of 50% amorphous complex and 50% crystalline compound. Such a mixture of solid forms may be beneficial as a drug product, for example, by providing an amorphous component having improved biopharmaceutical properties along with the crystalline component. The amorphous component would be more readily bioavailable while the crystalline component would have a delayed bioavailability. Such a mixture may provide both rapid and extended exposure to the active compound.

As used herein, the term "complex" refers to a combination of a pharmaceutically active compound and an additional molecular species that forms or produces a new chemical species in a solid form. In some instances, the complex may be a salt, i.e. where the additional molecular species provides an acid/base counter ion to an acid/base group of the compound resulting in an acid:base interaction that forms a typical salt. While such salt forms are typically substantially crystalline, they can also be partially crystalline, substantially amorphous, or amorphous forms. In some instances, the additional molecular species, in combination with the pharmaceutically active compound, forms a non-salt co-crystal, i.e. the compound and molecular species do not interact by way of a typical acid:base interaction, but still form a substantially crystalline structure. Co-crystals may also be formed from a salt of the compound and an additional molecular species. In some instances, the complex is a substantially amorphous complex, which may contain salt-like acid:base interactions that do not form typical salt crystals, but instead form a substantially amorphous solid, i.e. a solid whose X-ray powder diffraction pattern exhibits no sharp peaks (e.g. exhibits an amorphous halo).

As used herein, the term "stoichiometry" refers to the molar ratio of two or more reactants that combine to form a complex, for example, the molar ratio of acid or base to compound that form an amorphous complex. For example, a 1:1 mixture of acid or base with compound (i.e. 1 mole acid or base per mole of compound) resulting in an amorphous solid form has a 1:1 stoichiometry.

As used herein, the term "composition" refers to a pharmaceutical preparation suitable for administration to an intended subject for therapeutic purposes that contains at least one pharmaceutically active compound, including any solid form thereof. The composition may include at least one pharmaceutically acceptable component to provide an improved formulation of the compound, such as a suitable carrier or excipient.

As used herein, the term "subject" refers to a living organism that is treated with compounds as described herein, including, but not limited to, any mammal, such as a human, other primates, sports animals, animals of commercial interest such as cattle, farm animals such as horses, or pets such as dogs and cats.

As used herein, the term "biopharmaceutical properties" refers to the pharmacokinetic action of a compound or complex of the present disclosure, including the dissolution, absorption and distribution of the compound on administration to a subject. As such, certain solid forms of compounds of the disclosure, such as amorphous complexes of compounds of the disclosure, are intended to provide improved dissolution and absorption of the active compound, which is typically reflected in improved $C_{max}$ (i.e. the maximum achieved concentration in the plasma after administration of the drug) and improved AUC (i.e. area under the curve of drug plasma concentration vs. time after administration of the drug).

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectables.

Certain compounds contemplated for use in accordance with the present disclosure can exist in unsolvated forms as well as solvated forms, including hydrated forms. "Hydrate" refers to a complex formed by combination of water molecules with molecules or ions of the solute. "Solvate" refers to a complex formed by combination of solvent molecules with molecules or ions of the solute. The solvent can be an organic compound, an inorganic compound, or a mixture of both. Solvate is meant to include hydrate. Some examples of solvents include, but are not limited to, methanol, N,N-dimethylformamide, tetrahydrofuran, dimethylsulfoxide, and water. In general, the solvated forms are equivalent to unsolvated forms and are encompassed within the scope of the present disclosure. Certain compounds contemplated for use in accordance with the present disclosure may exist in multiple crystalline or amorphous forms. In general, all physical forms are equivalent for the uses contemplated by the present disclosure and are intended to be within the scope of the present disclosure.

In the present context, the term "therapeutically effective" or "effective amount" indicates that the materials or amount of material is effective to prevent, alleviate, or ameliorate one or more symptoms of a disease or medical condition, and/or to prolong the survival of the subject being treated. The therapeutically effective amount will vary depending on the compound, the disorder or condition and its severity and the age, weight, etc., of the mammal to be treated. For example, an effective amount is an amount sufficient to effectuate a beneficial or desired clinical result. The effective amounts can be provided all at once in a single administration or in fractional amounts that provide the effective amount in several administrations. The precise determination of what would be considered an effective amount may be based on factors individual to each subject, including their size, age, injury, and/or disease or injury being treated, and amount of time since the injury occurred or the disease began. One skilled in the art will be able to determine the effective amount for a given subject based on these considerations which are routine in the art.

In the present context, the terms "synergistically effective" or "synergistic effect" indicate that two or more compounds that are therapeutically effective, when used in combination, provide improved therapeutic effects greater than the additive effect that would be expected based on the effect of each compound used by itself.

By "assaying" is meant the creation of experimental conditions and the gathering of data regarding a particular result of the experimental conditions. For example, enzymes can be assayed based on their ability to act upon a detectable substrate. A compound can be assayed based on its ability to bind to a particular target molecule or molecules.

As used herein, the term "modulating" or "modulate" refers to an effect of altering a biological activity, especially a biological activity associated with a particular biomolecule such as a protein kinase. For example, an inhibitor of a particular biomolecule modulates the activity of that biomolecule, e.g., an enzyme, by decreasing the activity of the biomolecule, such as an enzyme. Such activity is typically indicated in terms of an inhibitory concentration ($IC_{50}$) of the compound for an inhibitor with respect to, for example, an enzyme.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

"Pain" or a "pain condition" can be acute and/or chronic pain, including, without limitation, arachnoiditis; arthritis (e.g. osteoarthritis, rheumatoid arthritis, ankylosing spondylitis, gout); back pain (e.g. sciatica, ruptured disc, spondylolisthesis, radiculopathy); burn pain; cancer pain; dysmenorrhea; headaches (e.g. migraine, cluster headaches, tension headaches); head and facial pain (e.g. cranial neuralgia, trigeminal neuralgia); hyperalgesia; hyperpathia; inflammatory pain (e.g. pain associated with irritable bowel syndrome, inflammatory bowel disease, ulcerative colitis, Crohn's disease, cystitis, pain from bacterial, fungal or viral infection); keloid or scar tissue formation; labor or delivery pain; muscle pain (e.g. as a result of polymyositis, dermatomyositis, inclusion body myositis, repetitive stress injury (e.g. writer's cramp, carpal tunnel syndrome, tendonitis, tenosynovitis)); myofascial pain syndromes (e.g. fibromyalgia); neuropathic pain (e.g. diabetic neuropathy, causalgia, entrapment neuropathy, brachial plexus avulsion, occipital neuralgia, gout, reflex sympathetic dystrophy syndrome, muscular dystrophy, duchenne muscular dystrophy, phantom limb or post-amputation pain, postherpetic neuralgia, central pain syndrome, or nerve pain resulting from trauma (e.g. nerve injury), disease (e.g. diabetes, multiple sclerosis, Guillan-Barre Syndrome, myasthenia gravis, neurodegenerative diseases such as Parkinson's disease, Alzheimer's disease, amyotrophic lateral sclerosis, or cancer treatment); pain associated with skin disorders (e.g. shingles, herpes simplex, skin tumors, cysts, neurofibromatosis); sports injuries (e.g. cuts, sprains, strains, bruises, dislocations, fractures, spinal chord, head); spinal stenosis; surgical pain; tactile allodynia; temporomandibular disorders; vascular disease or injury (e.g. vasculitis, coronary artery disease, reperfusion injury (e.g. following ischemia, stroke, or myocardial infarcts)); other specific organ or tissue pain (e.g. ocular pain, corneal pain, bone pain, heart pain, visceral pain (e.g. kidney, gall bladder, gastrointestinal), joint pain, dental pain, pelvic hypersensitivity, pelvic pain, renal colic, urinary incontinence); other disease associated pain (e.g. sickle cell anemia, AIDS, herpes zoster, psoriasis, endometriosis, asthma, chronic obstructive pulmonary disease (COPD), silicosis, pulmonary sarcoidosis, esophagitis, heart burn, gastroesophageal reflux disorder, stomach and duodenal ulcers, functional dyspepsia, bone resorption disease, osteoporosis, cerebral malaria, bacterial meningitis); or pain due to graft v. host rejection or allograft rejections.

Alternative Compound Forms or Derivatives

Compounds contemplated for use herein are described with reference to both generic formulae and specific compounds. In addition, compounds contemplated for use herein may exist in a number of different forms or derivatives, all within the scope of the present disclosure. Alternative forms or derivatives, include, for example, (a) prodrugs, and active metabolites (b) tautomers, isomers (including stereoisomers and regioisomers), and racemic mixtures (c) pharmaceutically acceptable salts and (d) solid forms, including different crystal forms, polymorphic or amorphous solids, including hydrates and solvates thereof, and other forms.

(a) Prodrugs and Metabolites

In addition to the present formulae and compounds described herein, the disclosure also includes prodrugs (generally pharmaceutically acceptable prodrugs), active metabolic derivatives (active metabolites), and their pharmaceutically acceptable salts.

Prodrugs are compounds or pharmaceutically acceptable salts thereof which, when metabolized under physiological conditions or when converted by solvolysis, yield the desired active compound. Prodrugs include, without limitation, esters, amides, carbamates, carbonates, ureides, solvates, or hydrates of the active compound. Typically, the prodrug is inactive, or less active than the active compound, but may provide one or more advantageous handling, administration, and/or metabolic properties. For example, some prodrugs are esters of the active compound; during metabolysis, the ester group is cleaved to yield the active drug. Esters include, for example, esters of a carboxylic acid group, or S-acyl or O-acyl derivatives of thiol, alcohol, or phenol groups. In this context, a common example is an alkyl ester of a carboxylic acid. Prodrugs may also include variants wherein an —NH group of the compound has undergone acylation, such as the 7-position of the pyrrolo [2,3-d]pyrimidine ring or the 1-position of the 1H-pyrrolo [2,3-b]pyridine ring of compounds as described herein, where cleavage of the acyl group provides the free —NH group of the active drug. Some prodrugs are activated enzymatically to yield the active compound, or a compound may undergo further chemical reaction to yield the active compound. Prodrugs may proceed from prodrug form to active form in a single step or may have one or more intermediate forms which may themselves have activity or may be inactive.

As described in *The Practice of Medicinal Chemistry*, Ch. 31-32 (Ed. Wermuth, Academic Press, San Diego, Calif., 2001), prodrugs can be conceptually divided into two non-exclusive categories, bioprecursor prodrugs and carrier prodrugs. Generally, bioprecursor prodrugs are compounds that are inactive or have low activity compared to the corresponding active drug compound, that contain one or more protective groups and are converted to an active form by metabolism or solvolysis. Both the active drug form and any released metabolic products should have acceptably low toxicity. Typically, the formation of active drug compound involves a metabolic process or reaction that is one of the following types:

Oxidative reactions: Oxidative reactions are exemplified without limitation by reactions such as oxidation of alcohol, carbonyl, and acid functionalities, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-dealkylation, oxidative 0- and S-dealkylation, oxidative deamination, as well as other oxidative reactions.

Reductive reactions: Reductive reactions are exemplified without limitation by reactions such as reduction of carbonyl functionalities, reduction of alcohol functionalities and carbon-carbon double bonds, reduction of nitrogen-containing functional groups, and other reduction reactions.

Reactions without change in the oxidation state: Reactions without change in the state of oxidation are exemplified without limitation to reactions such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improves uptake and/or localized delivery to a site(s) of action. Desirably for such a carrier prodrug, the linkage between the drug moiety and the transport moiety is a covalent bond, the prodrug is inactive or less active than the drug compound, the prodrug and any release transport moiety are acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. (See, e.g., Cheng et al., U.S. Patent Publ. No. 20040077595, application Ser. No. 10/656, 838, incorporated herein by reference.) Such carrier prodrugs are often advantageous for orally administered drugs. In some instances, the transport moiety provides targeted delivery of the drug, for example the drug may be conjugated to an antibody or antibody fragment. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of hydroxyl groups with lipophilic carboxylic acids, or of carboxylic acid groups with alcohols, e.g., aliphatic alcohols. Wermuth, supra.

Metabolites, e.g., active metabolites, overlap with prodrugs as described above, e.g., bioprecursor prodrugs. Thus, such metabolites are pharmacologically active compounds or compounds that further metabolize to pharmacologically active compounds that are derivatives resulting from metabolic processes in the body of a subject. Of these, active metabolites are such pharmacologically active derivative compounds. For prodrugs, the prodrug compound is generally inactive or of lower activity than the metabolic product. For active metabolites, the parent compound may be either an active compound or may be an inactive prodrug. For example, in some compounds, one or more alkoxy groups can be metabolized to hydroxyl groups while retaining pharmacologic activity and/or carboxyl groups can be esterified, e.g., glucuronidation. In some cases, there can be more than one metabolite, where an intermediate metabolite(s) is further metabolized to provide an active metabolite. For example, in some cases a derivative compound resulting from metabolic glucuronidation may be inactive or of low activity, and can be further metabolized to provide an active metabolite.

Metabolites of a compound may be identified using routine techniques known in the art, and their activities determined using tests such as those described herein. See, e.g., Bertolini et al., 1997, *J. Med. Chem.*, 40:2011-2016; Shan et al., 1997, *J Pharm Sci* 86(7):756-757; Bagshawe, 1995, *Drug Dev. Res.*, 34:220-230; Wermuth, supra.

(b) Tautomers, Stereoisomers, and Regioisomers

It is understood that some compounds may exhibit tautomerism. In such cases, the formulae provided herein expressly depict only one of the possible tautomeric forms. It is therefore to be understood that the formulae provided herein are intended to represent any tautomeric form of the depicted compounds and are not to be limited merely to the specific tautomeric form depicted by the drawings of the formulae.

Likewise, some of the compounds contemplated for use according to the present disclosure may exist as stereoisomers, i.e. having the same atomic connectivity of covalently bonded atoms yet differing in the spatial orientation of the atoms. For example, compounds may be optical stereoisomers, which contain one or more chiral centers, and therefore, may exist in two or more stereoisomeric forms (e.g. enantiomers or diastereomers). Thus, such compounds may be present as single stereoisomers (i.e., essentially free of other stereoisomers), racemates, and/or mixtures of enantiomers and/or diastereomers. As another example, stereoisomers include geometric isomers, such as cis- or trans-orientation of substituents on adjacent carbons of a double bond. All such single stereoisomers, racemates and mixtures thereof are intended to be within the scope of the present disclosure. Unless specified to the contrary, all such stereoisomeric forms are included within the formulae provided herein.

In some embodiments, a chiral compound contemplated for use in accordance with the present disclosure is in a form that contains at least 80% of a single isomer (60% enantiomeric excess ("e.e.") or diastereomeric excess ("d.e.")), or at least 85% (70% e.e. or d.e.), 90% (80% e.e. or d.e.), 95% (90% e.e. or d.e.), 97.5% (95% e.e. or d.e.), or 99% (98% e.e. or d.e.). As generally understood by those skilled in the art, an optically pure compound having one chiral center is one that consists essentially of one of the two possible enantiomers (i.e., is enantiomerically pure), and an optically pure compound having more than one chiral center is one that is both diastereomerically pure and enantiomerically pure. In some embodiments, the compound is present in optically pure form, such optically pure form being prepared and/or isolated by methods known in the art (e.g. by recrystallization techniques, chiral synthetic techniques (including synthesis from optically pure starting materials), and chromatographic separation using a chiral column.

(c) Pharmaceutically Acceptable Salts

Unless specified to the contrary, specification of a compound herein includes pharmaceutically acceptable salts of such compound. Thus, compounds described herein can be in the form of pharmaceutically acceptable salts, or can be formulated as pharmaceutically acceptable salts. Contemplated pharmaceutically acceptable salt forms include, without limitation, mono, bis, tris, tetrakis, and so on. Pharmaceutically acceptable salts are non-toxic in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug. A compound of the disclosure may possess a sufficiently acidic, a sufficiently basic, or both functional groups, and accordingly can react with any of a number of inorganic or organic bases, and inorganic and organic acids, to form a pharmaceutically acceptable salt.

Pharmaceutically acceptable salts include acid addition salts such as those containing chloride, bromide, iodide, hydrochloride, acetate, phenylacetate, acrylate, ascorbate, aspartate, benzoate, 2-phenoxybenzoate, 2-acetoxybenzoate, dinitrobenzoate, hydroxybenzoate, methoxybenzoate, methylbenzoate, bicarbonate, butyne-1,4 dioate, hexyne-1, 6-dioate, caproate, caprylate, chlorobenzoate, cinnamate, citrate, decanoate, formate, fumarate, glycolate, gluconate, glucarate, glucuronate, glucose-6-phosphate, glutamate, heptanoate, hexanoate, isethionate, isobutyrate, gamma-hydroxybutyrate, phenylbutyrate, lactate, malate, maleate, hydroxymaleate, methylmaleate, malonate, mandelate, nicotinate, nitrate, isonicotinate, octanoate, oleate, oxalate, pamoate, phosphate, monohydrogenphosphate, dihydrogenphosphate, orthophosphate, metaphosphate, pyrophosphate, 2-phosphoglycerate, 3-phosphoglycerate, phthalate, propionate, phenylpropionate, propiolate, pyruvate, quinate, salicylate, 4-aminosalicylate, sebacate, stearate, suberate, succinate, sulfate, pyrosulfate, bisulfate, sulfite, bisulfite, sulfamate, sulfonate, benzenesulfonate (i.e. besylate), ethanesulfonate (i.e. esylate), ethane-1,2-disulfonate, 2-hydroxyethanesulfonate (i.e. isethionate), methanesulfonate (i.e. mesylate), naphthalene-1-sulfonate, naphthalene-2-sulfonate (i.e. napsylate), propanesulfonate, p-toluenesulfonate (i.e. tosylate), xylenesulfonates, cyclohexylsulfamate, tartrate, and trifluoroacetate. These pharmaceutically acceptable acid addition salts can be prepared using the appropriate corresponding acid.

When acidic functional groups, such as carboxylic acid or phenol are present, pharmaceutically acceptable salts also include basic addition salts such as those containing benzathine, chloroprocaine, choline, ethanolamine, diethanolamine, triethanolamine, t-butylamine, dicyclohexylamine, ethylenediamine, N,N'-dibenzylethylenediamine, meglumine, hydroxyethylpyrrolidine, piperidine, morpholine, piperazine, procaine, aluminum, calcium, copper, iron, lithium, magnesium, manganese, potassium, sodium, zinc, ammonium, and mono-, di-, or tri-alkylamines (e.g. diethylamine), or salts derived from amino acids such as L-histidine, L-glycine, L-lysine, and L-arginine. For example, see *Remington's Pharmaceutical Sciences*, 19$^{th}$ ed., Mack Publishing Co., Easton, Pa., Vol. 2, p. 1457, 1995. These pharmaceutically acceptable base addition salts can be prepared using the appropriate corresponding base.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. In another example, a salt can be prepared by reacting the free base and acid in an organic solvent. If the particular compound is an acid, the desired pharmaceutically acceptable salt may be prepared by any suitable method, for example, treatment of the free acid with an appropriate inorganic or organic base.

(d) Other Compound Forms

In the case of agents that are solids, it is understood by those skilled in the art that the compounds and salts contemplated for use in accordance with the present disclosure may exist in different crystal or polymorphic forms, or may be formulated as co-crystals, or may be in an amorphous form, or may be any combination thereof (e.g. partially crystalline, partially amorphous, or mixtures of polymorphs) all of which are intended to be within the scope of the present disclosure and specified formulae. Whereas salts are formed by acid/base addition, i.e. a free base or free acid of the compound of interest forms an acid/base reaction with a corresponding addition base or addition acid, respectively, resulting in an ionic charge interaction, co-crystals are a new chemical species that is formed between neutral compounds, resulting in the compound and an additional molecular species in the same crystal structure.

In some instances, compounds contemplated for use according to the present disclosure are complexed with an acid or a base, including base addition salts such as ammonium, diethylamine, ethanolamine, ethylenediamine, diethanolamine, t-butylamine, piperazine, meglumine; acid addition salts, such as acetate, acetylsalicylate, besylate, camsylate, citrate, formate, fumarate, glutarate, hydrochlorate, maleate, mesylate, nitrate, oxalate, phosphate, succinate, sulfate, tartrate, thiocyanate and tosylate; and amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine. In combining the compound of the disclosure with the acid or base, an amorphous complex is preferably formed rather than a crystalline material such as a typical salt or co-crystal. In some instances, the amorphous form of the complex is facilitated by additional processing, such as by spray-drying, mechanochemical methods such as roller compaction, or microwave irradiation of the parent compound mixed with the acid or base. Such methods may also include addition of ionic and/or non-ionic polymer systems, including, but not limited to, hydroxypropyl methyl cellulose acetate succinate (HPMCAS) and methacrylic acid copolymer (e.g. Eudragit® L100-55), that further stabilize the amorphous nature of the complex. Such amorphous complexes provide several advantages. For example, lowering of the melting temperature relative to the free base facilitates additional processing, such as hot melt extrusion, to further improve the biopharmaceutical properties of the compound. Also, the amorphous complex is readily friable, which provides improved compression for loading of the solid into capsule or tablet form.

Additionally, the formulae are intended to cover hydrated or solvated as well as unhydrated or unsolvated forms of the identified structures. For example, the indicated compounds include both hydrated and non-hydrated forms. Other examples of solvates include the structures in combination with a suitable solvent, such as isopropanol, ethanol, methanol, DMSO, ethyl acetate, acetic acid, or ethanolamine.

II. Methods

The compounds described herein have been disclosed in PCT Patent Publication Nos.: WO 2008/064255, WO 2008/064265 and WO 2011/057022, and in US Patent Application Publication Nos.: US 2009/0076046 and US 2011/0112127, the disclosure of each of these patent publications is incorporated by reference in its entirety for all purposes.

In one aspect, the disclosure provides a method for treating a disease or condition in a subject in need thereof, by administering to the subject a therapeutically effective amount of any one or more compound(s) as described herein, a prodrug of such compound, a pharmaceutically acceptable salt of such compound or prodrug, or a pharmaceutically acceptable formulation of such compound or prodrug. The compound can be alone or can be part of a composition. In one embodiment, the disclosure provides a method of treating a disease or condition in a subject in need thereof, by administering to the subject a therapeutically effective amount of any one or more compound(s) as described herein, a prodrug of such compound, a pharmaceutically acceptable salt of such compound or prodrug, or a pharmaceutically acceptable formulation of such compound or prodrug in combination with one or more other suitable therapies for the disease or condition.

In some embodiments, the disclosure provides a method for treating a subject suffering from a disease or condition mediated by c-fms, c-kit, flt3, infiltration or activation of macrophages and/or microglias or combinations thereof. The method includes administering to the subject an effective amount of a compound of formulas I', I, II', II, IIa, III', III, or IV or any compound as described herein, or a pharmaceutically acceptable salt, a prodrug, a tautomer or a stereoisomer thereof, or a combination of a compound of formulas I', I, II', II, IIa, III', III, or IV or any compound as described herein or a pharmaceutically acceptable salt, a prodrug, a tautomer or a stereoisomer thereof and an agent or a drug as described herein. In certain embodiments, the method involves administering to the subject an effective amount of a compound as described herein in combination with one or more other suitable therapies for the disease or condition. In some embodiments, the disclosure provides a method for treating a subject suffering from a disease or condition mediated by tumor-associated macrophages (TAM). In certain embodiments, the disclosure provides a method for treating a subject suffering from a disease or condition, such as a tumor, where tumor-associated macrophages play a role in tumor proliferation, survival, and metastasis. In some embodiments, the disclosure provides a method for treating a subject suffering from a disease or condition, where reduction/depletion of macrophages or microglia provides a benefit. In certain instances, the disease or condition is as described herein. The method includes administering to the subject an effective amount of a compound of formulas I', I, II', II, IIa, III', III, or IV or any compound as described herein, or a pharmaceutically acceptable salt, a prodrug, a tautomer or a stereoisomer thereof, or a combination of a compound of formulas I', I, II', II, IIa, III', III, or IV or any compound as described herein or a pharmaceutically acceptable salt, a prodrug, a tautomer or a stereoisomer thereof and an agent or a drug as described herein. In some embodiments, the disclosure provides methods for treating a subject suffering from tumors that express aberrantly or otherwise Fms, CSF1R, CSF1 or IL-34, or activating mutations or translocations of any of the foregoing.

In some embodiments, the diseases treatable with the compounds as described herein are c-fms mediated disease selected from the group consisting of immune disorders, including, but not limiting to, rheumatoid arthritis, systemic lupus erythematosis (SLE), and transplant rejection; stem cell ablation and myelopreparation for stem cell transplant; inflammatory diseases including, but not limited to, osteoarthritis, inflammatory bowel syndrome, ulcerative colitis, Crohn's disease, chronic obstructive pulmonary disease (COPD), emphysema, Kawasaki's Disease, hemophagocytic syndrome (macrophage activation syndrome), multicentric reticulohistiocytosis, and atherosclerosis; metabolic disorders, including, but not limited to, Type I diabetes, Type II diabetes, insulin resistance, hyperglycemia, obesity, and lipolysis; disorders of bone structure, mineralization and bone formation and resorption, including, but not limited to, osteoporosis, increased risk of fracture, Paget's disease, hypercalcemia, infection-mediated osteolysis (e.g. osteomyelitis), peri-prosthetic or wear-debris-mediated osteolysis, and metastasis of cancer to bone; kidney and genitourinary diseases, including, but not limited to, endometriosis, nephritis (e.g. glomerulonephritis, interstitial nephritis, Lupus nephritis), tubular necrosis, diabetes-associated renal complications (e.g. diabetic nephropathy), and renal hypertrophy; disorders of the central nervous system, including, but not limited to, multiple sclerosis, stroke, Alzheimer's disease and Parkinson's disease; inflammatory and chronic pain, including, but not limited to, bone pain; and cancers, including, but not limited to, multiple myeloma, acute myeloid leukemia (AML), chronic myeloid leukemia (CML), monocytic leukemia, prostate cancer, breast cancer, ovarian cancer, melanoma, glioblastoma multiforme, metastasis of tumors to other tissues, and other chronic myeloproliferative diseases such as myelofibrosis. In some embodiments, the c-fms mediated diseases include tumors that express aberrantly or otherwise Fms, CSF1R, CSF1 or IL-34, or activating mutations or translocations of any of the foregoing.

In other embodiments, the disease or condition is mediated by c-fms and c-kit and is selected from the group consisting of mast cell tumors, small cell lung cancer, testicular cancer, gastrointestinal stromal tumors, glioblastoma, astrocytoma, neuroblastoma, carcinomas of the female genital tract, sarcomas of neuroectodermal origin, colorectal carcinoma, carcinoma in situ, Schwann cell neoplasia, malignant peripheral nerve cell tumors, malignant peripheral nerve sheath tumors, pheochromocytomas cutaneous and plexiform neurofibromas, neurofibromatosis, neurofibronatosis-1 (NF1), leiomyo-adenomatoid tumor, leiormyo sarcoma. acute myeloid leukemia, acute lymphocytic leukemia, chronic myelogenous leukemia, multiple myeloma, mastocytosis, melanoma, breast cancer, ovarian cancer, prostate cancer, canine mast cell tumors, metastasis of cancer to bone or other tissues, chronic myeloproliferative diseases such as myelofibrosis, renal hypertrophy, asthma, rheumatoid arthritis, allergic rhinitis, multiple sclerosis, osteoarthritis, inflammatory bowel syndrome, transplant rejection, systemic lupus erythematosis, ulcerative colitis, Crohn's disease, chronic obstructive pulmonary disease, emphysema, Kawasaki's Disease, hemophagocytic syndrome (macrophage activation syndrome), multicentric reticulohistiocytosis, atherosclerosis, Type I diabetes, Type II diabetes, insulin resistance, hyperglycemia, obesity, lipolysis, hypereosinophilia, osteoporosis, increased risk of fracture, Paget's disease, hypercalcemia, infection-mediated osteolysis (e.g. osteomyelitis), peri-prosthetic or wear-debris-mediated osteolysis, endometriosis, glomerulonephritis, interstitial nephritis, Lupus nephritis, tubular necrosis, diabetic nephropathy, stroke, Alzheimer's disease, Parkinson's disease, inflammatory pain, chronic pain, and bone pain.

In some embodiments, the disease or condition treatable with the compounds or compositions as described herein is selected from stem cell ablation and myelopreparation for stem cell transplant, primary progressive multiple sclerosis, complex regional pain syndrome, reflex sympathetic dystrophy, muscular dystrophy, duchenne muscular dystrophy, causalgia, neuro-inflammation, neuroinflammatory disorders, benign forgetfulness, binswager type dementia, dementia with lewy bodie, prosencephaly, microencepahy, cerebral palsy, congenital hydrocephalus, abdominal dropsy, progressive supranuclear palsy, glaucoma, addiction disorders, dependencies, alcoholism, tremors, Wilson's disease, vascular dementias, multi infarct dementia, frontotemporal dementia, pseudo-dementia, bladder cancer, basal cell carcinoma, cholangiocarcinoma, colon cancer, endometrial cancer, esophageal cancer, Ewing's sarcoma, gastric cancer, glioma, hepatocellular carcinoma, Hodgkin lymphoma, laryngeal carcinoma, leukemia, liver cancer, lung cancer, melanoma, mesothelioma, pancreatic cancer, rectal cancer, renal cancer, squamous cell carcinoma, t cell lymphoma, thyroid cancer, monocytic leukemia, pheochromocytoma, malignant peripheral nerve cell tumors, malignant peripheral nerve sheath tumors (MPNST), cutaneous and plexiform neurofibromas, leiomyoadenomatoid tumor, fibroids, uterine fibroids, leiomyosarcoma, papillary thyroid cancer, anaplastic thyroid cancer, medullary thyroid cancer, follicular thyroid cancer, hurthle cell carcinoma, thyroid cancer, ascites, malignant ascites, mesothelioma, salivary gland tumors, mucoepidermoid carcinoma of the salivary gland, acinic cell carcinoma of the salivary gland, gastrointestinal stromal tumors (GIST), tumors that cause effusions in potential spaces of the body, pleural effusions, pericardial effusions, peritoneal effusions aka ascites, giant cell tumors (GCT), GCT of bone, pigmented villonodular synovitis (PVNS), tenosynovial giant cell tumor (TGCT), TCGT of tendon sheath (TGCT-TS), other sarcomas; tumor angiogenesis and paracrine tumor growth; and tumors that express aberrantly or otherwise Fms, CSF1R, CSF1 or IL-34, or activating mutations or translocations of any of the foregoing.

In some embodiments, the disease or condition treatable with the compounds or compositions as described herein is selected from primary progressive multiple sclerosis, malignant peripheral nerve sheath tumors (MPNST), plexiform neurofibromas, mesothelioma, multi infarct dementia, fronto temporal dementia, mucoepidermoid carcinoma of the salivary gland, gastrointestinal stromal tumors (GIST), pigmented villonodular synovitis (PVNS) or tenosynovial giant cell tumor (TGCT).

In aspects and embodiments involving treatment of a disease or condition with one or more of the compounds described herein, the disclosure provides methods for treating a Kit-mediated disease or condition in a subject in need thereof (e.g. a mammal such as a human, other primates, sports animals, animals of commercial interest such as cattle, farm animals such as horses, or pets such as dogs and cats), e.g., a disease or condition characterized by abnormal Kit activity (e.g. kinase activity). In some embodiments, the methods may involve administering to the subject suffering from or at risk of a c-kit-mediated disease or condition an effective amount of one or more compound(s) as described herein. In one embodiment, the Kit mediated disease is selected from the group consisting of malignancies, including, but not limited to, mast cell tumors, small cell lung cancer, non-small cell lung cancer (NSCLC), testicular cancer, pancreatic cancer, breast cancer, merkel cell carcinoma, carcinomas of the female genital tract, sarcomas of neuroectodermal origin, colorectal carcinoma, carcinoma in situ, gastrointestinal stromal tumors (GISTs), tumor angiogenesis, glioblastoma, astrocytoma, neuroblastoma, neurofibromatosis (including Schwann cell neoplasia associated with neurofibromatosis), acute myeloid leukemia, acute lymphocytic leukemia, chronic myeloid leukemia, mastocytosis, melanoma, and canine mast cell tumors; cardiovascular disease, including but not limited to atherosclerosis, cardiomyopathy, heart failure, pulmonary arterial hypertension and pulmonary fibrosis; inflammatory and autoimmune indications, including, but not limited to, allergy, anaphylaxis, asthma, rheumatoid arthritis, allergic rhinitis, multiple sclerosis, inflammatory bowel disease, transplant rejection, hypereosinophilia, urticaria and dermatitis; gastrointestinal indications, including but not limited to gastroesophageal reflux disease (GERD), esophagitis, and gastrointestinal tract ulcers; ophthalmic indications, including but not limited to uveitis and retinitis; and neurologic indications, including, but not limiting to migraine and tumors that express aberrantly or otherwise Kit, SCFR, SCF, or activating mutations or translocations of any of the foregoing.

In aspects and embodiments involving treatment of a disease or condition with one or more of the compounds described herein, the disclosure provides methods for treating a Fms-mediated disease or condition in a subject in need thereof (e.g. a mammal such as a human, other primates, sports animals, animals of commercial interest such as cattle, farm animals such as horses, or pets such as dogs and cats), e.g., a disease or condition characterized by abnormal Fms activity (e.g. kinase activity). In some embodiments, the methods may involve administering to the subject suffering from or at risk of a Fms-mediated disease or condition an effective amount of one or more compound(s) as described herein. In one embodiment, the Fms mediated disease is selected from the group consisting of inflammatory and autoimmune indications, including, but not limited to, rheumatoid arthritis, osteoarthritis, psoriatic arthritis, psoriasis, dermatitis, ankylosing spondylitis, polymyositis, dermatomyositis, systemic sclerosis, juvenile idiopathic arthritis, polymyalgia rheumatica, Sjogren's disease, Langerhan's cell histiocytosis (LCH), Still's disease, inflammatory bowel disease, ulcerative colitis, Crohn's disease, systemic lupus erythematosis (SLE), immune thrombocytopenic purpura (ITP), myelopreparation for autologous transplantation, transplant rejection, chronic obstructive pulmonary disease (COPD), emphysema, Kawasaki's Disease, hemophagocytic syndrome (macrophage activation syndrome), multicentric reticulohistiocytosis, and atherosclerosis; metabolic disorders, including, but not limited to, Type I diabetes, Type II diabetes, insulin resistance, hyperglycemia, obesity, and lipolysis; disorders of bone structure, mineralization and bone formation and resorption, including, but not limited to, osteoporosis, osteodystrophy, increased risk of fracture, Paget's disease, hypercalcemia, infection-mediated osteolysis (e.g. osteomyelitis), and peri-prosthetic or wear-debris-mediated osteolysis; kidney and genitourinary diseases, including, but not limited to, endometriosis, nephritis (e.g. glomerulonephritis, interstitial nephritis, Lupus nephritis), tubular necrosis, diabetes-associated renal complications (e.g. diabetic nephropathy), and renal hypertrophy; disorders of the nervous system, including, but not limited to, demyelinating disorders (e.g. multiple sclerosis, Charcot Marie Tooth syndrome), amyotrophic lateral sclerosis (ALS), myasthenia gravis, chronic demyelinating polyneuropathy, other demyelinating disorders, stroke, Alzheimer's disease and Parkinson's disease; pain, including, but not limited to, chronic pain, acute pain, inflammatory pain, neuropathic pain, bone pain; malignancies, including, but not limited to, multiple myeloma, acute myeloid leukemia (AML), chronic myeloid leukemia (CML), lung cancer, pancreatic cancer, prostate cancer, breast cancer, ovarian cancer, neuroblastoma, sarcoma, osteosarcoma, giant cell tumors, (e.g. giant cell tumor of bone, giant cell tumor of tendon sheath (TGCT)), pigmented villonodular synovitis (PVNS), tumor angiogenesis, melanoma, glioblastoma multiforme, a subset of glioblastoma, proneural subset of glioblastoma, glioma, other tumors of the central nervous system, metastasis of tumors to other tissues, osteolytic bone metastases, and other chronic myeloproliferative diseases such as myelofibrosis; vasculitis, including but not limited to collagen vascular disease, polyarteritis nodosa, Behcet's disease, sarcoidosis, familiar Mediterranean fever, Churg-Strauss vasculitis, temporal arteritis, giant cell arteritis, Takayasu's arteritis; ophthalmic indications, including but not limited to uveitis, scleritis, retinitis, age related macular degeneration, choroidal neovascularization, diabetic retinopathy; inherited disorders, including but not limited to cherubism, neurofibromatosis; infectious disease indications, including but not limited to infections associated with human immunodeficiency virus, hepatitis B virus, hepatitis C virus, human granulocytic anaplasmosis; lysosomal storage disorders, including but not limited to Gaucher's disease, Fabry's disease, Niemann-Pick disease; gastrointestinal indications, including but not limited to liver cirrhosis; pulmonary indications, including but not limited to pulmonary fibrosis, acute lung injury (e.g. ventilator-induced, smoke- or toxin-induced); surgical indications, including but not limited to (cardiopulmonary) bypass surgery, vascular surgery, and vascular grafts; and tumors that express aberrantly or otherwise Fms, CSF1R, CSF1 or IL-34, or activating mutations or translocations of any of the foregoing.

In aspects and embodiments involving treatment of a disease or condition with one or more of the compounds described herein, the disclosure provides methods for treating a disease or condition mediated by Fms and Kit in a subject in need thereof (e.g. a mammal such as a human, other primates, sports animals, animals of commercial interest such as cattle, farm animals such as horses, or pets such as dogs and cats), e.g., a disease or condition characterized by abnormal Fms activity and Kit activity (e.g. kinase activity). In some embodiments, the methods may involve administering to the subject suffering from or at risk of a disease or condition mediated by Fms and Kit an effective amount of one or more compound(s) as described herein. In one embodiment, the condition mediated by Fms and Kit is selected from the group consisting of rheumatoid arthritis, osteoarthritis, psoriatic arthritis, psoriasis, dermatitis, allergy, anaphylaxis, asthma, allergic rhinitis, ankylosing spondylitis, polymyositis, dermatomyositis, systemic sclerosis, juvenile idiopathic arthritis, polymyalgia rheumatica, Sjogren's disease, Langerhan's cell histiocytosis, Still's disease, inflammatory bowel disease, ulcerative colitis, Crohn's disease, systemic lupus erythematosis, immune thrombocytopenic purpura, myelopreparation for autologous transplantation, transplant rejection, chronic obstructive pulmonary disease, emphysema, Kawasaki's Disease, hemophagocytic syndrome, multicentric reticulohistiocytosis, hypereosinophilia, and urticaria type I diabetes, type II diabetes, insulin resistance, hyperglycemia, obesity, and lipolysis, osteoporosis, osteodystrophy, increased risk of fracture, Paget's disease, hypercalcemia, infection-mediated osteolysis, and peri-prosthetic or wear-debris-mediated osteolysis, endometriosis, nephritis, tubular necrosis, diabetes-associated renal complications, and renal hypertrophy, multiple sclerosis, Charcot Marie Tooth syndrome, amyotrophic lateral sclerosis, myasthenia gravis, chronic demyelinating polyneuropathy, other demyelinating disorders, stroke, Alzheimer's disease and Parkinson's disease, acute pain, neuropathic pain, inflammatory pain, chronic pain, migraine, multiple myeloma, acute lymphocytic leukemia, acute myeloid leukemia, chronic myeloid leukemia, mast cell tumors, canine mast cell tumors, lung cancer, testicular cancer, pancreatic cancer, prostate cancer, breast cancer, ovarian cancer, merkel cell carcinoma, carcinomas of the female genital tract, colorectal carcinoma, carcinoma in situ, gastrointestinal stromal tumors, tumor angiogenesis, astrocytoma, neuroblastoma, sarcoma, osteosarcoma, sarcomas of neuroectodermal origin, giant cell tumor of bone, giant cell tumor of tendon sheath, pigmented villonodular synovitis, melanoma, glioblastoma, glioblastoma multiforme, glioma, other tumors of the central nervous system, neurofibromatosis (including Schwann cell neoplasia associated with neurofibromatosis), mastocytosis, metastasis of tumors to other tissues, osteolytic bone metastases, and other chronic myeloproliferative diseases such as myelofibrosis, collagen vascular disease, polyarteritis nodosa, Behcet's disease, sarcoidosis, familiar Mediterranean fever, Churg-Strauss vasculitis, temporal arteritis, giant cell arteritis, Takayasu's arteritis, uveitis, scleritis, retinitis, age related macular degeneration, choroidal neovascularization, diabetic retinopathy, cherubism, neurofibromatosis, infections associated with human immunodeficiency virus, hepatitis B virus, hepatitis C virus, human granulocytic anaplasmosis, Gaucher's disease, Fabry's disease, Niemann-Pick disease, liver cirrhosis, gastroesophageal reflux disease, esophagitis, and gastrointestinal tract ulcers, pulmonary fibrosis, acute lung injury, bypass surgery, vascular surgery, and vascular grafts, atherosclerosis, cardiomyopathy, heart failure, and pulmonary arterial hypertension.

In aspects and embodiments involving treatment of a disease or condition with one or more of the compounds described herein, the disclosure provides methods for treating a disease or condition mediated by Fms and Flt-3 in a subject in need thereof (e.g. a mammal such as a human, other primates, sports animals, animals of commercial interest such as cattle, farm animals such as horses, or pets such as dogs and cats), e.g., a disease or condition characterized by abnormal Fms activity and flt-3 activity (e.g. kinase activity). In some embodiments, the methods may involve administering to the subject suffering from or at risk of a disease or condition mediated by Fms and Flt-3 an effective amount of one or more compound(s) as described herein. In one embodiment, the condition mediated by Fms and Flt-3 is acute myeloid leukemia.

In aspects and embodiments involving treatment of a disease or condition with one or more of the compounds described herein, the methods may involve administering an effective amount of one or more compound(s) as described herein to a subject in need thereof suffering from or at risk of a disease or condition selected from the group consisting of rheumatoid arthritis, osteoarthritis, osteoporosis, peri-prosthetic osteolysis, systemic sclerosis, demyelinating disorders, multiple sclerosis, Charcot Marie Tooth syndrome, amyotrophic lateral sclerosis, Alzheimer's disease, Parkinson's disease, ulcerative colitis, Crohn's disease, immune thrombocytopenic purpura, atherosclerosis, systemic lupus erythematosis, myelopreparation for autologous transplantation, transplant rejection, glomerulonephritis, interstitial nephritis, Lupus nephritis, tubular necrosis, diabetic nephropathy, renal hypertrophy, type I diabetes, acute pain, inflammatory pain, neuropathic pain, acute myeloid leukemia, melanoma, multiple myeloma, metastatic breast cancer, prostate cancer, pancreatic cancer, lung cancer, ovarian cancer, gliomas, glioblastomas, neurofibromatosis, osteolytic bone metastases, brain metastases, gastrointestinal stromal tumors, and giant cell tumors.

In some embodiments, the disclosure provides a method for treating a disease or condition as described herein by administering to a subject a compound of Formula I':

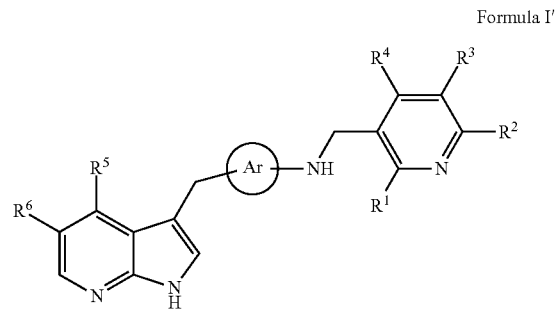

Formula I' or a salt, a prodrug, a tautomer or a stereoisomer thereof, wherein:

Ar is selected from the group consisting of:

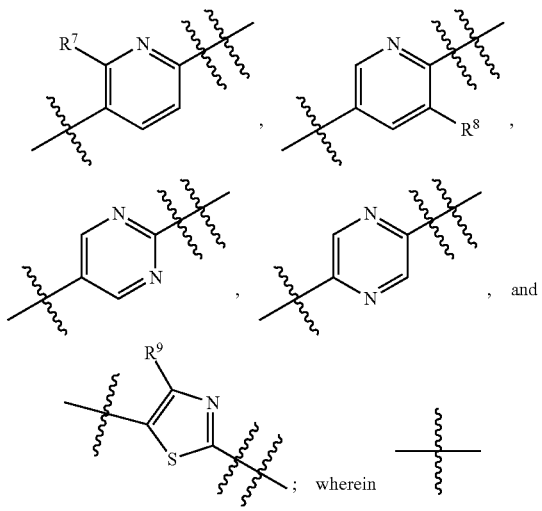

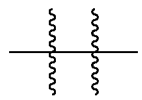 [SMILES: **]

; wherein indicates the point of attachment of Ar to —CH$_2$— of Formula I' and wherein indicates the point of attachment of Ar to —NH— of Formula I';

$R^1$, $R^2$, $R^3$ and $R^4$ are each independently selected from the group consisting of —H, halogen, lower alkyl, halogen substituted lower alkyl, halogen substituted lower alkoxy, alkoxy substituted lower alkyl, cycloalkylamino, —CN, —O—$R^{40}$, —S(O)$_2$—$R^{41}$, —S(O)$_2$—N(H)—$R^{42}$, —N(H)—$R^{42}$, —N($R^{42}$)$_2$, and —N(H)—S(O)$_2$—$R^{43}$, provided that at least two of $R^1$, $R^2$, $R^3$ and $R^4$ are —H and one of $R^1$, $R^2$, $R^3$ and $R^4$ is other than hydrogen, wherein:

$R^{40}$ is lower alkyl, fluoro substituted lower alkyl, methoxy substituted lower alkyl, or cycloalkyl;

$R^{41}$, $R^{42}$ and $R^{43}$ are lower alkyl;

$R^5$ is selected from the group consisting of —H, —F, —Cl, —Br, lower alkyl, halogen substituted alkyl, lower alkenyl, lower alkynyl, cycloalkyl, phenyl, pyrazolyl, —CN, —O—$R^{10}$, —C(O)—N(H)—$R^{11}$, —C(O)—O—$R^{11}$, —S(O)$_2$—$R^{12}$, —S(O)$_2$—N(H)—$R^{11}$, —N(H)—C(O)—

$R^{12}$, and —N(H)—S(O)$_2$—$R^{12}$, wherein pyrazolyl is optionally substituted with lower alkyl or heterocycloalkyl;

$R^6$ is selected from the group consisting of H, halogen, lower alkyl, halogen substituted alkyl, lower alkenyl, lower alkynyl, cycloalkyl, phenyl, pyrazolyl, —CN, —O—$R^{13}$, —C(O)—N(H)—$R^{14}$, —C(O)—O—$R^{14}$, —S(O)$_2$—$R^{15}$, —S(O)$_2$—N(H)—$R^{14}$, —N(H)—C(O)—$R^{15}$, and —N(H)—S(O)$_2$—$R^{15}$, wherein pyrazolyl is optionally substituted with lower alkyl or heterocycloalkyl;

$R^7$ is H, halogen, or lower alkyl;

$R^8$ is H, halogen, or lower alkoxy;

$R^9$ is H or halogen;

$R^{10}$ and $R^{13}$ are independently —H, lower alkyl, lower alkyl substituted with —O—CH$_3$, lower alkyl substituted with di-alklylamine, or lower alkyl substituted with heterocycloalkyl;

$R^{11}$ and $R^{14}$ are independently hydrogen or lower alkyl; and $R^{12}$ and $R^{15}$ are each independently lower alkyl. In some instances, the compound is other than those set forth in Table 1.

In some embodiments, $R^1$, $R^3$ and $R^4$ are each independently selected from the group consisting of —H, lower alkoxy, halogen, halogen substituted lower alkyl, alkoxy substituted lower alkyl, cycloalkylamino, —CN, —O—$R^{40}$, —S(O)$_2$—$R^{41}$, —S(O)$_2$—N(H)—$R^{42}$, —N(H)—$R^{42}$, —N($R^{42}$)$_2$, and —N(H)—S(O)$_2$—$R^{43}$, provided that at least two of $R^1$, $R^2$, $R^3$ and $R^4$ are —H and $R^2$ is —F, —Cl or —Br; or $R^1$, $R^2$, $R^3$ and $R^4$ are —H and $R^2$ is —CF$_3$; or $R^1$ and $R^4$ are —H, $R^2$ is —O—CH$_3$, and $R^3$ is —F; or $R^2$ and $R^4$ are —H, $R^1$ is —O—CH$_3$, and $R^3$ is —F;

$R^5$ is selected from the group consisting of —H, —F, —Cl, —Br, lower alkyl, fluoro substituted lower alkyl, lower alkenyl, lower alkynyl, cycloalkyl, phenyl, pyrazolyl, —CN, —O—$R^{10}$, —C(O)—N(H)—$R^{11}$, —C(O)—O—$R^{11}$, —S(O)$_2$—$R^{12}$, —S(O)$_2$—N(H)—$R^{11}$, —N(H)—C(O)—$R^{12}$, and —N(H)—S(O)$_2$—$R^{12}$, wherein pyrazolyl is optionally substituted with lower alkyl or heterocycloalkyl;

$R^6$ is selected from the group consisting of —H, —F, —Cl, —Br, lower alkyl, fluoro substituted lower alkyl, lower alkenyl, lower alkynyl, cycloalkyl, phenyl, pyrazolyl, —CN, —O—$R^{13}$, —C(O)—N(H)—$R^{14}$, —C(O)—O—$R^{14}$, —S(O)$_2$—$R^{15}$, —S(O)$_2$—N(H)—$R^{14}$, —N(H)—C(O)—$R^{15}$, and —N(H)—S(O)$_2$—$R^{15}$, wherein pyrazolyl is optionally substituted with lower alkyl or heterocycloalkyl;

$R^7$ is —H, —F, —Cl, or —CH$_3$;

$R^8$ is —H, —F, —CH$_3$, or —O—CH$_3$;

$R^9$ is —H or —Cl;

$R^{10}$ and $R^{13}$ are independently —H, lower alkyl, lower alkyl substituted with —O—CH$_3$, lower alkyl substituted with di-alklylamine, or lower alkyl substituted with heterocycloalkyl;

$R^{11}$ and $R^{14}$ are independently hydrogen or lower alkyl; and $R^{12}$ and $R^{15}$ are independently lower alkyl.

In some embodiments, Ar is:

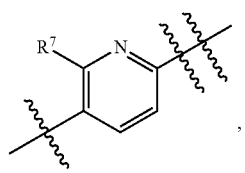

wherein $R^7$ is as defined herein.

In some embodiments, Ar is

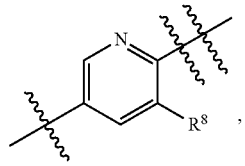

wherein $R^8$ is as defined herein.

In some embodiments, Ar is

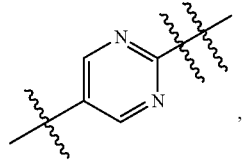

In some embodiments, Ar is

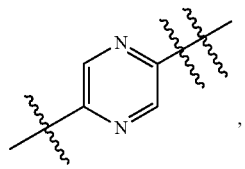

In some embodiments,

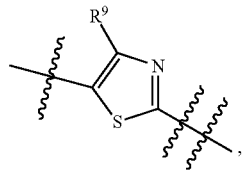

wherein $R^9$ is as defined herein.

In some embodiments, $R^1$, $R^3$ and $R^4$ are H and $R^2$ is halogen. In other embodiments, $R^1$, $R^2$ and $R^3$ are —H and $R^4$ is halo substituted lower alkyl. In other embodiments, $R^1$ and $R^4$ are —H and $R^2$ is lower alkoxy. In some embodiments, $R^3$ is halogen. In yet other embodiments, $R^2$ and $R^4$ are —H, $R^1$ is lower alkoxy and $R^3$ is halogen. In still another embodiment, $R^1$ and $R^4$ are —H, $R^3$ is halogen and $R^2$ is lower alkoxy. In certain instances, i) $R^1$, $R^2$ and $R^3$ are —H and $R^4$ is CF$_3$; or ii) $R^1$ and $R^4$ are —H and $R^2$ is —OCH$_3$; or iii) $R^3$ is F; iv) $R^2$ and $R^4$ are —H, $R^1$ is OCH$_3$ and $R^3$ is F; or v) $R^1$ and $R^4$ are —H, $R^3$ is F and $R^2$ is OCH3. The variables $R^5$, $R^6$ and Ar are as defined herein.

In some embodiments of compounds of Formula I', $R^5$ is —H, —F, —Cl, —Br, lower alkyl, fluoro substituted lower alkyl, lower alkenyl, lower alkynyl, cycloalkyl, phenyl, pyrazolyl, —CN, —O—$R^{10}$, —C(O)—N(H)—$R^{11}$, —C(O)—O—$R^{11}$, —S(O)$_2$—$R^{12}$, —S(O)$_2$—N(H)—$R^{11}$, —N(H)—C(O)—$R^{12}$, and —N(H)—S(O)$_2$—$R^{12}$, wherein pyrazolyl is optionally substituted with lower alkyl or heterocycloalkyl. In certain instances, $R^5$ is H. All the other variables are as defined herein.

In some embodiments of compounds of Formula I', $R^5$ is —H. In some embodiments, $R^5$ is —H and $R^6$ is —H, —F, —Cl, —CH$_3$, —CF$_3$, —CN, —O—CH$_3$, —S(O)$_2$—CH$_3$, —C(O)—NH—CH$_3$, —C(O)—O—CH$_3$, —NHC(O)CH$_3$, —NHS(O)$_2$CH$_3$, or cyclopropyl. All the other variables are as defined herein.

In some embodiments of compounds of Formula I', $R^6$ is selected from the group consisting of H, halo, lower alkyl, lower alkoxy, fluoro substituted lower alkyl, lower alkenyl, lower alkynyl, cycloalkyl, phenyl, pyrazolyl, —CN, —O—R$^{13}$, —C(O)—N(H)—R$^{14}$, —C(O)—O—R$^{14}$, —S(O)$_2$—R$^{15}$, —S(O)$_2$—N(H)—R$^{14}$, —N(H)—C(O)—R$^{15}$, and —N(H)—S(O)$_2$—R$^{15}$, wherein pyrazolyl is optionally substituted with lower alkyl or heterocycloalkyl. In certain instances, $R^6$ is halo, lower alkyl or fluoro substituted lower alkyl. All the other variables are as defined herein.

In some embodiments of compounds of Formula I', $R^6$ is —H. In some embodiments, $R^6$ is —H and $R^5$ is —H, —Cl, —CN, —C≡CH, —O—CH$_3$, or phenyl. In other embodiments, $R^6$ is halo, lower alkyl lower alkoxy, or fluoro substituted lower alkyl. In yet other embodiments, $R^6$ is halogen, methyl, methoxy, trifluoromethyl, or CN. All the other variables are as defined herein.

In some embodiments of compounds of Formula I', $R^7$ is H, halogen or lower alkyl. In other embodiments, $R^7$ is H, —F, —Cl, Br or —CH$_3$. All the other variables are as defined herein.

In some embodiments of compounds of Formula I', $R^8$ is H, halogen or lower alkoxy. In other embodiments, $R^8$ is H, —F, —Cl, Br or —OCH$_3$. All the other variables are as defined herein.

In some embodiments of compounds of Formula I', $R^9$ is H or halogen. In other embodiments, $R^9$ is —H or —Cl. All the other variables are as defined herein.

In some embodiments of compounds of Formula I', $R^1$, $R^3$ and $R^4$ are —H; $R^2$ is —F, —Cl or —Br; and $R^5$ is —H. In some embodiments, $R^1$, $R^3$ and $R^4$ are —H; $R^2$ is —F, —Cl or —Br; $R^5$ is —H; and $R^6$ is —H, —F, —Cl, —CH$_3$, —CF$_3$, —CN, —O—CH$_3$, —S(O)$_2$—CH$_3$, —C(O)—NH—CH$_3$, —C(O)—O—CH$_3$, —NHC(O)CH$_3$, —NHS(O)$_2$CH$_3$, or cyclopropyl. All the other variables are as defined herein.

In some embodiments of compounds of Formula I', $R^1$, $R^3$ and $R^4$ are —H; $R^2$ is —F, —Cl or —Br; and $R^6$ is —H. In some embodiments, $R^1$, $R^3$ and $R^4$ are —H; $R^2$ is —F, —Cl or —Br; $R^6$ is —H; and $R^5$ is —H, —Cl, —CN, —C≡CH, —O—CH$_3$, or phenyl. All the other variables are as defined herein.

In some embodiments of compounds of Formula I', $R^1$, $R^2$ and $R^3$ are —H; and $R^4$ is —CF$_3$; and $R^5$ is —H. In some embodiments, $R^1$, $R^2$ and $R^3$ are —H; and $R^4$ is —CF$_3$; $R^5$ is —H; and $R^6$ is —H, —F, —Cl, —CH$_3$, —CF$_3$, —CN, —O—CH$_3$, —S(O)$_2$—CH$_3$, —C(O)—NH—CH$_3$, —C(O)—O—CH$_3$, —NHC(O)CH$_3$, —NHS(O)$_2$CH$_3$, or cyclopropyl. All the other variables are as defined herein.

In some embodiments of compounds of Formula I', $R^1$, $R^2$ and $R^3$ are —H; and $R^4$ is —CF$_3$; and $R^6$ is —H. In some embodiments, $R^1$, $R^2$ and $R^3$ are —H; and $R^4$ is —CF$_3$; $R^6$ is —H; and $R^5$ is —H, —Cl, —CN, —C≡CH, —O—CH$_3$, or phenyl. All the other variables are as defined herein.

In some embodiments of compounds of Formula I', $R^1$ and $R^4$ are —H; $R^2$ is —O—CH$_3$; $R^3$ is —F; and $R^5$ is —H. In some embodiments, $R^1$ and $R^4$ are —H; $R^2$ is —O—CH$_3$; $R^3$ is —F; $R^5$ is —H; and $R^6$ is —H, —F, —Cl, —CH$_3$, —CF$_3$, —CN, —O—CH$_3$, —S(O)$_2$—CH$_3$, —C(O)—NH—CH$_3$, —C(O)—O—CH$_3$, —NHC(O)CH$_3$, —NHS(O)$_2$CH$_3$, or cyclopropyl. All the other variables are as defined herein.

In some embodiments of compounds of Formula I', $R^1$ and $R^4$ are —H; $R^2$ is —O—CH$_3$; $R^3$ is —F; and $R^6$ is —H. In some embodiments, $R^1$ and $R^4$ are —H; $R^2$ is —O—CH$_3$; $R^3$ is —F; $R^6$ is —H; and $R^5$ is —H, —Cl, —CN, —C≡CH, —O—CH$_3$, or phenyl. All the other variables are as defined herein.

In some embodiments of compounds of Formula I', $R^2$ and $R^4$ are —H; $R^1$ is —O—CH$_3$; $R^3$ is —F; and $R^5$ is —H. In some embodiments, $R^2$ and $R^4$ are —H; $R^1$ is —O—CH$_3$; $R^3$ is —F; $R^5$ is —H; and $R^6$ is —H, —F, —Cl, —CH$_3$, —CF$_3$, —CN, —O—CH$_3$, —S(O)$_2$—CH$_3$, —C(O)—NH—CH$_3$, —C(O)—O—CH$_3$, —NHC(O)CH$_3$, —NHS(O)$_2$CH$_3$, or cyclopropyl. All the other variables are as defined herein.

In some embodiments of compounds of Formula I', $R^2$ and $R^4$ are —H; $R^1$ is —O—CH$_3$; $R^3$ is —F; and $R^6$ is —H. In some embodiments, $R^2$ and $R^4$ are —H; $R^1$ is —O—CH$_3$; $R^3$ is —F; $R^6$ is —H; and $R^5$ is —H, —Cl, —CN, —C≡CH, —O—CH$_3$, or phenyl. All the other variables are as defined herein.

In other embodiments, the disclosure provides a method for treating a disease or condition as described herein by administering to a subject a compound of formula I:

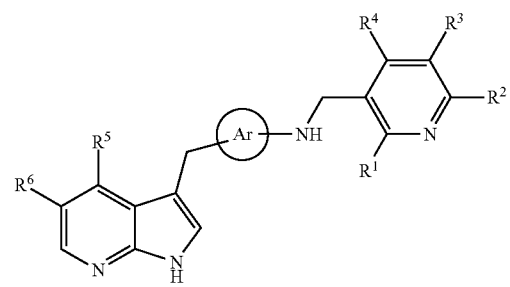

Formula I or a salt, a prodrug, a tautomer or a stereoisomer thereof, wherein:

Ar is selected from the group consisting of:

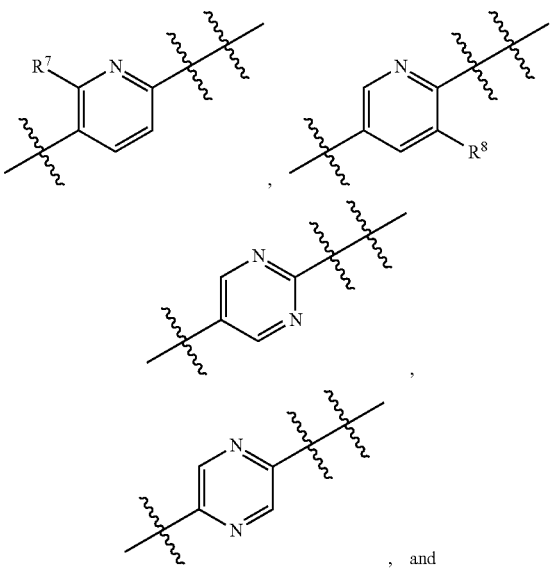

, and

-continued

; wherein indicates the point of attachment of Ar to —CH$_2$— of Formula I and wherein indicates the point of attachment of Ar to —NH— of Formula I;

$R^1$, $R^3$ and $R^4$ are —H and $R^2$ is —F, —Cl or —Br; or $R^1$, $R^2$ and $R^3$ are —H and $R^4$ is —CF$_3$; or $R^1$ and $R^4$ are —H, $R^2$ is —O—CH$_3$, and $R^3$ is —F; or $R^2$ and $R^4$ are —H, $R^1$ is —O—CH$_3$, and $R^3$ is —F;

$R^5$ is selected from the group consisting of —H, —F, —Cl, —Br, lower alkyl, fluoro substituted lower alkyl, lower alkenyl, lower alkynyl, cycloalkyl, phenyl, pyrazolyl, —CN, —O—R$^{10}$, —C(O)—N(H)—R$^{11}$, —C(O)—O—R$^{11}$, —S(O)$_2$—R$^{12}$, —S(O)$_2$—N(H)—R$^{11}$, —N(H)—C(O)—R$^{12}$, and —N(H)—S(O)$_2$—R$^{12}$, wherein pyrazolyl is optionally substituted with lower alkyl or heterocycloalkyl;

$R^6$ is selected from the group consisting of —H, —F, —Cl, —Br, lower alkyl, fluoro substituted lower alkyl, lower alkenyl, lower alkynyl, cycloalkyl, phenyl, pyrazolyl, —CN, —O—R$^{13}$, —C(O)—N(H)—R$^{14}$, —C(O)—O—R$^{14}$, —S(O)$_2$—R$^{15}$, —S(O)$_2$—N(H)—R$^{14}$, —N(H)—C(O)—R$^{15}$, and —N(H)—S(O)$_2$—R$^{15}$, wherein pyrazolyl is optionally substituted with lower alkyl or heterocycloalkyl;

$R^7$ is —H, —F, —Cl, or —CH$_3$;
$R^8$ is —H, —F, —CH$_3$, or —O—CH$_3$;
$R^9$ is —H or —Cl;
$R^{10}$ and $R^{13}$ are independently —H, lower alkyl, lower alkyl substituted with —O—CH$_3$, lower alkyl substituted with di-alklylamine, or lower alkyl substituted with heterocycloalkyl;
$R^{11}$ and $R^{14}$ are independently hydrogen or lower alkyl; and
$R^{12}$ and $R^{15}$ are independently lower alkyl.

In some embodiments of compounds of Formula I, $R^5$ is —H. In some embodiments, $R^5$ is —H and $R^6$ is —H, —F, —Cl, —CH$_3$, —CF$_3$, —CN, —O—CH$_3$, —S(O)$_2$—CH$_3$, —C(O)—NH—CH$_3$, —C(O)—O—CH$_3$, —NHC(O)CH$_3$, —NHS(O)$_2$CH$_3$, or cyclopropyl.

In some embodiments of compounds of Formula I, $R^6$ is —H. In some embodiments, $R^6$ is —H and $R^5$ is —H, —Cl, —CN, —C≡CH, —O—CH$_3$, or phenyl.

In some embodiments of compounds of Formula I, $R^1$, $R^3$ and $R^4$ are —H; $R^2$ is —F, —Cl or —Br; and $R^5$ is —H. In some embodiments, $R^1$, $R^3$ and $R^4$ are —H; $R^2$ is —F, —Cl or —Br; $R^5$ is —H; and $R^6$ is —H, —F, —Cl, —CH$_3$, —CF$_3$, —CN, —O—CH$_3$, —S(O)$_2$—CH$_3$, —C(O)—NH—CH$_3$, —C(O)—O—CH$_3$, —NHC(O)CH$_3$, —NHS(O)$_2$CH$_3$, or cyclopropyl.

In some embodiments of compounds of Formula I, $R^1$, $R^3$ and $R^4$ are —H; $R^2$ is —F, —Cl or —Br; and $R^6$ is —H. In some embodiments, $R^1$, $R^3$ and $R^4$ are —H; $R^2$ is —F, —Cl or —Br; $R^6$ is —H; and $R^5$ is —H, —Cl, —CN, —C≡CH, —O—CH$_3$, or phenyl.

In some embodiments of compounds of Formula I, $R^1$, $R^2$ and $R^3$ are —H; and $R^4$ is —CF$_3$; and $R^5$ is —H. In some embodiments, $R^1$, $R^2$ and $R^3$ are —H; and $R^4$ is —CF$_3$; $R^5$ is —H; and $R^6$ is —H, —F, —Cl, —CH$_3$, —CF$_3$, —CN, —O—CH$_3$, —S(O)$_2$—CH$_3$, —C(O)—NH—CH$_3$, —C(O)—O—CH$_3$, —NHC(O)CH$_3$, —NHS(O)$_2$CH$_3$, or cyclopropyl.

In some embodiments of compounds of Formula I, $R^1$, $R^2$ and $R^3$ are —H; and $R^4$ is —CF$_3$; and $R^6$ is —H. In some embodiments, $R^1$, $R^2$ and $R^3$ are —H; and $R^4$ is —CF$_3$; $R^6$ is —H; and $R^5$ is —H, —Cl, —CN, —C≡CH, —O—CH$_3$, or phenyl.

In some embodiments of compounds of Formula I, $R^1$ and $R^4$ are —H; $R^2$ is —O—CH$_3$; $R^3$ is —F; and $R^5$ is —H. In some embodiments, $R^1$ and $R^4$ are —H; $R^2$ is —O—CH$_3$; $R^3$ is —F; $R^5$ is —H; and $R^6$ is —H, —F, —Cl, —CH$_3$, —CF$_3$, —CN, —O—CH$_3$, —S(O)$_2$—CH$_3$, —C(O)—NH—CH$_3$, —C(O)—O—CH$_3$, —NHC(O)CH$_3$, —NHS(O)$_2$CH$_3$, or cyclopropyl.

In some embodiments of compounds of Formula I, $R^1$ and $R^4$ are —H; $R^2$ is —O—CH$_3$; $R^3$ is —F; and $R^6$ is —H. In some embodiments, $R^1$ and $R^4$ are —H; $R^2$ is —O—CH$_3$; $R^3$ is —F; $R^6$ is —H; and $R^1$ is —H, —Cl, —CN, —C≡CH, —O—CH$_3$, or phenyl.

In some embodiments of compounds of Formula I, $R^2$ and $R^4$ are —H; $R^1$ is —O—CH$_3$; $R^3$ is —F; and $R^5$ is —H. In some embodiments, $R^2$ and $R^4$ are —H; $R^1$ is —O—CH$_3$; $R^3$ is —F; $R^1$ is —H; and $R^6$ is —H, —F, —Cl, —CH$_3$, —CF$_3$, —CN, —O—CH$_3$, —S(O)$_2$—CH$_3$, —C(O)—NH—CH$_3$, —C(O)—O—CH$_3$, —NHC(O)CH$_3$, —NHS(O)$_2$CH$_3$, or cyclopropyl.

In some embodiments of compounds of Formula I, $R^2$ and $R^4$ are —H; $R^1$ is —O—CH$_3$; $R^3$ is —F; and $R^6$ is —H. In some embodiments, $R^2$ and $R^4$ are —H; $R^1$ is —O—CH$_3$; $R^3$ is —F; $R^6$ is —H; and $R^5$ is —H, —Cl, —CN, —C≡CH, —O—CH$_3$, or phenyl.

In some embodiments of compounds of Formulae I and I', $R^7$ is other than hydrogen. All the other variables are as defined herein.

In one group of embodiments of compounds of Formulae I and I', $R^6$ and $R^7$ are not simultaneously H. All the other variables are as defined herein.

In another group of embodiments of compounds of Formulae I and I', when $R^7$ is halogen, $R^6$ is other than H, halogen, heteroaryl, CN or lower alkyl. In certain instances, when $R^7$ is Cl, $R^6$ is other than H, Cl, pyrazolyl, CN or CH$_3$. All the other variables are as defined herein.

In another group of embodiments of compounds of Formulae I and I', when $R^7$ is halogen, $R^6$ is other than halo substituted lower alkyl. In certain instances, when $R^7$ is Cl, $R^6$ is other than CF$_3$. All the other variables are as defined herein.

In one group of embodiments of compounds of Formulae I and I', when $R^7$ is halogen, $R^2$ is other than halogen substituted lower alkyl or lower alkoxy. In certain instances, when $R^7$ is F, $R^2$ is other than CF$_3$ or —OCH$_3$. All the other variables are as defined herein.

In another group of embodiments of compounds of Formulae I and I', when $R^7$ is halogen, $R^6$ is other than halogen, lower alkoxy, hydrogen or CN. In certain instances, when $R^7$ is —F, $R^6$ is other than Cl, OCH$_3$, hydrogen or CN. In other instances, when $R^7$ is —F, $R^3$ is other than F. All the other variables are as defined herein.

In one group of embodiments of compounds of Formulae I and I', when $R^7$ is hydrogen, $R^6$ is other than halogen, hydrogen, lower alkyl, CN, or lower alkoxy. In certain instances, when $R^7$ is hydrogen, $R^6$ is other than H, Cl, F, CH$_3$, CN, —OCH$_3$. All the other variables are as defined herein.

In another group of embodiments of compounds of Formulae I and I', when $R^9$ is halogen, $R^6$ is other than H or halogen. In certain instances, when $R^9$ is Cl, $R^6$ is other than H or Cl. All the other variables are as defined herein.

In another group of embodiments of compounds of Formulae I and I', when Ar is

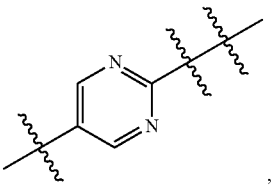

$R^6$ is other than hydrogen. All the other variables are as defined herein.

In another group of embodiments of compounds of Formulae I and I', when Ar is

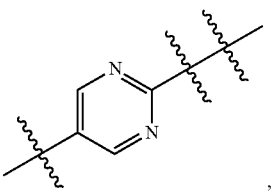

$R^1$, $R^2$, $R^3$ and $R^4$ are not simultaneously hydrogen. All the other variables are as defined herein.

In another group of embodiments of compounds of Formulae I and I', when Ar is

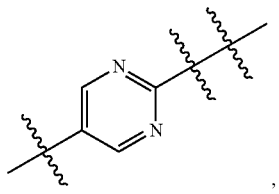

$R^2$ is other than halo substituted lower alkyl, for example, in one embodiment, $R^2$ is other than CF$_3$. All the other variables are as defined herein.

In some embodiments, the disclosure provides a method for treating a disease or condition as described herein by administering to a subject a compound of Formula I' or Formula I, wherein the compound is other than those are listed in Tables 1 and 10 below.

In some embodiments, the disclosure provides a method for treating a disease or condition as described herein by administering to a subject a compound listed in Table 1 or a pharmaceutically acceptable salt thereof.

TABLE 1

[6-Chloro-5-(1H-pyrrolo[2,3-b]pyridin-3-ylmethyl)-pyridin-2-yl]-(6-trifluoromethyl-pyridin-3-ylmethyl)-amine (P-0174),
[6-Chloro-5-(5-chloro-1H-pyrrolo[2,3-b]pyridin-3-ylmethyl)-pyridin-2-yl]-(6-trifluoromethyl-pyridin-3-ylmethyl)-amine (P-0176),
{6-Chloro-5-[5-(1-methyl-1H-pyrazol-4-yl)-1H-pyrrolo[2,3-b]pyridin-3-ylmethyl]-pyridin-2-yl}-(6-trifluoromethyl-pyridin-3-ylmethyl)-amine (P-0179),
[5-(5-Chloro-1H-pyrrolo[2,3-b]pyridin-3-ylmethyl)-6-fluoro-pyridin-2-yl]-(6-trifluoromethyl-pyridin-3-ylmethyl)-amine (P-0186),
[6-Fluoro-5-(5-methoxy-1H-pyrrolo[2,3-b]pyridin-3-ylmethyl)-pyridin-2-yl]-(6-trifluoromethyl-pyridin-3-ylmethyl)-amine (P-0187),
[6-Fluoro-5-(1H-pyrrolo[2,3-b]pyridin-3-ylmethyl)-pyridin-2-yl]-(6-trifluoromethyl-pyridin-3-ylmethyl)-amine (P-0188),
3-{2-Chloro-6-[(6-trifluoromethyl-pyridin-3-ylmethyl)-amino]-pyridin-3-ylmethyl}-1H-pyrrolo[2,3-b]pyridine-5-carbonitrile (P-0232),
[6-Chloro-5-(5-methyl-1H-pyrrolo[2,3-b]pyridin-3-ylmethyl)-pyridin-2-yl]-(6-trifluoromethyl-pyridin-3-ylmethyl)-amine (P-0233),
[6-Chloro-5-(5-methyl-1H-pyrrolo[2,3-b]pyridin-3-ylmethyl)-pyridin-2-yl]-(6-trifluoromethyl-pyridin-3-ylmethyl)-amine (P-0234),
[6-Fluoro-5-(1H-pyrrolo[2,3-b]pyridin-3-ylmethyl)-pyridin-2-yl]-(6-methoxy-pyridin-3-ylmethyl)-amine (P-0378),
[5-(5-Chloro-1H-pyrrolo[2,3-b]pyridin-3-ylmethyl)-6-fluoro-pyridin-2-yl]-(6-methoxy-pyridin-3-ylmethyl)-amine (P-0379),
(5-Fluoro-pyridin-3-ylmethyl)-[6-fluoro-5-(1H-pyrrolo[2,3-b]pyridin-3-ylmethyl)-pyridin-2-yl]-amine (P-0414),
3-{2-Fluoro-6-[(5-fluoro-pyridin-3-ylmethyl)-amino]-pyridin-3-ylmethyl}-1H-pyrrolo[2,3-b]pyridine-5-carbonitrile (P-0415),
3-[6-(4-Chloro-benzylamino)-2-fluoro-pyridin-3-ylmethyl]-1H-pyrrolo[2,3-b]pyridine-5-carbonitrile (P-0432),
Pyridin-3-ylmethyl-[5-(1H-pyrrolo[2,3-b]pyridin-3-ylmethyl)-pyridin-2-yl]-amine (P-0094),
(2-Methoxy-pyridin-3-ylmethyl)-[5-(1H-pyrrolo[2,3-b]pyridin-3-ylmethyl)-pyridin-2-yl]-amine (P-0215),
(6-Methoxy-pyridin-3-ylmethyl)-[5-(1H-pyrrolo[2,3-b]pyridin-3-ylmethyl)-pyridin-2-yl]-amine (P-0219),
(5-Methoxy-pyridin-3-ylmethyl)-[5-(1H-pyrrolo[2,3-b]pyridin-3-ylmethyl)-pyridin-2-yl]-amine (P-0222), TABLE 1-continued (5-Fluoro-pyridin-3-ylmethyl)-[5-(1H-pyrrolo[2,3-b]pyridin-3-ylmethyl)-pyridin-2-yl]-amine (P-0230),
3-{6-[(6-Trifluoromethyl-pyridin-3-ylmethyl)-amino]-pyridin-3-ylmethyl}-1H-pyrrolo[2,3-b]pyridine-5-carbonitrile (P-0273),
(6-Methoxy-pyridin-3-ylmethyl)-[5-(5-methyl-1H-pyrrolo[2,3-b]pyridin-3-ylmethyl)-pyridin-2-yl]-amine (P-0282),
3-{6-[(6-Methoxy-pyridin-3-ylmethyl)-amino]-pyridin-3-ylmethyl}-1H-pyrrolo[2,3-b]pyridine-5-carbonitrile (P-0284),
(2-Methoxy-pyridin-3-ylmethyl)-[5-(5-methyl-1H-pyrrolo[2,3-b]pyridin-3-ylmethyl)-pyridin-2-yl]-amine (P-0285),
[5-(5-Chloro-1H-pyrrolo[2,3-b]pyridin-3-ylmethyl)-pyridin-2-yl]-(2-methoxy-pyridin-3-ylmethyl)-amine (P-0286),
3-{6-[(2-Methoxy-pyridin-3-ylmethyl)-amino]-pyridin-3-ylmethyl}-1H-pyrrolo[2,3-b]pyridine-5-carbonitrile (P-0287),
[5-(5-Chloro-1H-pyrrolo[2,3-b]pyridin-3-ylmethyl)-pyridin-2-yl]-(5-fluoro-pyridin-3-ylmethyl)-amine (P-0324),
[5-(5-Fluoro-1H-pyrrolo[2,3-b]pyridin-3-ylmethyl)-pyridin-2-yl]-(6-methoxy-pyridin-3-ylmethyl)-amine (P-0331),
(6-Methoxy-pyridin-3-ylmethyl)-[5-(5-methoxy-1H-pyrrolo[2,3-b]pyridin-3-ylmethyl)-pyridin-2-yl]-amine (P-0332),
(2-Morpholin-4-yl-pyridin-3-ylmethyl)-[5-(1H-pyrrolo[2,3-b]pyridin-3-ylmethyl)-pyridin-2-yl]-amine (P-0347),
(2,6-Dimethoxy-pyridin-3-ylmethyl)-[5-(1H-pyrrolo[2,3-b]pyridin-3-ylmethyl)-pyridin-2-yl]-amine (P-0370),
(6-Cyclopentyloxy-pyridin-3-ylmethyl)-[5-(1H-pyrrolo[2,3-b]pyridin-3-ylmethyl)-pyridin-2-yl]-amine (P-0374),
[5-(1H-Pyrrolo[2,3-b]pyridin-3-ylmethyl)-pyridin-2-yl]-[2-(2,2,2-trifluoro-ethoxy)-pyridin-3-ylmethyl]-amine (P-0376),
(5-Chloro-pyridin-3-ylmethyl)-[5-(1H-pyrrolo[2,3-b]pyridin-3-ylmethyl)-pyridin-2-yl]-amine (P-0400),
[5-(5-Chloro-1H-pyrrolo[2,3-b]pyridin-3-ylmethyl)-pyridin-2-yl]-[6-(2,2,2-trifluoro-ethoxy)-pyridin-3-ylmethyl]-amine (P-0409),
[5-(5-Chloro-1H-pyrrolo[2,3-b]pyridin-3-ylmethyl)-pyridin-2-yl]-(6-trifluoromethyl-pyridin-3-ylmethyl)-amine (P-0181),
[5-(1H-Pyrrolo[2,3-b]pyridin-3-ylmethyl)-pyridin-2-yl]-(6-trifluoromethyl-pyridin-3-ylmethyl)-amine (P-0182),
[4-Chloro-5-(1H-pyrrolo[2,3-b]pyridin-3-ylmethyl)-thiazol-2-yl]-pyridin-3-ylmethyl-amine (P-0164),
[4-Chloro-5-(1H-pyrrolo[2,3-b]pyridin-3-ylmethyl)-thiazol-2-yl]-(6-trifluoromethyl-pyridin-3-ylmethyl)-amine (P-0173),
2,2-Dimethyl-N-(3-{[5-(1H-pyrrolo[2,3-b]pyridin-3-ylmethyl)-pyridin-2-ylamino]-methyl}-pyridin-2-yl)-propionamide (P-0384),
Methyl-(3-{[5-(1H-pyrrolo[2,3-b]pyridin-3-ylmethyl)-pyridin-2-ylamino]-methyl}-pyridin-2-yl)-amine (P-0385) and
Dimethyl-(3-{[5-(1H-pyrrolo[2,3-b]pyridin-3-ylmethyl)-pyridin-2-ylamino]-methyl}-pyridin-2-yl)-amine (P-0399).

In some embodiments, the disclosure provides a method for treating a disease or condition as described herein by administering to a subject a compound selected from those set forth in Table 1 or any salt, prodrug, tautomer, or stereoisomer thereof.

In some embodiments, the disclosure provides a method for treating a disease or condition as described herein by administering to a subject a compound selected from those set forth in Table 4 or any salt, prodrug, tautomer, or stereoisomer thereof.

TABLE 4

[5-(5-Bromo-1H-pyrrolo[2,3-b]pyridin-3-ylmethyl)-6-fluoro-pyridin-2-yl]-(5-fluoro-2-methoxy-pyridin-3-ylmethyl)-amine (P-1497),
(6-Chloro-pyridin-3-ylmethyl)-[5-(1H-pyrrolo[2,3-b]pyridin-3-ylmethyl)-pyridin-2-yl]-amine (P-1498),
(6-Chloro-pyridin-3-ylmethyl)-[6-fluoro-5-(1H-pyrrolo[2,3-b]pyridin-3-ylmethyl)-pyridin-2-yl]-amine (P-1499),
(5-Fluoro-2-methoxy-pyridin-3-ylmethyl)-[6-fluoro-5-(1H-pyrrolo[2,3-b]pyridin-3-ylmethyl)-pyridin-2-yl]-amine (P-1500),
[6-Fluoro-5-(1H-pyrrolo[2,3-b]pyridin-3-ylmethyl)-pyridin-2-yl]-(4-trifluoromethyl-pyridin-3-ylmethyl)-amine (P-1501),
(5-Fluoro-6-methoxy-pyridin-3-ylmethyl)-[5-(1H-pyrrolo[2,3-b]pyridin-3-ylmethyl)-pyridin-2-yl]-amine (P-1502),
(5-Fluoro-2-methoxy-pyridin-3-ylmethyl)-[5-(1H-pyrrolo[2,3-b]pyridin-3-ylmethyl)-pyridin-2-yl]-amine (P-1403),
[5-(1H-Pyrrolo[2,3-b]pyridin-3-ylmethyl)-pyridin-2-yl]-(4-trifluoromethyl-pyridin-3-ylmethyl)-amine (P-1504),
[5-(5-Chloro-1H-pyrrolo[2,3-b]pyridin-3-ylmethyl)-pyridin-2-yl]-(5-fluoro-2-methoxy-pyridin-3-ylmethyl)-amine (P-1505),
[6-Chloro-5-(1H-pyrrolo[2,3-b]pyridin-3-ylmethyl)-pyridin-2-yl]-(5-fluoro-6-methoxy-pyridin-3-ylmethyl)-amine (P-1506),
(6-Chloro-pyridin-3-ylmethyl)-[6-chloro-5-(1H-pyrrolo[2,3-b]pyridin-3-ylmethyl)-pyridin-2-yl]-amine (P-1508),
[6-Chloro-5-(1H-pyrrolo[2,3-b]pyridin-3-ylmethyl)-pyridin-2-yl]-(5-fluoro-2-methoxy-pyridin-3-ylmethyl)-amine (P-1509),
[6-Chloro-5-(1H-pyrrolo[2,3-b]pyridin-3-ylmethyl)-pyridin-2-yl]-(4-trifluoromethyl-pyridin-3-ylmethyl)-amine (P-1510), TABLE 4-continued (5-Fluoro-6-methoxy-pyridin-3-ylmethyl)-[5-(1H-pyrrolo[2,3-b]pyridin-3-ylmethyl)-pyrimidin-2-yl]-amine (P-1513),
(6-Chloro-pyridin-3-ylmethyl)-[5-(1H-pyrrolo[2,3-b]pyridin-3-ylmethyl)-pyrimidin-2-yl]-amine (P-1515),
[5-(1H-Pyrrolo[2,3-b]pyridin-3-ylmethyl)-pyrimidin-2-yl]-(4-trifluoromethyl-pyridin-3-ylmethyl)-amine (P-1516),
(5-Fluoro-2-methoxy-pyridin-3-ylmethyl)-[5-(1H-pyrrolo[2,3-b]pyridin-3-ylmethyl)-pyrimidin-2-yl]-amine (P-1520),
[4-Chloro-5-(1H-pyrrolo[2,3-b]pyridin-3-ylmethyl)-thiazol-2-yl]-(5-fluoro-6-methoxy-pyridin-3-ylmethyl)-amine (P-1521),
(6-Chloro-pyridin-3-ylmethyl)-[4-chloro-5-(1H-pyrrolo[2,3-b]pyridin-3-ylmethyl)-thiazol-2-yl]-amine (P-1523),
[4-Chloro-5-(1H-pyrrolo[2,3-b]pyridin-3-ylmethyl)-thiazol-2-yl]-(5-fluoro-2-methoxy-pyridin-3-ylmethyl)-amine (P-1524),
[4-Chloro-5-(1H-pyrrolo[2,3-b]pyridin-3-ylmethyl)-thiazol-2-yl]-(4-trifluoromethyl-pyridin-3-ylmethyl)-amine (P-1525),
(5-Fluoro-2-methoxy-pyridin-3-ylmethyl)-[5-(5-methyl-1H-pyrrolo[2,3-b]pyridin-3-ylmethyl)-pyridin-2-yl]-amine (P-1528),
(5-Fluoro-6-methoxy-pyridin-3-ylmethyl)-[5-(5-methyl-1H-pyrrolo[2,3-b]pyridin-3-ylmethyl)-pyridin-2-yl]-amine (P-1529),
(6-Chloro-pyridin-3-ylmethyl)-[5-(5-methyl-1H-pyrrolo[2,3-b]pyridin-3-ylmethyl)-pyridin-2-yl]-amine (P-1531),
(5-Fluoro-6-methoxy-pyridin-3-ylmethyl)-[6-methyl-5-(5-methyl-1H-pyrrolo[2,3-b]pyridin-3-ylmethyl)-pyridin-2-yl]-amine (P-1533),
(6-Chloro-pyridin-3-ylmethyl)-[6-methyl-5-(5-methyl-1H-pyrrolo[2,3-b]pyridin-3-ylmethyl)-pyridin-2-yl]-amine (P-1535),
(5-Fluoro-2-methoxy-pyridin-3-ylmethyl)-[6-methyl-5-(5-methyl-1H-pyrrolo[2,3-b]pyridin-3-ylmethyl)-pyridin-2-yl]-amine (P-1536),
[6-Methyl-5-(5-methyl-1H-pyrrolo[2,3-b]pyridin-3-ylmethyl)-pyridin-2-yl]-(4-trifluoromethyl-pyridin-3-ylmethyl)-amine (P-1537),
[6-Chloro-5-(5-methyl-1H-pyrrolo[2,3-b]pyridin-3-ylmethyl)-pyridin-2-yl]-(5-fluoro-6-methoxy-pyridin-3-ylmethyl)-amine (P-1540),
[6-Chloro-5-(5-methyl-1H-pyrrolo[2,3-b]pyridin-3-ylmethyl)-pyridin-2-yl]-(6-chloro-pyridin-3-ylmethyl)-amine (P-1542),
[6-Chloro-5-(5-methyl-1H-pyrrolo[2,3-b]pyridin-3-ylmethyl)-pyridin-2-yl]-(5-fluoro-2-methoxy-pyridin-3-ylmethyl)-amine (P-1543),
[6-Chloro-5-(5-methyl-1H-pyrrolo[2,3-b]pyridin-3-ylmethyl)-pyridin-2-yl]-(4-trifluoromethyl-pyridin-3-ylmethyl)-amine (P-1544),
(5-Fluoro-2-methoxy-pyridin-3-ylmethyl)-[3-methoxy-5-(5-methyl-1H-pyrrolo[2,3-b]pyridin-3-ylmethyl)-pyridin-2-yl]-amine (P-1547),
(5-Fluoro-6-methoxy-pyridin-3-ylmethyl)-[3-methoxy-5-(5-methyl-1H-pyrrolo[2,3-b]pyridin-3-ylmethyl)-pyridin-2-yl]-amine (P-1548),
(6-Chloro-pyridin-3-ylmethyl)-[3-methoxy-5-(5-methyl-1H-pyrrolo[2,3-b]pyridin-3-ylmethyl)-pyridin-2-yl]-amine (P-1550),
[3-Methoxy-5-(5-methyl-1H-pyrrolo[2,3-b]pyridin-3-ylmethyl)-pyridin-2-yl]-(4-trifluoromethyl-pyridin-3-ylmethyl)-amine (P-1551),
(5-Fluoro-6-methoxy-pyridin-3-ylmethyl)-[3-methyl-5-(5-methyl-1H-pyrrolo[2,3-b]pyridin-3-ylmethyl)-pyridin-2-yl]-amine (P-1555),
(6-Chloro-pyridin-3-ylmethyl)-[3-methyl-5-(5-methyl-1H-pyrrolo[2,3-b]pyridin-3-ylmethyl)-pyridin-2-yl]-amine (P-1557),
(5-Fluoro-2-methoxy-pyridin-3-ylmethyl)-[3-methyl-5-(5-methyl-1H-pyrrolo[2,3-b]pyridin-3-ylmethyl)-pyridin-2-yl]-amine (P-1558),
[3-Methyl-5-(5-methyl-1H-pyrrolo[2,3-b]pyridin-3-ylmethyl)-pyridin-2-yl]-(4-trifluoromethyl-pyridin-3-ylmethyl)-amine (P-1559),
(5-Fluoro-6-methoxy-pyridin-3-ylmethyl)-[3-fluoro-5-(5-methyl-1H-pyrrolo[2,3-b]pyridin-3-ylmethyl)-pyridin-2-yl]-amine (P-1563),
(6-Chloro-pyridin-3-ylmethyl)-[3-fluoro-5-(5-methyl-1H-pyrrolo[2,3-b]pyridin-3-ylmethyl)-pyridin-2-yl]-amine (P-1565),
(5-Fluoro-2-methoxy-pyridin-3-ylmethyl)-[3-fluoro-5-(5-methyl-1H-pyrrolo[2,3-b]pyridin-3-ylmethyl)-pyridin-2-yl]-amine (P-1566),
[3-Fluoro-5-(5-methyl-1H-pyrrolo[2,3-b]pyridin-3-ylmethyl)-pyridin-2-yl]-(4-trifluoromethyl-pyridin-3-ylmethyl)-amine (P-1567),
[5-(5-Methyl-1H-pyrrolo[2,3-b]pyridin-3-ylmethyl)-pyrimidin-2-yl]-(4-trifluoromethyl-pyridin-3-ylmethyl)-amine (P-1570),
(5-Fluoro-6-methoxy-pyridin-3-ylmethyl)-[5-(5-methyl-1H-pyrrolo[2,3-b]pyridin-3-ylmethyl)-thiazol-2-yl]-amine (P-1579),
(6-Chloro-pyridin-3-ylmethyl)-[5-(5-methyl-1H-pyrrolo[2,3-b]pyridin-3-ylmethyl)-thiazol-2-yl]-amine (P-1581),
[5-(5-Methyl-1H-pyrrolo[2,3-b]pyridin-3-ylmethyl)-thiazol-2-yl]-(4-trifluoromethyl-pyridin-3-ylmethyl)-amine (P-1582),
(5-Fluoro-6-methoxy-pyridin-3-ylmethyl)-[5-(5-methoxy-1H-pyrrolo[2,3-b]pyridin-3-ylmethyl)-pyridin-2-yl]-amine (P-1584),
(6-Chloro-pyridin-3-ylmethyl)-[5-(5-methoxy-1H-pyrrolo[2,3-b]pyridin-3-ylmethyl)-pyridin-2-yl]-amine (P-1586),
(5-Fluoro-2-methoxy-pyridin-3-ylmethyl)-[5-(5-methoxy-1H-pyrrolo[2,3-b]pyridin-3-ylmethyl)-pyridin-2-yl]-amine (P-1587),
[5-(5-Methoxy-1H-pyrrolo[2,3-b]pyridin-3-ylmethyl)-pyridin-2-yl]-(4-trifluoromethyl-pyridin-3-ylmethyl)-amine (P-1588),
[6-Chloro-5-(5-methoxy-1H-pyrrolo[2,3-b]pyridin-3-ylmethyl)-pyridin-2-yl]-(5-fluoro-6-methoxy-pyridin-3-ylmethyl)-amine (P-1590),

TABLE 4-continued

[6-Chloro-5-(5-methoxy-1H-pyrrolo[2,3-b]pyridin-3-ylmethyl)-pyridin-2-yl]-(6-chloro-pyridin-3-ylmethyl)-amine (P-1592),
[6-Chloro-5-(5-methoxy-1H-pyrrolo[2,3-b]pyridin-3-ylmethyl)-pyridin-2-yl]-(5-fluoro-2-methoxy-pyridin-3-ylmethyl)-amine (P-1593),
[6-Chloro-5-(5-methoxy-1H-pyrrolo[2,3-b]pyridin-3-ylmethyl)-pyridin-2-yl]-(4-trifluoromethyl-pyridin-3-ylmethyl)-amine (P-1594),
(6-Chloro-pyridin-3-ylmethyl)-[6-fluoro-5-(5-methoxy-1H-pyrrolo[2,3-b]pyridin-3-ylmethyl)-pyridin-2-yl]-amine (P-1597),
[6-Fluoro-5-(5-methoxy-1H-pyrrolo[2,3-b]pyridin-3-ylmethyl)-pyridin-2-yl]-(4-trifluoromethyl-pyridin-3-ylmethyl)-amine (P-1598),
(5-Fluoro-2-methoxy-pyridin-3-ylmethyl)-[5-(5-methoxy-1H-pyrrolo[2,3-b]pyridin-3-ylmethyl)-pyrimidin-2-yl]-amine (P-1599),
(5-Fluoro-6-methoxy-pyridin-3-ylmethyl)-[5-(5-methoxy-1H-pyrrolo[2,3-b]pyridin-3-ylmethyl)-pyrimidin-2-yl]-amine (P-1600),
(6-Chloro-pyridin-3-ylmethyl)-[5-(5-methoxy-1H-pyrrolo[2,3-b]pyridin-3-ylmethyl)-pyrimidin-2-yl]-amine (P-1602),
[5-(5-Methoxy-1H-pyrrolo[2,3-b]pyridin-3-ylmethyl)-pyrimidin-2-yl]-(4-trifluoromethyl-pyridin-3-ylmethyl)-amine (P-1603),
(6-Chloro-pyridin-3-ylmethyl)-[5-(5-chloro-1H-pyrrolo[2,3-b]pyridin-3-ylmethyl)-6-fluoro-pyridin-2-yl]-amine (P-1607),
[5-(5-Chloro-1H-pyrrolo[2,3-b]pyridin-3-ylmethyl)-6-fluoro-pyridin-2-yl]-(4-trifluoromethyl-pyridin-3-ylmethyl)-amine (P-1608),
[5-(5-Chloro-1H-pyrrolo[2,3-b]pyridin-3-ylmethyl)-pyrimidin-2-yl]-(5-fluoro-6-methoxy-pyridin-3-ylmethyl)-amine (P-1611),
(6-Chloro-pyridin-3-ylmethyl)-[5-(5-chloro-1H-pyrrolo[2,3-b]pyridin-3-ylmethyl)-pyrimidin-2-yl]-amine (P-1612),
[5-(5-Chloro-1H-pyrrolo[2,3-b]pyridin-3-ylmethyl)-pyrimidin-2-yl]-(4-trifluoromethyl-pyridin-3-ylmethyl)-amine (P-1613),
[6-Fluoro-5-(5-fluoro-1H-pyrrolo[2,3-b]pyridin-3-ylmethyl)-pyridin-2-yl]-(5-fluoro-6-methoxy-pyridin-3-ylmethyl)-amine (P-1623),
(6-Chloro-pyridin-3-ylmethyl)-[6-fluoro-5-(5-fluoro-1H-pyrrolo[2,3-b]pyridin-3-ylmethyl)-pyridin-2-yl]-amine (P-1625),
[6-Fluoro-5-(5-fluoro-1H-pyrrolo[2,3-b]pyridin-3-ylmethyl)-pyridin-2-yl]-(5-fluoro-2-methoxy-pyridin-3-ylmethyl)-amine (P-1626),
[6-Fluoro-5-(5-fluoro-1H-pyrrolo[2,3-b]pyridin-3-ylmethyl)-pyridin-2-yl]-(4-trifluoromethyl-pyridin-3-ylmethyl)-amine (P-1627),
(5-Fluoro-6-methoxy-pyridin-3-ylmethyl)-[5-(5-fluoro-1H-pyrrolo[2,3-b]pyridin-3-ylmethyl)-pyrimidin-2-yl]-amine (P-1630),
(6-Chloro-pyridin-3-ylmethyl)-[5-(5-fluoro-1H-pyrrolo[2,3-b]pyridin-3-ylmethyl)-pyrimidin-2-yl]-amine (P-1632),
(5-Fluoro-2-methoxy-pyridin-3-ylmethyl)-[5-(5-fluoro-1H-pyrrolo[2,3-b]pyridin-3-ylmethyl)-pyrimidin-2-yl]-amine (P-1633),
[5-(5-Fluoro-1H-pyrrolo[2,3-b]pyridin-3-ylmethyl)-pyrimidin-2-yl]-(4-trifluoromethyl-pyridin-3-ylmethyl)-amine (P-1634),
(5-Fluoro-6-methoxy-pyridin-3-ylmethyl)-[5-(5-trifluoromethyl-1H-pyrrolo[2,3-b]pyridin-3-ylmethyl)-pyridin-2-yl]-amine (P-1638),
(6-Chloro-pyridin-3-ylmethyl)-[5-(5-trifluoromethyl-1H-pyrrolo[2,3-b]pyridin-3-ylmethyl)-pyridin-2-yl]-amine (P-1640),
(5-Fluoro-2-methoxy-pyridin-3-ylmethyl)-[5-(5-trifluoromethyl-1H-pyrrolo[2,3-b]pyridin-3-ylmethyl)-pyridin-2-yl]-amine (P-1641),
(4-Trifluoromethyl-pyridin-3-ylmethyl)-[5-(5-trifluoromethyl-1H-pyrrolo[2,3-b]pyridin-3-ylmethyl)-pyridin-2-yl]-amine (P-1642),
(5-Fluoro-6-methoxy-pyridin-3-ylmethyl)-[6-fluoro-5-(5-trifluoromethyl-1H-pyrrolo[2,3-b]pyridin-3-ylmethyl)-pyridin-2-yl]-amine (P-1646),
(6-Chloro-pyridin-3-ylmethyl)-[6-fluoro-5-(5-trifluoromethyl-1H-pyrrolo[2,3-b]pyridin-3-ylmethyl)-pyridin-2-yl]-amine (P-1648),
(5-Fluoro-2-methoxy-pyridin-3-ylmethyl)-[6-fluoro-5-(5-trifluoromethyl-1H-pyrrolo[2,3-b]pyridin-3-ylmethyl)-pyridin-2-yl]-amine (P-1649),
[6-Fluoro-5-(5-trifluoromethyl-1H-pyrrolo[2,3-b]pyridin-3-ylmethyl)-pyridin-2-yl]-(4-trifluoromethyl-pyridin-3-ylmethyl)-amine (P-1650),
3-{2-Fluoro-6-[(5-fluoro-6-methoxy-pyridin-3-ylmethyl)-amino]-pyridin-3-ylmethyl}-1H-pyrrolo[2,3-b]pyridine-5-carbonitrile (P-1654),
3-{6-[(6-Chloro-pyridin-3-ylmethyl)-amino]-2-fluoro-pyridin-3-ylmethyl}-1H-pyrrolo[2,3-b]pyridine-5-carbonitrile (P-1655),
3-{2-Fluoro-6-[(5-fluoro-2-methoxy-pyridin-3-ylmethyl)-amino]-pyridin-3-ylmethyl}-1H-pyrrolo[2,3-b]pyridine-5-carbonitrile (P-1656),
3-{2-Fluoro-6-[(4-trifluoromethyl-pyridin-3-ylmethyl)-amino]-pyridin-3-ylmethyl}-1H-pyrrolo[2,3-b]pyridine-5-carbonitrile (P-1657),
[5-(5-Cyclopropyl-1H-pyrrolo[2,3-b]pyridin-3-ylmethyl)-pyridin-2-yl]-(5-fluoro-6-methoxy-pyridin-3-ylmethyl)-amine (P-1661),
(6-Chloro-pyridin-3-ylmethyl)-[5-(5-cyclopropyl-1H-pyrrolo[2,3-b]pyridin-3-ylmethyl)-pyridin-2-yl]-amine (P-1663),
[5-(5-Cyclopropyl-1H-pyrrolo[2,3-b]pyridin-3-ylmethyl)-pyridin-2-yl]-(5-fluoro-2-methoxy-pyridin-3-ylmethyl)-amine (P-1664),
[5-(5-Cyclopropyl-1H-pyrrolo[2,3-b]pyridin-3-ylmethyl)-pyridin-2-yl]-(4-trifluoromethyl-pyridin-3-ylmethyl)-amine (P-1665),
N-(3-{2-Fluoro-6-[(5-fluoro-6-methoxy-pyridin-3-ylmethyl)-amino]-pyridin-3-ylmethyl}-1H-pyrrolo[2,3-b]pyridin-5-yl)-acetamide (P-1670),
N-(3-{6-[(6-Chloro-pyridin-3-ylmethyl)-amino]-2-fluoro-pyridin-3-ylmethyl}-1H-pyrrolo[2,3-b]pyridin-5-yl)-acetamide (P-1672), TABLE 4-continued N-(3-{2-Fluoro-6-[(4-trifluoromethyl-pyridin-3-ylmethyl)-amino]-pyridin-3-ylmethyl}-1H-pyrrolo[2,3-b]pyridin-5-yl)-acetamide (P-1673),
N-(3-{2-Fluoro-6-[(5-fluoro-6-methoxy-pyridin-3-ylmethyl)-amino]-pyridin-3-ylmethyl}-1H-pyrrolo[2,3-b]pyridin-5-yl)-methanesulfonamide (P-1677),
N-(3-{2-Fluoro-6-[(5-fluoro-2-methoxy-pyridin-3-ylmethyl)-amino]-pyridin-3-ylmethyl}-1H-pyrrolo[2,3-b]pyridin-5-yl)-methanesulfonamide (P-1680),
N-(3-{2-Fluoro-6-[(4-trifluoromethyl-pyridin-3-ylmethyl)-amino]-pyridin-3-ylmethyl}-1H-pyrrolo[2,3-b]pyridin-5-yl)-methanesulfonamide (P-1681),
[6-Fluoro-5-(5-methanesulfonyl-1H-pyrrolo[2,3-b]pyridin-3-ylmethyl)-pyridin-2-yl]-(5-fluoro-6-methoxy-pyridin-3-ylmethyl)-amine (P-1685),
(6-Chloro-pyridin-3-ylmethyl)-[6-fluoro-5-(5-methanesulfonyl-1H-pyrrolo[2,3-b]pyridin-3-ylmethyl)-pyridin-2-yl]-amine (P-1687),
[6-Fluoro-5-(5-methanesulfonyl-1H-pyrrolo[2,3-b]pyridin-3-ylmethyl)-pyridin-2-yl]-(5-fluoro-2-methoxy-pyridin-3-ylmethyl)-amine (P-1688),
[6-Fluoro-5-(5-methanesulfonyl-1H-pyrrolo[2,3-b]pyridin-3-ylmethyl)-pyridin-2-yl]-(4-trifluoromethyl-pyridin-3-ylmethyl)-amine (P-1689),
3-{2-Fluoro-6-[(5-fluoro-2-methoxy-pyridin-3-ylmethyl)-amino]-pyridin-3-ylmethyl}-1H-pyrrolo[2,3-b]pyridine-5-carboxylic acid methyl ester (P-1693),
3-{2-Fluoro-6-[(5-fluoro-6-methoxy-pyridin-3-ylmethyl)-amino]-pyridin-3-ylmethyl}-1H-pyrrolo[2,3-b]pyridine-5-carboxylic acid methylamide (P-1694),
3-{2-Fluoro-6-[(5-fluoro-2-methoxy-pyridin-3-ylmethyl)-amino]-pyridin-3-ylmethyl}-1H-pyrrolo[2,3-b]pyridine-5-carboxylic acid methylamide (P-1696),
3-{6-[(6-Chloro-pyridin-3-ylmethyl)-amino]-2-fluoro-pyridin-3-ylmethyl}-1H-pyrrolo[2,3-b]pyridine-5-carboxylic acid methylamide (P-1697),
3-{2-Fluoro-6-[(4-trifluoromethyl-pyridin-3-ylmethyl)-amino]-pyridin-3-ylmethyl}-1H-pyrrolo[2,3-b]pyridine-5-carboxylic acid methylamide (P-1698),
(5-Fluoro-2-methoxy-pyridin-3-ylmethyl)-{6-fluoro-5-[5-(1-piperidin-4-yl-1H-pyrazol-4-yl)-1H-pyrrolo[2,3-b]pyridin-3-ylmethyl]-pyridin-2-yl}-amine (P-1703),
(5-Fluoro-6-methoxy-pyridin-3-ylmethyl)-{6-fluoro-5-[5-(1-piperidin-4-yl-1H-pyrazol-4-yl)-1H-pyrrolo[2,3-b]pyridin-3-ylmethyl]-pyridin-2-yl}-amine (P-1704),
(6-Chloro-pyridin-3-ylmethyl)-{6-fluoro-5-[5-(1-piperidin-4-yl-1H-pyrazol-4-yl)-1H-pyrrolo[2,3-b]pyridin-3-ylmethyl]-pyridin-2-yl}-amine (P-1706),
{6-Fluoro-5-[5-(1-piperidin-4-yl-1H-pyrazol-4-yl)-1H-pyrrolo[2,3-b]pyridin-3-ylmethyl]-pyridin-2-yl}-(4-trifluoromethyl-pyridin-3-ylmethyl)-amine (P-1707),
[5-(4-Ethynyl-1H-pyrrolo[2,3-b]pyridin-3-ylmethyl)-pyridin-2-yl]-(5-fluoro-6-methoxy-pyridin-3-ylmethyl)-amine (P-1711),
(6-Chloro-pyridin-3-ylmethyl)-[5-(4-ethynyl-1H-pyrrolo[2,3-b]pyridin-3-ylmethyl)-pyridin-2-yl]-amine (P-1713),
[5-(4-Ethynyl-1H-pyrrolo[2,3-b]pyridin-3-ylmethyl)-pyridin-2-yl]-(5-fluoro-2-methoxy-pyridin-3-ylmethyl)-amine (P-1714),
[5-(4-Ethynyl-1H-pyrrolo[2,3-b]pyridin-3-ylmethyl)-pyridin-2-yl]-(4-trifluoromethyl-pyridin-3-ylmethyl)-amine (P-1715),
3-{6-[(6-Chloro-pyridin-3-ylmethyl)-amino]-pyridin-3-ylmethyl}-1H-pyrrolo[2,3-b]pyridine-4-carbonitrile (P-1720),
3-{6-[(5-Fluoro-2-methoxy-pyridin-3-ylmethyl)-amino]-pyridin-3-ylmethyl}-1H-pyrrolo[2,3-b]pyridine-4-carbonitrile (P-1721),
3-{6-[(4-Trifluoromethyl-pyridin-3-ylmethyl)-amino]-pyridin-3-ylmethyl}-1H-pyrrolo[2,3-b]pyridine-4-carbonitrile (P-1722),
3-{6-[(5-Fluoro-6-methoxy-pyridin-3-ylmethyl)-amino]-pyridin-3-ylmethyl}-1H-pyrrolo[2,3-b]pyridine-4-carbonitrile (P-1726),
(6-Bromo-pyridin-3-ylmethyl)-[5-(5-chloro-1H-pyrrolo[2,3-b]pyridin-3-ylmethyl)-pyridin-2-yl]-amine (P-2002),
(6-Chloro-pyridin-3-ylmethyl)-[5-(5-chloro-1H-pyrrolo[2,3-b]pyridin-3-ylmethyl)-pyridin-2-yl]-amine (P-2003),
[5-(5-Chloro-1H-pyrrolo[2,3-b]pyridin-3-ylmethyl)-pyridin-2-yl]-(6-fluoro-pyridin-3-ylmethyl)-amine (P-2004),
(5-Fluoro-6-methoxy-pyridin-3-ylmethyl)-[6-fluoro-5-(5-methoxy-1H-pyrrolo[2,3-b]pyridin-3-ylmethyl)-pyridin-2-yl]-amine (P-2040),
(5-Fluoro-6-methoxy-pyridin-3-ylmethyl)-[6-fluoro-5-(1H-pyrrolo[2,3-b]pyridin-3-ylmethyl)-pyridin-2-yl]-amine (P-2041),
(5-Fluoro-2-methoxy-pyridin-3-ylmethyl)-[6-fluoro-5-(5-methoxy-1H-pyrrolo[2,3-b]pyridin-3-ylmethyl)-pyridin-2-yl]-amine (P-2042),
(5-Fluoro-6-methoxy-pyridin-3-ylmethyl)-[6-fluoro-5-(5-methyl-1H-pyrrolo[2,3-b]pyridin-3-ylmethyl)-pyridin-2-yl]-amine (P-2048),
(5-Fluoro-2-methoxy-pyridin-3-ylmethyl)-[6-fluoro-5-(5-methyl-1H-pyrrolo[2,3-b]pyridin-3-ylmethyl)-pyridin-2-yl]-amine (P-2049),
(5-Fluoro-2-methoxy-pyridin-3-ylmethyl)-[5-(5-methyl-1H-pyrrolo[2,3-b]pyridin-3-ylmethyl)-pyrimidin-2-yl]-amine (P-2061),
[6-Fluoro-5-(5-methyl-1H-pyrrolo[2,3-b]pyridin-3-ylmethyl)-pyridin-2-yl]-(4-trifluoromethyl-pyridin-3-ylmethyl)-amine (P-2062),
[5-(5-Chloro-1H-pyrrolo[2,3-b]pyridin-3-ylmethyl)-pyridin-2-yl]-(4-trifluoromethyl-pyridin-3-ylmethyl)-amine (P-2063),
[5-(5-Chloro-1H-pyrrolo[2,3-b]pyridin-3-ylmethyl)-pyrimidin-2-yl]-(5-fluoro-2-methoxy-pyridin-3-ylmethyl)-amine (P-2064),
[5-(5-Methyl-1H-pyrrolo[2,3-b]pyridin-3-ylmethyl)-pyridin-2-yl]-(4-trifluoromethyl-pyridin-3-ylmethyl)-amine (P-2070),
(5-Fluoro-6-methoxy-pyridin-3-ylmethyl)-[5-(5-methyl-1H-pyrrolo[2,3-b]pyridin-3-ylmethyl)-pyrimidin-2-yl]-amine (P-2073),
(6-Chloro-pyridin-3-ylmethyl)-[5-(5-methyl-1H-pyrrolo[2,3-b]pyridin-3-ylmethyl)-pyrimidin-2-yl]-amine (P-2078), TABLE 4-continued (6-Chloro-pyridin-3-ylmethyl)-[6-fluoro-5-(5-methyl-1H-pyrrolo[2,3-b]pyridin-3-ylmethyl)-pyridin-2-yl]-amine (P-2088),
[5-(5-Chloro-1H-pyrrolo[2,3-b]pyridin-3-ylmethyl)-thiazol-2-yl]-(5-fluoro-2-methoxy-pyridin-3-ylmethyl)-amine (P-2152),
(5-Fluoro-2-methoxy-pyridin-3-ylmethyl)-[5-(5-methyl-1H-pyrrolo[2,3-b]pyridin-3-ylmethyl)-thiazol-2-yl]-amine (P-2153),
[5-(5-Chloro-1H-pyrrolo[2,3-b]pyridin-3-ylmethyl)-6-fluoro-pyridin-2-yl]-(5-fluoro-6-methoxy-pyridin-3-ylmethyl)-amine (P-2165),
[5-(4-Chloro-1H-pyrrolo[2,3-b]pyridin-3-ylmethyl)-pyridin-2-yl]-(5-fluoro-2-methoxy-pyridin-3-ylmethyl)-amine (P-2170),
(5-Fluoro-2-methoxy-pyridin-3-ylmethyl)-[5-(4-phenyl-1H-pyrrolo[2,3-b]pyridin-3-ylmethyl)-pyridin-2-yl]-amine (P-2171),
5-[(5-bromo-1H-pyrrolo[2,3-b]pyridin-3-yl)methyl]-6-fluoro-N-[(5-fluoro-6-methoxy-3-pyridyl)methyl]pyridin-2-amine (P-2203),
3-[[2-fluoro-6-[(5-fluoro-6-methoxy-3-pyridyl)methylamino]-3-pyridyl]methyl]-1H-pyrrolo[2,3-b]pyridine-5-carbonitrile (P-2204),
6-chloro-N-[(5-fluoro-2-methoxy-3-pyridyl)methyl]-5-[(5-methyl-1H-pyrrolo[2,3-b]pyridin-3-yl)methyl]pyridin-2-amine (P-2205),
6-fluoro-N-[(5-fluoro-6-methoxy-3-pyridyl)methyl]-5-[[5-(trifluoromethyl)-1H-pyrrolo[2,3-b]pyridin-3-yl]methyl]pyridin-2-amine (P-2206),
5-[(5-chloro-1H-pyrrolo[2,3-b]pyridin-3-yl)methyl]-6-fluoro-N-[(5-fluoro-6-methoxy-3-pyridyl)methyl]pyridin-2-amine (P-2207).

In some embodiments, the disclosure provides a method for treating a disease or condition as described herein by administering to a subject a compound of Formula II':

In some embodiments, the disclosure provides a method for treating a disease or condition as described herein by administering to a subject a compound of Formula II:

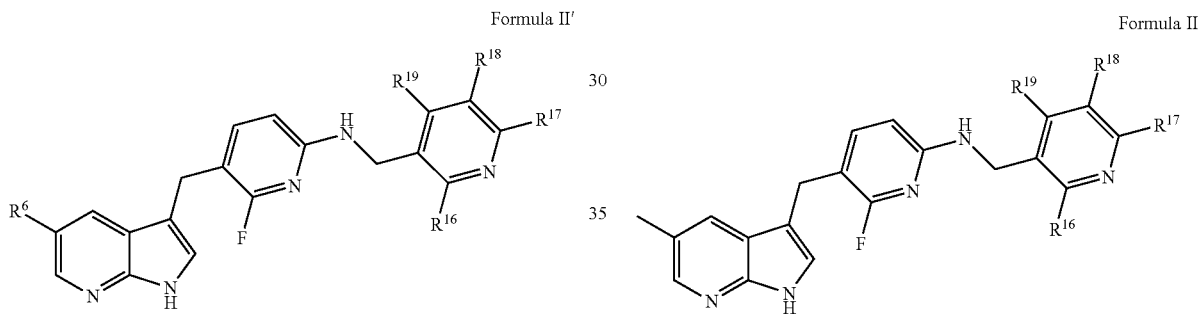

Formula II'

Formula II or a salt, a prodrug, a tautomer or a stereoisomer thereof, wherein:
$R^{16}$, $R^{17}$, $R^{18}$ and $R^{19}$ are each independently selected from the group consisting of H, halogen, lower alkyl, lower alkoxy, halo substituted lower alkyl, alkoxy substituted lower alkyl, cycloalkylamino, —CN, —O—$R^{20}$, —S(O)$_2$—$R^{21}$, —S(O)$_2$—N(H)—$R^{22}$, —N(H)—$R^{22}$, —N($R^{22}$)$_2$, and —N(H)—S(O)$_2$—$R^{23}$, provided that at least two of $R^{16}$, $R^{17}$, $R^{18}$ and $R^{19}$ are —H;
$R^{20}$ is lower alkyl, fluoro substituted lower alkyl, methoxy substituted lower alkyl, or cycloalkyl;
$R^{21}$ is lower alkyl;
$R^{22}$ is lower alkyl; and
$R^{23}$ is lower alkyl.

In some embodiments of compounds of Formula II', $R^6$ is selected from the group consisting of halogen, lower alkyl, fluoro substituted lower alkyl, lower alkenyl, lower alkynyl, cycloalkyl, phenyl, pyrazolyl, —CN, —O—$R^{13}$, —C(O)—N(H)—$R^{14}$, —C(O)—O—$R^{14}$, —S(O)$_2$—$R^{15}$, —S(O)$_2$—N(H)—$R^{14}$, —N(H)—C(O)—$R^{11}$, and —N(H)—S(O)$_2$—$R^5$, wherein pyrazolyl is optionally substituted with lower alkyl or heterocycloalkyl. In certain instances, $R^6$ is F, Cl, Br, lower alkyl, fluoro substituted lower alkyl, lower alkenyl, —CN, —C(O)—N(H)—$R^4$, —N(H)—C(O)—$R^{15}$, —C(O)—O—$R^{14}$, —S(O)$_2$—$R^{15}$, —S(O)$_2$—N(H)—$R^{14}$ or —N(H)—S(O)$_2$—$R^{15}$. In other instances, $R^6$ is methyl, ethyl, propyl, butyl, pentyl or hexyl. All other variables are as defined herein.

or a salt, a prodrug, a tautomer or a stereoisomer thereof, wherein:
$R^{16}$, $R^{17}$, $R^{18}$ and $R^{19}$ are independently selected from the group consisting of —H, —F, —Cl, —Br, lower alkyl, fluoro substituted lower alkyl, methoxy substituted lower alkyl, cycloalkylamino, —CN, —O—$R^{20}$, —S(O)$_2$—$R^{21}$, —S(O)$_2$—N(H)—$R^{22}$, —N(H)—$R^{22}$, —N($R^{22}$)$_2$, and —N(H)—S(O)$_2$—$R^{23}$, provided that at least two of $R^{16}$, $R^{17}$, $R^{18}$ and $R^{19}$ are —H;
$R^{20}$ is lower alkyl, fluoro substituted lower alkyl, methoxy substituted lower alkyl, or cycloalkyl;
$R^{21}$ is lower alkyl;
$R^{22}$ is lower alkyl; and
$R^{23}$ is lower alkyl.

In some embodiments of compounds of Formulae II and II', $R^{16}$, $R^{17}$, $R^{18}$ and $R^{19}$ are each independently selected from the group consisting of —H, —F, —Cl, —Br, lower alkyl, fluoro substituted lower alkyl, methoxy substituted lower alkyl, cycloalkylamino, —CN, —O—$R^{20}$, —S(O)$_2$—$R^{21}$, —S(O)$_2$—N(H)—$R^{22}$, —N(H)—$R^{22}$, —N($R^{22}$)$_2$, and —N(H)—S(O)$_2$—$R^{23}$, provided that at least two of $R^{16}$, $R^{17}$, $R^{18}$ and $R^{19}$ are —H. In some embodiments, $R^{17}$ and $R^{19}$ are H, halogen or lower alkyl. All other variables are as defined herein.

In other embodiments of compounds of Formulae II and II', $R^{16}$, $R^{17}$, $R^{18}$ and $R^{19}$ are each independently selected from H, halogen, lower alkyl, lower alkoxy, halo substituted lower alkyl, —OR$^{20}$, or alkoxy substituted lower alkyl, provided that at least two of R$^{16}$, R$^{17}$, R$^{18}$ and R$^{19}$ are —H. All other variables are as defined herein.

In some embodiments of compounds of Formulae II and II', R$^{16}$, R$^{17}$, and R$^{18}$ are H and R$^{19}$ is —F, —Cl, —Br, lower alkyl, fluoro substituted lower alkyl, methoxy substituted lower alkyl, cycloalkylamino, —CN, —O—R$^{20}$, —S(O)$_2$—R$^{21}$, —N(H)—R$^{22}$, —N(R$^{22}$)$_2$, or —N(H)—S(O)$_2$—R$^{23}$. In some embodiments R$^{16}$, R$^{17}$, and R$^{18}$ are H and R$^{19}$ is —F, —Cl, lower alkyl, fluoro substituted lower alkyl, cycloalkylamino, —O—R$^{20}$, —N(H)—R$^{22}$, or —N(R$^{22}$)$_2$. In some embodiments R$^{16}$, R$^{17}$, and R$^{18}$ are H and R$^{19}$ is fluoro substituted lower alkyl or —O—R$^{20}$. In some embodiments R$^{16}$, R$^{17}$, and R$^{18}$ are H and R$^{19}$ is —CF$_3$ or —O—CH$_3$. All other variables are as defined herein.

In some embodiments of compounds of Formulae II and II', R$^{16}$, R$^{17}$, and R$^{19}$ are H and R$^{18}$ is —F, —Cl, —Br, lower alkyl, fluoro substituted lower alkyl, methoxy substituted lower alkyl, cycloalkylamino, —CN, —O—R$^{20}$, —S(O)$_2$—R$^{21}$, —N(H)—R$^{22}$, —N(R$^{22}$)$_2$, or —N(H)—S(O)$_2$—R$^{23}$. In some embodiments R$^{16}$, R$^{17}$, and R$^{19}$ are H and R$^{18}$ is —F, —Cl, lower alkyl, fluoro substituted lower alkyl, cycloalkylamino, —O—R$^{20}$, —N(H)—R$^{22}$, or —N(R$^{22}$)$_2$. In some embodiments R$^{16}$, R$^{17}$, and R$^{19}$ are H and R$^{18}$ is —F, —Cl, or —O—R$^{20}$. In some embodiments R$^{16}$, R$^{17}$, and R$^{19}$ are H and R$^{18}$ is —F, —Cl, or —O—CH$_3$. All other variables are as defined herein.

In some embodiments of compounds of Formulae II and II', R$^{16}$, R$^{18}$, and R$^{19}$ are H and R$^{17}$ is —F, —Cl, —Br, lower alkyl, fluoro substituted lower alkyl, methoxy substituted lower alkyl, cycloalkylamino, —CN, —O—R$^{20}$, —S(O)$_2$—R$^{21}$, —N(H)—R$^{22}$, —N(R$^{22}$)$_2$, or —N(H)—S(O)$_2$—R$^{23}$. In some embodiments R$^{16}$, R$^{18}$, and R$^{19}$ are H and R$^{17}$ is —F, —Cl, lower alkyl, fluoro substituted lower alkyl, cycloalkylamino, —O—R$^{20}$, —N(H)—R$^{22}$, or —N(R$^{22}$)$_2$. In some embodiments R$^{16}$, R$^{18}$, and R$^{19}$ are H and R$^{17}$ is —Cl, fluoro substituted lower alkyl, cycloalkylamino, or —O—R$^{20}$. In some embodiments R$^{16}$, R$^{18}$, and R$^{19}$ are H and R$^{17}$ is —Cl, —CF$_3$, —O—CH$_3$, or morpholin-4-yl. All other variables are as defined herein.

In some embodiments of compounds of Formulae II and II', R$^{17}$, R$^{18}$, and R$^{19}$ are H and R$^{16}$ is —F, —Cl, —Br, lower alkyl, fluoro substituted lower alkyl, methoxy substituted lower alkyl, cycloalkylamino, —CN, —O—R$^{20}$, —S(O)$_2$—R$^{21}$, —N(H)—R$^{22}$, —N(R$^{22}$)$_2$, or —N(H)—S(O)$_2$—R$^{23}$. In some embodiments R$^{17}$, R$^{18}$, and R$^{19}$ are H and R$^{16}$ is —F, —Cl, lower alkyl, fluoro substituted lower alkyl, cycloalkylamino, —O—R$^{20}$, —N(H)—R$^{22}$, or —N(R$^{22}$)$_2$. In some embodiments R$^{17}$, R$^{18}$, and R$^{19}$ are H and R$^{16}$ is —F, —CF$_3$, morpholin-4-yl, —O—CH$_3$, —O—CH$_2$CH$_3$, —O—CH(CH$_3$)$_2$, —O—CH$_2$CF$_3$, —O-cyclopentyl, —O-cyclohexyl, or —N(H)—CH$_3$. In some embodiments R$^{17}$, R$^{18}$, and R$^{19}$ are H and R$^{16}$ is —F, —CF$_3$, or —O—CH$_3$. All other variables are as defined herein.

In some embodiments of compounds of Formulae II and II', R$^{16}$ and R$^{17}$ are H; and R$^{18}$ and R$^{19}$ are independently —F, —Cl, —Br, lower alkyl, fluoro substituted lower alkyl, methoxy substituted lower alkyl, cycloalkylamino, —CN, —O—R$^{20}$, —S(O)$_2$—R$^{21}$, —N(H)—R$^{22}$, —N(R$^{22}$)$_2$, or —N(H)—S(O)$_2$—R$^{23}$. In some embodiments R$^{16}$ and R$^{17}$ are H; and R$^{18}$ and R$^{19}$ are independently —F, —Cl, lower alkyl, fluoro substituted lower alkyl, cycloalkylamino, —O—R$^{20}$, or —N(H)—R$^{22}$, or —N(R$^{22}$)$_2$. In some embodiments R$^{16}$ and R$^{17}$ are H; and R$^{18}$ and R$^{19}$ are independently —F, —Cl, CF$_3$, —O—CH$_3$, or —N(CH$_3$)$_2$. All other variables are as defined herein.

In some embodiments of compounds of Formulae II and II', R$^{16}$ and R$^{18}$ are H; and R$^{17}$ and R$^{19}$ are independently —F, —Cl, —Br, lower alkyl, fluoro substituted lower alkyl, methoxy substituted lower alkyl, cycloalkylamino, —CN, —O—R$^{20}$, —S(O)$_2$—R$^{21}$, —N(H)—R$^{22}$, —N(R$^{22}$)$_2$, or —N(H)—S(O)$_2$—R$^{23}$. In some embodiments R$^{16}$ and R$^{18}$ are H; and R$^{17}$ and R$^{19}$ are independently —F, —Cl, lower alkyl, fluoro substituted lower alkyl, cycloalkylamino, —O—R$^{20}$, —N(H)—R$^{22}$, or —N(R$^{22}$)$_2$. In some embodiments R$^{16}$ and R$^{18}$ are H; and R$^{17}$ and R$^{19}$ are independently —F, —Cl, CF$_3$, —O—CH$_3$, or —N(CH$_3$)$_2$. In some embodiments R$^{16}$ and R$^{18}$ are H; and R$^{17}$ and R$^{19}$ are independently —CF$_3$ or —O—CH$_3$. All other variables are as defined herein.

In some embodiments of compounds of Formulae II and II', R$^{16}$ and R$^{19}$ are H; and R$^{7}$ and R$^{18}$ are independently —F, —Cl, —Br, lower alkyl, fluoro substituted lower alkyl, methoxy substituted lower alkyl, cycloalkylamino, —CN, —O—R$^{20}$, —S(O)$_2$—R$^{21}$, —N(H)—R$^{22}$, —N(R$^{22}$)$_2$, or —N(H)—S(O)$_2$—R$^{23}$. In some embodiments R$^{16}$ and R$^{19}$ are H; and R$^{17}$ and R$^{18}$ are independently —F, —Cl, lower alkyl, fluoro substituted lower alkyl, cycloalkylamino, —O—R$^{20}$, —N(H)—R$^{22}$, or —N(R$^{22}$)$_2$. In some embodiments R$^{16}$ and R$^{19}$ are H; and R$^{17}$ and R$^{18}$ are independently —F, —Cl, CF$_3$, —O—CH$_3$, or —N(CH$_3$)$_2$. In some embodiments R$^{16}$ and R$^{19}$ are H; and R$^{17}$ and R$^{18}$ are independently —F or —O—CH$_3$. All other variables are as defined herein.

In some embodiments of compounds of Formulae II and II', R$^{7}$ and R$^{18}$ are H; and R$^{16}$ and R$^{19}$ are independently —F, —Cl, —Br, lower alkyl, fluoro substituted lower alkyl, methoxy substituted lower alkyl, cycloalkylamino, —CN, —O—R$^{20}$, —S(O)$_2$—R$^{21}$, —N(H)—R$^{22}$, —N(R$^{22}$)$_2$, or —N(H)—S(O)$_2$—R$^{23}$. In some embodiments R$^{17}$ and R$^{18}$ are H; and R$^{16}$ and R$^{19}$ are independently —F, —Cl, lower alkyl, fluoro substituted lower alkyl, cycloalkylamino, —O—R$^{20}$, —N(H)—R$^{22}$, or —N(R$^{22}$)$_2$. In some embodiments R$^{17}$ and R$^{18}$ are H; and R$^{16}$ and R$^{19}$ are independently —F, —Cl, CF$_3$, —O—CH$_3$, or —N(CH$_3$)$_2$. All other variables are as defined herein.

In some embodiments of compounds of Formula II, R$^{17}$ and R$^{19}$ are H; and R$^{16}$ and R$^{18}$ are independently —F, —Cl, —Br, lower alkyl, fluoro substituted lower alkyl, methoxy substituted lower alkyl, cycloalkylamino, —CN, —O—R$^{20}$, —S(O)$_2$—R$^{21}$, —N(H)—R$^{22}$, —N(R$^{22}$)$_2$, or —N(H)—S(O)$_2$—R$^{23}$. In some embodiments R$^{17}$ and R$^{19}$ are H; and R$^{16}$ and R$^{18}$ are independently —F, —Cl, lower alkyl, fluoro substituted lower alkyl, cycloalkylamino, —O—R$^{20}$, —N(H)—R$^{22}$, or —N(R$^{22}$)$_2$. In some embodiments R$^{17}$ and R$^{19}$ are H; and R$^{16}$ and R$^{18}$ are independently —F, —Cl, CF$_3$, —O—CH$_3$, or —N(CH$_3$)$_2$. In some embodiments R$^{17}$ and R$^{19}$ are H; and R$^{16}$ and R$^{18}$ are independently —F, —Cl, or —O—CH$_3$. All other variables are as defined herein.

In some embodiments of compounds of Formulae II and II', R$^{18}$ and R$^{19}$ are H; and R$^{16}$ and R$^{17}$ are independently —F, —Cl, —Br, lower alkyl, fluoro substituted lower alkyl, methoxy substituted lower alkyl, cycloalkylamino, —CN, —O—R$^{20}$, —S(O)$_2$—R$^{21}$, —N(H)—R$^{22}$, —N(R$^{22}$)$_2$, or —N(H)—S(O)$_2$—R$^{23}$. In some embodiments R$^{118}$ and R$^{19}$ are H; and R$^{16}$ and R$^{17}$ are independently —F, —Cl, lower alkyl, fluoro substituted lower alkyl, cycloalkylamino, —O—R$^{20}$, —N(H)—R$^{22}$, or —N(R$^{22}$)$_2$. In some embodiments R$^{18}$ and R$^{19}$ are H; and R$^{16}$ and R$^{17}$ are independently —F, —Cl, CF$_3$, —O—CH$_3$, or —N(CH$_3$)$_2$. In some embodiments R$^{18}$ and R$^{19}$ are H; and R$^{16}$ and R$^{17}$ are independently —CF$_3$, —O—CH$_3$, or —N(CH$_3$)$_2$. All other variables are as defined herein.

In some embodiments, the disclosure provides a method for treating a disease or condition as described herein by administering to a subject a compound of Formula Iia:

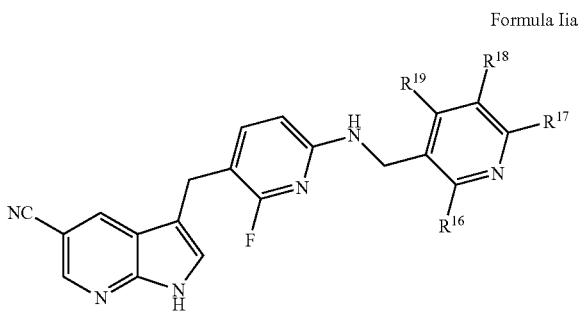

Formula Iia or a salt, a prodrug, a tautomer or a stereoisomer thereof, wherein:
R$^{16}$, R$^{17}$, R$^{18}$ and R$^{19}$ are independently selected from the group consisting of —H, —F, —Cl, —Br, lower alkyl, fluoro substituted lower alkyl, methoxy substituted lower alkyl,
cycloalkylamino, —CN, —O—R$^{20}$, —S(O)$_2$—R$^{21}$, —S(O)$_2$—N(H)—R$^{22}$, —N(H)—R$^{22}$, —N(R$^{22}$)$_2$, and —N(H)—S(O)$_2$—R$^{23}$, provided that at least two of R$^{16}$, R$^{17}$, R$^{18}$ and R$^{19}$ are —H;
R$^{20}$ is lower alkyl, fluoro substituted lower alkyl, methoxy substituted lower alkyl, or cycloalkyl;
R$^{21}$ is lower alkyl;
R$^{22}$ is lower alkyl; and
R$^{23}$ is lower alkyl.

In some embodiments of compounds of Formula Iia, R$^{16}$, R$^{17}$, R$^{18}$ and R$^{19}$ are each independently from the group consisting of —H, —F, —Cl, —Br, lower alkyl, fluoro substituted lower alkyl, methoxy substituted lower alkyl, cycloalkylamino, —CN, —O—R$^{20}$, —S(O)$_2$—R$^{21}$, —S(O)$_2$—N(H)—R$^{22}$, —N(H)—R$^{22}$, —N(R$^{22}$)$_2$, and —N(H)—S(O)$_2$—R$^{23}$, provided that at least two of R$^{16}$, R$^{17}$, R$^{18}$ and R$^{19}$ are —H. In some embodiments, R$^{17}$ and R$^{19}$ are H, halogen or lower alkyl. All other variables are as defined herein.

In other embodiments of compounds of Formula Iia, R$^{16}$, R$^{17}$, R$^{18}$ and R$^{19}$ are each independently selected from H, halogen, lower alkyl, lower alkoxy, halo substituted lower alkyl, —OR$^{20}$, or alkoxy substituted lower alkyl, provided that at least two of R$^{16}$, R$^{17}$, R$^{18}$ and R$^{19}$ are —H. All other variables are as defined herein.

In some embodiments of compounds of Formula Iia, R$^{16}$, R$^{17}$, and R$^{18}$ are H and R$^{19}$ is —F, —Cl, —Br, lower alkyl, fluoro substituted lower alkyl, methoxy substituted lower alkyl,
cycloalkylamino, —CN, —O—R$^{20}$, —S(O)$_2$—R$^{21}$, —N(H)—R$^{22}$, —N(R$^{22}$)$_2$, or —N(H)—S(O)$_2$—R$^{23}$. In some embodiments R$^{16}$, R$^{17}$, and R$^{18}$ are H and R$^{19}$ is —F, —Cl, lower alkyl, fluoro substituted lower alkyl, cycloalkylamino, —O—R$^{20}$, —N(H)—R$^{22}$, or —N(R$^{22}$)$_2$. In some embodiments R$^{16}$, R$^{17}$, and R$^{18}$ are H and R$^{19}$ is fluoro substituted lower alkyl or —O—R$^{20}$. In some embodiments R$^{16}$, R$^{17}$, and R$^{18}$ are H and R$^{19}$ is —CF$_3$ or —O—CH$_3$. All other variables are as defined herein.

In some embodiments of compounds of Formula Iia, R$^{16}$, R$^{17}$, and R$^{19}$ are H and R$^{18}$ is —F, —Cl, —Br, lower alkyl, fluoro substituted lower alkyl, methoxy substituted lower alkyl,
cycloalkylamino, —CN, —O—R$^{20}$, —S(O)$_2$—R$^{21}$, —N(H)—R$^{22}$, —N(R$^{22}$)$_2$, or —N(H)—S(O)$_2$—R$^{23}$. In some embodiments R$^{16}$, R$^{17}$, and R$^{19}$ are H and R$^{18}$ is —F, —Cl, lower alkyl, fluoro substituted lower alkyl, cycloalkylamino, —O—R$^{20}$, —N(H)—R$^{22}$, or —N(R$^{22}$)$_2$. In some embodiments R$^{16}$, R$^{17}$, and R$^{19}$ are H and R$^{18}$ is —F, —Cl, or —O—R$^{20}$. In some embodiments R$^{16}$, R$^{17}$, and R$^{19}$ are H and R$^{18}$ is —F, —Cl, or —O—CH$_3$. All other variables are as defined herein.

In some embodiments of compounds of Formula Iia, R$^{16}$, R$^{18}$, and R$^{19}$ are H and R$^7$ is —F, —Cl, —Br, lower alkyl, fluoro substituted lower alkyl, methoxy substituted lower alkyl,
cycloalkylamino, —CN, —O—R$^{20}$, —S(O)$_2$—R$^{21}$, —N(H)—R$^{22}$, —N(R$^{22}$)$_2$, or —N(H)—S(O)$_2$—R$^{23}$. In some embodiments R$^{16}$, R$^{18}$, and R$^{19}$ are H and R$^{17}$ is —F, —Cl, lower alkyl, fluoro substituted lower alkyl, cycloalkylamino, —O—R$^{20}$, —N(H)—R$^{22}$, or —N(R$^{22}$)$_2$. In some embodiments R$^{16}$, R$^{18}$, and R$^{19}$ are H and R$^{17}$ is —Cl, fluoro substituted lower alkyl, cycloalkylamino, or —O—R$^{20}$. In some embodiments R$^{16}$, R$^{18}$, and R$^{19}$ are H and R$^{17}$ is —Cl, —CF$_3$, —O—CH$_3$, or morpholin-4-yl. All other variables are as defined herein.

In some embodiments of compounds of Formula Iia, R$^{17}$, R$^{18}$, and R$^{19}$ are H and R$^{16}$ is —F, —Cl, —Br, lower alkyl, fluoro substituted lower alkyl, methoxy substituted lower alkyl,
cycloalkylamino, —CN, —O—R$^{20}$, —S(O)$_2$—R$^{21}$, —N(H)—R$^{22}$, —N(R$^{22}$)$_2$, or —N(H)—S(O)$_2$—R$^{23}$. In some embodiments R$^{17}$, R$^{18}$, and R$^{19}$ are H and R$^{16}$ is —F, —Cl, lower alkyl, fluoro substituted lower alkyl, cycloalkylamino, —O—R$^{20}$, —N(H)—R$^{22}$, or —N(R$^{22}$)$_2$. In some embodiments R$^{17}$, R$^{18}$, and R$^{19}$ are H and R$^{16}$ is —F, —CF$_3$, morpholin-4-yl, —O—CH$_3$, —O—CH$_2$CH$_3$, —O—CH(CH$_3$)$_2$, —O—CH$_2$CF$_3$, —O-cyclopentyl, —O-cyclohexyl, or —N(H)—CH$_3$. In some embodiments R$^{17}$, R$^{18}$, and R$^{19}$ are H and R$^{16}$ is —F, —CF$_3$, or —O—CH$_3$. All other variables are as defined herein.

In some embodiments of compounds of Formula Iia, R$^{16}$ and R$^{17}$ are H; and R$^{18}$ and R$^{19}$ are independently —F, —Cl, —Br, lower alkyl, fluoro substituted lower alkyl, methoxy substituted lower alkyl, cycloalkylamino, —CN, —O—R$^{20}$, —S(O)$_2$—R$^{21}$, —N(H)—R$^{22}$, —N(R$^{22}$)$_2$, or —N(H)—S(O)$_2$—R$^{23}$. In some embodiments R$^{16}$ and R$^{17}$ are H; and R$^{18}$ and R$^{19}$ are independently —F, —Cl, lower alkyl, fluoro substituted lower alkyl, cycloalkylamino, —O—R$^{20}$, —N(H)—R$^{22}$, or —N(R$^{22}$)$_2$. In some embodiments R$^{16}$ and R$^{17}$ are H; and R$^{18}$ and R$^{19}$ are independently —F, —Cl, CF$_3$, —O—CH$_3$, or —N(CH$_3$)$_2$. All other variables are as defined herein.

In some embodiments of compounds of Formula Iia, R$^{16}$ and R$^{18}$ are H; and R$^{17}$ and R$^{19}$ are independently —F, —Cl, —Br, lower alkyl, fluoro substituted lower alkyl, methoxy substituted lower alkyl, cycloalkylamino, —CN, —O—R$^{20}$, —S(O)$_2$—R$^{21}$, —N(H)—R$^{22}$, —N(R$^{22}$)$_2$, or —N(H)—S(O)$_2$—R$^{23}$. In some embodiments R$^{16}$ and R$^{18}$ are H; and R$^{17}$ and R$^{19}$ are independently —F, —Cl, lower alkyl, fluoro substituted lower alkyl, cycloalkylamino, —O—R$^{20}$, —N(H)—R$^{22}$, or —N(R$^{22}$)$_2$. In some embodiments R$^{16}$ and R$^{18}$ are H; and R$^{17}$ and R$^{19}$ are independently —F, —Cl, CF$_3$, —O—CH$_3$, or —N(CH$_3$)$_2$. All other variables are as defined herein.

In some embodiments of compounds of Formula IIa, $R^{16}$ and $R^{19}$ are H; and $R^7$ and $R^{18}$ are independently —F, —Cl, —Br, lower alkyl, fluoro substituted lower alkyl, methoxy substituted lower alkyl, cycloalkylamino, —CN, —O—$R^{20}$, —S(O)$_2$—$R^{21}$, —N(H)—$R^{22}$, —N($R^{22}$)$_2$, or —N(H)—S(O)$_2$—$R^{23}$. In some embodiments $R^{16}$ and $R^{19}$ are H; and $R^{17}$ and $R^{18}$ are independently —F, —Cl, lower alkyl, fluoro substituted lower alkyl, cycloalkylamino, —O—$R^{20}$, —N(H)—$R^{22}$, or —N($R^{22}$)$_2$. In some embodiments $R^{16}$ and $R^{19}$ are H; and $R^{17}$ and $R^{18}$ are independently —F, —Cl, CF$_3$, —O—CH$_3$, or —N(CH$_3$)$_2$. In some embodiments $R^{16}$ and $R^{19}$ are H; and $R^{17}$ and $R^{18}$ are independently —F or —O—CH$_3$. All other variables are as defined herein.

In some embodiments of compounds of Formula IIa, $R^{17}$ and $R^{18}$ are H; and $R^{16}$ and $R^{19}$ are independently —F, —Cl, —Br, lower alkyl, fluoro substituted lower alkyl, methoxy substituted lower alkyl, cycloalkylamino, —CN, —O—$R^{20}$, —S(O)$_2$—$R^{21}$, —N(H)—$R^{22}$, —N($R^{22}$)$_2$, or —N(H)—S(O)$_2$—$R^{23}$. In some embodiments $R^{17}$ and $R^{18}$ are H; and $R^{16}$ and $R^{19}$ are independently —F, —Cl, lower alkyl, fluoro substituted lower alkyl, cycloalkylamino, —O—$R^{20}$, —N(H)—$R^{22}$, or —N($R^{22}$)$_2$. In some embodiments $R^{17}$ and $R^{18}$ are H; and $R^{16}$ and $R^{19}$ are independently —F, —Cl, CF$_3$, —O—CH$_3$, or —N(CH$_3$)$_2$. All the other variables are as defined herein.

In some embodiments of compounds of Formula IIa, $R^{17}$ and $R^{19}$ are H; and $R^{16}$ and $R^{18}$ are independently —F, —Cl, —Br, lower alkyl, fluoro substituted lower alkyl, methoxy substituted lower alkyl, cycloalkylamino, —CN, —O—$R^{20}$, —S(O)$_2$—$R^{21}$, —N(H)—$R^{22}$, —N($R^{22}$)$_2$, or —N(H)—S(O)$_2$—$R^{23}$. In some embodiments $R^{17}$ and $R^{19}$ are H; and $R^{16}$ and $R^{18}$ are independently —F, —Cl, lower alkyl, fluoro substituted lower alkyl, cycloalkylamino, —O—$R^{20}$, —N(H)—$R^{22}$, or —N($R^{22}$)$_2$. In some embodiments $R^{17}$ and $R^{19}$ are H; and $R^{16}$ and $R^{18}$ are independently —F, —Cl, CF$_3$, —O—CH$_3$, or —N(CH$_3$)$_2$. In some embodiments $R^{17}$ and $R^{19}$ are H; and $R^{16}$ and $R^{18}$ are independently —F, —Cl, or —O—CH$_3$. All the other variables are as defined herein.

In some embodiments of compounds of Formula IIa, $R^{18}$ and $R^{19}$ are H; and $R^{16}$ and $R^{17}$ are independently —F, —Cl, —Br, lower alkyl, fluoro substituted lower alkyl, methoxy substituted lower alkyl, cycloalkylamino, —CN, —O—$R^{20}$, —S(O)$_2$—$R^{21}$, —N(H)—$R^{22}$, —N($R^{22}$)$_2$, or —N(H)—S(O)$_2$—$R^{23}$. In some embodiments $R^{18}$ and $R^{19}$ are H; and $R^{16}$ and $R^{17}$ are independently —F, —Cl, lower alkyl, fluoro substituted lower alkyl, cycloalkylamino, —O—$R^{20}$, —N(H)—$R^{22}$, or —N($R^{22}$)$_2$. In some embodiments $R^{18}$ and $R^{19}$ are H; and $R^{16}$ and $R^{17}$ are independently —F, —Cl, CF$_3$, —O—CH$_3$, or —N(CH$_3$)$_2$. In some embodiments $R^{18}$ and $R^{19}$ are H; and $R^{16}$ and $R^{17}$ are independently —CF$_3$, —O—CH$_3$, or —N(CH$_3$)$_2$. All the other variables are as defined herein.

In some embodiments, the disclosure provides a method for treating a disease or condition as described herein by administering to a subject a compound of Formulae II and II' and IIa, wherein the compound is selected from those set forth in Table 5 or any salt, prodrug, tautomer, or stereoisomer thereof.

TABLE 5

[6-Fluoro-5-(5-methyl-1H-pyrrolo[2,3-b]pyridin-3-ylmethyl)-pyridin-2-yl]-(5-fluoro-pyridin-3-ylmethyl)-amine (P-2027),
[6-Fluoro-5-(5-methyl-1H-pyrrolo[2,3-b]pyridin-3-ylmethyl)-pyridin-2-yl]-(6-methoxy-pyridin-3-ylmethyl)-amine (P-2029),
[6-Fluoro-5-(5-methyl-1H-pyrrolo[2,3-b]pyridin-3-ylmethyl)-pyridin-2-yl]-(6-trifluoromethyl-pyridin-3-ylmethyl)-amine (P-2031),
(5-Chloro-pyridin-2-ylmethyl)-[6-fluoro-5-(5-methyl-1H-pyrrolo[2,3-b]pyridin-3-ylmethyl)-pyridin-2-yl]-amine (P-2047),
(5-Fluoro-6-methoxy-pyridin-3-ylmethyl)-[6-fluoro-5-(5-methyl-1H-pyrrolo[2,3-b]pyridin-3-ylmethyl)-pyridin-2-yl]-amine (P-2048),
(5-Fluoro-2-methoxy-pyridin-3-ylmethyl)-[6-fluoro-5-(5-methyl-1H-pyrrolo[2,3-b]pyridin-3-ylmethyl)-pyridin-2-yl]-amine (P-2049),
(4-Chloro-benzyl)-[6-fluoro-5-(5-methyl-1H-pyrrolo[2,3-b]pyridin-3-ylmethyl)-pyridin-2-yl]-amine (P-2050),
(2-Chloro-benzyl)-[6-fluoro-5-(5-methyl-1H-pyrrolo[2,3-b]pyridin-3-ylmethyl)-pyridin-2-yl]-amine (P-2051),
[6-Fluoro-5-(5-methyl-1H-pyrrolo[2,3-b]pyridin-3-ylmethyl)-pyridin-2-yl]-(2-methoxy-pyridin-3-ylmethyl)-amine (P-2052),
[6-Fluoro-5-(5-methyl-1H-pyrrolo[2,3-b]pyridin-3-ylmethyl)-pyridin-2-yl]-[(S)-1-(4-fluoro-phenyl)-ethyl]-amine (P-2058),
[6-Fluoro-5-(5-methyl-1H-pyrrolo[2,3-b]pyridin-3-ylmethyl)-pyridin-2-yl]-(4-trifluoromethyl-pyridin-3-ylmethyl)-amine (P-2062),
[6-Fluoro-5-(5-methyl-1H-pyrrolo[2,3-b]pyridin-3-ylmethyl)-pyridin-2-yl]-(2-methoxy-pyridin-4-ylmethyl)-amine (P-2065),
[6-Fluoro-5-(5-methyl-1H-pyrrolo[2,3-b]pyridin-3-ylmethyl)-pyridin-2-yl]-(2-methyl-pyridin-4-ylmethyl)-amine (P-2067),
(5-Fluoro-2-methoxy-pyridin-4-ylmethyl)-[6-fluoro-5-(5-methyl-1H-pyrrolo[2,3-b]pyridin-3-ylmethyl)-pyridin-2-yl]-amine (P-2071),
(2,5-Dimethoxy-benzyl)-[6-fluoro-5-(5-methyl-1H-pyrrolo[2,3-b]pyridin-3-ylmethyl)-pyridin-2-yl]-amine (P-2086),
(3,5-Dimethoxy-benzyl)-[6-fluoro-5-(5-methyl-1H-pyrrolo[2,3-b]pyridin-3-ylmethyl)-pyridin-2-yl]-amine (P-2087),
(6-Chloro-pyridin-3-ylmethyl)-[6-fluoro-5-(5-methyl-1H-pyrrolo[2,3-b]pyridin-3-ylmethyl)-pyridin-2-yl]-amine (P-2088),
(3-Bromo-pyridin-4-ylmethyl)-[6-fluoro-5-(5-methyl-1H-pyrrolo[2,3-b]pyridin-3-ylmethyl)-pyridin-2-yl]-amine (P-2089),
[6-Fluoro-5-(5-methyl-1H-pyrrolo[2,3-b]pyridin-3-ylmethyl)-pyridin-2-yl]-(2-morpholin-4-yl-pyridin-3-ylmethyl)-amine (P-2090),
[6-Fluoro-5-(5-methyl-1H-pyrrolo[2,3-b]pyridin-3-ylmethyl)-pyridin-2-yl]-(6-morpholin-4-yl-pyridin-3-ylmethyl)-amine (P-2091),
(3-Chloro-pyridin-4-ylmethyl)-[6-fluoro-5-(5-methyl-1H-pyrrolo[2,3-b]pyridin-3-ylmethyl)-pyridin-2-yl]-amine (P-2092),

TABLE 5-continued

[6-Fluoro-5-(5-methyl-1H-pyrrolo[2,3-b]pyridin-3-ylmethyl)-pyridin-2-yl]-(5-fluoro-pyridin-2-ylmethyl)-amine (P-2093),
[6-Fluoro-5-(5-methyl-1H-pyrrolo[2,3-b]pyridin-3-ylmethyl)-pyridin-2-yl]-(3-fluoro-pyridin-4-ylmethyl)-amine (P-2094),
(5-{[6-Fluoro-5-(5-methyl-1H-pyrrolo[2,3-b]pyridin-3-ylmethyl)-pyridin-2-ylamino]-methyl}-pyrimidin-2-yl)-methyl-amine (P-2095),
[6-Fluoro-5-(5-methyl-1H-pyrrolo[2,3-b]pyridin-3-ylmethyl)-pyridin-2-yl]-[2-(2,2,2-trifluoro-ethoxy)-pyridin-3-ylmethyl]-amine (P-2096),
(2,6-Dimethoxy-pyridin-3-ylmethyl)-[6-fluoro-5-(5-methyl-1H-pyrrolo[2,3-b]pyridin-3-ylmethyl)-pyridin-2-yl]-amine (P-2097),
(5-Fluoro-2-methanesulfonyl-benzyl)-[6-fluoro-5-(5-methyl-1H-pyrrolo[2,3-b]pyridin-3-ylmethyl)-pyridin-2-yl]-amine (P-2098),
(5-Chloro-pyridin-3-ylmethyl)-[6-fluoro-5-(5-methyl-1H-pyrrolo[2,3-b]pyridin-3-ylmethyl)-pyridin-2-yl]-amine (P-2099),
(5-Bromo-pyridin-2-ylmethyl)-[6-fluoro-5-(5-methyl-1H-pyrrolo[2,3-b]pyridin-3-ylmethyl)-pyridin-2-yl]-amine (P-2100),
[6-Fluoro-5-(5-methyl-1H-pyrrolo[2,3-b]pyridin-3-ylmethyl)-pyridin-2-yl]-(3-methyl-pyridin-4-ylmethyl)-amine (P-2101),
(3-Chloro-5-fluoro-benzyl)-[6-fluoro-5-(5-methyl-1H-pyrrolo[2,3-b]pyridin-3-ylmethyl)-pyridin-2-yl]-amine (P-2102),
[6-Fluoro-5-(5-methyl-1H-pyrrolo[2,3-b]pyridin-3-ylmethyl)-pyridin-2-yl]-(2-fluoro-pyridin-3-ylmethyl)-amine (P-2103),
(3,5-Dimethyl-benzyl)-[6-fluoro-5-(5-methyl-1H-pyrrolo[2,3-b]pyridin-3-ylmethyl)-pyridin-2-yl]-amine (P-2104),
[6-Fluoro-5-(5-methyl-1H-pyrrolo[2,3-b]pyridin-3-ylmethyl)-pyridin-2-yl]-(5-methoxy-pyridin-3-ylmethyl)-amine (P-2105),
[6-Fluoro-5-(5-methyl-1H-pyrrolo[2,3-b]pyridin-3-ylmethyl)-pyridin-2-yl]-(2-methyl-pyrimidin-5-ylmethyl)-amine (P-2106),
[6-Fluoro-5-(5-methyl-1H-pyrrolo[2,3-b]pyridin-3-ylmethyl)-pyridin-2-yl]-(2-methylamino-pyridin-3-ylmethyl)-amine (P-2107),
(3,5-Bis-trifluoromethyl-benzyl)-[6-fluoro-5-(5-methyl-1H-pyrrolo[2,3-b]pyridin-3-ylmethyl)-pyridin-2-yl]-amine (P-2108),
[6-Fluoro-5-(5-methyl-1H-pyrrolo[2,3-b]pyridin-3-ylmethyl)-pyridin-2-yl]-(4-methoxy-pyridin-3-ylmethyl)-amine (P-2109),
(2-Ethoxy-pyridin-3-ylmethyl)-[6-fluoro-5-(5-methyl-1H-pyrrolo[2,3-b]pyridin-3-ylmethyl)-pyridin-2-yl]-amine (P-2110),
[6-Fluoro-5-(5-methyl-1H-pyrrolo[2,3-b]pyridin-3-ylmethyl)-pyridin-2-yl]-(2-isopropoxy-pyridin-3-ylmethyl)-amine (P-2111),
[6-Fluoro-5-(5-methyl-1H-pyrrolo[2,3-b]pyridin-3-ylmethyl)-pyridin-2-yl]-(4-methyl-pyridin-2-ylmethyl)-amine (P-2112),
(2-Cyclopentyloxy-pyridin-3-ylmethyl)-[6-fluoro-5-(5-methyl-1H-pyrrolo[2,3-b]pyridin-3-ylmethyl)-pyridin-2-yl]-amine (P-2113),
(2-Cyclohexyloxy-pyridin-3-ylmethyl)-[6-fluoro-5-(5-methyl-1H-pyrrolo[2,3-b]pyridin-3-ylmethyl)-pyridin-2-yl]-amine (P-2114),
[6-Fluoro-5-(5-methyl-1H-pyrrolo[2,3-b]pyridin-3-ylmethyl)-pyridin-2-yl]-(2-trifluoromethyl-pyridin-3-ylmethyl)-amine (P-2115),
(2-Chloro-5-fluoro-pyridin-4-ylmethyl)-[6-fluoro-5-(5-methyl-1H-pyrrolo[2,3-b]pyridin-3-ylmethyl)-pyridin-2-yl]-amine (P-2116),
4-{[6-Fluoro-5-(5-methyl-1H-pyrrolo[2,3-b]pyridin-3-ylmethyl)-pyridin-2-ylamino]-methyl}-pyridine-2-carbonitrile (P-2117),
[6-Fluoro-5-(5-methyl-1H-pyrrolo[2,3-b]pyridin-3-ylmethyl)-pyridin-2-yl]-(2-fluoro-pyridin-4-ylmethyl)-amine (P-2118),
[6-Fluoro-5-(5-methyl-1H-pyrrolo[2,3-b]pyridin-3-ylmethyl)-pyridin-2-yl]-(2-trifluoromethyl-pyridin-4-ylmethyl)-amine (P-2119),
(2-Chloro-pyridin-4-ylmethyl)-[6-fluoro-5-(5-methyl-1H-pyrrolo[2,3-b]pyridin-3-ylmethyl)-pyridin-2-yl]-amine (P-2120),
[6-Fluoro-5-(5-methyl-1H-pyrrolo[2,3-b]pyridin-3-ylmethyl)-pyridin-2-yl]-(2-morpholin-4-yl-pyridin-4-ylmethyl)-amine (P-2121),
[6-Fluoro-5-(5-methyl-1H-pyrrolo[2,3-b]pyridin-3-ylmethyl)-pyridin-2-yl]-(2-pyrrolidin-1-yl-pyridin-4-ylmethyl)-amine (P-2122),
(5-Chloro-2-fluoro-pyridin-3-ylmethyl)-[6-fluoro-5-(5-methyl-1H-pyrrolo[2,3-b]pyridin-3-ylmethyl)-pyridin-2-yl]-amine (P-2123),
(4-Chloro-2-methanesulfonyl-benzyl)-[6-fluoro-5-(5-methyl-1H-pyrrolo[2,3-b]pyridin-3-ylmethyl)-pyridin-2-yl]-amine (P-2124),
(2-Dimethylamino-benzyl)-[6-fluoro-5-(5-methyl-1H-pyrrolo[2,3-b]pyridin-3-ylmethyl)-pyridin-2-yl]-amine (P-2125),
(2-Ethyl-pyrimidin-5-ylmethyl)-[6-fluoro-5-(5-methyl-1H-pyrrolo[2,3-b]pyridin-3-ylmethyl)-pyridin-2-yl]-amine (P-2126),
[6-Fluoro-5-(5-methyl-1H-pyrrolo[2,3-b]pyridin-3-ylmethyl)-pyridin-2-yl]-(2-propyl-pyrimidin-5-ylmethyl)-amine (P-2127),
[6-Fluoro-5-(5-methyl-1H-pyrrolo[2,3-b]pyridin-3-ylmethyl)-pyridin-2-yl]-(2-isopropyl-pyrimidin-5-ylmethyl)-amine (P-2128),
[6-Fluoro-5-(5-methyl-1H-pyrrolo[2,3-b]pyridin-3-ylmethyl)-pyridin-2-yl]-[2-(2-methoxy-ethyl)-pyrimidin-5-ylmethyl]-amine (P-2129),
(2-Butyl-pyrimidin-5-ylmethyl)-[6-fluoro-5-(5-methyl-1H-pyrrolo[2,3-b]pyridin-3-ylmethyl)-pyridin-2-yl]-amine (P-2130),
[6-Fluoro-5-(5-methyl-1H-pyrrolo[2,3-b]pyridin-3-ylmethyl)-pyridin-2-yl]-(5-methyl-pyridin-2-ylmethyl)-amine (P-2131),
(3-Fluoro-5-methyl-benzyl)-[6-fluoro-5-(5-methyl-1H-pyrrolo[2,3-b]pyridin-3-ylmethyl)-pyridin-2-yl]-amine (P-2132),

TABLE 5-continued

[6-Fluoro-5-(5-methyl-1H-pyrrolo[2,3-b]pyridin-3-ylmethyl)-pyridin-2-yl]-(3-methoxy-5-trifluoromethyl-benzyl)-amine (P-2133),
(3-Fluoro-5-methoxy-benzyl)-[6-fluoro-5-(5-methyl-1H-pyrrolo[2,3-b]pyridin-3-ylmethyl)-pyridin-2-yl]-amine (P-2134),
[6-Fluoro-5-(5-methyl-1H-pyrrolo[2,3-b]pyridin-3-ylmethyl)-pyridin-2-yl]-(3,4,5-trimethoxy-benzyl)-amine (P-2150),
[6-Fluoro-5-(5-methyl-1H-pyrrolo[2,3-b]pyridin-3-ylmethyl)-pyridin-2-yl]-(5-pyrrolidin-1-yl-pyridin-2-ylmethyl)-amine (P-2151),
5-Fluoro-3-{[6-fluoro-5-(5-methyl-1H-pyrrolo[2,3-b]pyridin-3-ylmethyl)-pyridin-2-ylamino]-methyl}-1-methyl-1H-pyridin-2-one (P-2156),
[5-(5-Chloro-1H-pyrrolo[2,3-b]pyridin-3-ylmethyl)-6-fluoro-pyridin-2-yl]-(5-fluoro-6-methoxy-pyridin-3-ylmethyl)-amine (P-2165),
[6-Fluoro-5-(5-methyl-1H-pyrrolo[2,3-b]pyridin-3-ylmethyl)-pyridin-2-yl]-(2-methoxy-6-trifluoromethyl-pyridin-3-ylmethyl)-amine (P-2166),
[6-Fluoro-5-(5-methyl-1H-pyrrolo[2,3-b]pyridin-3-ylmethyl)-pyridin-2-yl]-(2-dimethylamino-6-trifluoromethyl-pyridin-3-ylmethyl)-amine (P-2167),
[6-Fluoro-5-(5-methyl-1H-pyrrolo[2,3-b]pyridin-3-ylmethyl)-pyridin-2-yl]-(6-methoxy-4-trifluoromethyl-pyridin-3-ylmethyl)-amine (P-2186),
Ethanesulfonic acid (2-{[6-fluoro-5-(5-methyl-1H-pyrrolo[2,3-b]pyridin-3-ylmethyl)-pyridin-2-ylamino]-methyl}-phenyl)-amide (P-2198),
Ethanesulfonic acid (4-fluoro-3-{[6-fluoro-5-(5-methyl-1H-pyrrolo[2,3-b]pyridin-3-ylmethyl)-pyridin-2-ylamino]-methyl}-phenyl)-amide (P-2199),
Ethanesulfonic acid (3-fluoro-5-{[6-fluoro-5-(5-methyl-1H-pyrrolo[2,3-b]pyridin-3-ylmethyl)-pyridin-2-ylamino]-methyl}-phenyl)-amide (P-2202),
5-[(5-bromo-1H-pyrrolo[2,3-b]pyridin-3-yl)methyl]-6-fluoro-N-[(5-fluoro-6-methoxy-3-pyridyl)methyl]pyridin-2-amine (P-2203),
3-[[2-fluoro-6-[(5-fluoro-6-methoxy-3-pyridyl)methylamino]-3-pyridyl]methyl]-1H-pyrrolo[2,3-b]pyridine-5-carbonitrile (P-2204),
6-chloro-N-[(5-fluoro-2-methoxy-3-pyridyl)methyl]-5-[(5-methyl-1H-pyrrolo[2,3-b]pyridin-3-yl)methyl]pyridin-2-amine (P-2205),
6-fluoro-N-[(5-fluoro-6-methoxy-3-pyridyl)methyl]-5-[[5-(trifluoromethyl)-1H-pyrrolo[2,3-b]pyridin-3-yl]methyl]pyridin-2-amine (P-2206),
5-[(5-chloro-1H-pyrrolo[2,3-b]pyridin-3-yl)methyl]-6-fluoro-N-[(5-fluoro-6-methoxy-3-pyridyl)methyl]pyridin-2-amine (P-2207).

In some embodiments, the disclosure provides a method for treating a disease or condition as described herein by administering to a subject a compound of Formula III':

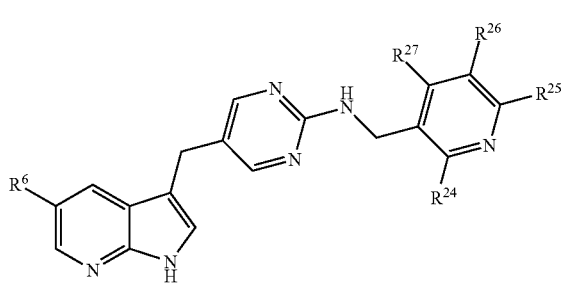

Formula III' or a salt, a prodrug, a tautomer or a stereoisomer thereof, wherein:
$R^{24}$, $R^{25}$, $R^{26}$ and $R^{27}$ are each independently selected from the group consisting of —H, halogen, lower alkyl, lower alkoxy, halo substituted lower alkyl, lower alkoxy, alkoxy substituted lower alkyl, cycloalkylamino, —CN, —O—$R^{28}$, —S(O)$_2$—$R^{29}$, —S(O)$_2$—N(H)—$R^{30}$, —N(H)—$R^{30}$, —N($R^{30}$)$_2$, and —N(H)—S(O)$_2$—$R^{31}$, provided that at least two of $R^{24}$, $R^{25}$, $R^{26}$ and $R^{27}$ are —H;
$R^{28}$ is lower alkyl, fluoro substituted lower alkyl, methoxy substituted lower alkyl, or cycloalkyl;
$R^{29}$ is lower alkyl;
$R^{30}$ is lower alkyl; and
$R^{31}$ is lower alkyl.
In some embodiments of compounds of Formula III', $R^6$ is selected from the group consisting of halogen, lower alkyl, lower alkoxy, fluoro substituted lower alkyl, lower alkenyl, lower alkynyl, cycloalkyl, phenyl, pyrazolyl, —CN, —O—$R^{13}$, —C(O)—N(H)—$R^{14}$, —C(O)—O—$R^{14}$, —S(O)$_2$—$R^{15}$, —S(O)$_2$—N(H)—$R^{14}$, —N(H)—C(O)—$R^{15}$, and —N(H)—S(O)$_2$—$R^{15}$, wherein pyrazolyl is optionally substituted with lower alkyl or heterocycloalkyl. In other embodiments of compounds of Formula III', $R^6$ is F, Cl, Br, lower alkyl, fluoro substituted lower alkyl, lower alkenyl, —CN, —C(O)—N(H)—$R^{14}$, —N(H)—C(O)—$R^{15}$, —C(O)—O—$R^4$, —S(O)$_2$—$R^{15}$, —S(O)$_2$—N(H)—$R^{14}$ or —N(H)—S(O)$_2$—$R^5$. In some embodiments, $R^6$ is methyl, ethyl, propyl, butyl, pentyl or hexyl. All other variables are as defined herein.

In some embodiments, the disclosure provides a method for treating a disease or condition as described herein by administering to a subject a compound of Formula III:

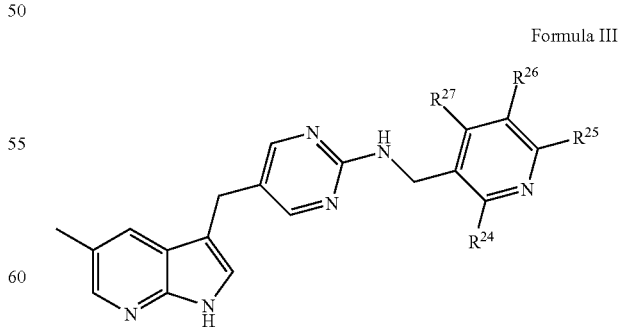

Formula III or a salt, a prodrug, a tautomer or a stereoisomer thereof, wherein:
$R^{24}$, $R^{25}$, $R^{26}$ and $R^{27}$ are independently selected from the group consisting of —H, —F, —Cl, —Br, lower alkyl, fluoro substituted lower alkyl, methoxy substituted lower alkyl, cycloalkylamino, —CN, —O—R$^{28}$, —S(O)$_2$—R$^{29}$, —S(O)$_2$—N(H)—R$^{30}$, —N(H)—R$^{30}$, —N(R$^{30}$)$_2$, and —N(H)—S(O)$_2$—R$^{31}$, provided that at least two of R$^{24}$, R$^{25}$, R$^{26}$ and R$^{27}$ are —H;

R$^{28}$ is lower alkyl, fluoro substituted lower alkyl, methoxy substituted lower alkyl, or cycloalkyl;

R$^{29}$ is lower alkyl;

R$^{30}$ is lower alkyl; and

R$^{31}$ is lower alkyl.

In some embodiments of compounds of Formulae III and III', R$^{24}$, R$^{25}$, R$^{26}$ and R$^{27}$ are each independently selected from the group consisting of —H, —F, —Cl, —Br, lower alkyl, fluoro substituted lower alkyl, lower alkoxy, methoxy substituted lower alkyl,
cycloalkylamino, —CN, —O—R$^{20}$, —S(O)$_2$—R$^{21}$, —S(O)$_2$ —N(H)—R$^{22}$, —N(H)—R$^{22}$, —N(R$^{22}$)$_2$, and —N(H)—S(O)$_2$—R$^{23}$, provided that at least two of R$^{24}$, R$^{25}$, R$^{26}$ and R$^{27}$ are —H. In some embodiments, R$^{24}$, R$^{25}$, R$^{26}$ and R$^{27}$ are each independently selected from H, halogen, lower alkyl, lower alkoxy, halo substituted lower alkyl, —OR$^{20}$, or alkoxy substituted lower alkyl. All other variables are as defined herein.

In some embodiments of compounds of Formulae III and III', R$^{24}$, R$^{25}$, and R$^{26}$ are H and R$^{27}$ is —F, —Cl, —Br, lower alkyl, fluoro substituted lower alkyl, methoxy substituted lower alkyl,
cycloalkylamino, —CN, —O—R$^{28}$, —S(O)$_2$—R$^{29}$, —N(H)—R$^{30}$, —N(R$^{30}$)$_2$, or —N(H)—S(O)$_2$—R$^{31}$. In some embodiments R$^{24}$, R$^{25}$, and R$^{26}$ are H and R$^{27}$ is —F, —Cl, lower alkyl, fluoro substituted lower alkyl, cycloalkylamino, —O—R$^{28}$, —N(H)—R$^{30}$, or —N(R$^{30}$)$_2$. In some embodiments R$^{24}$, R$^{25}$, and R$^{26}$ are H and R$^{27}$ is fluoro substituted lower alkyl or —O—R$^{28}$. In some embodiments R$^{24}$, R$^{25}$, and R$^{26}$ are H and R$^{27}$ is —CF$_3$ or —O—CH$_3$. All other variables are as defined herein.

In some embodiments of compounds of Formulae III and III', R$^{24}$, R$^{25}$, and R$^{27}$ are H and R$^{26}$ is —F, —Cl, —Br, lower alkyl, fluoro substituted lower alkyl, methoxy substituted lower alkyl,
cycloalkylamino, —CN, —O—R$^{28}$, —S(O)$_2$—R$^{29}$, —N(H)—R$^{30}$, —N(R$^{30}$)$_2$, or —N(H)—S(O)$_2$—R$^{31}$. In some embodiments R$^{24}$, R$^{25}$, and R$^{27}$ are H and R$^{26}$ is —F, —Cl, lower alkyl, fluoro substituted lower alkyl, cycloalkylamino, —O—R$^{28}$, —N(H)—R$^{30}$, or —N(R$^{30}$)$_2$. In some embodiments R$^{24}$, R$^{25}$, and R$^{27}$ are H and R$^{26}$ is —F, —Cl, or —O—R$^{28}$. In some embodiments R$^{24}$, R$^{25}$, and R$^{27}$ are H and R$^{26}$ is —F, —Cl, or —O—CH$_3$. All other variables are as defined herein.

In some embodiments of compounds of Formulae III and III', R$^{24}$, R$^{26}$, and R$^{27}$ are H and R$^{25}$ is —F, —Cl, —Br, lower alkyl, fluoro substituted lower alkyl, methoxy substituted lower alkyl,
cycloalkylamino, —CN, —O—R$^{28}$, —S(O)$_2$—R$^{29}$, —N(H)—R$^{30}$, —N(R$^{30}$)$_2$, or —N(H)—S(O)$_2$—R$^{31}$. In some embodiments R$^{24}$, R$^{26}$, and R$^{27}$ are H and R$^{25}$ is —F, —Cl, lower alkyl, fluoro substituted lower alkyl, cycloalkylamino, —O—R$^{28}$, —N(H)—R$^{30}$, or —N(R$^{30}$)$_2$. In some embodiments R$^{24}$, R$^{26}$, and R$^{27}$ are H and R$^{25}$ is —Cl, fluoro substituted lower alkyl, cycloalkylamino, or —O—R$^{28}$. In some embodiments R$^{24}$, R$^{26}$, and R$^{27}$ are H and R$^{25}$ is —Cl, —CF$_3$, —O—CH$_3$, or 4-methyl-piperazin-1-yl. All other variables are as defined herein.

In some embodiments of compounds of Formulae III and III', R$^{25}$, R$^{26}$, and R$^{27}$ are H and R$^{24}$ is —F, —Cl, —Br, lower alkyl, fluoro substituted lower alkyl, methoxy substituted lower alkyl,
cycloalkylamino, —CN, —O—R$^{28}$, —S(O)$_2$—R$^{29}$, —N(H)—R$^{30}$, —N(R$^{30}$)$_2$, or —N(H)—S(O)$_2$—R$^{31}$. In some embodiments R$^{25}$, R$^{26}$, and R$^{27}$ are H and R$^{24}$ is —F, —Cl, lower alkyl, fluoro substituted lower alkyl, cycloalkylamino, —O—R$^{28}$, —N(H)—R$^{30}$, or —N(R$^{30}$)$_2$. In some embodiments R$^{25}$, R$^{26}$, and R$^{27}$ are H and R$^{24}$ is —F, —CF$_3$, morpholin-4-yl, —O—CH$_3$, —O—CH$_2$CH$_3$, —O—CH(CH$_3$)$_2$, —O—CH$_2$CF$_3$, —O-cyclopentyl, —O-cyclohexyl, or —N(H)—CH$_3$. In some embodiments R$^{25}$, R$^{26}$, and R$^{27}$ are H and R$^{24}$ is —F, —CF$_3$, —O—CH$_3$, —O—CH$_2$CH$_3$, or —O-cyclopentyl. All other variables are as defined herein.

In some embodiments of compounds of Formulae III and III', R$^{24}$ and R$^{25}$ are H; and R$^{26}$ and R$^{27}$ are independently —F, —Cl, —Br, lower alkyl, fluoro substituted lower alkyl, methoxy substituted lower alkyl, cycloalkylamino, —CN, —O—R$^{28}$, —S(O)$_2$—R$^{29}$, —N(H)—R$^{30}$, —N(R$^{30}$)$_2$, or —N(H)—S(O)$_2$—R$^{31}$. In some embodiments R$^{24}$ and R$^{25}$ are H; and R$^{26}$ and R$^{27}$ are independently —F, —Cl, lower alkyl, fluoro substituted lower alkyl, cycloalkylamino, —O—R$^{28}$, —N(H)—R$^{30}$, or —N(R$^{30}$)$_2$. In some embodiments R$^{24}$ and R$^{25}$ are H; and R$^{26}$ and R$^{27}$ are independently —F, —Cl, CF$_3$, —O—CH$_3$, or —N(CH$_3$)$_2$. All other variables are as defined herein.

In some embodiments of compounds of Formulae III and III', R$^{24}$ and R$^{26}$ are H; and R$^{25}$ and R$^{27}$ are independently —F, —Cl, —Br, lower alkyl, fluoro substituted lower alkyl, methoxy substituted lower alkyl, cycloalkylamino, —CN, —O—R$^{28}$, —S(O)$_2$—R$^{29}$, —N(H)—R$^{30}$, —N(R$^{30}$)$_2$, or —N(H)—S(O)$_2$—R$^{31}$. In some embodiments R$^{24}$ and R$^{26}$ are H; and R$^{25}$ and R$^{27}$ are independently —F, —Cl, lower alkyl, fluoro substituted lower alkyl, cycloalkylamino, —O—R$^{28}$, —N(H)—R$^{30}$, or —N(R$^{30}$)$_2$. In some embodiments R$^{24}$ and R$^{26}$ are H; and R$^{25}$ and R$^{27}$ are independently —F, —Cl, CF$_3$, —O—CH$_3$, or —N(CH$_3$)$_2$. In some embodiments R$^{24}$ and R$^{26}$ are H; and R$^{25}$ and R$^{27}$ are independently —CF$_3$ or —O—CH$_3$. All other variables are as defined herein.

In some embodiments of compounds of Formulae III and III', R$^{24}$ and R$^{27}$ are H; and R$^{25}$ and R$^{26}$ are independently —F, —Cl, —Br, lower alkyl, fluoro substituted lower alkyl, methoxy substituted lower alkyl, cycloalkylamino, —CN, —O—R$^{28}$, —S(O)$_2$—R$^{29}$, —N(H)—R$^{30}$, —N(R$^{30}$)$_2$, or —N(H)—S(O)$_2$—R$^{31}$. In some embodiments R$^{24}$ and R$^{27}$ are H; and R$^{25}$ and R$^{26}$ are independently —F, —Cl, lower alkyl, fluoro substituted lower alkyl, cycloalkylamino, —O—R$^{28}$, —N(H)—R$^{30}$, or —N(R$^{30}$)$_2$. In some embodiments R$^{24}$ and R$^{27}$ are H; and R$^{25}$ and R$^{26}$ are independently —F, —Cl, CF$_3$, —O—CH$_3$, or —N(CH$_3$)$_2$. In some embodiments R$^{24}$ and R$^{27}$ are H; and R$^{25}$ and R$^{26}$ are independently —F or —O—CH$_3$. All other variables are as defined herein.

In some embodiments of compounds of Formulae III and III', R$^{25}$ and R$^{26}$ are H; and R$^{24}$ and R$^{27}$ are independently —F, —Cl, —Br, lower alkyl, fluoro substituted lower alkyl, methoxy substituted lower alkyl, cycloalkylamino, —CN, —O—R$^{28}$, —S(O)$_2$—R$^{29}$, —N(H)—R$^{30}$, —N(R$^{30}$)$_2$, or —N(H)—S(O)$_2$—R$^{31}$. In some embodiments R$^{25}$ and R$^{26}$ are H; and R$^{24}$ and R$^{27}$ are independently —F, —Cl, lower alkyl, fluoro substituted lower alkyl, cycloalkylamino, —O—R$^{28}$, —N(H)—R$^{30}$, or —N(R$^{30}$)$_2$. In some embodiments R$^{25}$ and R$^{26}$ are H; and R$^{24}$ and R$^{27}$ are independently —F, —Cl, CF$_3$, —O—CH$_3$, or —N(CH$_3$)$_2$. All other variables are as defined herein.

In some embodiments of compounds of Formulae III and III', R$^{25}$ and R$^{27}$ are H; and R$^{24}$ and R$^{26}$ are independently —F, —Cl, —Br, lower alkyl, fluoro substituted lower alkyl, methoxy substituted lower alkyl, cycloalkylamino, —CN, —O—$R^{28}$, —S(O)$_2$—$R^{29}$, —N(H)—$R^{30}$, —N($R^{30}$)$_2$, or —N(H)—S(O)$_2$—$R^{31}$. In some embodiments $R^{25}$ and $R^{27}$ are H; and $R^{24}$ and $R^{26}$ are independently —F, —Cl, lower alkyl, fluoro substituted lower alkyl, cycloalkylamino, —O—$R^{28}$, —N(H)—$R^{30}$, or —N($R^{30}$)$_2$. In some embodiments $R^{25}$ and $R^{27}$ are H; and $R^{24}$ and $R^{26}$ are independently —F, —Cl, $CF_3$, —O—$CH_3$, or —N($CH_3$)$_2$. In some embodiments $R^{25}$ and $R^{27}$ are H; and $R^{24}$ and $R^{26}$ are independently —F or —O—$CH_3$. All other variables are as defined herein.

In some embodiments of compounds of Formulae III and III', $R^{26}$ and $R^{27}$ are H; and $R^{24}$ and $R^{25}$ are independently —F, —Cl, —Br, lower alkyl, fluoro substituted lower alkyl, methoxy substituted lower alkyl, cycloalkylamino, —CN, —O—$R^{28}$, —S(O)$_2$—$R^{29}$, —N(H)—$R^{30}$, —N($R^{30}$)$_2$, or —N(H)—S(O)$_2$—$R^{31}$. In some embodiments $R^{26}$ and $R^{27}$ are H; and $R^{24}$ and $R^{25}$ are independently —F, —Cl, lower alkyl, fluoro substituted lower alkyl, cycloalkylamino, —O—$R^{28}$, —N(H)—$R^{30}$, or —N($R^{30}$)$_2$. In some embodiments $R^{26}$ and $R^{27}$ are H; and $R^{24}$ and $R^{25}$ are independently —F, —Cl, $CF_3$, —O—$CH_3$, or —N($CH_3$)$_2$. In some embodiments $R^{26}$ and $R^{27}$ are H; and $R^{24}$ and $R^{25}$ are independently —$CF_3$, —O—$CH_3$, or —N($CH_3$)$_2$. All other variables are as defined herein.

In some embodiments, the disclosure provides a method for treating a disease or condition as described herein by administering to a subject a compound of Formulae III and III', wherein the compound is selected from the group consisting of:
(5-Fluoro-pyridin-3-ylmethyl)-[5-(5-methyl-1H-pyrrolo[2,3-b]pyridin-3-ylmethyl)-pyrimidin-2-yl]-amine (P-1569),
[5-(5-Methyl-1H-pyrrolo[2,3-b]pyridin-3-ylmethyl)-pyrimidin-2-yl]-(4-trifluoromethyl-pyridin-3-ylmethyl)-amine (P-1570),
(6-Methoxy-pyridin-3-ylmethyl)-[5-(5-methyl-1H-pyrrolo[2,3-b]pyridin-3-ylmethyl)-pyrimidin-2-yl]-amine (P-2057),
(5-Fluoro-2-methoxy-pyridin-3-ylmethyl)-[5-(5-methyl-1H-pyrrolo[2,3-b]pyridin-3-ylmethyl)-pyrimidin-2-yl]-amine (P-2061),
(2-Methoxy-pyridin-4-ylmethyl)-[5-(5-methyl-1H-pyrrolo[2,3-b]pyridin-3-ylmethyl)-pyrimidin-2-yl]-amine (P-2069),
(5-Fluoro-2-methoxy-pyridin-4-ylmethyl)-[5-(5-methyl-1H-pyrrolo[2,3-b]pyridin-3-ylmethyl)-pyrimidin-2-yl]-amine (P-2072),
(5-Fluoro-6-methoxy-pyridin-3-ylmethyl)-[5-(5-methyl-1H-pyrrolo[2,3-b]pyridin-3-ylmethyl)-pyrimidin-2-yl]-amine (P-2073),
[5-(5-Methyl-1H-pyrrolo[2,3-b]pyridin-3-ylmethyl)-pyrimidin-2-yl]-pyridin-2-ylmethyl-amine (P-2076),
[5-(5-Methyl-1H-pyrrolo[2,3-b]pyridin-3-ylmethyl)-pyrimidin-2-yl]-pyridin-3-ylmethyl-amine (P-2077),
(6-Chloro-pyridin-3-ylmethyl)-[5-(5-methyl-1H-pyrrolo[2,3-b]pyridin-3-ylmethyl)-pyrimidin-2-yl]-amine (P-2078),
(6-Methyl-pyridin-2-ylmethyl)-[5-(5-methyl-1H-pyrrolo[2,3-b]pyridin-3-ylmethyl)-pyrimidin-2-yl]-amine (P-2079),
[5-(5-Methyl-1H-pyrrolo[2,3-b]pyridin-3-ylmethyl)-pyrimidin-2-yl]-(6-trifluoromethyl-pyridin-3-ylmethyl)-amine (P-2080),
[5-(5-Methyl-1H-pyrrolo[2,3-b]pyridin-3-ylmethyl)-pyrimidin-2-yl]-(6-morpholin-4-yl-pyridin-2-ylmethyl)-amine (P-2081),
[5-(5-Methyl-1H-pyrrolo[2,3-b]pyridin-3-ylmethyl)-pyrimidin-2-yl]-(6-pyrrolidin-1-yl-pyridin-2-ylmethyl)-amine (P-2082),
(5-Ethyl-pyridin-2-ylmethyl)-[5-(5-methyl-1H-pyrrolo[2,3-b]pyridin-3-ylmethyl)-pyrimidin-2-yl]-amine (P-2083),
(3-Methyl-pyridin-4-ylmethyl)-[5-(5-methyl-1H-pyrrolo[2,3-b]pyridin-3-ylmethyl)-pyrimidin-2-yl]-amine (P-2084),
[5-(5-Methyl-1H-pyrrolo[2,3-b]pyridin-3-ylmethyl)-pyrimidin-2-yl]-(2-morpholin-4-yl-pyridin-4-ylmethyl)-amine (P-2085),
[5-(5-Methyl-1H-pyrrolo[2,3-b]pyridin-3-ylmethyl)-pyrimidin-2-yl]-pyridin-4-ylmethyl-amine (P-2138),
(2-Methoxy-pyridin-3-ylmethyl)-[5-(5-methyl-1H-pyrrolo[2,3-b]pyridin-3-ylmethyl)-pyrimidin-2-yl]-amine (P-2139),
[6-(4-Methyl-piperazin-1-yl)-pyridin-3-ylmethyl]-[5-(5-methyl-1H-pyrrolo[2,3-b]pyridin-3-ylmethyl)-pyrimidin-2-yl]-amine (P-2140),
(2-Methyl-pyridin-4-ylmethyl)-[5-(5-methyl-1H-pyrrolo[2,3-b]pyridin-3-ylmethyl)-pyrimidin-2-yl]-amine (P-2141),
(2-Ethoxy-pyridin-3-ylmethyl)-[5-(5-methyl-1H-pyrrolo[2,3-b]pyridin-3-ylmethyl)-pyrimidin-2-yl]-amine (P-2142),
(2-Cyclopentyloxy-pyridin-3-ylmethyl)-[5-(5-methyl-1H-pyrrolo[2,3-b]pyridin-3-ylmethyl)-pyrimidin-2-yl]-amine (P-2148),
(2-Cyclopentyloxy-pyridin-4-ylmethyl)-[5-(5-methyl-1H-pyrrolo[2,3-b]pyridin-3-ylmethyl)-pyrimidin-2-yl]-amine (P-2149), and
any salt, prodrug, tautomer, or stereoisomer thereof.

In some embodiments, the disclosure provides a method for treating a disease or condition as described herein by administering to a subject a compound selected from those set forth in Table 6.

TABLE 6

[5-(5-Chloro-1H-pyrrolo[2,3-b]pyridin-3-ylmethyl)-pyridin-2-yl]-(2,6-dimethoxy-pyridin-3-ylmethyl)-amine (P-1496),
[6-Chloro-5-(1H-pyrrolo[2,3-b]pyridin-3-ylmethyl)-pyridin-2-yl]-(5-fluoro-pyridin-3-ylmethyl)-amine (P-1507),
[6-Chloro-5-(1H-pyrrolo[2,3-b]pyridin-3-ylmethyl)-pyridin-2-yl]-(6-methoxy-pyridin-3-ylmethyl)-amine (P-1511),
[6-Chloro-5-(1H-pyrrolo[2,3-b]pyridin-3-ylmethyl)-pyridin-2-yl]-(2-methoxy-pyridin-3-ylmethyl)-amine (P-1512),
(5-Fluoro-pyridin-3-ylmethyl)-[5-(1H-pyrrolo[2,3-b]pyridin-3-ylmethyl)-pyrimidin-2-yl]-amine (P-1514),
(6-Methoxy-pyridin-3-ylmethyl)-[5-(1H-pyrrolo[2,3-b]pyridin-3-ylmethyl)-pyrimidin-2-yl]-amine (P-1517),
[5-(1H-Pyrrolo[2,3-b]pyridin-3-ylmethyl)-pyrimidin-2-yl]-(6-trifluoromethyl-pyridin-3-ylmethyl)-amine (P-1518),
(2-Methoxy-pyridin-3-ylmethyl)-[5-(1H-pyrrolo[2,3-b]pyridin-3-ylmethyl)-pyrimidin-2-yl]-amine (P-1519),
[4-Chloro-5-(1H-pyrrolo[2,3-b]pyridin-3-ylmethyl)-thiazol-2-yl]-(5-fluoro-pyridin-3-ylmethyl)-amine (P-1522),
[4-Chloro-5-(1H-pyrrolo[2,3-b]pyridin-3-ylmethyl)-thiazol-2-yl]-(6-methoxy-pyridin-3-ylmethyl)-amine (P-1526), TABLE 6-continued

[4-Chloro-5-(1H-pyrrolo[2,3-b]pyridin-3-ylmethyl)-thiazol-2-yl]-(2-methoxy-pyridin-3-ylmethyl)-amine (P-1527),
(5-Fluoro-pyridin-3-ylmethyl)-[5-(5-methyl-1H-pyrrolo[2,3-b]pyridin-3-ylmethyl)-pyridin-2-yl]-amine (P-1530),
(6-Methoxy-pyridin-3-ylmethyl)-[6-methyl-5-(5-methyl-1H-pyrrolo[2,3-b]pyridin-3-ylmethyl)-pyridin-2-yl]-amine (P-1532),
(5-Fluoro-pyridin-3-ylmethyl)-[6-methyl-5-(5-methyl-1H-pyrrolo[2,3-b]pyridin-3-ylmethyl)-pyridin-2-yl]-amine (P-1534),
[6-Methyl-5-(5-methyl-1H-pyrrolo[2,3-b]pyridin-3-ylmethyl)-pyridin-2-yl]-(6-trifluoromethyl-pyridin-3-ylmethyl)-amine (P-1538),
(2-Methoxy-pyridin-3-ylmethyl)-[6-methyl-5-(5-methyl-1H-pyrrolo[2,3-b]pyridin-3-ylmethyl)-pyridin-2-yl]-amine (P-1539),
[6-Chloro-5-(5-methyl-1H-pyrrolo[2,3-b]pyridin-3-ylmethyl)-pyridin-2-yl]-(5-fluoro-pyridin-3-ylmethyl)-amine (P-1541),
[6-Chloro-5-(5-methyl-1H-pyrrolo[2,3-b]pyridin-3-ylmethyl)-pyridin-2-yl]-(6-methoxy-pyridin-3-ylmethyl)-amine (P-1545),
[6-Chloro-5-(5-methyl-1H-pyrrolo[2,3-b]pyridin-3-ylmethyl)-pyridin-2-yl]-(2-methoxy-pyridin-3-ylmethyl)-amine (P-1546),
(5-Fluoro-pyridin-3-ylmethyl)-[3-methoxy-5-(5-methyl-1H-pyrrolo[2,3-b]pyridin-3-ylmethyl)-pyridin-2-yl]-amine (P-1549),
[3-Methoxy-5-(5-methyl-1H-pyrrolo[2,3-b]pyridin-3-ylmethyl)-pyridin-2-yl]-(6-methoxy-pyridin-3-ylmethyl)-amine (P-1552),
[3-Methoxy-5-(5-methyl-1H-pyrrolo[2,3-b]pyridin-3-ylmethyl)-pyridin-2-yl]-(2-methoxy-pyridin-3-ylmethyl)-amine (P-1553),
(6-Methoxy-pyridin-3-ylmethyl)-[3-methyl-5-(5-methyl-1H-pyrrolo[2,3-b]pyridin-3-ylmethyl)-pyridin-2-yl]-amine (P-1554),
(5-Fluoro-pyridin-3-ylmethyl)-[3-methyl-5-(5-methyl-1H-pyrrolo[2,3-b]pyridin-3-ylmethyl)-pyridin-2-yl]-amine (P-1556),
[3-Methyl-5-(5-methyl-1H-pyrrolo[2,3-b]pyridin-3-ylmethyl)-pyridin-2-yl]-(6-trifluoromethyl-pyridin-3-ylmethyl)-amine (P-1560),
(2-Methoxy-pyridin-3-ylmethyl)-[3-methyl-5-(5-methyl-1H-pyrrolo[2,3-b]pyridin-3-ylmethyl)-pyridin-2-yl]-amine (P-1561),
[3-Fluoro-5-(5-methyl-1H-pyrrolo[2,3-b]pyridin-3-ylmethyl)-pyridin-2-yl]-(6-methoxy-pyridin-3-ylmethyl)-amine (P-1562),
[3-Fluoro-5-(5-methyl-1H-pyrrolo[2,3-b]pyridin-3-ylmethyl)-pyridin-2-yl]-(5-fluoro-pyridin-3-ylmethyl)-amine (P-1564),
[3-Fluoro-5-(5-methyl-1H-pyrrolo[2,3-b]pyridin-3-ylmethyl)-pyridin-2-yl]-(2-methoxy-pyridin-3-ylmethyl)-amine (P-1568),
(5-Fluoro-pyridin-3-ylmethyl)-[5-(5-methyl-1H-pyrrolo[2,3-b]pyridin-3-ylmethyl)-thiazol-2-yl]-amine (P-1580),
[5-(5-Methoxy-1H-pyrrolo[2,3-b]pyridin-3-ylmethyl)-pyridin-2-yl]-(6-trifluoromethyl-pyridin-3-ylmethyl)-amine (P-1583),
(5-Fluoro-pyridin-3-ylmethyl)-[5-(5-methoxy-1H-pyrrolo[2,3-b]pyridin-3-ylmethyl)-pyridin-2-yl]-amine (P-1585),
(2-Methoxy-pyridin-3-ylmethyl)-[5-(5-methoxy-1H-pyrrolo[2,3-b]pyridin-3-ylmethyl)-pyridin-2-yl]-amine (P-1589),
[6-Chloro-5-(5-methoxy-1H-pyrrolo[2,3-b]pyridin-3-ylmethyl)-pyridin-2-yl]-(5-fluoro-pyridin-3-ylmethyl)-amine (P-1591),
[6-Chloro-5-(5-methoxy-1H-pyrrolo[2,3-b]pyridin-3-ylmethyl)-pyridin-2-yl]-(6-methoxy-pyridin-3-ylmethyl)-amine (P-1595),
[6-Chloro-5-(5-methoxy-1H-pyrrolo[2,3-b]pyridin-3-ylmethyl)-pyridin-2-yl]-(2-methoxy-pyridin-3-ylmethyl)-amine (P-1596),
(5-Fluoro-pyridin-3-ylmethyl)-[5-(5-methoxy-1H-pyrrolo[2,3-b]pyridin-3-ylmethyl)-pyrimidin-2-yl]-amine (P-1601),
(6-Methoxy-pyridin-3-ylmethyl)-[5-(5-methoxy-1H-pyrrolo[2,3-b]pyridin-3-ylmethyl)-pyrimidin-2-yl]-amine (P-1604),
[5-(5-Methoxy-1H-pyrrolo[2,3-b]pyridin-3-ylmethyl)-pyrimidin-2-yl]-(6-trifluoromethyl-pyridin-3-ylmethyl)-amine (P-1605),
(2-Methoxy-pyridin-3-ylmethyl)-[5-(5-methoxy-1H-pyrrolo[2,3-b]pyridin-3-ylmethyl)-pyrimidin-2-yl]-amine (P-1606),
[5-(5-Chloro-1H-pyrrolo[2,3-b]pyridin-3-ylmethyl)-6-fluoro-pyridin-2-yl]-(2-methoxy-pyridin-3-ylmethyl)-amine (P-1609),
[5-(5-Chloro-1H-pyrrolo[2,3-b]pyridin-3-ylmethyl)-pyrimidin-2-yl]-(2-methoxy-pyridin-3-ylmethyl)-amine (P-1614),
[6-Fluoro-5-(5-fluoro-1H-pyrrolo[2,3-b]pyridin-3-ylmethyl)-pyridin-2-yl]-(6-methoxy-pyridin-3-ylmethyl)-amine (P-1622),
[6-Fluoro-5-(5-fluoro-1H-pyrrolo[2,3-b]pyridin-3-ylmethyl)-pyridin-2-yl]-(5-fluoro-pyridin-3-ylmethyl)-amine (P-1624),
[6-Fluoro-5-(5-fluoro-1H-pyrrolo[2,3-b]pyridin-3-ylmethyl)-pyridin-2-yl]-(6-trifluoromethyl-pyridin-3-ylmethyl)-amine (P-1628),
[6-Fluoro-5-(5-fluoro-1H-pyrrolo[2,3-b]pyridin-3-ylmethyl)-pyridin-2-yl]-(2-methoxy-pyridin-3-ylmethyl)-amine (P-1629),
(5-Fluoro-pyridin-3-ylmethyl)-[5-(5-fluoro-1H-pyrrolo[2,3-b]pyridin-3-ylmethyl)-pyrimidin-2-yl]-amine (P-1631),
[5-(5-Fluoro-1H-pyrrolo[2,3-b]pyridin-3-ylmethyl)-pyrimidin-2-yl]-(6-methoxy-pyridin-3-ylmethyl)-amine (P-1635),
[5-(5-Fluoro-1H-pyrrolo[2,3-b]pyridin-3-ylmethyl)-pyrimidin-2-yl]-(6-trifluoromethyl-pyridin-3-ylmethyl)-amine (P-1636),
[5-(5-Fluoro-1H-pyrrolo[2,3-b]pyridin-3-ylmethyl)-pyrimidin-2-yl]-(2-methoxy-pyridin-3-ylmethyl)-amine (P-1637), TABLE 6-continued (5-Fluoro-pyridin-3-ylmethyl)-[5-(5-trifluoromethyl-1H-pyrrolo[2,3-b]pyridin-3-ylmethyl)-pyridin-2-yl]-amine (P-1639),
(6-Methoxy-pyridin-3-ylmethyl)-[5-(5-trifluoromethyl-1H-pyrrolo[2,3-b]pyridin-3-ylmethyl)-pyridin-2-yl]-amine (P-1643),
(6-Trifluoromethyl-pyridin-3-ylmethyl)-[5-(5-trifluoromethyl-1H-pyrrolo[2,3-b]pyridin-3-ylmethyl)-pyridin-2-yl]-amine (P-1644),
(2-Methoxy-pyridin-3-ylmethyl)-[5-(5-trifluoromethyl-1H-pyrrolo[2,3-b]pyridin-3-ylmethyl)-pyridin-2-yl]-amine (P-1645),
(5-Fluoro-pyridin-3-ylmethyl)-[6-fluoro-5-(5-trifluoromethyl-1H-pyrrolo[2,3-b]pyridin-3-ylmethyl)-pyridin-2-yl]-amine (P-1647),
[6-Fluoro-5-(5-trifluoromethyl-1H-pyrrolo[2,3-b]pyridin-3-ylmethyl)-pyridin-2-yl]-(6-methoxy-pyridin-3-ylmethyl)-amine (P-1651),
[6-Fluoro-5-(5-trifluoromethyl-1H-pyrrolo[2,3-b]pyridin-3-ylmethyl)-pyridin-2-yl]-(6-trifluoromethyl-pyridin-3-ylmethyl)-amine (P-1652),
[6-Fluoro-5-(5-trifluoromethyl-1H-pyrrolo[2,3-b]pyridin-3-ylmethyl)-pyridin-2-yl]-(2-methoxy-pyridin-3-ylmethyl)-amine (P-1653),
3-{2-Fluoro-6-[(6-methoxy-pyridin-3-ylmethyl)-amino]-pyridin-3-ylmethyl}-1H-pyrrolo[2,3-b]pyridine-5-carbonitrile (P-1658),
3-{2-Fluoro-6-[(6-trifluoromethyl-pyridin-3-ylmethyl)-amino]-pyridin-3-ylmethyl}-1H-pyrrolo[2,3-b]pyridine-5-carbonitrile (P-1659),
3-{2-Fluoro-6-[(2-methoxy-pyridin-3-ylmethyl)-amino]-pyridin-3-ylmethyl}-1H-pyrrolo[2,3-b]pyridine-5-carbonitrile (P-1660),
[5-(5-Cyclopropyl-1H-pyrrolo[2,3-b]pyridin-3-ylmethyl)-pyridin-2-yl]-(5-fluoro-pyridin-3-ylmethyl)-amine (P-1662),
[5-(5-Cyclopropyl-1H-pyrrolo[2,3-b]pyridin-3-ylmethyl)-pyridin-2-yl]-(6-methoxy-pyridin-3-ylmethyl)-amine (P-1666),
[5-(5-Cyclopropyl-1H-pyrrolo[2,3-b]pyridin-3-ylmethyl)-pyridin-2-yl]-(6-trifluoromethyl-pyridin-3-ylmethyl)-amine (P-1667),
[5-(5-Cyclopropyl-1H-pyrrolo[2,3-b]pyridin-3-ylmethyl)-pyridin-2-yl]-(2-methoxy-pyridin-3-ylmethyl)-amine (P-1668),
N-(3-{2-Fluoro-6-[(5-fluoro-pyridin-3-ylmethyl)-amino]-pyridin-3-ylmethyl}-1H-pyrrolo[2,3-b]pyridin-5-yl)-acetamide (P-1671),
N-(3-{2-Fluoro-6-[(6-methoxy-pyridin-3-ylmethyl)-amino]-pyridin-3-ylmethyl}-1H-pyrrolo[2,3-b]pyridin-5-yl)-acetamide (P-1674),
N-(3-{2-Fluoro-6-[(6-trifluoromethyl-pyridin-3-ylmethyl)-amino]-pyridin-3-ylmethyl}-1H-pyrrolo[2,3-b]pyridin-5-yl)-acetamide (P-1675),
N-(3-{2-Fluoro-6-[(2-methoxy-pyridin-3-ylmethyl)-amino]-pyridin-3-ylmethyl}-1H-pyrrolo[2,3-b]pyridin-5-yl)-acetamide (P-1676),
N-(3-{2-Fluoro-6-[(5-fluoro-pyridin-3-ylmethyl)-amino]-pyridin-3-ylmethyl}-1H-pyrrolo[2,3-b]pyridin-5-yl)-methanesulfonamide (P-1678),
N-(3-{2-Fluoro-6-[(6-methoxy-pyridin-3-ylmethyl)-amino]-pyridin-3-ylmethyl}-1H-pyrrolo[2,3-b]pyridin-5-yl)-methanesulfonamide (P-1682),
N-(3-{2-Fluoro-6-[(6-trifluoromethyl-pyridin-3-ylmethyl)-amino]-pyridin-3-ylmethyl}-1H-pyrrolo[2,3-b]pyridin-5-yl)-methanesulfonamide (P-1683),
N-(3-{2-Fluoro-6-[(2-methoxy-pyridin-3-ylmethyl)-amino]-pyridin-3-ylmethyl}-1H-pyrrolo[2,3-b]pyridin-5-yl)-methanesulfonamide (P-1684),
[6-Fluoro-5-(5-methanesulfonyl-1H-pyrrolo[2,3-b]pyridin-3-ylmethyl)-pyridin-2-yl]-(5-fluoro-pyridin-3-ylmethyl)-amine (P-1686),
[6-Fluoro-5-(5-methanesulfonyl-1H-pyrrolo[2,3-b]pyridin-3-ylmethyl)-pyridin-2-yl]-(6-methoxy-pyridin-3-ylmethyl)-amine (P-1690),
[6-Fluoro-5-(5-methanesulfonyl-1H-pyrrolo[2,3-b]pyridin-3-ylmethyl)-pyridin-2-yl]-(6-trifluoromethyl-pyridin-3-ylmethyl)-amine (P-1691),
[6-Fluoro-5-(5-methanesulfonyl-1H-pyrrolo[2,3-b]pyridin-3-ylmethyl)-pyridin-2-yl]-(2-methoxy-pyridin-3-ylmethyl)-amine (P-1692),
3-{2-Fluoro-6-[(5-fluoro-pyridin-3-ylmethyl)-amino]-pyridin-3-ylmethyl}-1H-pyrrolo[2,3-b]pyridine-5-carboxylic acid methylamide (P-1695),
3-{2-Fluoro-6-[(6-methoxy-pyridin-3-ylmethyl)-amino]-pyridin-3-ylmethyl}-1H-pyrrolo[2,3-b]pyridine-5-carboxylic acid methylamide (P-1699),
3-{2-Fluoro-6-[(6-trifluoromethyl-pyridin-3-ylmethyl)-amino]-pyridin-3-ylmethyl}-1H-pyrrolo[2,3-b]pyridine-5-carboxylic acid methylamide (P-1700),
3-{2-Fluoro-6-[(2-methoxy-pyridin-3-ylmethyl)-amino]-pyridin-3-ylmethyl}-1H-pyrrolo[2,3-b]pyridine-5-carboxylic acid methylamide (P-1701),
4-[4-(3-{2-Fluoro-6-[(5-fluoro-2-methoxy-pyridin-3-ylmethyl)-amino]-pyridin-3-ylmethyl}-1H-pyrrolo[2,3-b]pyridin-5-yl)-pyrazol-1-yl]-piperidine-1-carboxylic acid tert-butyl ester (P-1702),
{6-Fluoro-5-[5-(1-piperidin-4-yl-1H-pyrazol-4-yl)-1H-pyrrolo[2,3-b]pyridin-3-ylmethyl]-pyridin-2-yl}-(5-fluoro-pyridin-3-ylmethyl)-amine (P-1705),
{6-Fluoro-5-[5-(1-piperidin-4-yl-1H-pyrazol-4-yl)-1H-pyrrolo[2,3-b]pyridin-3-ylmethyl]-pyridin-2-yl}-(6-methoxy-pyridin-3-ylmethyl)-amine (P-1708),
{6-Fluoro-5-[5-(1-piperidin-4-yl-1H-pyrazol-4-yl)-1H-pyrrolo[2,3-b]pyridin-3-ylmethyl]-pyridin-2-yl}-(6-trifluoromethyl-pyridin-3-ylmethyl)-amine (P-1709),
{6-Fluoro-5-[5-(1-piperidin-4-yl-1H-pyrazol-4-yl)-1H-pyrrolo[2,3-b]pyridin-3-ylmethyl]-pyridin-2-yl}-(2-methoxy-pyridin-3-ylmethyl)-amine (P-1710),
[5-(4-Ethynyl-1H-pyrrolo[2,3-b]pyridin-3-ylmethyl)-pyridin-2-yl]-(5-fluoro-pyridin-3-ylmethyl)-amine (P-1712),
[5-(4-Ethynyl-1H-pyrrolo[2,3-b]pyridin-3-ylmethyl)-pyridin-2-yl]-(6-methoxy-pyridin-3-ylmethyl)-amine (P-1716),
[5-(4-Ethynyl-1H-pyrrolo[2,3-b]pyridin-3-ylmethyl)-pyridin-2-yl]-(6-trifluoromethyl-pyridin-3-ylmethyl)-amine (P-1717),
[5-(4-Ethynyl-1H-pyrrolo[2,3-b]pyridin-3-ylmethyl)-pyridin-2-yl]-(2-methoxy-pyridin-3-ylmethyl)-amine (P-1718), TABLE 6-continued 3-{6-[(5-Fluoro-pyridin-3-ylmethyl)-amino]-pyridin-3-ylmethyl}-1H-pyrrolo[2,3-b]pyridine-4-carbonitrile (P-1719),
3-{6-[(6-Methoxy-pyridin-3-ylmethyl)-amino]-pyridin-3-ylmethyl}-1H-pyrrolo[2,3-b]pyridine-4-carbonitrile (P-1723),
3-{6-[(6-Trifluoromethyl-pyridin-3-ylmethyl)-amino]-pyridin-3-ylmethyl}-1H-pyrrolo[2,3-b]pyridine-4-carbonitrile (P-1724),
3-{6-[(2-Methoxy-pyridin-3-ylmethyl)-amino]-pyridin-3-ylmethyl}-1H-pyrrolo[2,3-b]pyridine-4-carbonitrile (P-1725),
[6-Fluoro-5-(4-methyl-7H-pyrrolo[2,3-d]pyrimidin-5-ylmethyl)-pyridin-2-yl]-(5-fluoro-pyridin-3-ylmethyl)-amine (P-1727),
(6-Chloro-pyridin-3-ylmethyl)-[6-fluoro-5-(4-methyl-7H-pyrrolo[2,3-d]pyrimidin-5-ylmethyl)-pyridin-2-yl]-amine (P-1728),
(5-Fluoro-2-methoxy-pyridin-3-ylmethyl)-[6-fluoro-5-(4-methyl-7H-pyrrolo[2,3-d]pyrimidin-5-ylmethyl)-pyridin-2-yl]-amine (P-1729),
[6-Fluoro-5-(4-methyl-7H-pyrrolo[2,3-d]pyrimidin-5-ylmethyl)-pyridin-2-yl]-(4-trifluoromethyl-pyridin-3-ylmethyl)-amine (P-1730),
[6-Fluoro-5-(4-methyl-7H-pyrrolo[2,3-d]pyrimidin-5-ylmethyl)-pyridin-2-yl]-(6-methoxy-pyridin-3-ylmethyl)-amine (P-1731),
[6-Fluoro-5-(4-methyl-7H-pyrrolo[2,3-d]pyrimidin-5-ylmethyl)-pyridin-2-yl]-(6-trifluoromethyl-pyridin-3-ylmethyl)-amine (P-1732),
(5-Fluoro-6-methoxy-pyridin-3-ylmethyl)-[6-fluoro-5-(4-methyl-7H-pyrrolo[2,3-d]pyrimidin-5-ylmethyl)-pyridin-2-yl]-amine (P-1733),
[6-Fluoro-5-(4-methyl-7H-pyrrolo[2,3-d]pyrimidin-5-ylmethyl)-pyridin-2-yl]-(2-methoxy-pyridin-3-ylmethyl)-amine (P-1734),
[5-(5-Chloro-1H-pyrrolo[2,3-b]pyridin-3-ylmethyl)-6-fluoro-pyridin-2-yl]-(5-fluoro-pyridin-3-ylmethyl)-amine (P-2001),
[5-(5-Chloro-1H-pyrrolo[2,3-b]pyridin-3-ylmethyl)-pyrimidin-2-yl]-[(S)-1-(4-fluoro-phenyl)-ethyl]-amine (P-2005),
(3-Chloro-benzyl)-[5-(5-fluoro-1H-pyrrolo[2,3-b]pyridin-3-ylmethyl)-1-methyl-1H-pyrazol-3-yl]-amine (P-2006),
(3-Chloro-4-methyl-benzyl)-[5-(5-chloro-1H-pyrrolo[2,3-b]pyridin-3-ylmethyl)-pyrimidin-2-yl]-amine (P-2007),
[5-(5-Chloro-1H-pyrrolo[2,3-b]pyridin-3-ylmethyl)-pyrimidin-2-yl]-(3,4-difluoro-benzyl)-amine (P-2008),
[5-(5-Chloro-1H-pyrrolo[2,3-b]pyridin-3-ylmethyl)-pyrimidin-2-yl]-(3-fluoro-5-trifluoromethyl-benzyl)-amine (P-2009),
[5-(5-Chloro-1H-pyrrolo[2,3-b]pyridin-3-ylmethyl)-pyrimidin-2-yl]-(3-trifluoromethoxy-benzyl)-amine (P-2010),
[5-(5-Chloro-1H-pyrrolo[2,3-b]pyridin-3-ylmethyl)-pyrimidin-2-yl]-(3-fluoro-4-trifluoromethyl-benzyl)-amine (P-2011),
(4-Chloro-benzyl)-[5-(5-chloro-1H-pyrrolo[2,3-b]pyridin-3-ylmethyl)-pyrimidin-2-yl]-methyl-amine (P-2012),
[5-(5-Chloro-1H-pyrrolo[2,3-b]pyridin-3-ylmethyl)-pyrimidin-2-yl]-(3-methyl-benzyl)-amine (P-2013),
[5-(5-Chloro-1H-pyrrolo[2,3-b]pyridin-3-ylmethyl)-pyrimidin-2-yl]-(3-fluoro-4-methyl-benzyl)-amine (P-2014),
[2-(3-Chloro-phenyl)-ethyl]-[5-(5-chloro-1H-pyrrolo[2,3-b]pyridin-3-ylmethyl)-pyrimidin-2-yl]-amine (P-2015),
[5-(5-Chloro-1H-pyrrolo[2,3-b]pyridin-3-ylmethyl)-1H-pyrazol-3-yl]-(4-fluoro-benzyl)-amine (P-2016),
[5-(5-Bromo-1H-pyrrolo[2,3-b]pyridin-3-ylmethyl)-pyridin-2-yl]-(6-methoxy-pyridin-3-ylmethyl)-amine (P-2017),
[5-(4-Methoxy-1H-pyrrolo[2,3-b]pyridin-3-ylmethyl)-pyridin-2-yl]-(6-trifluoromethyl-pyridin-3-ylmethyl)-amine (P-2018),
[5-(5-Methyl-1H-pyrrolo[2,3-b]pyridin-3-ylmethyl)-pyridin-2-yl]-(6-trifluoromethyl-pyridin-3-ylmethyl)-amine (P-2019),
[2-(2-Chloro-phenyl)-ethyl]-[5-(5-chloro-1H-pyrrolo[2,3-b]pyridin-3-ylmethyl)-pyrimidin-2-yl]-amine (P-2020),
[5-(5-Chloro-1H-pyrrolo[2,3-b]pyridin-3-ylmethyl)-pyrimidin-2-yl]-[2-(4-fluoro-phenyl)-ethyl]-amine (P-2021),
[5-(5-Chloro-1H-pyrrolo[2,3-b]pyridin-3-ylmethyl)-pyrimidin-2-yl]-[2-(6-methyl-pyridin-2-yl)-ethyl]-amine (P-2022),
[5-(5-Fluoro-1H-pyrrolo[2,3-b]pyridin-3-ylmethyl)-pyridin-2-yl]-(6-trifluoromethyl-pyridin-3-ylmethyl)-amine (P-2023),
[5-(5-Methoxy-1H-pyrrolo[2,3-b]pyridin-3-ylmethyl)-pyridin-2-yl]-(6-trifluoromethyl-pyridin-3-ylmethyl)-amine (P-2024),
Butyl-[5-(5-chloro-1H-pyrrolo[2,3-b]pyridin-3-ylmethyl)-pyrimidin-2-yl]-amine (P-2026),
[6-Fluoro-5-(5-methoxy-1H-pyrrolo[2,3-b]pyridin-3-ylmethyl)-pyridin-2-yl]-(5-fluoro-pyridin-3-ylmethyl)-amine (P-2028),
[6-Fluoro-5-(5-methoxy-1H-pyrrolo[2,3-b]pyridin-3-ylmethyl)-pyridin-2-yl]-(6-methoxy-pyridin-3-ylmethyl)-amine (P-2030),
(4-Chloro-benzyl)-[6-fluoro-5-(5-methoxy-1H-pyrrolo[2,3-b]pyridin-3-ylmethyl)-pyridin-2-yl]-amine (P-2032),
(2-Fluoro-benzyl)-[5-(4-methoxy-1H-pyrrolo[2,3-b]pyridin-3-ylmethyl)-pyridin-2-yl]-amine (P-2033),
(2-Chloro-benzyl)-[6-fluoro-5-(5-methoxy-1H-pyrrolo[2,3-b]pyridin-3-ylmethyl)-pyridin-2-yl]-amine (P-2034),
(2-Chloro-benzyl)-[6-fluoro-5-(4-methoxy-1H-pyrrolo[2,3-b]pyridin-3-ylmethyl)-pyridin-2-yl]-amine (P-2035),
(2-Chloro-benzyl)-[5-(4-methoxy-1H-pyrrolo[2,3-b]pyridin-3-ylmethyl)-pyridin-2-yl]-amine (P-2036),
(4-Chloro-benzyl)-[6-fluoro-5-(4-methoxy-1H-pyrrolo[2,3-b]pyridin-3-ylmethyl)-pyridin-2-yl]-amine (P-2037),
[5-(5-Chloro-1H-pyrrolo[2,3-b]pyridin-3-ylmethyl)-pyrimidin-2-yl]-(6-methoxy-pyridin-3-ylmethyl)-amine (P-2038), TABLE 6-continued

[5-(5-Fluoro-1H-pyrrolo[2,3-b]pyridin-3-ylmethyl)-pyrimidin-2-yl]-(1-thiazol-2-yl-ethyl)-amine (P-2039),
[6-Fluoro-5-(5-methoxy-1H-pyrrolo[2,3-b]pyridin-3-ylmethyl)-pyridin-2-yl]-(2-methoxy-pyridin-3-ylmethyl)-amine (P-2043),
(5-Chloro-pyridin-2-ylmethyl)-[6-fluoro-5-(1H-pyrrolo[2,3-b]pyridin-3-ylmethyl)-pyridin-2-yl]-amine (P-2044),
[6-Fluoro-5-(1H-pyrrolo[2,3-b]pyridin-3-ylmethyl)-pyridin-2-yl]-(2-methoxy-pyridin-3-ylmethyl)-amine (P-2045),
[1-(4-Fluoro-phenyl)-propyl]-[5-(5-fluoro-1H-pyrrolo[2,3-b]pyridin-3-ylmethyl)-pyrimidin-2-yl]-amine (P-2053),
[1-(4-Fluoro-phenyl)-cyclopropyl]-[5-(5-fluoro-1H-pyrrolo[2,3-b]pyridin-3-ylmethyl)-pyrimidin-2-yl]-amine (P-2055),
[(S)-1-(4-Fluoro-phenyl)-ethyl]-[5-(5-fluoro-1H-pyrrolo[2,3-b]pyridin-3-ylmethyl)-pyrimidin-2-yl]-amine (P-2056),
[5-(5-Chloro-1H-pyrrolo[2,3-b]pyridin-3-ylmethyl)-pyrimidin-2-yl]-(2-methoxy-pyridin-4-ylmethyl)-amine (P-2074),
[5-(5-Chloro-1H-pyrrolo[2,3-b]pyridin-3-ylmethyl)-6-fluoro-pyridin-2-yl]-(2-methyl-pyridin-4-ylmethyl)-amine (P-2075),
(5-Fluoro-2-methoxy-pyridin-4-ylmethyl)-[5-(1H-pyrrolo[2,3-b]pyridin-3-ylmethyl)-pyrimidin-2-yl]-amine (P-2135),
(5-Fluoro-2-methoxy-pyridin-4-ylmethyl)-[5-(5-methoxy-1H-pyrrolo[2,3-b]pyridin-3-ylmethyl)-pyrimidin-2-yl]-amine (P-2136),
[3-Methoxy-5-(5-methyl-1H-pyrrolo[2,3-b]pyridin-3-ylmethyl)-pyridin-2-yl]-(6-trifluoromethyl-pyridin-3-ylmethyl)-amine (P-2143),
[5-(5-Chloro-1H-pyrrolo[2,3-b]pyridin-3-ylmethyl)-thiazol-2-yl]-(6-trifluoromethyl-pyridin-3-ylmethyl)-amine (P-2144),
[5-(5-Methyl-1H-pyrrolo[2,3-b]pyridin-3-ylmethyl)-thiazol-2-yl]-(6-trifluoromethyl-pyridin-3-ylmethyl)-amine (P-2145),
[3-Fluoro-5-(5-methyl-1H-pyrrolo[2,3-b]pyridin-3-ylmethyl)-pyridin-2-yl]-(6-trifluoromethyl-pyridin-3-ylmethyl)-amine (P-2146),
[3-Fluoro-5-(5-methoxy-1H-pyrrolo[2,3-b]pyridin-3-ylmethyl)-pyridin-2-yl]-(6-trifluoromethyl-pyridin-3-ylmethyl)-amine (P-2147),
[5-(5-Chloro-1H-pyrrolo[2,3-b]pyridin-3-ylmethyl)-thiazol-2-yl]-(6-methoxy-pyridin-3-ylmethyl)-amine (P-2154),
(6-Methoxy-pyridin-3-ylmethyl)-[5-(5-methyl-1H-pyrrolo[2,3-b]pyridin-3-ylmethyl)-thiazol-2-yl]-amine (P-2155),
3-{[5-(5-Chloro-1H-pyrrolo[2,3-b]pyridin-3-ylmethyl)-pyrimidin-2-ylamino]-methyl}-5-fluoro-1-methyl-1H-pyridin-2-one (P-2157),
[5-(5-Chloro-1H-pyrrolo[2,3-b]pyridin-3-ylmethyl)-thiazol-2-yl]-(2-methoxy-pyridin-3-ylmethyl)-amine (P-2158),
(2-Methoxy-pyridin-3-ylmethyl)-[5-(5-methyl-1H-pyrrolo[2,3-b]pyridin-3-ylmethyl)-thiazol-2-yl]-amine (P-2159),
(6-Methoxy-pyridin-2-ylmethyl)-[5-(5-methyl-1H-pyrrolo[2,3-b]pyridin-3-ylmethyl)-thiazol-2-yl]-amine (P-2162),
[5-(5-Chloro-1H-pyrrolo[2,3-b]pyridin-3-ylmethyl)-thiazol-2-yl]-(6-methoxy-pyridin-2-ylmethyl)-amine (P-2163),
[5-(5-Chloro-1H-pyrrolo[2,3-b]pyridin-3-ylmethyl)-thiazol-2-yl]-(2,6-dimethoxy-pyridin-3-ylmethyl)-amine (P-2164),
5-Fluoro-N-[6-fluoro-5-(5-methyl-1H-pyrrolo[2,3-b]pyridin-3-ylmethyl)-pyridin-2-yl]-2-methoxy-nicotinamide (P-2168),
[5-(5-Chloro-1H-pyrrolo[2,3-b]pyridin-3-ylmethyl)-3-fluoro-pyridin-2-yl]-(6-trifluoromethyl-pyridin-3-ylmethyl)-amine (P-2172),
[5-(5-Chloro-1H-pyrrolo[2,3-b]pyridin-3-ylmethyl)-pyrimidin-2-yl]-(5-fluoro-pyridin-3-ylmethyl)-amine (P-2176),
N-[6-Fluoro-5-(5-methyl-1H-pyrrolo[2,3-b]pyridin-3-ylmethyl)-pyridin-2-yl]-C-phenyl-methanesulfonamide (P-2181), and
any salt, prodrug, tautomer, or stereoisomer thereof.

In some embodiments, the disclosure provides a method for treating a disease or condition as described herein by administering to a subject a compound of Formula IV:

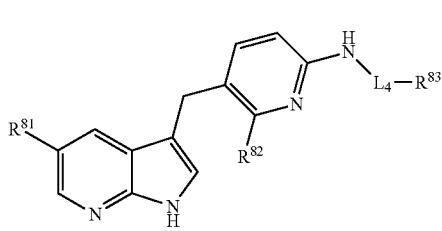

IV all salts, prodrugs, tautomers, and isomers thereof, wherein:

$L_4$ is —CH$_2$—, —CH$_2$CH$_2$—, —CH(R$^{50}$)—, —C(O)— or —C(O)NH—;

$R^{81}$ is selected from the group consisting of hydrogen, —OR$^{51}$, —CN, fluoro, chloro, lower alkyl, fluoro substituted lower alkyl, cycloalkyl, heterocycloalkyl, aryl and heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{51}$, —NR$^{51}$R$^{51}$, —OR$^{51}$ and —S(O)$_2$R$^{51}$;

$R^{82}$ is selected from the group consisting of hydrogen, fluoro, C$_{1-3}$ alkyl, fluoro substituted C$_{2-3}$ alkyl, OH, C$_{1-3}$ alkoxy, and fluoro substituted C$_{1-3}$ alkoxy;

$R^{83}$ is heterocycloalkyl, heteroaryl, or

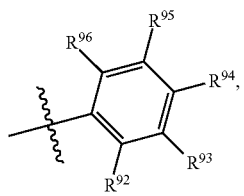

in which

indicates the attachment point of $R^{83}$ to $L_4$ of Formula III, wherein heterocycloalkyl or heteroaryl are optionally substituted with one or more substituents selected from the group consisting of halogen, lower alkyl, fluoro substituted lower alkyl, cycloalkylamino, —NHR$^{51}$, —NR$^{51}$R$^{51}$, —OR$^{51}$ and —S(O)$_2$R$^{51}$;

$R^{92}$, $R^{93}$, $R^{94}$, $R^{95}$, and $R^{96}$ are independently selected from the group consisting of hydrogen, halogen, lower alkyl, fluoro substituted lower alkyl, cycloalkylamino, —NHS(O)$_2$R$^{51}$, —NHC(O)R$^{51}$, —NHR$^{51}$, —NR$^{51}$R$^{51}$, —OR$^{51}$ and —S(O)$_2$R$^{51}$;

$R^{50}$ is lower alkyl or fluoro substituted lower alkyl;

$R^{51}$ at each occurrence is independently selected from the group consisting of lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, and heteroaryl as $R^{51}$ or as substituents of lower alkyl are optionally substituted with one or more substituents selected from the group consisting of —OH, —NH$_2$, —CN, —NO$_2$, —S(O)$_2$NH$_2$, —C(O)NH$_2$, —OR$^{52}$, —SR$^{52}$, —NHR$^{52}$, —NR$^{52}$R$^{52}$, —NR$^{49}$C(O)R$^{52}$, —NR$^{49}$S(O)$_2$R$^{52}$, —S(O)$_2$R$^{52}$, halogen, lower alkyl, fluoro substituted lower alkyl, and cycloalkylamino;

$R^{49}$ at each occurrence is independently hydrogen or lower alkyl;

$R^{52}$ at each occurrence is independently selected from the group consisting of lower alkyl, heterocycloalkyl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, and wherein heterocycloalkyl and heteroaryl are optionally substituted with one or more substituents selected from the group consisting of halogen, —CN, lower alkyl, fluoro substituted lower alkyl, lower alkoxy and fluoro substituted lower alkoxy. In certain instances, the compound is not those listed in Table 2 below.

TABLE 2

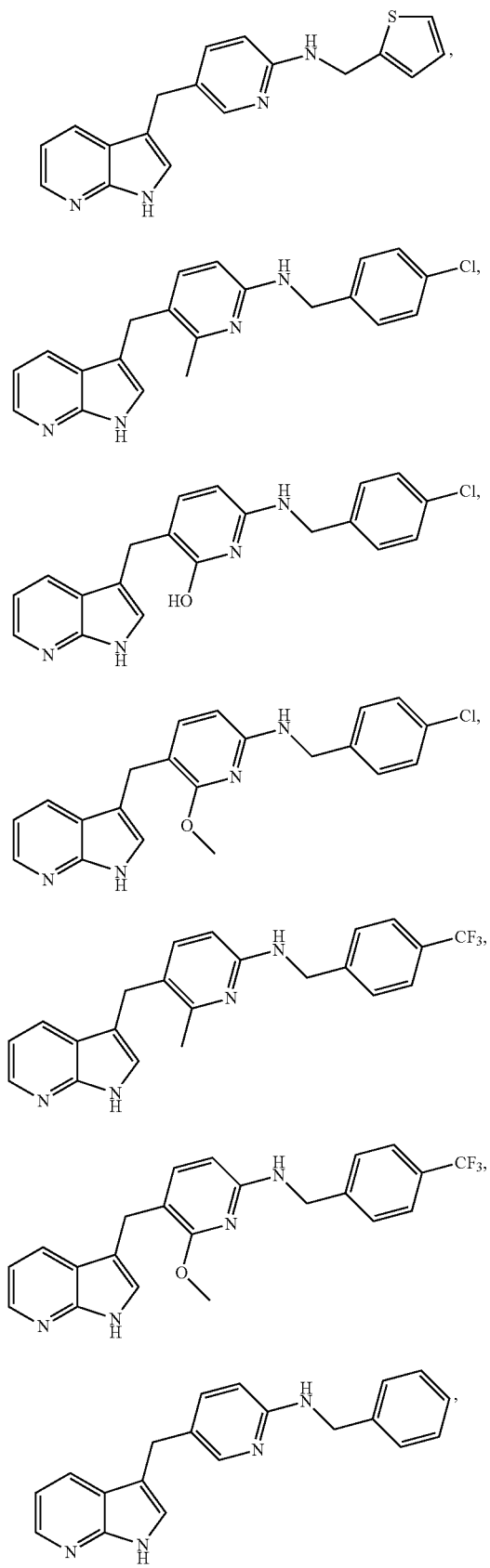

TABLE 2-continued
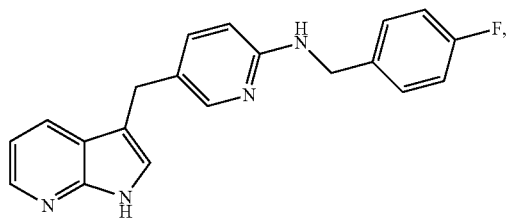 [SMILES: Fc1ccc(CNc2ccc(Cc3c[nH]c4ncccc34)cn2)cc1]
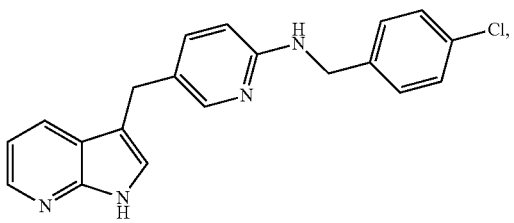 [SMILES: Clc1ccc(CNc2ccc(Cc3c[nH]c4ncccc34)cn2)cc1]
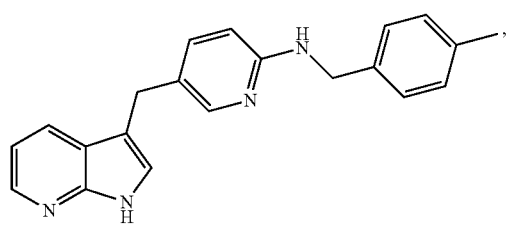 [SMILES: Cc1ccc(CNc2ccc(Cc3c[nH]c4ncccc34)cn2)cc1]
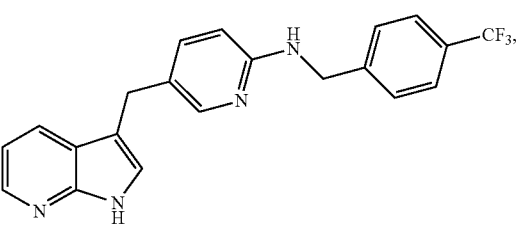 [SMILES: FC(F)(F)c1ccc(CNc2ccc(Cc3c[nH]c4ncccc34)cn2)cc1]
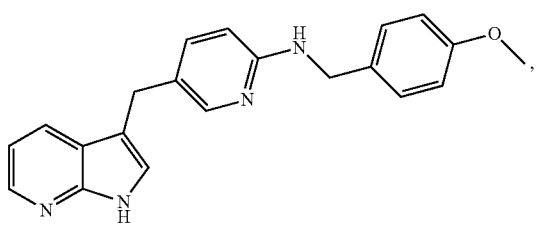 [SMILES: COc1ccc(CNc2ccc(Cc3c[nH]c4ncccc34)cn2)cc1]
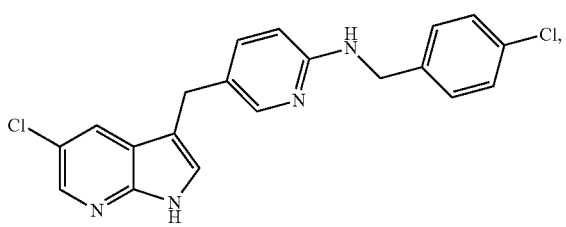 [SMILES: Clc1ccc(CNc2ccc(Cc3c[nH]c4ncc(Cl)cc34)cn2)cc1]
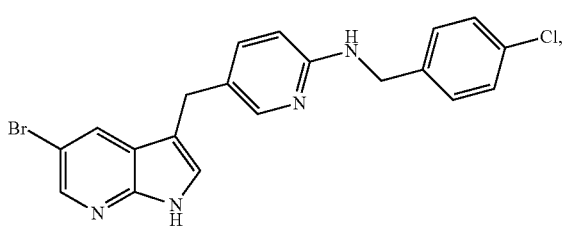
TABLE 2-continued
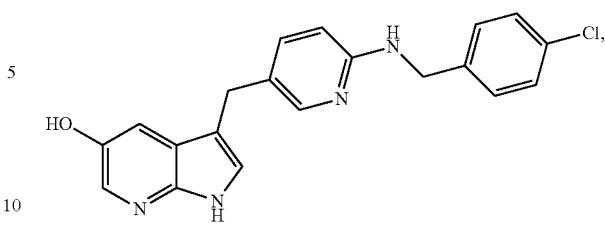
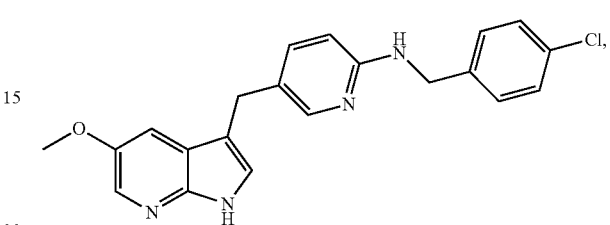
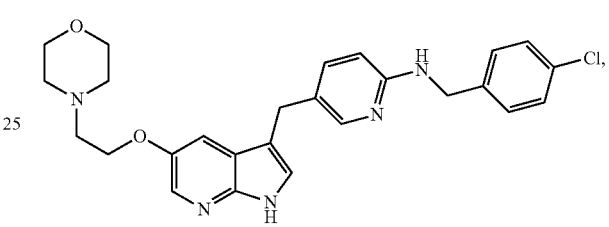
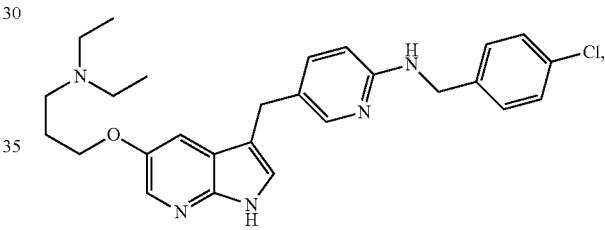
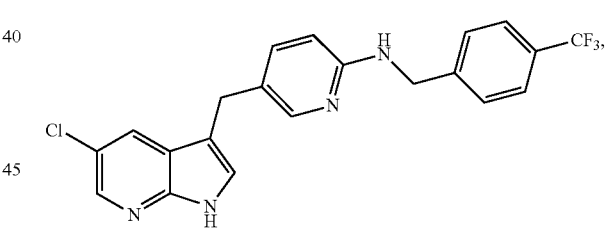
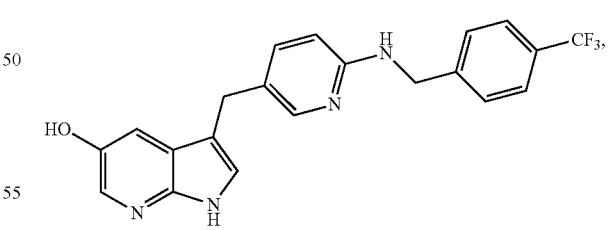
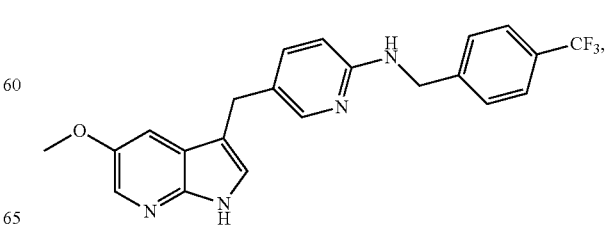

TABLE 2-continued

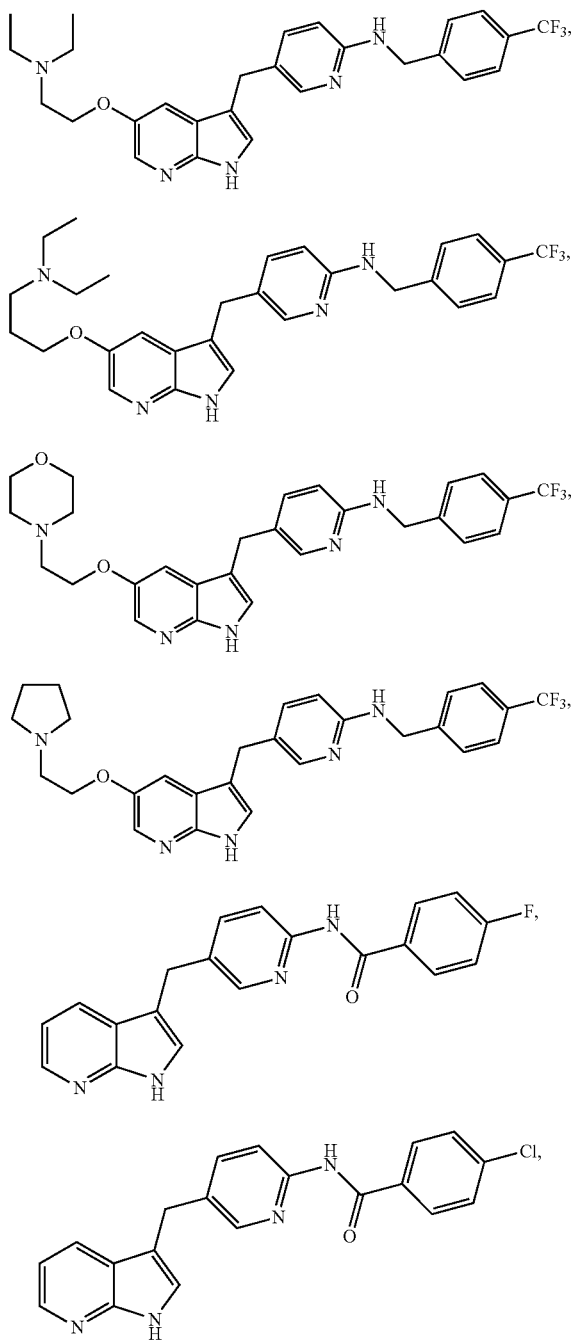

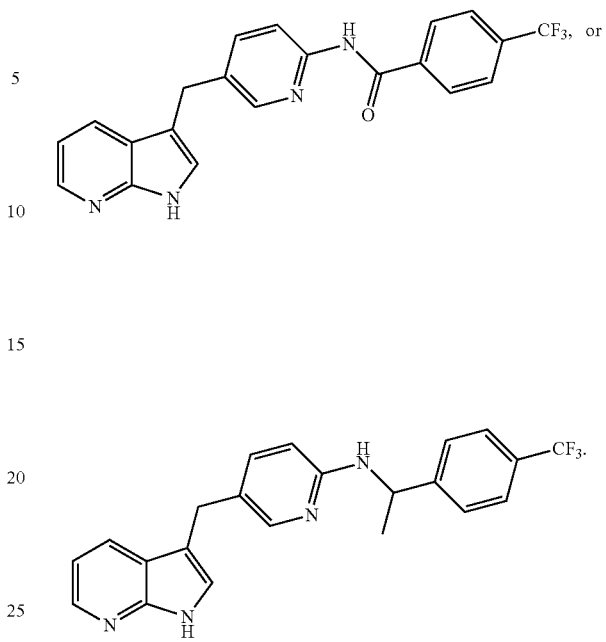

In certain embodiments, the disclosure provide a method for treating a disease or condition as described herein by administering to a subject a compound of Formula IV, wherein $L_4$ is —$CH_2$— or —C(O)—; $R^{81}$ is selected from the group consisting of hydrogen, —CN, fluoro, chloro, lower alkyl, fluoro substituted lower alkyl, lower alkoxy, and fluoro substituted lower alkoxy; $R^{82}$ is hydrogen or fluoro; $R^{83}$ is a nitrogen containing heteroaryl, wherein nitrogen containing heteroaryl is optionally substituted with one or two substituents selected from the group consisting of halogen, lower alkyl, fluoro substituted lower alkyl, cycloalkylamino, —$NHR^{51}$, —$NR^{51}R^{51}$, —$OR^{51}$ and —$S(O)_2R^{51}$; and $R^{51}$ at each occurrence is independently lower alkyl or cycloalkyl, wherein lower alkyl is optionally substituted with one or more fluoro. In one instance, $L_4$ is $CH_2$. In one instance, $R^{82}$ is fluoro. In other instances, $R^3$ is pyridyl optionally substituted with one or two substituents selected from the group consisting of halogen, lower alkyl or fluoro substituted lower alkyl. In other instances, $R^{82}$ is hydrogen, fluoro or chloro.

In some embodiments, the disclosure provides a method for treating a disease or condition as described herein by administering to a subject a compound selected from those set forth in Table 3 or any salts, prodrugs, tautomers, and isomers thereof.

TABLE 3

(4-Chloro-benzyl)-[6-(1H-pyrrolo[2,3-b]pyridin-3-ylmethyl)-pyridazin-3-yl]-amine (P-0092),
(4-Morpholin-4-ylmethyl-benzyl)-[5-(1H-pyrrolo[2,3-b]pyridin-3-ylmethyl)-pyridin-2-yl]-amine (P-0093)
Pyridin-3-ylmethyl-[5-(1H-pyrrolo[2,3-b]pyridin-3-ylmethyl)-pyridin-2-yl]-amine (P-0094),
(5-Methyl-isoxazol-3-ylmethyl)-[5-(1H-pyrrolo[2,3-b]pyridin-3-ylmethyl)-pyridin-2-yl]-amine (P-0095),
(2-Pyrrolidin-1-yl-ethyl)-[5-(1H-pyrrolo[2,3-b]pyridin-3-ylmethyl)-pyridin-2-yl]-amine (P-0096),
[1-(4-Methanesulfonyl-phenyl)-ethyl]-[5-(1H-pyrrolo[2,3-b]pyridin-3-ylmethyl)-pyridin-2-yl]-amine (P-0097),
(2-Methoxy-ethyl)-[5-(1H-pyrrolo[2,3-b]pyridin-3-ylmethyl)-pyridin-2-yl]-amine (P-0098),
(2-Morpholin-4-yl-ethyl)-[5-(1H-pyrrolo[2,3-b]pyridin-3-ylmethyl)-pyridin-2-yl]-amine (P-0099),
3,4-Dichloro-N-[5-(1H-pyrrolo[2,3-b]pyridin-3-ylmethyl)-pyridin-2-yl]-benzamide (P-0100),
2-Chloro-4-fluoro-N-[5-(1H-pyrrolo[2,3-b]pyridin-3-ylmethyl)-pyridin-2-yl]-benzamide (P-0101), TABLE 3-continued 2,5-Dimethyl-2H-pyrazole-3-carboxylic acid [5-(1H-pyrrolo[2,3-b]pyridin-3-ylmethyl)-pyridin-2-yl]-amide (P-0102),
Thiophene-2-carboxylic acid [5-(1H-pyrrolo[2,3-b]pyridin-3-ylmethyl)-pyridin-2-yl]-amide (P-0103),
2-Methoxy-N-[5-(1H-pyrrolo[2,3-b]pyridin-3-ylmethyl)-pyridin-2-yl]-isonicotinamide (P-0104),
N-[5-(1H-Pyrrolo[2,3-b]pyridin-3-ylmethyl)-pyridin-2-yl]-isonicotinamide (P-0105),
Pyrazine-2-carboxylic acid [5-(1H-pyrrolo[2,3-b]pyridin-3-ylmethyl)-pyridin-2-yl]-amide (P-0106),
Pyridine-2-carboxylic acid [5-(1H-pyrrolo[2,3-b]pyridin-3-ylmethyl)-pyridin-2-yl]-amide (P-0107),
6-Methyl-N-[5-(1H-pyrrolo[2,3-b]pyridin-3-ylmethyl)-pyridin-2-yl]-nicotinamide (P-0108),
4-Fluoro-3-methyl-N-[5-(1H-pyrrolo[2,3-b]pyridin-3-ylmethyl)-pyridin-2-yl]-benzamide (P-0109),
5-Methyl-pyrazine-2-carboxylic acid [5-(1H-pyrrolo[2,3-b]pyridin-3-ylmethyl)-pyridin-2-yl]-amide (P-0110),
3-Chloro-N-[5-(1H-pyrrolo[2,3-b]pyridin-3-ylmethyl)-pyridin-2-yl]-benzamide (P-0111),
4-Fluoro-N-[5-(1H-pyrrolo[2,3-b]pyridin-3-ylmethyl)-pyridin-2-yl]-3-trifluoromethyl-benzamide (P-0112),
N-[5-(1H-Pyrrolo[2,3-b]pyridin-3-ylmethyl)-pyridin-2-yl]-3-trifluoromethoxy-benzamide (P-0113),
N-[5-(1H-Pyrrolo[2,3-b]pyridin-3-ylmethyl)-pyridin-2-yl]-3-trifluoromethyl-benzamide (P-0114),
3-Chloro-4-fluoro-N-[5-(1H-pyrrolo[2,3-b]pyridin-3-ylmethyl)-pyridin-2-yl]-benzamide (P-0115),
3,4-Difluoro-N-[5-(1H-pyrrolo[2,3-b]pyridin-3-ylmethyl)-pyridin-2-yl]-benzamide (P-0116),
2-Chloro-N-[5-(1H-pyrrolo[2,3-b]pyridin-3-ylmethyl)-pyridin-2-yl]-benzamide (P-0117),
5-Fluoro-2-methyl-N-[5-(1H-pyrrolo[2,3-b]pyridin-3-ylmethyl)-pyridin-2-yl]-benzamide (P-0118),
2-Fluoro-N-[5-(1H-pyrrolo[2,3-b]pyridin-3-ylmethyl)-pyridin-2-yl]-benzamide (P-0119),
3-Methoxy-N-[5-(1H-pyrrolo[2,3-b]pyridin-3-ylmethyl)-pyridin-2-yl]-benzamide (P-0120),
3-Fluoro-N-[5-(1H-pyrrolo[2,3-b]pyridin-3-ylmethyl)-pyridin-2-yl]-benzamide (P-0121),
3-Methyl-N-[5-(1H-pyrrolo[2,3-b]pyridin-3-ylmethyl)-pyridin-2-yl]-benzamide (P-0122),
2-Chloro-N-[5-(1H-pyrrolo[2,3-b]pyridin-3-ylmethyl)-pyridin-2-yl]-isonicotinamide (P-0123),
((R)-1-Phenyl-ethyl)-[5-(1H-pyrrolo[2,3-b]pyridin-3-ylmethyl)-pyridin-2-yl]-amine (P-0125),
(3-Morpholin-4-yl-benzyl)-[5-(1H-pyrrolo[2,3-b]pyridin-3-ylmethyl)-pyridin-2-yl]-amine (P-0126),
[1-(2-Fluoro-phenyl)-ethyl]-[5-(1H-pyrrolo[2,3-b]pyridin-3-ylmethyl)-pyridin-2-yl]-amine (P-0127),
[2-(3-Fluoro-phenyl)-ethyl]-[5-(1H-pyrrolo[2,3-b]pyridin-3-ylmethyl)-pyridin-2-yl]-amine (P-0128),
(3-Chloro-benzyl)-[5-(1H-pyrrolo[2,3-b]pyridin-3-ylmethyl)-pyridin-2-yl]-amine (P-0129),
(1-Methyl-1H-imidazol-4-ylmethyl)-[5-(1H-pyrrolo[2,3-b]pyridin-3-ylmethyl)-pyridin-2-yl]-amine (P-0130),
(1,5-Dimethyl-1H-pyrazol-3-ylmethyl)-[5-(1H-pyrrolo[2,3-b]pyridin-3-ylmethyl)-pyridin-2-yl]-amine (P-0131),
[4-Chloro-1-ethyl-5-(1H-pyrrolo[2,3-b]pyridin-3-ylmethyl)-1H-pyrazol-3-yl]-[1-(4-fluoro-phenyl)-meth-(E)-ylidene]-amine (P-0166),
[5-(5-Chloro-1H-pyrrolo[2,3-b]pyridin-3-ylmethyl)-pyridin-2-yl]-(6-trifluoromethyl-pyridin-3-ylmethyl)-amine (P-0181),
[5-(1H-Pyrrolo[2,3-b]pyridin-3-ylmethyl)-pyridin-2-yl]-(6-trifluoromethyl-pyridin-3-ylmethyl)-amine (P-0182),
(3-Chloro-pyridin-4-ylmethyl)-[5-(1H-pyrrolo[2,3-b]pyridin-3-ylmethyl)-pyridin-2-yl]-amine (P-0183),
(2-Chloro-6-fluoro-benzyl)-[5-(1H-pyrrolo[2,3-b]pyridin-3-ylmethyl)-pyridin-2-yl]-amine (P-0210),
Phenethyl-[5-(1H-pyrrolo[2,3-b]pyridin-3-ylmethyl)-pyridin-2-yl]-amine (P-0211),
(2,4-Difluoro-benzyl)-[5-(1H-pyrrolo[2,3-b]pyridin-3-ylmethyl)-pyridin-2-yl]-amine (P-0212),
(2-Fluoro-benzyl)-[5-(1H-pyrrolo[2,3-b]pyridin-3-ylmethyl)-pyridin-2-yl]-amine (P-0213),
(3-Bromo-pyridin-4-ylmethyl)-[5-(1H-pyrrolo[2,3-b]pyridin-3-ylmethyl)-pyridin-2-yl]-amine (P-0214),
(2-Methoxy-pyridin-3-ylmethyl)-[5-(1H-pyrrolo[2,3-b]pyridin-3-ylmethyl)-pyridin-2-yl]-amine (P-0215),
(2-Chloro-benzyl)-[5-(1H-pyrrolo[2,3-b]pyridin-3-ylmethyl)-pyridin-2-yl]-amine (P-0216),
(2-Methyl-benzyl)-[5-(1H-pyrrolo[2,3-b]pyridin-3-ylmethyl)-pyridin-2-yl]-amine (P-0217),
(1-Methyl-1H-benzoimidazol-2-ylmethyl)-[5-(1H-pyrrolo[2,3-b]pyridin-3-ylmethyl)-pyridin-2-yl]-amine (P-0218),
(6-Methoxy-pyridin-3-ylmethyl)-[5-(1H-pyrrolo[2,3-b]pyridin-3-ylmethyl)-pyridin-2-yl]-amine (P-0219),
(1H-Benzoimidazol-2-ylmethyl)-[5-(1H-pyrrolo[2,3-b]pyridin-3-ylmethyl)-pyridin-2-yl]-amine (P-0220),
(2-Chloro-4-fluoro-benzyl)-[5-(1H-pyrrolo[2,3-b]pyridin-3-ylmethyl)-pyridin-2-yl]-amine (P-0221),
(5-Methoxy-pyridin-3-ylmethyl)-[5-(1H-pyrrolo[2,3-b]pyridin-3-ylmethyl)-pyridin-2-yl]-amine (P-0222),
(3-Fluoro-pyridin-4-ylmethyl)-[5-(1H-pyrrolo[2,3-b]pyridin-3-ylmethyl)-pyridin-2-yl]-amine (P-0223),
(6-Methoxy-pyridin-2-ylmethyl)-[5-(1H-pyrrolo[2,3-b]pyridin-3-ylmethyl)-pyridin-2-yl]-amine (P-0224),
(4-Fluoro-2-trifluoromethyl-benzyl)-[5-(1H-pyrrolo[2,3-b]pyridin-3-ylmethyl)-pyridin-2-yl]-amine (P-0225),
[5-(1H-Pyrrolo[2,3-b]pyridin-3-ylmethyl)-pyridin-2-yl]-(2-trifluoromethyl-benzyl)-amine (P-0226),
(3,5-Dichloro-pyridin-4-ylmethyl)-[5-(1H-pyrrolo[2,3-b]pyridin-3-ylmethyl)-pyridin-2-yl]-amine (P-0227),
(6-Morpholin-4-yl-pyridin-2-ylmethyl)-[5-(1H-pyrrolo[2,3-b]pyridin-3-ylmethyl)-pyridin-2-yl]-amine (P-0228),
(3-Fluoro-pyridin-2-ylmethyl)-[5-(1H-pyrrolo[2,3-b]pyridin-3-ylmethyl)-pyridin-2-yl]-amine (P-0229),
(5-Fluoro-pyridin-3-ylmethyl)-[5-(1H-pyrrolo[2,3-b]pyridin-3-ylmethyl)-pyridin-2-yl]-amine (P-0230),
(3-Chloro-pyridin-4-ylmethyl)-[5-(5-chloro-1H-pyrrolo[2,3-b]pyridin-3-ylmethyl)-pyridin-2-yl]-amine (P-0235),
3-{6-[(3-Chloro-pyridin-4-ylmethyl)-amino]-pyridin-3-ylmethyl}-1H-pyrrolo[2,3-b]pyridine-5-carbonitrile (P-0256),
3-[6-(4-Chloro-benzylamino)-pyridin-3-ylmethyl]-1H-pyrrolo[2,3-b]pyridine-5-carbonitrile (P-0257),
Propane-1-sulfonic acid (2,4-difluoro-3-{[5-(1H-pyrrolo[2,3-b]pyridin-3-ylmethyl)-pyridin-2-ylamino]-methyl}-phenyl)-amide (P-0258),
Propane-1-sulfonic acid (3-{[5-(5-chloro-1H-pyrrolo[2,3-b]pyridin-3-ylmethyl)-pyridin-2-ylamino]-methyl}-2,4-difluoro-phenyl)-amide (P-0259),
3-[6-(4-Trifluoromethyl-benzylamino)-pyridin-3-ylmethyl]-1H-pyrrolo[2,3-b]pyridine-5-carbonitrile (P-0269),
[5-(5-Chloro-1H-pyrrolo[2,3-b]pyridin-3-ylmethyl)-pyridin-2-yl]-(2-fluoro-benzyl)-amine (P-0270),
3-[6-(2-Fluoro-benzylamino)-pyridin-3-ylmethyl]-1H-pyrrolo[2,3-b]pyridine-5-carbonitrile (P-0271),
(2-Fluoro-benzyl)-[5-(5-methyl-1H-pyrrolo[2,3-b]pyridin-3-ylmethyl)-pyridin-2-yl]-amine (P-0272),
3-{6-[(6-Trifluoromethyl-pyridin-3-ylmethyl)-amino]-pyridin-3-ylmethyl}-1H-pyrrolo[2,3-b]pyridine-5-carbonitrile (P-0273),
3-[6-(2-Trifluoromethyl-benzylamino)-pyridin-3-ylmethyl]-1H-pyrrolo[2,3-b]pyridine-5-carbonitrile (P-0274),

TABLE 3-continued

[5-(5-Chloro-1H-pyrrolo[2,3-b]pyridin-3-ylmethyl)-pyridin-2-yl]-(2-trifluoromethyl-benzyl)-amine (P-0275),
[5-(5-Methyl-1H-pyrrolo[2,3-b]pyridin-3-ylmethyl)-pyridin-2-yl]-(2-trifluoromethyl-benzyl)-amine (P-0276),
3-[6-(2,6-Difluoro-benzylamino)-pyridin-3-ylmethyl]-1H-pyrrolo[2,3-b]pyridine-5-carbonitrile (P-0277),
[5-(5-Chloro-1H-pyrrolo[2,3-b]pyridin-3-ylmethyl)-pyridin-2-yl]-(2,6-difluoro-benzyl)-amine (P-0278),
(2-Chloro-benzyl)-[5-(5-methyl-1H-pyrrolo[2,3-b]pyridin-3-ylmethyl)-pyridin-2-yl]-amine (P-0279),
(2-Chloro-benzyl)-[5-(5-chloro-1H-pyrrolo[2,3-b]pyridin-3-ylmethyl)-pyridin-2-yl]-amine (P-0280),
3-[6-(2-Chloro-benzylamino)-pyridin-3-ylmethyl]-1H-pyrrolo[2,3-b]pyridine-5-carbonitrile (P-0281),
(6-Methoxy-pyridin-3-ylmethyl)-[5-(5-methyl-1H-pyrrolo[2,3-b]pyridin-3-ylmethyl)-pyridin-2-yl]-amine (P-0282),
[5-(5-Chloro-1H-pyrrolo[2,3-b]pyridin-3-ylmethyl)-pyridin-2-yl]-(6-methoxy-pyridin-3-ylmethyl)-amine (P-0283),
3-{6-[(6-Methoxy-pyridin-3-ylmethyl)-amino]-pyridin-3-ylmethyl}-1H-pyrrolo[2,3-b]pyridine-5-carbonitrile (P-0284),
(2-Methoxy-pyridin-3-ylmethyl)-[5-(5-methyl-1H-pyrrolo[2,3-b]pyridin-3-ylmethyl)-pyridin-2-yl]-amine (P-0285),
[5-(5-Chloro-1H-pyrrolo[2,3-b]pyridin-3-ylmethyl)-pyridin-2-yl]-(2-methoxy-pyridin-3-ylmethyl)-amine (P-0286),
3-{6-[(2-Methoxy-pyridin-3-ylmethyl)-amino]-pyridin-3-ylmethyl}-1H-pyrrolo[2,3-b]pyridine-5-carbonitrile (P-0287),
(2-Ethoxy-benzyl)-[5-(1H-pyrrolo[2,3-b]pyridin-3-ylmethyl)-pyridin-2-yl]-amine (P-0288),
(2,5-Difluoro-benzyl)-[5-(1H-pyrrolo[2,3-b]pyridin-3-ylmethyl)-pyridin-2-yl]-amine (P-0296),
(2,5-Difluoro-benzyl)-[5-(5-methyl-1H-pyrrolo[2,3-b]pyridin-3-ylmethyl)-pyridin-2-yl]-amine (P-0297),
[5-(5-Chloro-1H-pyrrolo[2,3-b]pyridin-3-ylmethyl)-pyridin-2-yl]-(2,5-difluoro-benzyl)-amine (P-0298),
3-[6-(2,5-Difluoro-benzylamino)-pyridin-3-ylmethyl]-1H-pyrrolo[2,3-b]pyridine-5-carbonitrile (P-0299),
3-[6-(2-Trifluoromethoxy-benzylamino)-pyridin-3-ylmethyl]-1H-pyrrolo[2,3-b]pyridine-5-carbonitrile (P-0321),
[5-(1H-Pyrrolo[2,3-b]pyridin-3-ylmethyl)-pyridin-2-yl]-(2-trifluoromethoxy-benzyl)-amine (P-0322),
3-[6-(2-Ethoxy-benzylamino)-pyridin-3-ylmethyl]-1H-pyrrolo[2,3-b]pyridine-5-carbonitrile (P-0323),
[5-(5-Chloro-1H-pyrrolo[2,3-b]pyridin-3-ylmethyl)-pyridin-2-yl]-(5-fluoro-pyridin-3-ylmethyl)-amine (P-0324),
[5-(5-Fluoro-1H-pyrrolo[2,3-b]pyridin-3-ylmethyl)-pyridin-2-yl]-(2-trifluoromethyl-benzyl)-amine (P-0325),
[5-(5-Methoxy-1H-pyrrolo[2,3-b]pyridin-3-ylmethyl)-pyridin-2-yl]-(2-trifluoromethyl-benzyl)-amine (P-0326),
(2-Chloro-benzyl)-[5-(5-fluoro-1H-pyrrolo[2,3-b]pyridin-3-ylmethyl)-pyridin-2-yl]-amine (P-0327),
(2-Chloro-benzyl)-[5-(5-methoxy-1H-pyrrolo[2,3-b]pyridin-3-ylmethyl)-pyridin-2-yl]-amine (P-0328),
(2,5-Difluoro-benzyl)-[5-(5-fluoro-1H-pyrrolo[2,3-b]pyridin-3-ylmethyl)-pyridin-2-yl]-amine (P-0329),
(2,5-Difluoro-benzyl)-[5-(5-methoxy-1H-pyrrolo[2,3-b]pyridin-3-ylmethyl)-pyridin-2-yl]-amine (P-0330),
[5-(5-Fluoro-1H-pyrrolo[2,3-b]pyridin-3-ylmethyl)-pyridin-2-yl]-(6-methoxy-pyridin-3-ylmethyl)-amine (P-0331),
(6-Methoxy-pyridin-3-ylmethyl)-[5-(5-methoxy-1H-pyrrolo[2,3-b]pyridin-3-ylmethyl)-pyridin-2-yl]-amine (P-0332),
(2,6-Difluoro-benzyl)-[5-(5-fluoro-1H-pyrrolo[2,3-b]pyridin-3-ylmethyl)-pyridin-2-yl]-amine (P-0333),
(2,6-Difluoro-benzyl)-[5-(5-methoxy-1H-pyrrolo[2,3-b]pyridin-3-ylmethyl)-pyridin-2-yl]-amine (P-0334),
(2-Methoxy-benzyl)-[5-(1H-pyrrolo[2,3-b]pyridin-3-ylmethyl)-pyridin-2-yl]-amine (P-0336),
3-[6-(2-Methoxy-benzylamino)-pyridin-3-ylmethyl]-1H-pyrrolo[2,3-b]pyridine-5-carbonitrile (P-0337),
[5-(5-Chloro-1H-pyrrolo[2,3-b]pyridin-3-ylmethyl)-pyridin-2-yl]-(2-difluoromethoxy-benzyl)-amine (P-0338),
3-[6-(2-Difluoromethoxy-benzylamino)-pyridin-3-ylmethyl]-1H-pyrrolo[2,3-b]pyridine-5-carbonitrile (P-0339),
(2,6-Difluoro-benzyl)-[5-(1H-pyrrolo[2,3-b]pyridin-3-ylmethyl)-pyridin-2-yl]-amine (P-0340),
(2,6-Difluoro-benzyl)-[5-(5-methyl-1H-pyrrolo[2,3-b]pyridin-3-ylmethyl)-pyridin-2-yl]-amine (P-0341),
(2,4-Dichloro-benzyl)-[5-(1H-pyrrolo[2,3-b]pyridin-3-ylmethyl)-pyridin-2-yl]-amine (P-0342),
(3-Fluoro-benzyl)-[5-(1H-pyrrolo[2,3-b]pyridin-3-ylmethyl)-pyridin-2-yl]-amine (P-0343),
(2-Fluoro-4-trifluoromethyl-benzyl)-[5-(1H-pyrrolo[2,3-b]pyridin-3-ylmethyl)-pyridin-2-yl]-amine (P-0344),
(4-Chloro-2-fluoro-benzyl)-[5-(1H-pyrrolo[2,3-b]pyridin-3-ylmethyl)-pyridin-2-yl]-amine (P-0345),
(3-Fluoro-5-trifluoromethyl-benzyl)-[5-(1H-pyrrolo[2,3-b]pyridin-3-ylmethyl)-pyridin-2-yl]-amine (P-0346),
(2-Morpholin-4-yl-pyridin-3-ylmethyl)-[5-(1H-pyrrolo[2,3-b]pyridin-3-ylmethyl)-pyridin-2-yl]-amine (P-0347),
(4-Chloro-3-trifluoromethyl-benzyl)-[5-(1H-pyrrolo[2,3-b]pyridin-3-ylmethyl)-pyridin-2-yl]-amine (P-0348),
(2-Chloro-5-trifluoromethyl-benzyl)-[5-(1H-pyrrolo[2,3-b]pyridin-3-ylmethyl)-pyridin-2-yl]-amine (P-0349),
(2-Fluoro-5-trifluoromethyl-benzyl)-[5-(1H-pyrrolo[2,3-b]pyridin-3-ylmethyl)-pyridin-2-yl]-amine (P-0350),
(2,3-Dichloro-benzyl)-[5-(1H-pyrrolo[2,3-b]pyridin-3-ylmethyl)-pyridin-2-yl]-amine (P-0351),
(2-Fluoro-3-methoxy-benzyl)-[5-(1H-pyrrolo[2,3-b]pyridin-3-ylmethyl)-pyridin-2-yl]-amine (P-0352),
Dimethyl-(5-{[5-(1H-pyrrolo[2,3-b]pyridin-3-ylmethyl)-pyridin-2-ylamino]-methyl}-pyrimidin-2-yl)-amine (P-0353),
(3-Chloro-2-fluoro-benzyl)-[5-(1H-pyrrolo[2,3-b]pyridin-3-ylmethyl)-pyridin-2-yl]-amine (P-0354),
(5-Fluoro-pyridin-2-ylmethyl)-[5-(1H-pyrrolo[2,3-b]pyridin-3-ylmethyl)-pyridin-2-yl]-amine (P-0355),
(3,5-Difluoro-benzyl)-[5-(1H-pyrrolo[2,3-b]pyridin-3-ylmethyl)-pyridin-2-yl]-amine (P-0356),
(2-Propoxy-benzyl)-[5-(1H-pyrrolo[2,3-b]pyridin-3-ylmethyl)-pyridin-2-yl]-amine (P-0357),
(2-Morpholin-4-yl-benzyl)-[5-(1H-pyrrolo[2,3-b]pyridin-3-ylmethyl)-pyridin-2-yl]-amine (P-0358),
(2-Chloro-3-methoxy-benzyl)-[5-(1H-pyrrolo[2,3-b]pyridin-3-ylmethyl)-pyridin-2-yl]-amine (P-0359),
(2-Fluoro-6-trifluoromethyl-benzyl)-[5-(1H-pyrrolo[2,3-b]pyridin-3-ylmethyl)-pyridin-2-yl]-amine (P-0360),
[2-(2-Morpholin-4-yl-ethoxy)-benzyl]-[5-(1H-pyrrolo[2,3-b]pyridin-3-ylmethyl)-pyridin-2-yl]-amine (P-0361),
(2,3-Difluoro-benzyl)-[5-(1H-pyrrolo[2,3-b]pyridin-3-ylmethyl)-pyridin-2-yl]-amine (P-0362),
(2-Chloro-3-trifluoromethyl-benzyl)-[5-(1H-pyrrolo[2,3-b]pyridin-3-ylmethyl)-pyridin-2-yl]-amine (P-0363),
(2-Chloro-5-fluoro-benzyl)-[5-(1H-pyrrolo[2,3-b]pyridin-3-ylmethyl)-pyridin-2-yl]-amine (P-0364),
(2-Fluoro-3-trifluoromethyl-benzyl)-[5-(1H-pyrrolo[2,3-b]pyridin-3-ylmethyl)-pyridin-2-yl]-amine (P-0365),
(5-Fluoro-2-methoxy-benzyl)-[5-(1H-pyrrolo[2,3-b]pyridin-3-ylmethyl)-pyridin-2-yl]-amine (P-0366), TABLE 3-continued (2-Difluoromethoxy-benzyl)-[5-(1H-pyrrolo[2,3-b]pyridin-3-ylmethyl)-pyridin-2-yl]-amine (P-0367),
(2-Fluoro-4-methyl-benzyl)-[5-(1H-pyrrolo[2,3-b]pyridin-3-ylmethyl)-pyridin-2-yl]-amine (P-0368),
[2-(3-Dimethylamino-propoxy)-benzyl]-[5-(1H-pyrrolo[2,3-b]pyridin-3-ylmethyl)-pyridin-2-yl]-amine
(P-0369),
(2,6-Dimethoxy-pyridin-3-ylmethyl)-[5-(1H-pyrrolo[2,3-b]pyridin-3-ylmethyl)-pyridin-2-yl]-amine
(P-0370),
(2-Fluoro-5-methoxy-benzyl)-[5-(1H-pyrrolo[2,3-b]pyridin-3-ylmethyl)-pyridin-2-yl]-amine (P-0371),
(4-Fluoro-2-methyl-benzyl)-[5-(1H-pyrrolo[2,3-b]pyridin-3-ylmethyl)-pyridin-2-yl]-amine (P-0372),
(3-Chloro-5-fluoro-benzyl)-[5-(1H-pyrrolo[2,3-b]pyridin-3-ylmethyl)-pyridin-2-yl]-amine (P-0373),
(6-Cyclopentyloxy-pyridin-3-ylmethyl)-[5-(1H-pyrrolo[2,3-b]pyridin-3-ylmethyl)-pyridin-2-yl]-amine
(P-0374),
(5-Fluoro-2-trifluoromethyl-benzyl)-[5-(1H-pyrrolo[2,3-b]pyridin-3-ylmethyl)-pyridin-2-yl]-amine (P-0375),
[5-(1H-Pyrrolo[2,3-b]pyridin-3-ylmethyl)-pyridin-2-yl]-[2-(2,2,2-trifluoro-ethoxy)-pyridin-3-ylmethyl]-
amine (P-0376),
Propane-1-sulfonic acid (2-fluoro-3-{[5-(1H-pyrrolo[2,3-b]pyridin-3-ylmethyl)-pyridin-2-ylamino]-methyl}-
phenyl)-amide (P-0377),
(2,5-Dichloro-benzyl)-[5-(1H-pyrrolo[2,3-b]pyridin-3-ylmethyl)-pyridin-2-yl]-amine (P-0380),
Pyrimidin-5-ylmethyl-[5-(1H-pyrrolo[2,3-b]pyridin-3-ylmethyl)-pyridin-2-yl]-amine (P-0381),
(5-Chloro-2-fluoro-benzyl)-[5-(1H-pyrrolo[2,3-b]pyridin-3-ylmethyl)-pyridin-2-yl]-amine (P-0382),
(2-Ethyl-benzyl)-[5-(1H-pyrrolo[2,3-b]pyridin-3-ylmethyl)-pyridin-2-yl]-amine (P-0383),
2,2-Dimethyl-N-(3-{[5-(1H-pyrrolo[2,3-b]pyridin-3-ylmethyl)-pyridin-2-ylamino]-methyl}-pyridin-2-yl)-
propionamide (P-0384),
Methyl-(3-{[5-(1H-pyrrolo[2,3-b]pyridin-3-ylmethyl)-pyridin-2-ylamino]-methyl}-pyridin-2-yl)-amine
(P-0385),
Methyl-(5-{[5-(1H-pyrrolo[2,3-b]pyridin-3-ylmethyl)-pyridin-2-ylamino]-methyl}-pyrimidin-2-yl)-amine
(P-0386),
(2-Chloro-4-methanesulfonyl-benzyl)-[5-(1H-pyrrolo[2,3-b]pyridin-3-ylmethyl)-pyridin-2-yl]-amine
(P-0387),
{5-[1-(1H-Pyrrolo[2,3-b]pyridin-3-yl)-ethyl]-pyridin-2-yl}-(4-trifluoromethyl-benzyl)-amine (P-0388),
(5-Fluoro-2-methyl-benzyl)-[5-(1H-pyrrolo[2,3-b]pyridin-3-ylmethyl)-pyridin-2-yl]-amine (P-0397),
((2,2-Difluoro-benzo[1,3]dioxol-4-ylmethyl)-[5-(1H-pyrrolo[2,3-b]pyridin-3-ylmethyl)-pyridin-2-yl]-amine
(P-0398),
Dimethyl-(3-{[5-(1H-pyrrolo[2,3-b]pyridin-3-ylmethyl)-pyridin-2-ylamino]-methyl}-pyridin-2-yl)-amine
(P-0399),
(5-Chloro-pyridin-3-ylmethyl)-[5-(1H-pyrrolo[2,3-b]pyridin-3-ylmethyl)-pyridin-2-yl]-amine (P-0400),
(2-Methoxy-pyrimidin-5-ylmethyl)-[5-(1H-pyrrolo[2,3-b]pyridin-3-ylmethyl)-pyridin-2-yl]-amine (P-0401),
[5-(5-Chloro-1H-pyrrolo[2,3-b]pyridin-3-ylmethyl)-pyridin-2-yl]-[6-(2,2,2-trifluoro-ethoxy)-pyridin-3-
ylmethyl]-amine (P-0409),
1-(3-Fluoro-phenyl)-3-[5-(1H-pyrrolo[2,3-b]pyridin-3-ylmethyl)-pyridin-2-yl]-urea (P-0412), or
all salts, prodrugs, tautomers, and isomers thereof.

In reference to compounds herein, unless clearly indicated to the contrary, specification of a compound or group of compounds includes salts of such compound(s) (including pharmaceutically acceptable salts), formulations of such compound(s) (including pharmaceutically acceptable formulations), conjugates thereof, derivatives thereof, forms thereof, prodrugs thereof, and all stereoisomers thereof. In reference to compositions, kits, methods of use, etc. of compounds as described herein (i.e. compounds of the disclosure), it is understood (unless indicated otherwise) that a compound as described herein includes compounds of Formulae I and I' including all sub-embodiments thereof, compounds of Formulae II, II' and IIa, including all sub-embodiments thereof, compounds of Formulae III, III' and IV including all sub-embodiments thereof, and compounds as described herein.

In some embodiments, a compound as described herein will have an $IC_{50}$ of less than 500 nm, less than 100 nM, less than 50 nM, less than 20 nM, less than 10 nM, less than 5 nM, or less than 1 nM as determined in a generally accepted Fms kinase activity assay. In some embodiments, the compound is selective relative to other protein kinases, such that the ratio of $IC_{50}$ for another kinase assessed comparably, divided by the $IC_{50}$ for Fms kinase is >20, also >30, also >40, also >50, also >60, also >70, also >80, also >90, also >100, wherein the other protein kinase includes, but is not limited to CSK, Insulin receptor kinase, AMPK, PDGFR or VEGFR.

In some embodiments, a compound as described herein will have an $IC_{50}$ of less than 500 nm, less than 100 nM, less than 50 nM, less than 20 nM, less than 10 nM, less than 5 nM, or less than 1 nM as determined in a generally accepted Kit kinase activity assay. In some embodiments, the compound is selective relative to other protein kinases, such that the ratio of $IC_{50}$ for another kinase assessed comparably divided by the $IC_{50}$ for Kit kinase is >20, also >30, also >40, also >50, also >60, also >70, also >80, also >90, also >100, wherein the other protein kinase includes, but is not limited to CSK, Insulin receptor kinase, AMPK, PDGFR or VEGFR.

In some embodiments, a compound as described herein is a dual Fms/Kit inhibitor, i.e. will be approximately equipotent with respect to inhibition of Fms kinase and Kit kinase. In some embodiments the compound will have an $IC_{50}$ of less than 500 nm, less than 100 nM, less than 50 nM, less than 20 nM, less than 10 nM, less than 5 nM, or less than 1 nM as determined in a generally accepted Fms kinase activity assay and will have an $IC_{50}$ of less than 500 nm, less than 100 nM, less than 50 nM, less than 20 nM, less than 10 nM, less than 5 nM, or less than 1 nM as determined in a comparable generally accepted Kit kinase activity assay, wherein the ratio of $IC_{50}$ for Kit kinase divided by the $IC_{50}$ for Fms kinase is in the range of 20 to 0.05, also 10 to 0.1, also 5 to 0.2. In some embodiments, the compound is selective relative to protein kinases other than Kit, such that the ratio of $IC_{50}$ for another kinase assessed comparably, divided by the $IC_{50}$ for Fms kinase is >20, also >30, also >40, also >50, also >60, also >70, also >80, also >90, also >100, wherein the other protein kinase includes, but is not limited to CSK, Insulin receptor kinase, AMPK, PDGFR or VEGFR. In one embodiment, the dual Fms/Kit inhibitor is a compound set forth in Table 7.

TABLE 7

(6-Methoxy-pyridin-3-ylmethyl)-[3-methyl-5-(5-methyl-1H-pyrrolo[2,3-b]pyridin-3-ylmethyl)-pyridin-2-yl]-amine (P-1554),
[3-Fluoro-5-(5-methyl-1H-pyrrolo[2,3-b]pyridin-3-ylmethyl)-pyridin-2-yl]-(6-methoxy-pyridin-3-ylmethyl)-amine (P-1562),
(6-Chloro-pyridin-3-ylmethyl)-[5-(5-chloro-1H-pyrrolo[2,3-b]pyridin-3-ylmethyl)-pyridin-2-yl]-amine (P-2003),
[5-(5-Chloro-1H-pyrrolo[2,3-b]pyridin-3-ylmethyl)-pyridin-2-yl]-(6-fluoro-pyridin-3-ylmethyl)-amine (P-2004),
[5-(5-Chloro-1H-pyrrolo[2,3-b]pyridin-3-ylmethyl)-pyrimidin-2-yl]-(3,4-difluoro-benzyl)-amine (P-2008),
[5-(5-Chloro-1H-pyrrolo[2,3-b]pyridin-3-ylmethyl)-pyrimidin-2-yl]-(3-methyl-benzyl)-amine (P-2013),
[5-(5-Methyl-1H-pyrrolo[2,3-b]pyridin-3-ylmethyl)-pyridin-2-yl]-(6-trifluoromethyl-pyridin-3-ylmethyl)-amine (P-2019),
[6-Fluoro-5-(5-methyl-1H-pyrrolo[2,3-b]pyridin-3-ylmethyl)-pyridin-2-yl]-(6-trifluoromethyl-pyridin-3-ylmethyl)-amine (P-2031),
(4-Chloro-benzyl)-[6-fluoro-5-(5-methoxy-1H-pyrrolo[2,3-b]pyridin-3-ylmethyl)-pyridin-2-yl]-amine (P-2032),
(4-Chloro-benzyl)-[6-fluoro-5-(4-methoxy-1H-pyrrolo[2,3-b]pyridin-3-ylmethyl)-pyridin-2-yl]-amine (P-2037),
(6-Methyl-pyridin-2-ylmethyl)-[5-(5-methyl-1H-pyrrolo[2,3-b]pyridin-3-ylmethyl)-pyrimidin-2-yl]-amine (P-2079),
[5-(5-Methyl-1H-pyrrolo[2,3-b]pyridin-3-ylmethyl)-pyrimidin-2-yl]-(6-morpholin-4-yl-pyridin-2-ylmethyl)-amine (P-2081),
[5-(5-Methyl-1H-pyrrolo[2,3-b]pyridin-3-ylmethyl)-pyrimidin-2-yl]-(6-pyrrolidin-1-yl-pyridin-2-ylmethyl)-amine (P-2082),
[6-Fluoro-5-(5-methyl-1H-pyrrolo[2,3-b]pyridin-3-ylmethyl)-pyridin-2-yl]-(5-methyl-pyridin-2-ylmethyl)-amine (P-2131),
[3-Fluoro-5-(5-methyl-1H-pyrrolo[2,3-b]pyridin-3-ylmethyl)-pyridin-2-yl]-(6-trifluoromethyl-pyridin-3-ylmethyl)-amine (P-2146),
[3-Fluoro-5-(5-methoxy-1H-pyrrolo[2,3-b]pyridin-3-ylmethyl)-pyridin-2-yl]-(6-trifluoromethyl-pyridin-3-ylmethyl)-amine (P-2147),
(2-Cyclopentyloxy-pyridin-3-ylmethyl)-[5-(5-methyl-1H-pyrrolo[2,3-b]pyridin-3-ylmethyl)-pyrimidin-2-yl]-amine (P-2148),
[5-(5-Chloro-1H-pyrrolo[2,3-b]pyridin-3-ylmethyl)-thiazol-2-yl]-(6-methoxy-pyridin-3-ylmethyl)-amine (P-2154),
[5-(5-Chloro-1H-pyrrolo[2,3-b]pyridin-3-ylmethyl)-thiazol-2-yl]-(6-methoxy-pyridin-2-ylmethyl)-amine (P-2163),
[5-(5-Chloro-1H-pyrrolo[2,3-b]pyridin-3-ylmethyl)-3-fluoro-pyridin-2-yl]-(6-trifluoromethyl-pyridin-3-ylmethyl)-amine (P-2172),
Ethanesulfonic acid (2-{[6-fluoro-5-(5-methyl-1H-pyrrolo[2,3-b]pyridin-3-ylmethyl)-pyridin-2-ylamino]-methyl}-phenyl)-amide (P-2198),
Ethanesulfonic acid (3-fluoro-5-{[6-fluoro-5-(5-methyl-1H-pyrrolo[2,3-b]pyridin-3-ylmethyl)-pyridin-2-ylamino]-methyl}-phenyl)-amide (P-2202),
5-[(5-bromo-1H-pyrrolo[2,3-b]pyridin-3-yl)methyl]-6-fluoro-N-[(5-fluoro-6-methoxy-3-pyridyl)methyl]pyridin-2-amine (P-2203),
3-[[2-fluoro-6-[(5-fluoro-6-methoxy-3-pyridyl)methylamino]-3-pyridyl]methyl]-1H-pyrrolo[2,3-b]pyridine-5-carbonitrile (P-2204),
6-chloro-N-[(5-fluoro-2-methoxy-3-pyridyl)methyl]-5-[(5-methyl-1H-pyrrolo[2,3-b]pyridin-3-yl)methyl]pyridin-2-amine (P-2205),
6-fluoro-N-[(5-fluoro-6-methoxy-3-pyridyl)methyl]-5-[[5-(trifluoromethyl)-1H-pyrrolo[2,3-b]pyridin-3-yl]methyl]pyridin-2-amine (P-2206), or
any salt, prodrug, tautomer, or stereoisomer thereof.

In some embodiments, a compound as described herein is a Fms selective inhibitor, i.e. will selectively inhibit Fms kinase relative to Kit kinase. In some embodiments the compound will have an $IC_{50}$ of less than 500 nm, less than 100 nM, less than 50 nM, less than 20 nM, less than 10 nM, less than 5 nM, or less than 1 nM as determined in a generally accepted Fms kinase activity assay and when determined in a comparable generally accepted Kit kinase activity assay will have a ratio of $IC_{50}$ for Kit kinase divided by the $IC_{50}$ for Fms kinase of >20, also >30, also >40, also >50, also >60, also >70, also >80, also >90, also >100. In some embodiments, the compound is also selective relative to protein kinases other than Kit, such that the ratio of $IC_{50}$ for another kinase assessed comparably, divided by the $IC_{50}$ for Fms kinase is >20, also >30, also >40, also >50, also >60, also >70, also >80, also >90, also >100, wherein the other protein kinase includes, but is not limited to Flt-3, CSK, Insulin receptor kinase, AMPK, PDGFR or VEGFR. In one embodiment, the Fms selective inhibitor is a compound set forth in Table 8.

TABLE 8

[5-(5-Chloro-1H-pyrrolo[2,3-b]pyridin-3-ylmethyl)-pyridin-2-yl]-(2,6-dimethoxy-pyridin-3-ylmethyl)-amine (P-1496),
[6-Fluoro-5-(5-fluoro-1H-pyrrolo[2,3-b]pyridin-3-ylmethyl)-pyridin-2-yl]-(6-methoxy-pyridin-3-ylmethyl)-amine (P-1622),
N-(3-{2-Fluoro-6-[(5-fluoro-2-methoxy-pyridin-3-ylmethyl)-amino]-pyridin-3-ylmethyl}-1H-pyrrolo[2,3-b]pyridin-5-yl)-acetamide (P-1669),
N-(3-{6-[(6-Chloro-pyridin-3-ylmethyl)-amino]-2-fluoro-pyridin-3-ylmethyl}-1H-pyrrolo[2,3-b]pyridin-5-yl)-methanesulfonamide (P-1679),
[5-(5-Chloro-1H-pyrrolo[2,3-b]pyridin-3-ylmethyl)-6-fluoro-pyridin-2-yl]-(5-fluoro-pyridin-3-ylmethyl)-amine (P-2001), TABLE 8-continued

[6-Fluoro-5-(5-methoxy-1H-pyrrolo[2,3-b]pyridin-3-ylmethyl)-pyridin-2-yl]-(5-fluoro-pyridin-3-ylmethyl)-amine (P-2028),
[6-Fluoro-5-(5-methyl-1H-pyrrolo[2,3-b]pyridin-3-ylmethyl)-pyridin-2-yl]-(6-methoxy-pyridin-3-ylmethyl)-amine (P-2029),
[6-Fluoro-5-(5-methoxy-1H-pyrrolo[2,3-b]pyridin-3-ylmethyl)-pyridin-2-yl]-(6-methoxy-pyridin-3-ylmethyl)-amine (P-2030),
[5-(5-Chloro-1H-pyrrolo[2,3-b]pyridin-3-ylmethyl)-pyrimidin-2-yl]-(6-methoxy-pyridin-3-ylmethyl)-amine (P-2038),
[6-Fluoro-5-(5-methoxy-1H-pyrrolo[2,3-b]pyridin-3-ylmethyl)-pyridin-2-yl]-(2-methoxy-pyridin-3-ylmethyl)-amine (P-2043),
[6-Fluoro-5-(1H-pyrrolo[2,3-b]pyridin-3-ylmethyl)-pyridin-2-yl]-(2-methoxy-pyridin-3-ylmethyl)-amine (P-2045),
(5-Fluoro-6-methoxy-pyridin-3-ylmethyl)-[6-fluoro-5-(5-methyl-1H-pyrrolo[2,3-b]pyridin-3-ylmethyl)-pyridin-2-yl]-amine (P-2048),
(5-Fluoro-2-methoxy-pyridin-3-ylmethyl)-[6-fluoro-5-(5-methyl-1H-pyrrolo[2,3-b]pyridin-3-ylmethyl)-pyridin-2-yl]-amine (P-2049),
[6-Fluoro-5-(5-methyl-1H-pyrrolo[2,3-b]pyridin-3-ylmethyl)-pyridin-2-yl]-(2-methoxy-pyridin-3-ylmethyl)-amine (P-2052),
(6-Methoxy-pyridin-3-ylmethyl)-[5-(5-methyl-1H-pyrrolo[2,3-b]pyridin-3-ylmethyl)-pyrimidin-2-yl]-amine (P-2057),
(5-Fluoro-2-methoxy-pyridin-3-ylmethyl)-[5-(5-methyl-1H-pyrrolo[2,3-b]pyridin-3-ylmethyl)-pyrimidin-2-yl]-amine (P-2061),
[6-Fluoro-5-(5-methyl-1H-pyrrolo[2,3-b]pyridin-3-ylmethyl)-pyridin-2-yl]-(4-trifluoromethyl-pyridin-3-ylmethyl)-amine (P-2062),
[5-(5-Chloro-1H-pyrrolo[2,3-b]pyridin-3-ylmethyl)-pyridin-2-yl]-(4-trifluoromethyl-pyridin-3-ylmethyl)-amine (P-2063),
[5-(5-Chloro-1H-pyrrolo[2,3-b]pyridin-3-ylmethyl)-pyrimidin-2-yl]-(5-fluoro-2-methoxy-pyridin-3-ylmethyl)-amine (P-2064),
[6-Fluoro-5-(5-methyl-1H-pyrrolo[2,3-b]pyridin-3-ylmethyl)-pyridin-2-yl]-(2-methyl-pyridin-4-ylmethyl)-amine (P-2067),
[5-(5-Methyl-1H-pyrrolo[2,3-b]pyridin-3-ylmethyl)-pyridin-2-yl]-(4-trifluoromethyl-pyridin-3-ylmethyl)-amine (P-2070),
(5-Fluoro-2-methoxy-pyridin-4-ylmethyl)-[6-fluoro-5-(5-methyl-1H-pyrrolo[2,3-b]pyridin-3-ylmethyl)-pyridin-2-yl]-amine (P-2071),
(5-Fluoro-6-methoxy-pyridin-3-ylmethyl)-[5-(5-methyl-1H-pyrrolo[2,3-b]pyridin-3-ylmethyl)-pyrimidin-2-yl]-amine (P-2073),
[5-(5-Chloro-1H-pyrrolo[2,3-b]pyridin-3-ylmethyl)-6-fluoro-pyridin-2-yl]-(2-methyl-pyridin-4-ylmethyl)-amine (P-2075),
(6-Chloro-pyridin-3-ylmethyl)-[5-(5-methyl-1H-pyrrolo[2,3-b]pyridin-3-ylmethyl)-pyrimidin-2-yl]-amine (P-2078),
(6-Chloro-pyridin-3-ylmethyl)-[6-fluoro-5-(5-methyl-1H-pyrrolo[2,3-b]pyridin-3-ylmethyl)-pyridin-2-yl]-amine (P-2088),
(2,6-Dimethoxy-pyridin-3-ylmethyl)-[6-fluoro-5-(5-methyl-1H-pyrrolo[2,3-b]pyridin-3-ylmethyl)-pyridin-2-yl]-amine (P-2097),
[6-Fluoro-5-(5-methyl-1H-pyrrolo[2,3-b]pyridin-3-ylmethyl)-pyridin-2-yl]-(2-fluoro-pyridin-3-ylmethyl)-amine (P-2103),
[6-Fluoro-5-(5-methyl-1H-pyrrolo[2,3-b]pyridin-3-ylmethyl)-pyridin-2-yl]-(2-fluoro-pyridin-4-ylmethyl)-amine (P-2118),
(2-Methoxy-pyridin-3-ylmethyl)-[5-(5-methyl-1H-pyrrolo[2,3-b]pyridin-3-ylmethyl)-pyrimidin-2-yl]-amine (P-2139),
3-{[5-(5-Chloro-1H-pyrrolo[2,3-b]pyridin-3-ylmethyl)-pyrimidin-2-ylamino]-methyl}-5-fluoro-1-methyl-1H-pyridin-2-one (P-2157),
[5-(5-Chloro-1H-pyrrolo[2,3-b]pyridin-3-ylmethyl)-6-fluoro-pyridin-2-yl]-(5-fluoro-6-methoxy-pyridin-3-ylmethyl)-amine (P-2165),
[5-(5-Chloro-1H-pyrrolo[2,3-b]pyridin-3-ylmethyl)-pyrimidin-2-yl]-(5-fluoro-pyridin-3-ylmethyl)-amine (P-2176),
3-{2-Fluoro-6-[(5-fluoro-2-methoxy-pyridin-3-ylmethyl)-amino]-pyridin-3-ylmethyl}-1H-pyrrolo[2,3-b]pyridine-5-carbonitrile (P-2193),
5-[(5-bromo-1H-pyrrolo[2,3-b]pyridin-3-yl)methyl]-6-fluoro-N-[(5-fluoro-6-methoxy-3-pyridyl)methyl]pyridin-2-amine (P-2203),
3-[[2-fluoro-6-[(5-fluoro-6-methoxy-3-pyridyl)methylamino]-3-pyridyl]methyl]-1H-pyrrolo[2,3-b]pyridine-5-carbonitrile (P-2204),
6-chloro-N-[(5-fluoro-2-methoxy-3-pyridyl)methyl]-5-[(5-methyl-1H-pyrrolo[2,3-b]pyridin-3-yl)methyl]pyridin-2-amine (P-2205),
6-fluoro-N-[(5-fluoro-6-methoxy-3-pyridyl)methyl]-5-[[5-(trifluoromethyl)-1H-pyrrolo[2,3-b]pyridin-3-yl]methyl]pyridin-2-amine (P-2206), or any salt, prodrug, tautomer, or stereoisomer thereof.

In some embodiments, a compound as described herein is a dual Fms/Flt-3 inhibitor, i.e. will be approximately equipotent with respect to inhibition of Fms kinase and Flt-3 kinase. In some embodiments the compound will have an $IC_{50}$ of less than 500 nm, less than 100 nM, less than 50 nM, less than 20 nM, less than 10 nM, less than 5 nM, or less than 1 nM as determined in a generally accepted Fms kinase activity assay and will have an $IC_{50}$ of less than 500 nm, less than 100 nM, less than 50 nM, less than 20 nM, less than 10 nM, less than 5 nM, or less than 1 nM as determined in a comparable generally accepted Flt-3 kinase activity assay, wherein the ratio of $IC_{50}$ for Flt-3 kinase divided by the $IC_{50}$ for Fms kinase is in the range of 20 to 0.05, also 10 to 0.1, also 5 to 0.2. In some embodiments, the compound is selective relative to protein kinases other than Flt-3, such that the ratio of $IC_{50}$ for another kinase assessed comparably, divided by the $IC_{50}$ for Fms kinase is >20, also >30, also >40, also >50, also >60, also >70, also >80, also >90, also >100, wherein the other protein kinase includes, but is not limited to CSK, Insulin receptor kinase, AMPK, PDGFR or VEGFR. In some embodiments, the dual Fms/Flt-3 inhibitor also inhibits Kit. In one embodiment, the dual Fms/Flt-3 inhibitor is a compound set forth in Table 9.

TABLE 9

(6-Trifluoromethyl-pyridin-3-ylmethyl)-[5-(5-trifluoromethyl-1H-pyrrolo[2,3-b]pyridin-3-ylmethyl)-pyridin-2-yl]-amine (P-1644),
(5-Fluoro-6-methoxy-pyridin-3-ylmethyl)-[6-fluoro-5-(5-trifluoromethyl-1H-pyrrolo[2,3-b]pyridin-3-ylmethyl)-pyridin-2-yl]-amine (P-1646),
[5-(5-Cyclopropyl-1H-pyrrolo[2,3-b]pyridin-3-ylmethyl)-pyridin-2-yl]-(6-trifluoromethyl-pyridin-3-ylmethyl)-amine (P-1667),
(6-Chloro-pyridin-3-ylmethyl)-[5-(5-chloro-1H-pyrrolo[2,3-b]pyridin-3-ylmethyl)-pyridin-2-yl]-amine (P-2003),
[5-(5-Chloro-1H-pyrrolo[2,3-b]pyridin-3-ylmethyl)-pyridin-2-yl]-(6-fluoro-pyridin-3-ylmethyl)-amine (P-2004),
[5-(5-Chloro-1H-pyrrolo[2,3-b]pyridin-3-ylmethyl)-pyrimidin-2-yl]-(3-fluoro-5-trifluoromethyl-benzyl)-amine (P-2009),
[5-(5-Methyl-1H-pyrrolo[2,3-b]pyridin-3-ylmethyl)-pyridin-2-yl]-(6-trifluoromethyl-pyridin-3-ylmethyl)-amine (P-2019),
[6-Fluoro-5-(5-methyl-1H-pyrrolo[2,3-b]pyridin-3-ylmethyl)-pyridin-2-yl]-(6-methoxy-pyridin-3-ylmethyl)-amine (P-2029),
[6-Fluoro-5-(5-methoxy-1H-pyrrolo[2,3-b]pyridin-3-ylmethyl)-pyridin-2-yl]-(6-methoxy-pyridin-3-ylmethyl)-amine (P-2030),
[6-Fluoro-5-(5-methyl-1H-pyrrolo[2,3-b]pyridin-3-ylmethyl)-pyridin-2-yl]-(6-trifluoromethyl-pyridin-3-ylmethyl)-amine (P-2031),
(4-Chloro-benzyl)-[6-fluoro-5-(5-methoxy-1H-pyrrolo[2,3-b]pyridin-3-ylmethyl)-pyridin-2-yl]-amine (P-2032),
(2-Chloro-benzyl)-[6-fluoro-5-(5-methoxy-1H-pyrrolo[2,3-b]pyridin-3-ylmethyl)-pyridin-2-yl]-amine (P-2034),
(4-Chloro-benzyl)-[6-fluoro-5-(4-methoxy-1H-pyrrolo[2,3-b]pyridin-3-ylmethyl)-pyridin-2-yl]-amine (P-2037),
[5-(5-Chloro-1H-pyrrolo[2,3-b]pyridin-3-ylmethyl)-pyrimidin-2-yl]-(6-methoxy-pyridin-3-ylmethyl)-amine (P-2038),
(5-Fluoro-6-methoxy-pyridin-3-ylmethyl)-[6-fluoro-5-(5-methoxy-1H-pyrrolo[2,3-b]pyridin-3-ylmethyl)-pyridin-2-yl]-amine (P-2040),
(5-Fluoro-6-methoxy-pyridin-3-ylmethyl)-[6-fluoro-5-(1H-pyrrolo[2,3-b]pyridin-3-ylmethyl)-pyridin-2-yl]-amine (P-2041),
(5-Chloro-pyridin-2-ylmethyl)-[6-fluoro-5-(1H-pyrrolo[2,3-b]pyridin-3-ylmethyl)-pyridin-2-yl]-amine (P-2044),
(5-Chloro-pyridin-2-ylmethyl)-[6-fluoro-5-(5-methyl-1H-pyrrolo[2,3-b]pyridin-3-ylmethyl)-pyridin-2-yl]-amine (P-2047),
(5-Fluoro-6-methoxy-pyridin-3-ylmethyl)-[6-fluoro-5-(5-methyl-1H-pyrrolo[2,3-b]pyridin-3-ylmethyl)-pyridin-2-yl]-amine (P-2048),
(4-Chloro-benzyl)-[6-fluoro-5-(5-methyl-1H-pyrrolo[2,3-b]pyridin-3-ylmethyl)-pyridin-2-yl]-amine (P-2050),
(6-Methoxy-pyridin-3-ylmethyl)-[5-(5-methyl-1H-pyrrolo[2,3-b]pyridin-3-ylmethyl)-pyrimidin-2-yl]-amine (P-2057),
[5-(5-Chloro-1H-pyrrolo[2,3-b]pyridin-3-ylmethyl)-6-fluoro-pyridin-2-yl]-(5-fluoro-6-methoxy-pyridin-3-ylmethyl)-amine (P-2165),
5-[(5-bromo-1H-pyrrolo[2,3-b]pyridin-3-yl)methyl]-6-fluoro-N-[(5-fluoro-6-methoxy-3-pyridyl)methyl]pyridin-2-amine (P-2203),
3-[[2-fluoro-6-[(5-fluoro-6-methoxy-3-pyridyl)methylamino]-3-pyridyl]methyl]-1H-pyrrolo[2,3-b]pyridine-5-carbonitrile (P-2204),
6-chloro-N-[(5-fluoro-2-methoxy-3-pyridyl)methyl]-5-[(5-methyl-1H-pyrrolo[2,3-b]pyridin-3-yl)methyl]pyridin-2-amine (P-2205),
6-fluoro-N-[(5-fluoro-6-methoxy-3-pyridyl)methyl]-5-[[5-[(trifluoromethyl)-1H-pyrrolo[2,3-b]pyridin-3-yl]methyl]pyridin-2-amine (P-2206), and
any salt, prodrug, tautomer, or stereoisomer thereof.

In one embodiment, the dual Fms/Flt-3 inhibitor is a compound selected from the group consisting of:
(6-Trifluoromethyl-pyridin-3-ylmethyl)-[5-(5-trifluoromethyl-1H-pyrrolo[2,3-b]pyridin-3-ylmethyl)-pyridin-2-yl]-amine (P-1644),
(5-Fluoro-6-methoxy-pyridin-3-ylmethyl)-[6-fluoro-5-(5-trifluoromethyl-1H-pyrrolo[2,3-b]pyridin-3-ylmethyl)-pyridin-2-yl]-amine (P-1646),
[5-(5-Cyclopropyl-1H-pyrrolo[2,3-b]pyridin-3-ylmethyl)-pyridin-2-yl]-(6-trifluoromethyl-pyridin-3-ylmethyl)-amine (P-1667),
[5-(5-Chloro-1H-pyrrolo[2,3-b]pyridin-3-ylmethyl)-pyrimidin-2-yl]-(3-fluoro-5-trifluoromethyl-benzyl)-amine (P-2009),
(2-Chloro-benzyl)-[6-fluoro-5-(5-methoxy-1H-pyrrolo[2,3-b]pyridin-3-ylmethyl)-pyridin-2-yl]-amine (P-2034),
(4-Chloro-benzyl)-[6-fluoro-5-(4-methoxy-1H-pyrrolo[2,3-b]pyridin-3-ylmethyl)-pyridin-2-yl]-amine (P-2037),
(5-Fluoro-6-methoxy-pyridin-3-ylmethyl)-[6-fluoro-5-(5-methoxy-1H-pyrrolo[2,3-b]pyridin-3-ylmethyl)-pyridin-2-yl]-amine (P-2040),
(5-Fluoro-6-methoxy-pyridin-3-ylmethyl)-[6-fluoro-5-(1H-pyrrolo[2,3-b]pyridin-3-ylmethyl)-pyridin-2-yl]-amine (P-2041),
(5-Chloro-pyridin-2-ylmethyl)-[6-fluoro-5-(1H-pyrrolo[2,3-b]pyridin-3-ylmethyl)-pyridin-2-yl]-amine (P-2044),
(5-Chloro-pyridin-2-ylmethyl)-[6-fluoro-5-(5-methyl-1H-pyrrolo[2,3-b]pyridin-3-ylmethyl)-pyridin-2-yl]-amine (P-2047),
(4-Chloro-benzyl)-[6-fluoro-5-(5-methyl-1H-pyrrolo[2,3-b]pyridin-3-ylmethyl)-pyridin-2-yl]-amine (P-2050),
5-[(5-bromo-1H-pyrrolo[2,3-b]pyridin-3-yl)methyl]-6-fluoro-N-[(5-fluoro-6-methoxy-3-pyridyl)methyl]pyridin-2-amine (P-2203),
3-[[2-fluoro-6-[(5-fluoro-6-methoxy-3-pyridyl)methylamino]-3-pyridyl]methyl]-1H-pyrrolo[2,3-b]pyridine-5-carbonitrile (P-2204),
6-chloro-N-[(5-fluoro-2-methoxy-3-pyridyl)methyl]-5-[(5-methyl-1H-pyrrolo[2,3-b]pyridin-3-yl)methyl]pyridin-2-amine (P-2205),
6-fluoro-N-[(5-fluoro-6-methoxy-3-pyridyl)methyl]-5-[[5-(trifluoromethyl)-1H-pyrrolo[2,3-b]pyridin-3-yl]methyl]pyridin-2-amine (P-2206), and any salt, prodrug, tautomer, or stereoisomer thereof.

In some embodiments, the disclosure provides a method for treating a disease or condition as described herein by administering to a subject a compound listed in Table 10 or a pharmaceutically acceptable salt thereof.

Further to any of the aspects and embodiments referred to herein, a compound as described herein also inhibits the effects of a mutation of the kinase (e.g. Fms mutant, Kit mutant, Flt-3 mutant, e.g., ITD), including, but not limiting to, a mutation that is related to a disease state, such as a cancer.

In aspects and embodiments involving treatment of a disease or condition with one or more of the compounds described herein, the methods involve administering an effective amount of one or more compound(s) as described herein or a composition to a subject in need thereof suffering from or at risk of a disease or condition selected from the group consisting of from stem cell ablation and myelopreparation for stem cell transplant, monocytic leukemia, primary progressive multiple sclerosis, complex regional pain syndrome, reflex sympathetic dystrophy, muscular dystrophy, duchenne muscular dystrophy, causalgia, malignant peripheral nerve cell tumors, malignant peripheral nerve sheath tumors, pheochromocytomas cutaneous and plexiform neurofibromas, neuro-inflammations, benign forgetfulness, HIV, binswager type dementia, dementia with lewy bodie, prosencephaly, microencepahy, cerebral palsy, congenital hydrocephalus, tremors, Wilson's disease, vascular dementias/multi infarct dementia, fronto temporal type, pseudodementia, papillary thyroid cancer, anaplastic thyroid cancer, medullary thyroid cancer, follicular thyroid cancer, hurthle cell carcinoma, thyroid cancer, ascites, malignant ascites, abdominal dropsy, progressive supranuclear palsy, glaucoma, mesothelioma, salivary gland tumors, mucoepidermoid carcinoma of the salivary gland, acinic cell carcinoma of the salivary gland, and others), gastrointestinal stromal tumors (GIST), tumors that cause effusions in potential spaces of the body, pleural effusions, pericardial effusions, peritoneal effusions aka ascites, giant cell tumors (GCT), GCT of bone, pigmented villonodular synovitis (PVNS), tenosynovial giant cell tumor (TGCT), TCGT of tendon sheath (TGCT-TS), other sarcomas, tumor angiogenesis and paracrine tumor growth; and tumors that express aberrantly or otherwise Fms, CSF1R, CSF1 or IL-34, or activating mutations or translocations of any of the foregoing, wherein the compound is an inhibitor of Kit, i.e. has an $IC_{50}$ of less than 500 nm, less than 100 nM, less than 50 nM, less than 20 nM, less than 10 nM, less than 5 nM, or less than 1 nM as determined in a generally accepted Kit kinase activity assay.

In aspects and embodiments involving treatment of a disease or condition with one or more of the compounds described herein, the methods may involve administering an

TABLE 10

[5-(5-Chloro-1H-pyrrolo[2,3-b]pyridin-3-ylmethyl)-pyrimidin-2-yl]-pyridin-3-ylmethyl-amine (P-0422),
[5-(5-Chloro-1H-pyrrolo[2,3-b]pyridin-3-ylmethyl)-pyrimidin-2-yl]-(6-trifluoromethyl-pyridin-3-ylmethyl)-amine (P-0429),
[4-Chloro-5-(5-chloro-1H-pyrrolo[2,3-b]pyridin-3-ylmethyl)-thiazol-2-yl]-(3-fluoro-pyridin-4-ylmethyl)-amine (P-0200),
[4-Chloro-5-(5-chloro-1H-pyrrolo[2,3-b]pyridin-3-ylmethyl)-thiazol-2-yl]-pyridin-3-ylmethyl-amine (P-0236),
[4-Chloro-5-(5-chloro-1H-pyrrolo[2,3-b]pyridin-3-ylmethyl)-thiazol-2-yl]-(5-methoxy-pyridin-3-ylmethyl)-amine (P-0241),
[4-Chloro-5-(5-chloro-1H-pyrrolo[2,3-b]pyridin-3-ylmethyl)-thiazol-2-yl]-(6-trifluoromethyl-pyridin-3-ylmethyl)-amine (P-0242),
[4-Chloro-5-(5-chloro-1H-pyrrolo[2,3-b]pyridin-3-ylmethyl)-thiazol-2-yl]-(2-methoxy-pyridin-3-ylmethyl)-amine (P-0247),
[4-Chloro-5-(1H-pyrrolo[2,3-b]pyridin-3-ylmethyl)-thiazol-2-yl]-(5-methoxy-pyridin-3-ylmethyl)-amine (P-0207).

effective amount of one or more compound(s) as described herein or a composition to a subject in need thereof suffering from or at risk of a disease or condition selected from the group consisting of from stem cell ablation and myelopreparation for stem cell transplant, primary progressive multiple sclerosis, complex regional pain syndrome, reflex sympathetic dystrophy, muscular dystrophy, duchenne muscular dystrophy, causalgia, neuro-inflammation, neuroinflammatory disorders, benign forgetfulness, HIV, binswager type dementia, dementia with lewy bodie, prosencephaly, microencepahy, cerebral palsy, congenital hydrocephalus, abdominal dropsy, progressive supranuclear palsy, glaucoma, addiction disorders, dependencies, alcoholism, tremors, Wilson's disease, vascular dementias, multi infarct dementia, fronto temporal dementia, pseudo-dementia, bladder cancer, basal cell carcinoma, cholangiocarcinoma, colon cancer, endometrial cancer, esophageal cancer, Ewing's sarcoma, gastric cancer, glioma, hepatocellular carcinoma, Hodgkin lymphoma, laryngeal carcinoma, leukemia, liver cancer, lung cancer, melanoma, mesothelioma, pancreatic cancer, rectal cancer, renal cancer, squamous cell carcinoma, t cell lymphoma, thyroid cancer, monocytic leukemia, pheochromocytoma, malignant peripheral nerve cell tumors, malignant peripheral nerve sheath tumors (MPNST), cutaneous and plexiform neurofibromas, leiomyoadenomatoid tumor, fibroids, uterine fibroids, leiomyosarcoma, papillary thyroid cancer, anaplastic thyroid cancer, medullary thyroid cancer, follicular thyroid cancer, hurthle cell carcinoma, thyroid cancer, ascites, malignant ascites, mesothelioma, salivary gland tumors, mucoepidermoid carcinoma of the salivary gland, acinic cell carcinoma of the salivary gland, gastrointestinal stromal tumors (GIST), tumors that cause effusions in potential spaces of the body, pleural effusions, pericardial effusions, peritoneal effusions aka ascites, giant cell tumors (GCT), GCT of bone, pigmented villonodular synovitis (PVNS), tenosynovial giant cell tumor (TGCT), TCGT of tendon sheath (TGCT-TS), and other sarcomas; tumor angiogenesis and paracrine tumor growth and tumors that express aberrantly or otherwise Fms, CSF1R, CSF1 or IL-34, or activating mutations or translocations of any of the foregoing, wherein the compound is a Fms selective inhibitor, i.e. has an $IC_{50}$ of less than 500 nm, less than 100 nM, less than 50 nM, less than 20 nM, less than 10 nM, less than 5 nM, or less than 1 nM as determined in a generally accepted Fms kinase activity assay and when determined in a comparable generally accepted Kit kinase activity assay will have a ratio of $IC_{50}$ for Kit kinase divided by the $IC_{50}$ for Fms kinase of >20, also >30, also >40, also >50, also >60, also >70, also >80, also >90, also >100; in some embodiments, the compound is also selective relative to protein kinases other than Kit, such that the ratio of $IC_{50}$ for another kinase assessed comparably, divided by the $IC_{50}$ for Fms kinase is >20, also >30, also >40, also >50, also >60, also >70, also >80, also >90, also >100, wherein the other protein kinase includes, but is not limited to Flt-3, CSK, Insulin receptor kinase, AMPK, PDGFR or VEGFR.

In aspects and embodiments involving treatment of a disease or condition with one or more of the compounds described herein, the methods may involve administering an effective amount of one or more compound(s) as described herein to a subject in need thereof suffering from or at risk of a disease or condition selected from the group consisting of stem cell ablation and myelopreparation for stem cell transplant, primary progressive multiple sclerosis, complex regional pain syndrome, reflex sympathetic dystrophy, muscular dystrophy, duchenne muscular dystrophy, causalgia, neuro-inflammation, neuroinflammatory disorders, benign forgetfulness, HIV, binswager type dementia, dementia with lewy bodie, prosencephaly, microencepahy, cerebral palsy, congenital hydrocephalus, abdominal dropsy, progressive supranuclear palsy, glaucoma, addiction disorders, dependencies, alcoholism, tremors, Wilson's disease, vascular dementias, multi infarct dementia, fronto temporal dementia, pseudo-dementia, bladder cancer, basal cell carcinoma, cholangiocarcinoma, colon cancer, endometrial cancer, esophageal cancer, Ewing's sarcoma, gastric cancer, glioma, hepatocellular carcinoma, Hodgkin lymphoma, laryngeal carcinoma, leukemia, liver cancer, lung cancer, melanoma, mesothelioma, pancreatic cancer, rectal cancer, renal cancer, squamous cell carcinoma, t cell lymphoma, thyroid cancer, monocytic leukemia, pheochromocytoma, malignant peripheral nerve cell tumors, malignant peripheral nerve sheath tumors (MPNST), cutaneous and plexiform neurofibromas, leiomyoadenomatoid tumor, fibroids, uterine fibroids, leiomyosarcoma, papillary thyroid cancer, anaplastic thyroid cancer, medullary thyroid cancer, follicular thyroid cancer, hurthle cell carcinoma, thyroid cancer, ascites, malignant ascites, mesothelioma, salivary gland tumors, mucoepidermoid carcinoma of the salivary gland, acinic cell carcinoma of the salivary gland, gastrointestinal stromal tumors (GIST), tumors that cause effusions in potential spaces of the body, pleural effusions, pericardial effusions, peritoneal effusions aka ascites, giant cell tumors (GCT), GCT of bone, pigmented villonodular synovitis (PVNS), tenosynovial giant cell tumor (TGCT), TCGT of tendon sheath (TGCT-TS), other sarcomas; tumor angiogenesis and paracrine tumor growth and tumors that express aberrantly or otherwise Fms, CSF1R, CSF1 or IL-34, or activating mutations or translocations of any of the foregoing, wherein the compound is a dual Fms/Kit inhibitor, i.e. has an $IC_{50}$ of less than 500 nm, less than 100 nM, less than 50 nM, less than 20 nM, less than 10 nM, less than 5 nM, or less than 1 nM as determined in a generally accepted Fms kinase activity assay and will have an $IC_{50}$ of less than 500 nm, less than 100 nM, less than 50 nM, less than 20 nM, less than 10 nM, less than 5 nM, or less than 1 nM as determined in a comparable generally accepted Kit kinase activity assay, wherein the ratio of $IC_{50}$ for Kit kinase divided by the $IC_{50}$ for Fms kinase is in the range of 20 to 0.05, also 10 to 0.1, also 5 to 0.2; in some embodiments, the compound is also selective relative to protein kinase other than Kit, such that the ratio of $IC_{50}$ for another kinase assessed comparably divided by the $IC_{50}$ for Fms kinase is >20, also >30, also >40, also >50, also >60, also >70, also >80, also >90, also >100, wherein the other protein kinase includes, but is not limited to CSK, Insulin receptor kinase, AMPK, PDGFR or VEGFR.

In aspects and embodiments involving treatment of a disease or condition with one or more of the compounds described herein, the methods may involve administering an effective amount of one or more compound(s) as described herein to a subject in need thereof suffering from or at risk of acute myeloid leukemia, wherein the compound is a dual Fms/Flt-3 inhibitor, i.e. has an $IC_{50}$ of less than 500 nm, less than 100 nM, less than 50 nM, less than 20 nM, less than 10 nM, less than 5 nM, or less than 1 nM as determined in a generally accepted Fms kinase activity assay and will have an $IC_{50}$ of less than 500 nm, less than 100 nM, less than 50 nM, less than 20 nM, less than 10 nM, less than 5 nM, or less than 1 nM as determined in a comparable generally accepted Flt-3 kinase activity assay, wherein the ratio of $IC_{50}$ for Flt-3 kinase divided by the $IC_{50}$ for Fms kinase is in the range of 20 to 0.05, also 10 to 0.1, also 5 to 0.2; in some embodiments, the compound is also selective relative to protein kinase other than Flt-3, such that the ratio of $IC_{50}$ for another kinase assessed comparably divided by the $IC_{50}$ for Fms kinase is >20, also >30, also >40, also >50, also >60, also >70, also >80, also >90, also >100, wherein the other protein kinase includes, but is not limited to CSK, Insulin receptor kinase, AMPK, PDGFR or VEGFR.

In another aspect, the disclosure provides kits that include a compound or composition thereof as described herein. In some embodiments, the compound or composition is packaged, e.g., in a vial, bottle, flask, which may be further packaged, e.g., within a box, envelope, or bag; the compound or composition is approved by the U.S. Food and Drug Administration or similar regulatory agency for administration to a mammal, e.g., a human; the compound or composition is approved for administration to a mammal, e.g., a human, for a Fms and/or Kit protein kinase mediated disease or condition; the disclosure kit includes written instructions for use and/or other indication that the compound or composition is suitable or approved for administration to a mammal, e.g., a human, for a Fms and/or Kit protein kinase-mediated disease or condition; and the compound or composition is packaged in unit dose or single dose form, e.g., single dose pills, capsules, or the like.

In yet another aspect, one or more compounds or compositions as described herein can be used in the preparation of a medicament for the treatment of a Kit-mediated disease or condition as described herein, a Fms-mediated disease or condition as described herein, a Fms-mediated and Kit-mediated disease or condition as described herein, a Flt3-mediated disease or condition as described herein or a Fms-mediated and Flt3-mediated disease or condition as described herein, wherein the Kit, Fms or Flt3 kinases can include any mutations thereof. In other embodiments, the disclosure provides one or more compounds or compositions as described herein for use in treating a Fms-mediated and Kit-mediated disease or condition as described herein. In yet other embodiments, the disclosure provides one or more compounds or compositions as described herein for use in treating a Kit-mediated disease or condition as described herein. In still other embodiments, the disclosure provides one or more compounds or compositions as described herein for use in treating a Fms-mediated disease or condition as described herein.

In some embodiments, one or more compounds as described herein can be used in the preparation of a medicament for the treatment of a disease or condition selected from the group consisting of stem cell ablation and myelo-preparation for stem cell transplant, primary progressive multiple sclerosis, complex regional pain syndrome, reflex sympathetic dystrophy, muscular dystrophy, duchenne muscular dystrophy, causalgia, neuro-inflammation, neuroinflammatory disorders, benign forgetfulness, HIV, binswager type dementia, dementia with lewy bodie, prosencephaly, microencepahy, cerebral palsy, congenital hydrocephalus, abdominal dropsy, progressive supranuclear palsy, glaucoma, addiction disorders, dependencies, alcoholism, tremors, Wilson's disease, vascular dementias, multi infarct dementia, fronto temporal dementia, pseudo-dementia, bladder cancer, basal cell carcinoma, cholangiocarcinoma, colon cancer, endometrial cancer, esophageal cancer, Ewing's sarcoma, gastric cancer, glioma, hepatocellular carcinoma, Hodgkin lymphoma, laryngeal carcinoma, leukemia, liver cancer, lung cancer, melanoma, mesothelioma, pancreatic cancer, rectal cancer, renal cancer, squamous cell carcinoma, t cell lymphoma, thyroid cancer, monocytic leukemia, pheochromocytoma, malignant peripheral nerve cell tumors, malignant peripheral nerve sheath tumors (MPNST), cutaneous and plexiform neurofibromas, leiomyoadenomatoid tumor, fibroids, uterine fibroids, leiomyosarcoma, papillary thyroid cancer, anaplastic thyroid cancer, medullary thyroid cancer, follicular thyroid cancer, hurthle cell carcinoma, thyroid cancer, ascites, malignant ascites, mesothelioma, salivary gland tumors, mucoepidermoid carcinoma of the salivary gland, acinic cell carcinoma of the salivary gland, gastrointestinal stromal tumors (GIST), tumors that cause effusions in potential spaces of the body, pleural effusions, pericardial effusions, peritoneal effusions aka ascites, giant cell tumors (GCT), GCT of bone, pigmented villonodular synovitis (PVNS), tenosynovial giant cell tumor (TGCT), TCGT of tendon sheath (TGCT-TS), other sarcomas; tumor angiogenesis and paracrine tumor growth; and tumors that express aberrantly or otherwise Fms, CSF1R, CSF1 or IL-34, or activating mutations or translocations of any of the foregoing.

In some embodiments, one or more compounds as described herein that are Kit inhibitors can be used in the preparation of a medicament for the treatment of neuro-inflammations, benign forgetfulness, HIV, binswager type dementia, dementia with lewy bodie, prosencephaly, microencepahy, cerebral palsy, congenital hydrocephalus, tremors, Wilson's disease, vascular dementias/multi infarct dementia, fronto temporal type, pseudo-dementia, papillary thyroid cancer, anaplastic thyroid cancer, medullary thyroid cancer, follicular thyroid cancer, hurthle cell carcinoma, thyroid cancer, ascites and malignant ascites.

In some embodiments, one or more compounds as described herein that are Fms selective inhibitors can be used in the preparation of a medicament for the treatment of neuro-inflammations, benign forgetfulness, HIV, binswager type dementia, dementia with lewy bodie, prosencephaly, microencepahy, cerebral palsy, congenital hydrocephalus, tremors, Wilson's disease, vascular dementias/multi infarct dementia, fronto temporal type, pseudo-dementia, papillary thyroid cancer, anaplastic thyroid cancer, medullary thyroid cancer, follicular thyroid cancer, hurthle cell carcinoma, thyroid cancer, ascites, and malignant ascites.

In some embodiments, one or more compounds as described herein that are Fms selective inhibitors that effectively cross the blood brain barrier can be used in the preparation of a medicament for the treatment of multiple sclerosis, glioblastoma, Alzheimer's disease, or Parkinson's disease.

In some embodiments, one or more compounds as described herein that are Fms selective inhibitors that do not effectively cross the blood brain barrier can be used in the preparation of a medicament for the treatment of rheumatoid arthritis, osteoarthritis, atherosclerosis, systemic lupus erythematosus, glomerulonephritis, interstitial nephritis, Lupus nephritis, tubular necrosis, diabetic nephropathy, or renal hypertrophy.

In some embodiments, one or more compounds as described herein that are dual Fms/Kit inhibitors can be used in the preparation of a medicament for the treatment of metastatic breast cancer, prostate cancer, multiple myeloma, melanoma, acute myeloid leukemia, brain metastases, neurofibromatosis, gastrointestinal stromal tumors, rheumatoid arthritis, or multiple sclerosis.

One or more compounds as described herein that are dual Fms/Kit inhibitors can be used in the preparation of a medicament for the treatment of neuro-inflammations, benign forgetfulness, HIV, binswager type dementia, dementia with lewy bodie, prosencephaly, microencepahy, cerebral palsy, congenital hydrocephalus, primary progressive multiple sclerosis, complex regional pain syndrome, reflex sympathetic dystrophy, muscular dystrophy, duchenne muscular dystrophy, causalgia, tremors, Wilson's disease, vascular dementias/multi infarct dementia, fronto temporal type, pseudo-dementia, papillary thyroid cancer, anaplastic thyroid cancer, medullary thyroid cancer, follicular thyroid cancer, hurthle cell carcinoma, thyroid cancer, ascites, and malignant ascites.

In some embodiments, one or more compounds as described herein that are dual Fms/Flt-3 inhibitors can be used in the preparation of a medicament for the treatment of acute myeloid leukemia.

In another aspect, one or more compounds or compositions as described herein can be used for the treatment of a Kit-mediated disease or condition as described herein, a Fms-mediated disease or condition as described herein, a Fms-mediated and Kit-mediated disease or condition as described herein, a Flt3-mediated disease or condition as described herein or a Fms-mediated and Flt3-mediated disease or condition as described herein, wherein the Kit, Fms or Flt3 kinases can include any mutations thereof. In other embodiments, the disclosure provides one or more compounds or compositions as described herein for use in treating a Fms-mediated and Kit-mediated disease or condition as described herein. In yet other embodiments, the disclosure provides one or more compounds or compositions as described herein for use in treating a Kit-mediated disease or condition as described herein. In still other embodiments, the disclosure provides one or more compounds or compositions as described herein for use in treating a Fms-mediated disease or condition as described herein.

In some embodiments, one or more compounds as described herein can be used for the treatment of a disease or condition selected from the group consisting of stem cell ablation and myelopreparation for stem cell transplant, primary progressive multiple sclerosis, complex regional pain syndrome, reflex sympathetic dystrophy, muscular dystrophy, duchenne muscular dystrophy, causalgia, neuro-inflammation, neuroinflammatory disorders, benign forgetfulness, HIV, binswager type dementia, dementia with lewy bodie, prosencephaly, microencepahy, cerebral palsy, congenital hydrocephalus, abdominal dropsy, progressive supranuclear palsy, glaucoma, addiction disorders, dependencies, alcoholism, tremors, Wilson's disease, vascular dementias, multi infarct dementia, fronto temporal dementia, pseudo-dementia, bladder cancer, basal cell carcinoma, cholangiocarcinoma, colon cancer, endometrial cancer, esophageal cancer, Ewing's sarcoma, gastric cancer, glioma, hepatocellular carcinoma, Hodgkin lymphoma, laryngeal carcinoma, leukemia, liver cancer, lung cancer, melanoma, mesothelioma, pancreatic cancer, rectal cancer, renal cancer, squamous cell carcinoma, t cell lymphoma, thyroid cancer, monocytic leukemia, pheochromocytoma, malignant peripheral nerve cell tumors, malignant peripheral nerve sheath tumors (MPNST), cutaneous and plexiform neurofibromas, leiomyoadenomatoid tumor, fibroids, uterine fibroids, leiomyosarcoma, papillary thyroid cancer, anaplastic thyroid cancer, medullary thyroid cancer, follicular thyroid cancer, hurthle cell carcinoma, thyroid cancer, ascites, malignant ascites, mesothelioma, salivary gland tumors, mucoepidermoid carcinoma of the salivary gland, acinic cell carcinoma of the salivary gland, gastrointestinal stromal tumors (GIST), tumors that cause effusions in potential spaces of the body, pleural effusions, pericardial effusions, peritoneal effusions aka ascites, giant cell tumors (GCT), GCT of bone, pigmented villonodular synovitis (PVNS), tenosynovial giant cell tumor (TGCT), TCGT of tendon sheath (TGCT-TS), other sarcomas, tumor angiogenesis and paracrine tumor growth. In some embodiments, one or more compounds as described herein can be used for the treatment of tumors that express aberrantly or otherwise Fms, CSF1R, CSF1 or IL-34, or activating mutations or translocations of any of the foregoing. In other embodiments, In some embodiments, one or more compounds as described herein can be used for the treatment of tumors that express aberrantly or otherwise Kit, SCFR, SCF, or activating mutations or translocations of any of the foregoing. In yet other embodiments, In some embodiments, one or more compounds as described herein can be used for the treatment of tumors that express aberrantly or otherwise Flt3, Flt3 ligand, or activating mutations or translocations of any of the foregoing.

In some embodiments, the disclosure provides a method for regulating/modulating tumor associated macrophages (TAM), for example, by depleting, inhibiting or reducing TAM or blocking proliferation, migration or activation of TAM in a subject. The method includes administering to the subject an effective amount of a compound of any of formulas (I), (I'), (II), (II'), (IIa), (III), (III') and (IV), or a compound set forth in any of Tables 1 and 3-10, or a compound or a composition as described herein. In certain embodiments, the disclosure provides a method for treating a cancer mediated or modulated by TAM. The method includes administering to the subject an effective amount of a compound of any of formulas (I), (I'), (II), (II'), (IIa), (III), (III') and (IV), or a compound set forth in any of Tables 1 and 3-10, or a compound or a composition as described herein. In other embodiments, the disclosure provides a method for inhibiting infiltrating macrophages. The methods include administering to the subject an effective amount of a compound of any of formulas (I), (I'), (II), (II'), (IIa), (III), (III') and (IV), or a compound set forth in any of Tables 1 and 3-10, or a compound or a composition as described herein.

In some embodiments, the disclosure provides a method for inhibiting, reducing, or blocking proliferation, migration or activation of microglia in a subject. The method includes administering to the subject an effective amount of a compound of any of formulas (I), (I'), (II), (II'), (IIa), (III), (III') and (IV), or a compound set forth in any of Tables 1 and 3-10, or a compound or a composition as described herein. In one embodiment, the disclosure provides a method for depleting and/or eliminating microglia in a subject. The method includes administering to the subject an effective amount of a compound of any of formulas (I), (I'), (II), (II'), (IIa), (III), (III') and (IV), or a compound set forth in any of Tables 1 and 3-10, or a compound or a composition as described herein.

In some embodiments, the disclosure provides a method for inhibiting, reducing, or blocking proliferation, migration or activation of monocytes in a subject. In certain instances, the monocytes are CD14+CD16++ monocytes. In another instance, the monocytes are CD11b+ monocytes. The method includes administering to the subject an effective amount of a compound of any of formulas (I), (I'), (II), (II'), (IIa), (III), (III') and (IV), or a compound set forth in any of Tables 1 and 3-10, or a compound or a composition as described herein.

In some embodiments, the disclosure provides a method for inhibiting, reducing, or blocking proliferation, migration or activation of mast cells in a subject. The method includes administering to the subject an effective amount of a compound of any of formulas (I), (I'), (II), (II'), (IIa), (III), (III') and (IV), or a compound set forth in any of Tables 1 and 3-10, or a compound or a composition as described herein.

In some embodiments, the disclosure provides a method for inhibiting, reducing, or blocking proliferation, migration or activation of osteoclasts in a subject. The method includes administering to the subject an effective amount of a compound of any of formulas (I), (I'), (II), (II'), (IIa), (III), (III') and (IV), or a compound set forth in any of Tables 1 and 3-10, or a compound or a composition as described herein.

In certain embodiments, the disclosure provides a method for treating bone osteolysis and/or bone pain. The method includes administering to the subject in need thereof an effective amount of a compound of any of formulas (I), (I'), (II), (II'), (IIa), (III), (III') and (IV), or a compound set forth in any of Tables 1 and 3-10, or a compound or a composition as described herein.

In certain embodiments, the disclosure provides a method for preventing bone and joint destruction and/or protecting bone damages from tumor cells. The method includes administering to the subject in need thereof an effective amount of a compound of any of formulas (I), (I'), (II), (II'), (IIa), (III), (III') and (IV), or a compound set forth in any of Tables 1 and 3-10, or a compound or a composition as described herein.

In certain aspects, one or more compounds as described herein can be used for the treatment of stem cell ablation and myelopreparation for stem cell transplant.

In certain aspects, one or more compounds as described herein can be used for the treatment of monocytic leukemia.

In certain aspects, one or more compounds as described herein can be used for the treatment of malignant peripheral nerve cell tumors.

In another aspect, one or more compounds as described herein can be used for the treatment of malignant peripheral nerve sheath tumors.

In certain aspects, one or more compounds as described herein can be used for the treatment of pheochromocytomas cutaneous and plexiform neurofibromas.

In certain aspects, one or more compounds as described herein can be used for the treatment of neuro-inflammation.

In certain aspects, one or more compounds as described herein can be used for the treatment of benign forgetfulness.

In certain aspects, one or more compounds as described herein can be used for the treatment of binswager type dementia.

In certain aspects, one or more compounds as described herein can be used for the treatment of dementia with lewy bodie.

In certain aspects, one or more compounds as described herein can be used for the treatment of prosencephaly.

In certain aspects, one or more compounds as described herein can be used for the treatment of microencepahy.

In certain aspects, one or more compounds as described herein can be used for the treatment of cerebral palsy.

In certain aspects, one or more compounds as described herein can be used for the treatment of congenital hydrocephalus.

In certain aspects, one or more compounds as described herein can be used for the treatment of tremors.

In certain aspects, one or more compounds as described herein can be used for the treatment of Wilson's disease.

In certain aspects, one or more compounds as described herein can be used for the treatment of vascular dementias/multi infarct dementia.

In certain aspects, one or more compounds as described herein can be used for the treatment of fronto temporal type, pseudo-dementia.

In certain aspects, one or more compounds as described herein can be used for the treatment of thyroid cancer.

In certain aspects, one or more compounds as described herein can be used for the treatment of papillary thyroid cancer.

In certain aspects, one or more compounds as described herein can be used for the treatment of anaplastic thyroid cancer.

In certain aspects, one or more compounds as described herein can be used for the treatment of medullary thyroid cancer.

In certain aspects, one or more compounds as described herein can be used for the treatment of follicular thyroid cancer.

In certain aspects, one or more compounds as described herein can be used for the treatment of hurthle cell carcinoma.

In certain aspects, one or more compounds as described herein can be used for the treatment of ascites.

In certain aspects, one or more compounds as described herein can be used for the treatment of malignant ascites.

In certain aspects, one or more compounds as described herein can be used for the treatment of abdominal dropsy.

In certain aspects, one or more compounds as described herein can be used for the treatment of progressive supranuclear palsy.

In certain aspects, one or more compounds as described herein can be used for the treatment of glaucoma.

In certain aspects, one or more compounds as described herein can be used for the treatment of mesothelioma.

In certain aspects, one or more compounds as described herein can be used for the treatment of salivary gland tumors.

In certain aspects, one or more compounds as described herein can be used for the treatment of mucoepidermoid carcinoma of the salivary gland.

In certain aspects, one or more compounds as described herein can be used for the treatment of acinic cell carcinoma of the salivary gland, and others.

In certain aspects, one or more compounds as described herein can be used for the treatment of gastrointestinal stromal tumors (GIST).

In certain aspects, one or more compounds as described herein can be used for the treatment of tumors that cause effusions in potential spaces of the body.

In certain aspects, one or more compounds as described herein can be used for the treatment of pleural effusions.

In certain aspects, one or more compounds as described herein can be used for the treatment of pericardial effusions.

In certain aspects, one or more compounds as described herein can be used for the treatment of peritoneal effusions aka ascites.

In certain aspects, one or more compounds as described herein can be used for the treatment of giant cell tumors (GCT).

In certain aspects, one or more compounds as described herein can be used for the treatment of GCT of bone.

In certain aspects, one or more compounds or a composition as described herein can be used for the treatment of pigmented villonodular synovitis (PVNS).

In certain aspects, one or more compounds as described herein can be used for the treatment of tenosynovial giant cell tumor (TGCT).

In certain aspects, one or more compounds as described herein can be used for the treatment of TCGT of tendon sheath (TGCT-TS).

In certain aspects, one or more compounds as described herein can be used for the treatment of sarcomas.

III. Combinations

In one aspect, the disclosure provides methods for treating a Fms protein kinase mediated disease or condition in an animal subject in need thereof, wherein the method involves administering to the subject an effective amount of any one or more compound(s) as described herein. In one embodiment, the method involves administering to the subject an effective amount of a compound as described herein in combination with one or more other therapies for the disease or condition.

In another aspect, the disclosure provides methods for treating a Kit protein kinase mediated disease or condition in an animal subject in need thereof, wherein the method involves administering to the subject an effective amount of any one or more compound(s) as described herein. In one embodiment, the method involves administering to the subject an effective amount of a compound described herein in combination with one or more other therapies for the disease or condition.

In another aspect, compositions are provided that include a therapeutically effective amount of any one or more compound(s) as described herein and at least one pharmaceutically acceptable carrier, excipient, and/or diluent, including combinations of any two or more compounds as described herein. The composition can further include a plurality of different pharmacologically active compounds, which can include a plurality of compounds as described herein. In certain embodiments, the composition can include any one or more compound(s) as described herein along with one or more compounds that are therapeutically effective for the same disease indication. In one aspect, the composition includes any one or more compound(s) as described herein along with one or more compounds that are therapeutically effective for the same disease indication, wherein the compounds have a synergistic effect on the disease indication. In one embodiment, the composition includes any one or more compound(s) as described herein effective in treating a cancer and one or more other compounds that are effective in treating the same cancer, further wherein the compounds are synergistically effective in treating the cancer. The compounds can be administered simultaneously or sequentially.

In another aspect, methods are provided for modulating the activity of a Fms and/or Kit and/or Flt-3 protein kinase, including any mutations thereof, by contacting the protein kinase with an effective amount of any one or more compound(s) as described herein.

In another aspect, the disclosure provides methods for treating a disease or condition mediated by Fms and/or Kit and/or Flt-3, including any mutations thereof, in a subject in need thereof by administering to the subject an effective amount of a compound as described herein or a composition including any one or more compound(s) as described herein. In one embodiment, the disclosure provides methods for treating a disease or condition mediated by Fms and/or Kit, including any mutations thereof, in a subject in need thereof by administering to the subject an effective amount of a compound as described herein or a composition including any one or more compound(s) as described herein in combination with one or more other suitable therapies for treating the disease.

In another aspect, the disclosure provides methods for treating a disease or condition mediated by Fms, including any mutations thereof, in a subject in need thereof by administering to the subject an effective amount of a compound as described herein or a composition including any one or more compound(s) as described herein. In one embodiment, the disclosure provides methods for treating a disease or condition mediated by Fms, including any mutations thereof, in a subject in need thereof by administering to the subject an effective amount of a compound as described herein or a composition including any one or more compound(s) as described herein in combination with one or more other suitable therapies for treating the disease.

In another aspect, the disclosure provides methods for treating a disease or condition mediated by Kit, including any mutations thereof, in a subject in need thereof by administering to the subject an effective amount of a compound as described herein or a composition including any one or more compound(s) as described herein. In one embodiment, the disclosure provides methods for treating a disease or condition mediated by Kit, including any mutations thereof, in a subject in need thereof by administering to the subject an effective amount of a compound as described herein or a composition including any one or more compound(s) as described herein in combination with one or more other suitable therapies for treating the disease.

In another aspect, the disclosure provides methods for treating a disease or condition mediated by Flt-3, including any mutations thereof, in a subject in need thereof by administering to the subject an effective amount of a compound as described herein or a composition including any one or more compound(s) as described herein. In one embodiment, the disclosure provides methods for treating a disease or condition mediated by Flt-3, including any mutations, such as an internal tandem duplication (ITD) mutation thereof, in a subject in need thereof by administering to the subject an effective amount of a composition including any one or more compound(s) as described herein in combination with one or more other suitable therapies for treating the disease. In some embodiments, the Flt3 mutant encoded by Flt3 gene with ITD mutations has one or more mutations at residues F691, D835, Y842 or combinations thereof. In some embodiments, the Flt3 mutant has one or more mutations selected from F691L, D835V/Y, Y842C/H or combinations thereof.

In another aspect, the disclosure provides methods for treating a disease or condition mediated by Fms and Flt-3, including any mutations thereof, in a subject in need thereof by administering to the subject an effective amount of a compound as described herein or a composition including any one or more compound(s) as described herein. In one embodiment, the disclosure provides methods for treating a disease or condition mediated by Fms and Flt-3, including any mutations thereof, in a subject in need thereof by administering to the subject an effective amount of a composition including any one or more compound(s) as described herein in combination with one or more other suitable therapies for treating the disease.

In another aspect, the disclosure provides methods for treating a disease or condition mediated by Fms and Kit, including any mutations thereof, in a subject in need thereof by administering to the subject an effective amount of a compound as described herein or a composition including any one or more compound(s) as described herein. In one embodiment, the disclosure provides methods for treating a disease or condition mediated by Fms and Kit, including any mutations thereof, in a subject in need thereof by administering to the subject an effective amount of a composition including any one or more compound(s) as described herein in combination with one or more other suitable therapies for treating the disease.

In some embodiments, the disclosure provides a method of treating a cancer in a subject in need thereof by administering to the subject an effective amount of a compound or a composition including any one or more compound(s) as described herein, in combination with one or more other therapies or medical procedures effective in treating the cancer. Other therapies or medical procedures include suitable anticancer therapy (e.g. drug therapy, vaccine therapy, gene therapy, photodynamic therapy) or medical procedure (e.g. surgery, radiation treatment, hyperthermia heating, bone marrow or stem cell transplant). In one embodiment, the one or more suitable anticancer therapies or medical procedures is selected from treatment with a chemotherapeutic agent (e.g. chemotherapeutic drug), radiation treatment (e.g. x-ray, γ-ray, or electron, proton, neutron, or α particle beam), hyperthermia heating (e.g. microwave, ultrasound, radiofrequency ablation), Vaccine therapy (e.g. AFP gene hepatocellular carcinoma vaccine, AFP adenoviral vector vaccine, AG-858, allogeneic GM-CSF-secretion breast cancer vaccine, dendritic cell peptide vaccines), gene therapy (e.g. Ad5CMV-p53 vector, adenovector encoding MDA7, adenovirus 5-tumor necrosis factor alpha), photodynamic therapy (e.g. aminolevulinic acid, motexafin lutetium), oncolytic viral or bacterial therapy, surgery, or bone marrow and stem cell transplantation. In certain embodiments, the disclosure provides a method of treating a cancer in a subject in need thereof by administering to the subject an effective amount of a compound as described herein and applying a radiation treatment as described herein either separately or simultaneously. In one embodiment, the disclosure provides a method for treating a cancer in a subject in need thereof by administering an effective amount of a compound as described herein to the subject followed by a radiation treatment (e.g. x-ray, γ-ray, or electron, proton, neutron, or α particle beam). In another embodiment, the disclosure provides a method for treating a cancer in a subject in need thereof by applying a radiation treatment (e.g. x-ray, γ-ray, or electron, proton, neutron, or α particle beam) to the subject followed by administering an effective amount of a compound as described herein to the subject. In yet another embodiment, the disclosure provides a method for treating a cancer in a subject in need thereof by administering a compound as described herein and a radiation therapy (e.g. x-ray, γ-ray, or electron, proton, neutron, or α particle beam) to the subject simultaneously.

In some embodiments, the disclosure provides a method for treating glioblastoma in a subject. The method includes applying a ionizing radiation treatment to the subject followed by administering to the subject a compound of any of formulas (I), (I'), (II), (II'), (IIa), (III), (III') and (IV), or a compound set forth in any of Tables 1 and 3-10, or a compound or a composition as described herein. In one instance, the treatment has a single dose of 12 Gy ionizing radiation. In another instance, a compound set forth in any of Tables 1 and 3-10, or a compound or a composition as described herein is administered to the subject at a dose of 40 mg/kg/day. In other instances, The method includes applying a ionizing radiation treatment to the subject followed by administering to the subject Temodar® and a compound of any of formulas (I), (I'), (II), (II'), (IIa), (III), (III') and (IV), or a compound set forth in any of Tables 1 and 3-10, or a compound or a composition as described herein.

In another aspect, the disclosure provides a method for treating a cancer in a subject in need thereof by administering to the subject an effective amount of a compound or a composition including any one or more compound(s) as described herein, in combination with one or more suitable chemotherapeutic agents. The compounds can be administered simultaneously or sequentially. In some embodiments, the cancer is any cancer mediated by a protein kinases selected from c-fms, c-kit, Flt3 or combinations thereof and/or macrophages or microglia or a cancer as described herein. In one embodiment, the one or more suitable chemotherapeutic agents is selected from an alkylating agent, including, but not limited to, adozelesin, altretamine, bendamustine, bizelesin, busulfan, carboplatin, carboquone, carmofur, carmustine, chlorambucil, cisplatin, cyclophosphamide, dacarbazine, estramustine, etoglucid, fotemustine, hepsulfam, ifosfamide, improsulfan, irofulven, lomustine, mannosulfan, mechlorethamine, melphalan, mitobronitol, nedaplatin, nimustine, oxaliplatin, piposulfan, prednimustine, procarbazine, ranimustine, satraplatin, semustine, streptozocin, temozolomide, thiotepa, treosulfan, triaziquone, triethylenemelamine, triplatin tetranitrate, trofosphamide, and uramustine; an antibiotic, including, but not limited to, aclarubicin, amrubicin, bleomycin, dactinomycin, daunorubicin, doxorubicin, elsamitrucin, epirubicin, idarubicin, menogaril, mitomycin, neocarzinostatin, pentostatin, pirarubicin, plicamycin, valrubicin, and zorubicin; an antimetabolite, including, but not limited to, aminopterin, azacitidine, azathioprine, capecitabine, cladribine, clofarabine, cytarabine, decitabine, floxuridine, fludarabine, 5-fluorouracil, gemcitabine, hydroxyurea, mercaptopurine, methotrexate, nelarabine, pemetrexed, raltitrexed, tegafur-uracil, thioguanine, trimethoprim, trimetrexate, and vidarabine; an immunotherapy, an antibody therapy, including, but not limited to, alemtuzumab, bevacizumab, cetuximab, galiximab, gemtuzumab, panitumumab, pertuzumab, rituximab, brentuximab, tositumomab, trastuzumab, 90 Y ibritumomab tiuxetan, ipilimumab, tremelimumab and anti-CTLA-4 antibodies; a hormone or hormone antagonist, including, but not limited to, anastrozole, androgens, buserelin, diethylstilbestrol, exemestane, flutamide, fulvestrant, goserelin, idoxifene, letrozole, leuprolide, magestrol, raloxifene, tamoxifen, and toremifene; a taxane, including, but not limited to, DJ-927, docetaxel, TPI 287, larotaxel, ortataxel, paclitaxel, DHA-paclitaxel, and tesetaxel; a retinoid, including, but not limited to, alitretinoin, bexarotene, fenretinide, isotretinoin, and tretinoin; an alkaloid, including, but not limited to, demecolcine, homoharringtonine, vinblastine, vincristine, vindesine, vinflunine, and vinorelbine; an antiangiogenic agent, including, but not limited to, AE-941 (GW786034, Neovastat), ABT-510, 2-methoxyestradiol, lenalidomide, and thalidomide; a topoisomerase inhibitor, including, but not limited to, amsacrine, belotecan, edotecarin, etoposide, etoposide phosphate, exatecan, irinotecan (also active metabolite SN-38 (7-ethyl-10-hydroxy-camptothecin)), lucanthone, mitoxantrone, pixantrone, rubitecan, teniposide, topotecan, and 9-aminocamptothecin; a kinase inhibitor, including, but not limited to, axitinib (AG 013736), dasatinib (BMS 354825), erlotinib, gefitinib, flavopiridol, imatinib mesylate, lapatinib, motesanib diphosphate (AMG 706), nilotinib (AMN107), seliciclib, sorafenib, sunitinib malate, AEE-788, BMS-599626, UCN-01 (7-hydroxystaurosporine), vemurafenib, dabrafenib, selumetinib, and vatalanib; a targeted signal transduction inhibitor including, but not limited to bortezomib, geldanamycin, and rapamycin; a biological response modifier, including, but not limited to, imiquimod, interferon-α, and interleukin-2; and other chemotherapeutics, including, but not limited to 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, mTOR inhibitors (e.g. sirolimus, temsirolimus, everolimus, deforolimus), PI3K inhibitors (e.g. BEZ235, GDC-0941, XL147, XL765), Cdk4 inhibitors (e.g. PD-332991), Akt inhibitors, Hsp90 inhibitors (e.g. geldanamycin, radicicol, tanespimycin), farnesyltransferase inhibitors (e.g. tipifarnib), and Aromatase inhibitors (anastrozole letrozole exemestane). Preferably, the method of treating a cancer involves administering to the subject an effective amount of a composition including any one or more compound(s) of Formulae I, I', II, II', IIa, III', III, IV, a compound listed in Tables 1, 3-10 or a compound as described herein in combination with a chemotherapeutic agent selected from capecitabine, 5-fluorouracil, carboplatin, dacarbazine, gefitinib, oxaliplatin, paclitaxel, SN-38, temozolomide, vinblastine, bevacizumab, cetuximab, interferon-α, interleukin-2, or erlotinib. In another embodiment, the chemotherapeutic agent is a Mek inhibitor. Exemplary Mek inhibitors include, but are not limited to, AS703026, AZD6244 (Selumetinib), AZD8330, BIX 02188, CI-1040 (PD184352), GSK1120212 (JTP-74057), PD0325901, PD318088, PD98059, RDEA119 (BAY 869766), TAK-733 and U0126-EtOH. In another embodiment, the chemotherapeutic agent is a tyrosine kinase inhibitor. Exemplary tyrosine kinase inhibitors include, but are not limited to, AEE788, AG-1478 (Tyrphostin AG-1478), AG-490, Apatinib (YN968D1), AV-412, AV-951 (Tivozanib), Axitinib, AZD8931, BIBF1120 (Vargatef), BIBW2992 (Afatinib), BMS794833, BMS-599626, Brivanib (BMS-540215), Brivanib alaninate (BMS-582664), Cediranib (AZD2171), Chrysophanic acid (Chrysophanol), Crenolanib (CP-868569), CUDC-101, CYC116, Dovitinib Dilactic acid (TKI258 Dilactic acid), E7080, Erlotinib Hydrochloride (Tarceva, CP-358774, OSI-774, NSC-718781), Foretinib (GSK1363089, XL880), Gefitinib (ZD-1839 or Iressa), Imatinib (Gleevec), Imatinib Mesylate, Ki8751, KRN 633, Lapatinib (Tykerb), Linifanib (ABT-869), Masitinib (Masivet, AB1010), MGCD-265, Motesanib (AMG-706), MP-470, Mubritinib (TAK 165), Neratinib (HKI-272), NVP-BHG712, OSI-420 (Desmethyl Erlotinib, CP-473420), OSI-930, Pazopanib HCl, PD-153035 HCl, PD173074, Pelitinib (EKB-569), PF299804, Ponatinib (AP24534), PP121, RAF265 (CHIR-265), Raf265 derivative, Regorafenib (BAY 73-4506), Sorafenib Tosylate (Nexavar), Sunitinib Malate (Sutent), Telatinib (BAY 57-9352), TSU-68 (SU6668), Vandetanib (Zactima), Vatalanib dihydrochloride (PTK787), WZ3146, WZ4002, WZ8040, XL-184 free base (Cabozantinib), XL647, EGFR siRNA, FLT4 siRNA, KDR siRNA, Antidiabetic agents such as metformin, PPAR agonists (rosiglitazone, pioglitazone, bezafibrate, ciprofibrate, clofibrate, gemfibrozil, fenofibrate, indeglitazar), and DPP4 inhibitors (sitagliptin, vildagliptin, saxagliptin, dutogliptin, gemigliptin, alogliptin). In another embodiment, the agent is an EGFR inhibitor. Exemplary EGFR inhibitors include, but are not limited to, AEE-788, AP-26113, BIBW-2992 (Tovok), CI-1033, GW-572016, Iressa, LY2874455, RO-5323441, Tarceva (Erlotinib, OSI-774), CUDC-101 and WZ4002.

In some embodiments, the disclosure provides a composition, which includes (i) a compound of formulas I', I, II', II, IIa, III', III or IV, or a compound listed in Tables 1 and 3-10, or a compound as described herein, or a salt, a hydrate, a solvate, an tautomer or an isomer thereof and (ii) a chemotherapeutic agent as described herein. The composition can be used for treating a disease or condition mediated by a protein kinases selected from c-fms, c-kit, Flt3 or combinations thereof and/or macrophages or microglia. Exemplary diseases or conditions include, but are not limited to, stem cell ablation and myelopreparation for stem cell transplant, primary progressive multiple sclerosis, complex regional pain syndrome, reflex sympathetic dystrophy, muscular dystrophy, duchenne muscular dystrophy, causalgia, neuro-inflammation, neuroinflammatory disorders, benign forgetfulness, HIV, binswager type dementia, dementia with lewy bodie, prosencephaly, microencepahy, cerebral palsy, congenital hydrocephalus, abdominal dropsy, progressive supranuclear palsy, glaucoma, addiction disorders, dependencies, alcoholism, tremors, Wilson's disease, vascular dementias, multi infarct dementia, fronto temporal dementia, pseudo-dementia, bladder cancer, basal cell carcinoma, cholangiocarcinoma, colon cancer, endometrial cancer, esophageal cancer, Ewing's sarcoma, gastric cancer, glioma, hepatocellular carcinoma, Hodgkin lymphoma, laryngeal carcinoma, leukemia, liver cancer, lung cancer, melanoma, mesothelioma, pancreatic cancer, rectal cancer, renal cancer, squamous cell carcinoma, t cell lymphoma, thyroid cancer, monocytic leukemia, pheochromocytoma, malignant peripheral nerve cell tumors, malignant peripheral nerve sheath tumors (MPNST), cutaneous and plexiform neurofibromas, leiomyoadenomatoid tumor, fibroids, uterine fibroids, leiomyosarcoma, papillary thyroid cancer, anaplastic thyroid cancer, medullary thyroid cancer, follicular thyroid cancer, hurthle cell carcinoma, thyroid cancer, ascites, malignant ascites, mesothelioma, salivary gland tumors, mucoepidermoid carcinoma of the salivary gland, acinic cell carcinoma of the salivary gland, gastrointestinal stromal tumors (GIST), tumors that cause effusions in potential spaces of the body, pleural effusions, pericardial effusions, peritoneal effusions aka ascites, giant cell tumors (GCT), GCT of bone, pigmented villonodular synovitis (PVNS), tenosynovial giant cell tumor (TGCT), TCGT of tendon sheath (TGCT-TS), other sarcomas, tumor angiogenesis, or paracrine tumor growth. In some embodiments, the compositions can be used to treat tumors that express aberrantly or otherwise Fms, CSF1R, CSF1 or IL-34, or activating mutations or translocations of any of the foregoing; or tumors that express aberrantly or otherwise Kit, SCFR, SCF, or activating mutations or translocations of any of the foregoing; or and tumors that express aberrantly or otherwise Flt3, Flt3 ligand, or activating mutations or translocations of any of the foregoing.

In some embodiments, the disclosure provides a composition including a Raf inhibitor and a compound of any of formulas (I), (I'), (II), (II'), (IIa), (III), (III') and (IV), or a compound set forth in any of Tables 1 and 3-10. In certain embodiments, the disclosure provides a composition including vemurafenib and a compound of any of formulas (I), (I'), (II), (II'), (IIa), (III), (III') and (IV), or a compound set forth in any of Tables 1 and 3-10, or a compound or a composition as described herein. In certain instances, the disclosure provide a composition including vemurafenib and a compound set forth in any of Tables 1 and 3-10, or a compound or a composition as described herein. In one embodiment, the disclosure provides a pharmaceutical composition comprising vemurafenib and a compound listed in Table 1. In certain embodiments, the disclosure provides a composition including dabrafenib and a compound listed in Table 1. In certain embodiments, the Raf inhibitor is a B-raf inhibitor as disclosed in U.S. Pat. No. 7,863,288, which is incorporated herein by reference in its entirety.

In some embodiments, the disclosure provides a method for treating a melanoma or a metastatic melanoma in a subject. The method includes administering a composition comprising a Raf inhibitor and a compound of any of formulas (I), (I'), (II), (II'), (IIa), (III), (III') and (IV), or a compound set forth in any of Tables 1 and 3-10. In certain embodiments, the method includes administering to the subject in need thereof an effective amount of a composition comprising vemurafenib and a compound of any of formulas (I), (I'), (II), (II'), (IIa), (III), (III') and (IV), or a compound set forth in any of Tables 1 and 3-10, or a compound or a composition as described herein. In certain instances, the method includes administering to the subject in need thereof an effective amount of a composition comprising vemurafenib and a compound set forth in Table 1. In some embodiments, vemurafenib and a compound listed in Table 1 can be administered simultaneously or separately. In certain embodiments, the disclosure provides a method for treating a metastatic melanoma in a subject. The method includes administering to the subject in need thereof vemurafenib followed by administering to the subject a compound of any of formulas (I), (I'), (II), (II'), (IIa), (III), (III') and (IV), or a compound set forth in any of Tables 1 and 3-10, or a compound or a composition as described herein. In certain instances, the method includes administering to the subject in need thereof vemurafenib followed by administering to the subject a compound listed in Table 1. In certain embodiments, the disclosure provides a method for treating a metastatic melanoma in a subject, wherein the method includes administering to the subject in need thereof a compound of any of formulas (I), (I'), (II), (II'), (IIa), (III), (III') and (IV), or a compound set forth in any of Tables 1 and 3-10, or a compound or a composition as described herein followed by administering vemurafenib to the subject. In certain instances, the method includes administering to the subject in need thereof an effective amount of a compound set forth in Table 1 followed by administering to the subject vemurafenib. In certain instances, the melanoma is mediated by a mutant B-rafprotein kinase. In other instances, the melanoma is mediated by a V600 mutant B-raf. In yet other instances, the melanoma is mediated by a V600A, V600M, V600R, V600E, V600K or V600G B-raf mutant. In other instances, the melanoma is mediated by a V600E mutant B-raf.

IV. Kinase Targets and Indications

Protein kinases play key roles in propagating biochemical signals in diverse biological pathways. More than 500 kinases have been described, and specific kinases have been implicated in a wide range of diseases or conditions (i.e., indications), including for example without limitation, cancer, cardiovascular disease, inflammatory disease, neurological disease, and other diseases. As such, kinases represent important control points for small molecule therapeutic intervention. Specific target protein kinases, i.e. Fms kinase and Kit kinase, contemplated for use in accordance with the present disclosure are described in the art, including, without limitation, as described in U.S. patent application Ser. No. 11/473,347 (see also, PCT publication No. WO2007002433), the disclosure of which is hereby incorporated by reference with respect to such kinase targets, as well as the following:

Fms: Target kinase Fms (i.e., feline McDonough sarcoma) is a member of the family of genes originally isolated from the Susan McDonough strain of feline sarcoma viruses. Fms is a transmembrane tyrosine kinase of 108.0 kDa coded by chromosome 5q33.2-q33.3 (symbol: CSF1R). The structure of the transmembrane receptor Fms comprises two Ig-like domains, a IgC2-like domain, two additional Ig-like domains, a TM domain, and the TK domain.

Fms is the receptor for the macrophage colony-stimulating factor (M-CSF), and is crucial for the growth and differentiation of the monocyte-macrophage lineage. Upon binding of M-CSF to the extracellular domain of Fms, the receptor dimerizes and trans-autophosphorylates cytoplasmic tyrosine residues.

M-CSF, first described by Robinson and co-workers (Blood. 1969, 33:396-9), is a cytokine that controls the production, differentiation, and function of macrophages. M-CSF stimulates differentiation of progenitor cells to mature monocytes, and prolongs the survival of monocytes. Furthermore, M-CSF enhances cytotoxicity, superoxide production, phagocytosis, chemotaxis, and secondary cytokine production of additional factors in monocytes and macrophages. Examples of such additional factors include granulocyte colony stimulating factor (G-CSF), interleukin-6 (IL-6), and interleukin-8 (IL-8). M-CSF stimulates hematopoiesis, promotes differentiation and proliferation of osteoclast progenitor cells, and has profound effects on lipid metabolism. Furthermore, M-CSF is important in pregnancy. Physiologically, large amounts of M-CSF are produced in the placenta, and M-CSF is believed to play an essential role in trophoblast differentiation (Motoyoshi, Int J Hematol. 1998, 67:109-22). The elevated serum M-CSF levels of early pregnancy may participate in the immunologic mechanisms responsible for the maintenance of the pregnancy (Flanagan & Lader, Curr Opin Hematol. 1998, 5:181-5).

Aberrant expression and/or activation of Fms has been implicated in acute myeloid leukemia, AML (Ridge et al, Proc. Nat. Acad. Sci., 1990, 87:1377-1380). Mutations at codon 301 are believed to lead to neoplastic transformation by ligand independence and constitutive tyrosine kinase activity of the receptor. The tyrosine residue at codon 969 has been shown to be involved in a negative regulatory activity, which is disrupted by amino acid substitutions. Accordingly, Fms mutations are most prevalent (20%) in chronic myelomonocytic leukemia and AML type M4 (23%), both of which are characterized by monocytic differentiation.

A condition related to AML is chronic myeloid leukemia (CML). During the myeloid blast crisis (BC) of CML, non-random additional chromosome abnormalities occur in over 80% of patients. However, these cytogenetic changes have been reported to precede the clinical signs of CML-BC by several months to years suggesting that other biological events may participate in the multistep process of acute transformation of CML. The autocrine production of growth factors has been shown to occur in several hematological malignancies and particularly in AML. Specchia et al [Br J Haematol. 1992 March; 80(3):310-6] have demonstrated that IL-1 beta gene is expressed in almost all cases of CML in myeloid blast crisis, and that a high proportion of cases showed constitutive expression of the M-CSF gene. Many of the same patients in the Specchia et al study demonstrated simultaneous co-expression of Fms. After exposure of leukemic cells to phorbol myristate acetate (PMA), release of M-CSF protein was documented in three of five patients studied; however, no significant interleukin-3 (IL-3), granulocyte-macrophage colony-stimulating factor (GM-CSF) or granulocyte colony-stimulating factor (G-CSF), was detected in these patients. This demonstrates that different patterns of growth factors secretion exist in AML and CML, and that distinct molecular events are likely involved in the control of leukemic proliferation.

The observation that production of M-CSF, the major macrophage growth factor, is increased in tissues during inflammation (Le Meur et al, J. Leukocyte Biology. 2002; 72:530-537) provides a role for Fms in certain diseases. For example, COPD is characterized by airflow limitation that is not fully reversible. The airflow limitation is usually progressive and associated with an abnormal inflammatory response of the lungs to noxious particles or gases. The chronic inflammation of COPD is observed through the airways, parenchyma, and pulmonary vasculature. The inflammatory cell population consists of neutrophils, macrophages, and T lymphocytes, along with eosinophils in some patients. Macrophages are postulated to play an orchestrating role in COPD inflammation by releasing mediators such as TNF-a, IL-8 and LTB4, which are capable of damaging lung structures and/or sustaining neutrophilic inflammation.

Further, M-CSF/fms signaling is critical to osteoclast formation and survival of osteoclast precursors. For example, estrogen loss in menopause results in increased M-CSF and thus increased osteoclast number and bone resorption which leads to increased risk of fracture and osteoporosis. Accordingly, blockage of this signal is a target for the inhibition of bone resorption (Teitelbaum, Science. 2000; 289:1504; Rohan, Science. 2000; 289:1508).

Atherosclerosis, an inflammatory disease of the vessel walls, is associated with significant morbidity and mortality. A effect for Fms inhibition in the treatment and prevention of atherosclerosis depends on several observations (Libby, Nature. 2002; 420:868-874). First, monocytes resident in the arterial intima increase expression of scavenger receptors and internalize modified lipoproteins. The resulting lipid-laden macrophages develop into foam cells characteristic of the atherosclerotic lesion. Macrophages in atheroma secrete cytokines and growth factors involved in lesion progression. Additionally, macrophages replicate within the intima. Through Fms, M-CSF activates the transition from monocyte to lipid-laden macrophage and augments expression of scavenger receptor A. Indeed, atherosclerotic plaques overexpress M-CSF which is critical for atherosclerotic progression. Mice deficient in M-CSF have been found to experience less severe atherosclerosis than mice with normal M-CSF (Rajavashisth, et. al., J. Clin. Invest. 1998; 101: 2702-2710; Qiao, et. al., Am. J. Path. 1997; 150:1687-1699). Accordingly, inhibitors of Fms disrupt M-CSF signaling, compromising monocyte to macrophage foam cell progression, macrophage survival and replication, and cytokine signaling that participates in lesion progression.

The role of M-CSF and Fms in emphysema appears to involve the regulation of elastin metabolism through control of matrix metalloproteins. M-CSF has a role in the modulation of the accumulation and function of alveolar macrophages (AMs) in vivo (Shibata et al, Blood 2001, 98: pp. 2845-2852). Osteopetrotic (Op/Op) mice have no detectable M-CSF and show variable tissue-specific reductions in macrophage numbers. Accordingly, it was hypothesized that AMs would be decreased in number and have altered function in Op/Op mice because of the absence of M-CSF. Shibata et al found that lung macrophages identified in lung sections were decreased in number in 20-day-old Op/Op mice but not Op/Op mice older than 4 months compared with findings in age-matched littermate controls. The numbers of AMs recovered by bronchoalveolar lavage (BAL) were also reduced in young but not adult Op/Op mice compared with controls. Importantly, AMs of Op/Op mice spontaneously release higher levels of matrix metalloproteinases (MMPs) than AMs of controls. Consistent with an increased release of MMP, Op/Op mice have abnormal elastin deposition and spontaneously develop emphysema in the absence of molecular or cellular evidence of lung inflammation. Accordingly, the modulation of metalloelastase activity in macrophages by M-CSF may control the degradation of elastin fibers in lungs or blood vessels.

Metastatic cancer cells cause bone destruction, with associated fracture, pain, deformation, and hypercalcaemia, due to production of osteoclasticogenic factors including M-CSF by tumor cells (Clohisy et al, Clin. Orthop. 2000, 373: 104-14). Binding of M-CSF to the Fms product stimulates formation of osteoclasts and osteolytic activity (Kodama et al, J. Exp. Med. 1991, 173: 269-72; Feng et al, Endocrinology 2002, 143: 4868-74). Accordingly, inhibition of osteoclast activity at the level of Fms offers a compelling target for amelioration of bone metastasis. Fms is also a target for amelioration of metastatic breast cancer (Lawicki et al., Clin Chim Acta. 2006, September, 371 (1-2): 112-6; Wyckoff et al., Cancer Res. 2007, March 15, 67(6):2649-56).

Nephritis is inflammation of the kidneys. It may be caused for example by a bacterial infection of the kidneys or exposure to a toxin. However, nephritis more commonly develops from an abnormal immune reaction, which can occur, for example, when an antibody attacks either the kidney itself or an antigen attached to kidney cells, or when an antigen-antibody complex formed elsewhere in the body attaches to cells in the kidney. Some types of nephritis involve infiltration of kidney tissues by white blood cells and deposits of antibodies. In other types of nephritis, inflammation may consist of tissue swelling or scarring without white blood cells or antibodies. Furthermore, nephritis can occur anywhere in the kidneys. With respect to the glomeruli, progressive damage to glomeruli causes urine production to fall and metabolic waste products to build up in the blood. When damage to glomeruli is severe, inflammatory cells and injured glomerular cells accumulate, compressing the capillaries within the glomerulus and interfering with filtration. Scarring may develop, impairing kidney function and reducing urine production. In some cases, microthrombi may form in the small blood vessels, further decreasing kidney function. Less commonly, nephritis involves the tubulointerstitial tissues; such inflammation is called tubulointerstitial nephritis. When inflammation damages the tubules and the tubulointerstitial tissues, the kidneys may become unable to concentrate urine, eliminate (excrete) metabolic waste products from the body, or balance the excretion of sodium and other electrolytes, such as potassium. When the tubules and tubulointerstitial tissues are damaged, kidney failure often develops. Accordingly, inhibition of Fms offers a target for therapeutic intervention in nephritis due to the modulation of the inflammatory response comprising the etiology of the disease.

Lupus nephritis, i.e., renal involvement in systemic lupus erythematosus (SLE), is a common disease manifestation with a poor prognosis. At least three potentially overlapping, immuno-pathogenic mechanisms for lupus nephritis are supported by experimental data. First, circulating immune complexes consisting chiefly of DNA and anti-DNA are deposited in the kidney. Resulting complement activation and chemotaxis of neutrophils leads to a local inflammatory process. Second, in situ formation of antigen and antibody complexes may similarly lead to complement activation and leukocyte mediated injury. Third, antibodies against specific cellular targets may produce renal injury. An additional mechanism is observed in SLE patients with the antiphospholipid antibody syndrome. Glomerular thrombosis can result from the hypercoagulability that accompanies antibodies directed against negatively charged phospholipid-protein complexes (e.g. biologic false positive VDRL, anti-cardiolipin antibodies, and lupus anticoagulant). Mesangial lupus nephritis is accompanied by normal diagnostic findings or with a mild degree of proteinuria but typically absence of hypertension or abnormal urinary sediment. Focal and diffuse proliferative lupus glomerulonephritis are often associated with the worst prognosis for renal survival and can be accompanied by nephrotic syndrome, significant hypertension and abnormal urine sediment. Membranous lupus nephritis often presents with proteinuria, moderate to high grade, but usually normal urinary sediment in the absence of hypertension. Mesangial lupus nephropathy is generally associated with an excellent prognosis, whereas proliferative lupus nephropathy, especially diffuse variant, is often characterized by hypertension, red cell casts and significant deterioration of renal function. Nephrotic syndrome in the absence of hypertension, active urinary sediment or significant hypocomplementemia suggest the membranous variant of lupus nephropathy. Membranous nephropathy generally is associated with a good prognosis and relative preservation of renal function. However, in the presence of persistent nephrotic range proteinuria, membranous lupus nephropathy can, in fact, lead to loss of renal function and end stage renal disease (ESRD). Accordingly, inhibition of Fms offers a target for therapeutic intervention in lupus due to the modulation of the inflammatory response comprising the etiology of the disease.

Macrophage accumulation is a prominent feature in many forms of glomerulonephritis. Local proliferation of macrophages within the kidney has been described in human and experimental glomerulonephritis and may have an important role in augmenting the inflammatory response. Isbel et al (Nephrol Dial Transplant 2001, 16: 1638-1647) examined the relationship between local macrophage proliferation and renal expression of M-CSF. Glomerular and tubulointerstitial M-CSF expression was found to be up-regulated in human glomerulonephritis, being most prominent in proliferative forms of disease. Because this correlates with local macrophage proliferation, it suggests that increased renal M-CSF production plays an important role in regulating local macrophage proliferation in human glomerulonephritis. In a model of renal inflammation (UUO— unilateral ureteric obstruction) anti-Fms antibody treatment reduced macrophage accumulation (Le Meur et al., J Leukocyte Biology, 2002, 72: 530-537). Accordingly, inhibition of Fms offers a target for therapeutic intervention in glomerulonephritis.

Insulin resistance and obesity are hallmark of type II diabetes and there is a strong correlation between insulin resistance and abdominal visceral fact accumulation (Bjorntrop, Diabetes Metab. Res. Rev., 1999, 15: 427-441). Current evidence indicates that macrophages accumulating in adipose tissue release TNF-a and other factors that cause adipocyte changes (hypertrophy, lipolysis, reduced insulin sensitivity) and also promote insulin resistance in surrounding tissues. Therefore, macrophage accumulation in type 2 diabetes is important for disease progression. Accordingly, inhibition of Fms has potential in preventing the development of insulin resistance and hyperglycemia.

Similarly, the observation that production of M-CSF, the major macrophage growth factor, is increased in tissues during inflammation points out a role for Fms in diseases, such as for example inflammatory diseases. More particularly, because elevated levels of M-CSF are found in the disease state, modulation of the activity of Fms can ameliorate disease associated with increased levels of M-CSF.

A Fms inhibitor may be useful in treating inflammatory and autoimmune indications, including, but not limited to, rheumatoid arthritis, osteoarthritis, psoriatic arthritis, psoriasis, dermatitis, ankylosing spondylitis, polymyositis, dermatomyositis, systemic sclerosis, juvenile idiopathic arthritis, polymyalgia rheumatica, Sjogren's disease, Langerhan's cell histiocytosis (LCH), Still's disease, inflammatory bowel syndrome, ulcerative colitis, Crohn's disease, systemic lupus erythematosis (SLE), transplant rejection, chronic obstructive pulmonary disease (COPD), emphysema, Kawasaki's Disease, hemophagocytic syndrome (macrophage activation syndrome), multicentric reticulohistiocytosis, and atherosclerosis; metabolic disorders, including, but not limited to, Type I diabetes, Type II diabetes, insulin resistance, hyperglycemia, obesity, and lipolysis; disorders of bone structure, mineralization and bone formation and resorption, including, but not limited to, osteoporosis, osteodystrophy, increased risk of fracture, Paget's disease, hypercalcemia, infection-mediated osteolysis (e.g. osteomyelitis), and periprosthetic or wear-debris-mediated osteolysis; kidney and genitourinary diseases, including, but not limited to, endometriosis, nephritis (e.g. glomerulonephritis, interstitial nephritis, Lupus nephritis), tubular necrosis, diabetes-associated renal complications (e.g. diabetic nephropathy), and renal hypertrophy; disorders of the central nervous system, including, but not limited to, multiple sclerosis, amyotrophic lateral sclerosis (ALS), myasthenia gravis, chronic demyelinating polyneuropathy, other demyelinating disorders, stroke, Alzheimer's disease and Parkinson's disease; inflammatory and chronic pain, including, but not limited to, bone pain; malignancies, including, but not limited to, multiple myeloma, acute myeloid leukemia (AML), chronic myeloid leukemia (CML), lung cancer, pancreatic cancer, prostate cancer, breast cancer, ovarian cancer, neuroblastoma, sarcoma, osteosarcoma, giant cell tumor of bone, giant cell tumor of tendon sheath (TGCT), pigmented villonodular synovitis (PVNS), tumor angiogenesis, melanoma, glioblastoma multiforme, glioma, other tumors of the central nervous system, metastasis of tumors to other tissues, and other chronic myeloproliferative diseases such as myelofibrosis; vasculitis, including but not limited to collagen vascular disease, polyarteritis nodosa, Behcet's disease, sarcoidosis, familiar Mediterranean fever, Churg-Strauss vasculitis, temporal arteritis, giant cell arteritis, Takayasu's arteritis; ophthalmic indications, including but not limited to uveitis, scleritis, retinitis, age related macular degeneration, choroidal neovascularization, diabetic retinopathy; inherited disorders, including but not limited to cherubism, neurofibromatosis; infectious disease indications, including but not limited to infections associated with human immunodeficiency virus, hepatitis B virus, hepatitis C virus, human granulocytic anaplasmosis; lysosomal storage disorders, including but not limited to Gaucher's disease, Fabry's disease, Niemann-Pick disease; gastrointestinal indications, including but not limited to liver cirrhosis; pulmonary indications, including but not limited to pulmonary fibrosis, acute lung injury (e.g. ventilator-induced, smoke- or toxin-induced); and surgical indications, including but not limited to (cardiopulmonary) bypass surgery, vascular surgery, and vascular grafts.

Kit: Target kinase Kit (i.e., feline Hardy-Zuckerman 4 sarcoma viral oncogene) is a 109.9 kDa transmembrane tyrosine kinase encoded by chromosome 4q12 (symbol: KIT). Receptor protein tyrosine kinases (RPTKs) regulate key signal transduction cascades that control cellular growth and proliferation. The Stem Cell Factor (SCF) receptor Kit is a type III transmembrane RPTK that includes five extracellular immunoglobulin (IG) domains, a single transmembrane domain, and a split cytoplasmic kinase domain separated by a kinase insert segment. Kit plays an important role in the development of melanocytes, mast, germ, and hematopoietic cells.

Stem Cell Factor (SCF) is a protein encoded by the S1 locus, and has also been called kit ligand (KL) and mast cell growth factor (MGF), based on the biological properties used to identify it (reviewed in Tsujimura, Pathol Int 1996, 46:933-938; Loveland, et al., J. Endocrinol 1997, 153:337-344; Vliagoftis, et al., Clin Immunol 1997, 100:435-440; Broudy, Blood 1997, 90:1345-1364; Pignon, Hermatol Cell Ther 1997, 39:114-116; and Lyman, et al., Blood 1998, 91:1101-1134). Herein the abbreviation SCF refers to the ligand for Kit.

SCF is synthesized as a transmembrane protein with a molecular weight of 220 or 248 Dalton, depending on alternative splicing of the mRNA to encode exon 6. The larger protein can be proteolytically cleaved to form a soluble, glycosylated protein which noncovalently dimerizes. Both the soluble and membrane-bound forms of SCF can bind to and activate Kit. For example, in the skin, SCF is predominantly expressed by fibroblasts, keratinocytes, and endothelial cells, which modulate the activity of melanocytes and mast cells expressing Kit. In bone, marrow stromal cells express SCF and regulate hematopoiesis of Kit expressing stem cells. In the gastrointestinal tract, intestinal epithelial cells express SCF and affect the interstitial cells of Cajal and intraepithelial lymphocytes. In the testis, sertoli cells and granulosa cells express SCF which regulates spermatogenesis by interaction with Kit on germ cells.

According to OMIM, signaling from Kit is essential for primordial germ cell growth both in vivo and in vitro. Many downstream effectors of the KIT signaling pathway have been identified in other cell types, but how these molecules control primordial germ cell survival and proliferation are unknown. Determination of the KIT effectors acting in primordial germ cells has been hampered by the lack of effective methods to manipulate easily gene expression in these cells. De Miguel et al. (2002) overcame this problem by testing the efficacy of retroviral-mediated gene transfer for manipulating gene expression in mammalian germ cells. They found that primordial germ cells can successfully be infected with a variety of types of retroviruses. They used this method to demonstrate an important role of the AKT1 in regulating primordial germ cell growth (OMIM MIM Number: 164920: Apr. 17, 2006).

Aberrant expression and/or activation of Kit has been implicated in a variety of pathologic states. For example, evidence for a contribution of Kit to neoplastic pathology includes its association with leukemias and mast cell tumors, small cell lung cancer, testicular cancer, and some cancers of the gastrointestinal tract and central nervous system. In addition, Kit has been implicated in playing a role in carcinogenesis of the female genital tract sarcomas of neuroectodermal origin, and Schwann cell neoplasia associated with neurofibromatosis. It was found that mast cells are involved in modifying the tumor microenvironment and enhancing tumor growth (Yang et al., J Clin Invest. 2003, 112:1851-1861; Viskochil, J Clin Invest. 2003, 112:1791-1793). Kit inhibitors can also be used to target melanoma (Smalley et al., Histol Histopathol. 2009, May, 24(5):643-50), gastrointestinal stromal tumors (Demetri, G D, Semin Oncol. 2001, October, 28(5 Suppl 17):19-26), neurofibromatosis (Yang et al., Cell, 2008, October 31, 135(3):437-48), and multiple sclerosis (Secor et al., J Exp Med. 2000, March 6, 191(5):813-22).

A Kit inhibitor may be useful in treating malignancies, including, but not limited to, mast cell tumors, small cell lung cancer, non-small cell lung cancer (NSCLC), testicular cancer, pancreatic cancer, breast cancer, merkel cell carcinoma, carcinomas of the female genital tract, sarcomas of neuroectodermal origin, colorectal carcinoma, carcinoma in situ, gastrointestinal stromal tumors (GISTs), tumor angiogenesis, glioblastoma, astrocytoma, neuroblastoma, neurofibromatosis (including Schwann cell neoplasia associated with neurofibromatosis), acute myelocytic leukemia, acute lymphocytic leukemia, chronic myelogenous leukemia, mastocytosis, melanoma, and canine mast cell tumors; cardiovascular disease, including but not limited to atherosclerosis, cardiomyopathy, heart failure, pulmonary arterial hypertension, and pulmonary fibrosis; inflammatory and autoimmune indications, including, but not limited to, allergy, anaphylaxis, asthma, rheumatoid arthritis, allergic rhinitis, multiple sclerosis, inflammatory bowel syndrome, transplant rejection, hypereosinophilia, urticaria and dermatitis; gastrointestinal indications, including but not limited to gastroesophageal reflux disease (GERD), esophagitis, and gastrointestinal tract ulcers; ophthalmic indications, including but not limited to uveitis and retinitis; and neurologic indications, including but not limited to migraine.

Flt3: Target kinase Flt3 (i.e., Fms-like tyrosine kinase 3) is a transmembrane tyrosine kinase of 112.8 kDa encoded by chromosome 13q12 (symbol: FLT3). According to OMIM, Rosnet et al. (Genomics 1991, 9: 380-385) isolated a novel member of the class 3 receptors discussed above. They demonstrated that this gene of the tyrosine kinase family, called FLT3, has strong sequence similarities with other members of the group. Lymphohematopoietic stem cells serve as a reservoir for virtually all blood cells but make up only approximately 0.01% of human or murine marrow cells. The ability to isolate and expand this population has clinical applications in bone marrow transplantations for cancer and genetic diseases. Small et al. (Proc. Nat. Acad. Sci. 1994, 91: 459-463) cloned the cDNA for stem cell tyrosine kinase 1, the human homolog of murine Flk2/Flt3, from a CD34+ hematopoietic stem cell-enriched library. The cDNA encoded a protein of 993 amino acids with 85% identity and 92% similarity to the murine homolog. STK1, which is identical to FLT3, is a member of the type III receptor tyrosine kinase family that includes KIT, FMS, and platelet-derived growth factor receptor. STK1 expression in human blood and marrow is restricted to CD34+ cells, a population greatly enriched by stem/progenitor cells. Antisense oligonucleotides directed against STK1 sequences inhibited hematopoietic colony formation, most strongly in long-term bone marrow cultures. The data suggested that STK1 may function as a growth factor receptor on hematopoietic stem and/or progenitor cells (OMIM MIM Number: 136351: Mar. 3, 2005).

Levis et al., state that Internal tandem duplication (ITD) mutations of the receptor tyrosine kinase FLT3 have been found in 20% to 30% of patients with acute myeloid leukemia (AML). These mutations constitutively activate the receptor and appear to be associated with a poor prognosis. In their study, dose-response cytotoxic assays were performed with AG1295, a tyrosine kinase inhibitor active against FLT3, on primary blasts from patients with AML, and they found that AG1295 was specifically cytotoxic to AML blasts harboring FLT3/ITD mutations. They suggest that these mutations contribute to the leukemic process and that the FLT3 receptor represents a therapeutic target in AML (Levis et al., Blood 2001, 98:885-887). An Flt3 inhibitor may be useful in treating acute myeloid leukemia, myelodysplastic syndrome, acute lymphoblastic leukemia.

Kinase Activity Assays

A number of different assays for kinase activity can be utilized for assaying for active modulators and/or determining specificity of a modulator for a particular kinase or group of kinases. In addition to the assays mentioned in the Examples below, one of ordinary skill in the art can readily identify other assays that can be utilized and can modify an assay for a particular application. For example, numerous papers concerning kinases describe assays that can be used.

Additional alternative assays can employ binding determinations. For example, this sort of assay can be formatted either in a fluorescence resonance energy transfer (FRET) format, or using an AlphaScreen (amplified luminescent proximity homogeneous assay) format by varying the donor and acceptor reagents that are attached to streptavidin or the phosphor-specific antibody.

V. Formulations and Administration

The methods and compounds will typically be used in therapy for human subjects. However, they may also be used to treat similar or identical indications in other animal subjects. Compounds described herein can be administered by different routes, including injection (i.e. parenteral, including intravenous, intraperitoneal, subcutaneous, and intramuscular), oral, transdermal, transmucosal, rectal, or inhalant. Such dosage forms should allow the compound to reach target cells. Other factors are well known in the art, and include considerations such as toxicity and dosage forms that retard the compound or composition from exerting its effects. Techniques and formulations generally may be found in Remington: *The Science and Practice of Pharmacy*, $21^{st}$ edition, Lippincott, Williams and Wilkins, Philadelphia, Pa., 2005 (hereby incorporated by reference herein).

In some embodiments, compositions used in the methods of the present disclosure will comprise pharmaceutically acceptable carriers or excipients, such as fillers, binders, disintegrants, glidants, lubricants, complexing agents, solubilizers, and surfactants, which may be chosen to facilitate administration of the compound by a particular route. Examples of carriers include calcium carbonate, calcium phosphate, various sugars such as lactose, glucose, or sucrose, types of starch, cellulose derivatives, gelatin, lipids, liposomes, nanoparticles, and the like. Carriers also include physiologically compatible liquids as solvents or for suspensions, including, for example, sterile solutions of water for injection (WFI), saline solution, dextrose solution, Hank's solution, Ringer's solution, vegetable oils, mineral oils, animal oils, polyethylene glycols, liquid paraffin, and the like. Excipients may also include, for example, colloidal silicon dioxide, silica gel, talc, magnesium silicate, calcium silicate, sodium aluminosilicate, magnesium trisilicate, powdered cellulose, macrocrystalline cellulose, carboxymethyl cellulose, cross-linked sodium carboxymethylcellulose, sodium benzoate, calcium carbonate, magnesium carbonate, stearic acid, aluminum stearate, calcium stearate, magnesium stearate, zinc stearate, sodium stearyl fumarate, syloid, stearowet C, magnesium oxide, starch, sodium starch glycolate, glyceryl monostearate, glyceryl dibehenate, glyceryl palmitostearate, hydrogenated vegetable oil, hydrogenated cotton seed oil, castor seed oil mineral oil, polyethylene glycol (e.g. PEG 4000-8000), polyoxyethylene glycol, poloxamers, povidone, crospovidone, croscarmellose sodium, alginic acid, casein, methacrylic acid divinylbenzene copolymer, sodium docusate, cyclodextrins (e.g. 2-hydroxypropyl-.delta.-cyclodextrin), polysorbates (e.g. polysorbate 80), cetrimide, TPGS (d-alpha-tocopheryl polyethylene glycol 1000 succinate), magnesium lauryl sulfate, sodium lauryl sulfate, polyethylene glycol ethers, di-fatty acid ester of polyethylene glycols, or a polyoxyalkylene sorbitan fatty acid ester (e.g., polyoxyethylene sorbitan ester Tween®), polyoxyethylene sorbitan fatty acid esters, sorbitan fatty acid ester, e.g. a sorbitan fatty acid ester from a fatty acid such as oleic, stearic or palmitic acid, mannitol, xylitol, sorbitol, maltose, lactose, lactose monohydrate or lactose spray dried, sucrose, fructose, calcium phosphate, dibasic calcium phosphate, tribasic calcium phosphate, calcium sulfate, dextrates, dextran, dextrin, dextrose, cellulose acetate, maltodextrin, simethicone, polydextrosem, chitosan, gelatin, HPMC (hydroxypropyl methyl celluloses), HPC (hydroxypropyl cellulose), hydroxyethyl cellulose, and the like.

In some embodiments, oral administration may be used. Pharmaceutical preparations for oral use can be formulated into conventional oral dosage forms such as capsules, tablets, and liquid preparations such as syrups, elixirs, and concentrated drops. Compounds described herein may be combined with solid excipients, optionally grinding a resulting mixture, and processing the mixture of granules, after adding suitable auxiliaries, if desired, to obtain, for example, tablets, coated tablets, hard capsules, soft capsules, solutions (e.g. aqueous, alcoholic, or oily solutions) and the like. Suitable excipients are, in particular, fillers such as sugars, including lactose, glucose, sucrose, mannitol, or sorbitol; cellulose preparations, for example, corn starch, wheat starch, rice starch, potato starch, gelatin, gum tragacanth, methyl cellulose, hydroxypropylmethyl-cellulose, sodium carboxymethylcellulose (CMC), and/or polyvinylpyrrolidone (PVP: povidone); oily excipients, including vegetable and animal oils, such as sunflower oil, olive oil, or codliver oil. The oral dosage formulations may also contain disintegrating agents, such as the cross-linked polyvinylpyrrolidone, agar, or alginic acid, or a salt thereof such as sodium alginate; a lubricant, such as talc or magnesium stearate; a plasticizer, such as glycerol or sorbitol; a sweetening such as sucrose, fructose, lactose, or aspartame; a natural or artificial flavoring agent, such as peppermint, oil of wintergreen, or cherry flavoring; or dye-stuffs or pigments, which may be used for identification or characterization of different doses or combinations. Also provided are dragee cores with suitable coatings. For this purpose, concentrated sugar solutions may be used, which may optionally contain, for example, gum arabic, talc, polyvinylpyrrolidone, carbopol gel, polyethylene glycol, and/or titanium dioxide, lacquer solutions, and suitable organic solvents or solvent mixtures.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols.

In some embodiments, injection (parenteral administration) may be used, e.g., intramuscular, intravenous, intraperitoneal, and/or subcutaneous. Compounds described herein for injection may be formulated in sterile liquid solutions, preferably in physiologically compatible buffers or solutions, such as saline solution, Hank's solution, or Ringer's solution. Dispersions may also be prepared in non-aqueous solutions, such as glycerol, propylene glycol, ethanol, liquid polyethylene glycols, triacetin, and vegetable oils. Solutions may also contain a preservative, such as methylparaben, propylparaben, chlorobutanol, phenol, sorbic acid, thimerosal, and the like. In addition, the compounds may be formulated in solid form, including, for example, lyophilized forms, and redissolved or suspended prior to use.

In some embodiments, transmucosal, topical or transdermal administration may be used. In such formulations of compounds described herein, penetrants appropriate to the barrier to be permeated are used. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal). Compositions of compounds described herein for topical administration may be formulated as oils, creams, lotions, ointments, and the like by choice of appropriate carriers known in the art. Suitable carriers include vegetable or mineral oils, white petrolatum (white soft paraffin), branched chain fats or oils, animal fats and high molecular weight alcohol (greater than $C_{12}$). In some embodiments, carriers are selected such that the active ingredient is soluble. Emulsifiers, stabilizers, humectants and antioxidants may also be included as well as agents imparting color or fragrance, if desired. Creams for topical application are preferably formulated from a mixture of mineral oil, self-emulsifying beeswax and water in which mixture the active ingredient, dissolved in a small amount of solvent (e.g., an oil), is admixed. Additionally, administration by transdermal means may comprise a transdermal patch or dressing such as a bandage impregnated with an active ingredient and optionally one or more carriers or diluents known in the art. To be administered in the form of a transdermal delivery system, the dosage administration will be continuous rather than intermittent throughout the dosage regimen.

In some embodiments, compounds are administered as inhalants. Compounds described herein may be formulated as dry powder or a suitable solution, suspension, or aerosol. Powders and solutions may be formulated with suitable additives known in the art. For example, powders may include a suitable powder base such as lactose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer, and the like. The compounds described herein may also be used in combination with other inhaled therapies, for example corticosteroids such as fluticasone propionate, beclomethasone dipropionate, triamcinolone acetonide, budesonide, and mometasone furoate; beta agonists such as albuterol, salmeterol, and formoterol; anticholinergic agents such as ipratroprium bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

The amounts of various compounds to be administered can be determined by standard procedures taking into account factors such as the compound activity (in vitro, e.g. the compound $IC_{50}$ vs. target, or in vivo activity in animal efficacy models), pharmacokinetic results in animal models (e.g. biological half-life or bioavailability), the age, size, and weight of the subject, and the disorder associated with the subject. The importance of these and other factors are well known to those of ordinary skill in the art. Generally, a dose will be in the range of about 0.01 to 50 mg/kg, also about 0.1 to 20 mg/kg of the subject being treated. Multiple doses may be used.

The compounds described herein may also be used in combination with other therapies for treating the same disease. Such combination use includes administration of the compounds and one or more other therapeutics at different times, or co-administration of the compound and one or more other therapies. In some embodiments, dosage may be modified for one or more of the compounds of the disclosure or other therapeutics used in combination, e.g., reduction in the amount dosed relative to a compound or therapy used alone, by methods well known to those of ordinary skill in the art.

The compounds of formulas I', I, II', II, IIa, III', III and IV and a compound of any of those listed in Tables 1 and 3-10 or described herein or a salt, a tautomer, an isomer thereof may be used in combination with another chemotherapeutic agent or drug or a kinase inhibitor as described herein for treating the same disease. Such combination can be a fixed dose composition or be administered at different times, or co-administration of the compound and anther agent, drug or kinase inhibitor simultaneously or separately. In some embodiments, dosage may be modified for one or more of the compounds of the disclosure or another agent, drug or kinase inhibitor used in combination, e.g., reduction or increase in the amount dosed relative to a compound used alone to improve safety and/or efficacy, by methods well known to those of ordinary skill in the art.

It is understood that use in combination includes use with other therapies, drugs, medical procedures etc., where the other therapy or procedure may be administered at different times (e.g. within a short time, such as within hours (e.g. 1, 2, 3, 4-24 hours), or within a longer time (e.g. 1-2 days, 2-4 days, 4-7 days, 1-4 weeks)) than a compound described herein, or at the same time as a compound described herein. Use in combination also includes use with a therapy or medical procedure that is administered once or infrequently, such as surgery, along with a compound described herein administered within a short time or longer time before or after the other therapy or procedure. In some embodiments, the present invention provides for delivery of a compound described herein and one or more other drug therapeutics delivered by a different route of administration or by the same route of administration. The use in combination for any route of administration includes delivery of a compound described herein and one or more other drug therapeutics delivered by the same route of administration together in any formulation, including formulations where the two compounds are chemically linked in such a way that they maintain their therapeutic activity when administered. In one aspect, the other drug therapy may be co-administered with a compound described herein. Use in combination by co-administration includes administration of co-formulations or formulations of chemically joined compounds, or administration of two or more compounds in separate formulations within a short time of each other (e.g. within an hour, 2 hours, 3 hours, up to 24 hours), administered by the same or different routes. Co-administration of separate formulations includes co-administration by delivery via one device, for example the same inhalant device, the same syringe, etc., or administration from separate devices within a short time of each other. Co-formulations of a compound described herein and one or more additional drug therapies delivered by the same route includes preparation of the materials together such that they can be administered by one device, including the separate compounds combined in one formulation, or compounds that are modified such that they are chemically joined, yet still maintain their biological activity. Such chemically joined compounds may have a linkage that is substantially maintained in vivo, or the linkage may break down in vivo, separating the two active components.

VI. Examples

Examples related to the present disclosure are described below. In most cases, alternative techniques can be used. The examples are intended to be illustrative and are not limiting or restrictive to the scope of the disclosure. Compound A as used herein and noted the Figures refers to a compound of Formulas I, I', II, II', IIa, III, and III' and IV; a compound listed in Tables 1 and 3-10; and a compound described in the Examples.

Example 1

Synthesis

The synthesis of the compounds described herein and those set forth in Tables 1, 3-10 was described in PCT Patent publication Nos.: WO 2008/064255; WO 2008/064265; and WO 2011/057022 and US Patent Application Publication Nos.: US 2009/0076046 and US 2011/0112127. A person of skill in the art is readily capable of preparing all the compounds encompassed by the generic formulas I', I, II, II', IIa, III', III and IV using the procedures described in the above-mentioned patent applications.

Example 2

Compound Forms and Formulations

The compounds disclosed herein can be prepared in additional forms, such as polymorphs, salt forms and complexes. Such solid forms can further improve the biopharmaceutical properties, and can be further formulated to enhance biopharmaceutical properties. For example, compounds of the disclosure form acid addition salts such as hydrochloride or tosylate salts or form a complex with polyprotic acids, such as citric acid, preferably wherein the complex is substantially amorphous. Such an amorphous complex can also be processed with addition of a polymer, such as HPMCAS, that further stabilizes the amorphous form. The process can also include spray drying of the material. Compound is dissolved in 400-500 mL of acetone and added with stirring and heat to 1 equivalent of citric acid dissolved in ethanol. The solution is spray dried to provide the dried complex. Additional material is formulated with addition of the compound/citrate complex to polymer in the same ratio of acetone/ethanol, for example using either HPMCAS or a mixture of Eudragit® L100-55 and Poloxamer 407. In one sample, components are combined in the weight ratios of 40-50% compound, 15-25% citric acid, 25-35% Eudragit® L100-55 and 1-10% Poloxamer 407. In one sample, components are combined in the weight ratios of 40-50% compound, 15-25% citric acid, and 30-40% HPMCAS. The amorphous nature of the resulting complex or formulation of the complex can be determined by X-Ray Powder Diffraction (XRPD), infra-red spectrometry, and differential scanning calorimetry. For example using a ShimadzuXRD-6000 X-ray powder diffractometer using Cu Kα radiation. The tube voltage and amperage are set to 40 kV and 40 mA, respectively. The divergence and scattering slits are set at 1° and the receiving slit was set at 0.15 mm. Diffracted radiation is detected by a NaI scintillation detector. A θ-2θ continuous scan at 3°/min (0.4 sec/0.02° step) from 2.5° to 40° 2θ is used. A silicon standard is analyzed to check the instrument alignment. Data are collected and analyzed using XRD-6100/7000 v.5.0. Sample is prepared for analysis by placing it in an aluminum holder with silicon insert. The DSC is used to demonstrate that the complexes lack a characteristic transition and have completely melted before any free base crystalline transition, further supporting that these complexes are amorphous.

Example 3

Compound Properties

While the inhibitory activity of the compounds on any of Fms, Flt-3 and Kit kinase is important to their activity in treating of disease, the compounds described herein show favorable properties that provide advantages as a pharmaceutical as well. In some instances, Fms selectivity relative to Kit and other kinases provides preferred activity for treating certain diseases, such as rheumatoid arthritis, Alzheimer's disease, Parkinson's disease, osteoarthritis, glomerulonephritis, interstitial nephritis, Lupus nephritis, tubular necrosis, diabetic nephropathy, or renal hypertrophy. In some instances, Fms selectivity of compounds in combination with the compounds inability to cross the blood brain barrier provides preferred activity for treating certain diseases, such as osteoarthritis, glomerulonephritis, interstitial nephritis, Lupus nephritis, tubular necrosis, diabetic nephropathy, or renal hypertrophy. In some instances, Fms selectivity of compounds in combination with the compounds ability to effectively cross the blood brain barrier provides preferred activity for treating certain diseases, such as rheumatoid arthritis, Alzheimer's disease, or Parkinson's disease. In some instances, dual Fms/Kit activity provides preferred activity for treating certain diseases, such as metastatic breast cancer, prostate cancer, multiple myeloma, melanoma, acute myeloid leukemia, brain metastases, neurofibromatosis, gastrointestinal stromal tumors, rheumatoid arthritis, or multiple sclerosis. In some instances, dual Fms/Flt-3 activity provides preferred activity for treating certain diseases, such as acute myeloid leukemia. In addition to demonstrating kinase inhibitory activity against Fms, Kit, Flt-3 or at least both Fms and Kit or at least both Fms and Flt-3 in both biochemical and cell based assays, compounds have improved solubility, improved pharmacokinetic properties, and low Cyp inhibition. The compounds are assessed in the following assays or similar assays available to one skilled in the art.

Assays for biochemical and cell based activity are known in the art, for example, U.S. Patent Application Publication Numbers, US 2007/0032519, US 2009/0076046 and US 2011/0112127, the disclosure of each of which is hereby incorporated by reference as it relates to such assays. In one assay the biochemical activity $IC_{50}$ values are determined with respect to inhibition of c-Kit kinase activity, where inhibition of phosphorylation of a peptide substrate is measured as a function of compound concentration. Compounds to be tested are dissolved in DMSO to a concentration of 20 mM. These are diluted 30 μL into 120 μL of DMSO (4 mM) and 1 μL is added to an assay plate. These are then serially diluted 1:2 (50 µL to 100 µL DMSO) for a total of 8 points. Plates are prepared such that each kinase reaction is 20 µL in 1× kinase buffer (25 mM HEPES, pH 7.5, 2 mM MgCl$_2$, 2 mM MnCl$_2$, 0.01% Tween-20, 1 mM DTT, 0.01% BSA), 5% DMSO and 100 µM ATP. Substrate is 30 nM biotin-(E4Y)10 (Millipore). C-kit kinase (obtained from Millipore (#14-559) or is prepared as described in U.S. Patent Application Publication Number 2009/0076046, the disclosure of which is hereby incorporated by reference as it relates to this assay) is at 0.75 ng per sample. After incubation of the kinase reaction for 1 hour at room temperature, 5 µL of donor beads (Streptavidin coated beads (Perkin Elmer Life Science) final concentration 10 µg/mL) in stop buffer (25 mM Hepes pH 7.5, 100 mM EDTA, 0.01% BSA) is added, the sample is mixed and incubated for 20 minutes at room temperature before adding 5 µL of acceptor beads (PY20 coated beads (Perkin Elmer Life Science) final concentration 10 µg/mL) in stop buffer. The samples are incubated for 60 minutes at room temperature and the signal per well is read on Envision reader. Phosphorylated substrate results in binding of the PY20 antibody and association of the donor and acceptor beads such that signal correlates with kinase activity. The signal vs. compound concentration is used to determine the IC$_{50}$.

In one assay the biochemical activity IC$_{50}$ values are determined with respect to inhibition of Fms kinase activity, where inhibition of phosphorylation of a peptide substrate is measured as a function of compound concentration. Compounds to be tested, dissolved in DMSO (1 µL), are added to a white 384-well plate (Costar #3705). Working stocks of Fms kinase (Invitrogen #PV3249), biotin-(E4Y)10 substrate (Upstate Biotech, Cat#12-440), and ATP (Sigma, Cat#A-3377) are prepared in 25 mM Hepes pH 7.5, 0.5 mM MgCl$_2$, 2 mM MnCl$_2$, 2 mM DTT, 0.01% BSA, and 0.01% Tween-20. All components are added to the 384-well plate for a final concentration of 1 ng/well Fms, 30 nM biotin-(E4Y)10 (Upstate Biotechnology) and 100 µM ATP in a volume of 20 µL. Each sample is at 5% DMSO. The plate is then incubated for 20 minutes at 30° C. Just before use, working stocks of donor and acceptor beads from the AlphaScreen PY20 Detection Kit (PerkinElmer, Cat#676601M) are prepared in 25 mM Hepes pH 7.5, pH 7.4, 100 mM EDTA, 0.01% BSA. To stop the reaction, the plate is uncovered in the dark and 5 µL of Donor Beads solution (Streptavidin beads) is added to each well. The plate is incubated at room temperature for 20 minutes. Five microliters of Acceptor Beads solution (PY20 coated beads) are then added to each well. The final concentration of each bead is 10 µg/mL. The plates are incubated at room temperature for 60 minutes. Fluorescence signal is recorded on the Envision reader. Phosphorylated substrate results in binding of the PY20 antibody and association of the donor and acceptor beads such that signal correlates with kinase activity. The signal vs. compound concentration is used to determine the IC$_{50}$.

In one assay the biochemical activity IC$_{50}$ values are determined with respect to inhibition of Flt-3 kinase activity, where inhibition of phosphorylation of a peptide substrate is measured as a function of compound concentration. Compounds to be tested, dissolved in DMSO (1 µL), are added to a white 384-well plate (Costar #3705). Working stocks of Flt-3 kinase (Invitrogen), biotin-(E4Y)10 substrate (Upstate Biotech, Cat#12-440), and ATP (Sigma, Cat#A-3377) are prepared in 25 mM Hepes pH 7.5, 5 mM MgCl$_2$, 5 mM MnCl$_2$, 1 mM DTT, and 0.01% Tween-20. All components are added to the 384-well plate for a final concentration of 1 ng/well Flt-3, 30 nM biotin-(E4Y)10 and 100 µM ATP in a volume of 20 µL. Each sample is at 5% DMSO. The plate is then incubated for 1 hour at room temperature. Just before use, working stocks of donor and acceptor beads from the AlphaScreen PY20 Detection Kit (PerkinElmer, Cat#676601M) are prepared in 25 mM Hepes pH 7.5, pH 7.4, 100 mM EDTA. 0.3% BSA. To stop the reaction, the plate is uncovered in the dark and 5 µL of Donor Beads solution (Streptavidin beads) is added to each well. The plate is incubated at room temperature for 20 minutes. Five microliters of Acceptor Beads solution (PY20 coated beads) are then added to each well. The final concentration of each bead is 10 µg/mL. The plates are incubated at room temperature for 60 minutes. Fluorescence signal is recorded on the Envision reader. Phosphorylated substrate results in binding of the PY20 antibody and association of the donor and acceptor beads such that signal correlates with kinase activity. The signal vs. compound concentration is used to determine the IC$_{50}$.

Compounds are assessed in a variety of cell based assays. For example BCR-FMS/BaF3, BCR-KIT/BaF3, M-NFS-60, M-07e, and BAC1.2F5 cell proliferation assays are used to assess inhibitory activity of Fms or Kit and MV-4-11 cell proliferation assay is used to assess inhibitory activity in Flt-3. Reagent and assay conditions are as follows:

BCR-FMS/BaF3 and BCR-KIT/BaF3 cells:
Maintained in RPMI containing 10% FBS, 1% PenStrep, 1% NEAA, and 1% L-Glutamine, supplemented with 1 mg/mL G418 and 5% WEHI-CM (or recombinant murine IL-3).
Confluent cells are split 1:50 to 1:100 every 3-4 days.

M-NFS-60 cells (ATCC #CRL-1838):
Maintained in RPMI containing 10% FBS, 1% Hepes, 1% NaPyruvate, and 0.45% Glucose, supplemented with 62 ng/mL murine M-CSF.
Confluent cells are split 1:20 every 3-4 days.

M-07e cells (DSMZ #ACC 104):
Maintained in IMDM containing 10% FBS, supplemented with either 200 ng/mL human SCF or 75 ng/µL SCF (R&D Systems 255-SC).
Confluent cells are split 1:5 to 1:10 every 3-4 days.

BAC1.2F5 cells:
Maintained in Alpha-MEM containing 10% Newborn Calf Serum (Invitrogen #26010-074) supplemented with 36 ng/mL murine M-CSF.
Confluent cells are split 1:4 every 3-4 days.

MV-4-11 cells:
Maintained in Iscove's Modified Dulbecco's Medium containing 10% FBS.
Confluent cells are split 1:4 every 3-4 days.

On day 1, cells are counted, then centrifuged in a conical tube for 5 minutes at 1000 rpm. The supernatant is removed and cells are re-suspended as follows:
BCR-FMS/BaF3 and BCR-KIT/BaF3: resuspend in growth media+1 mg/mL G418 (without WEHI/IL-3) to 2×10$^5$ cells/mL.
M-NFS-60: resuspend in growth media+62 ng/mL murine M-CSF to 5×10$^5$ cells/mL.
M-07e: resuspend in growth media+200 ng/mL human SCF to 5×10$^5$ cells/mL.
BAC1.2F5: resuspend in growth media+36 ng/mL murine M-CSF to 1.4×10$^5$ cells/mL.
MV-4-11: resuspend in growth media+10% FBS to 5×10$^5$ cells/mL.

The cells are plated (50 µL) in each well of a 96-well dish (Corning 3610) and incubated at 37° C. in 5% CO$_2$ overnight, cells plated to a final concentration of cells as follows:
BCR-FMS/BaF3 and BCR-KIT/BaF3: 10,000 cells per well.

M-NFS-60: 25,000 cells per well.
M-07e: 25,000 cells per well.
BAC1.2F5: 7,000 cells per well.
MV-4-11: 25,000 cells per well.

On day 2, compound at a maximum concentration of 5 mM is serially diluted 1:3 for a total of 8 point titration with DMSO as a control. A 1 µL aliquot of each dilution point is added to 249 µL growth media and 50 µL is added to a well containing cells, providing 10 µM compound for the maximum concentration point. The cells are incubated for 3 days at 37° C. in 5% $CO_2$.

On day 5, ATPlite 1 step Luminescence Assay System (Perkin Elmer #6016739) is brought to room temperature along with the cell cultures. ATPlite is added to each well as follows:

BCR-FMS/BaF3 and BCR-KIT/BaF3: 25 µL per well.
M-NFS-60: 25 µL per well.
M-07e: 40 µL per well.
BAC1.2F5: 50 µL per well.
MV-4-11: 40 µL per well.

The cells are incubated at room temperature for 10 minutes, then luminescence is read on Safire reader. The measured luminescence correlates directly with cell number, such that the reading as a function of compound concentration is used to determine the $IC_{50}$ value.

Further, an osteoclast differentiation assay is used to assess the efficacy of Fms inhibitors for treating bone disease such as osteoarthritis. On day 0, Osteoclast Medium BulletKit (Lonza catalog #PT-8001, containing Media, FBS, L-Glutamine, PenStrep, RANKL, and M-CSF) media is thawed and the FBS, L-glutamine and PenStrep from the kit is added to 100 mL of Osteoclast Precursor Basal medium to provide the Osteoclast Precursor Growth Medium (OPGM). This is warmed to 37° C. Osteoclast precursor cells (Lonza catalog #2T-110) frozen in cryovial are warmed to 37° C. and transferred to a 50 mL conical tube. The cryovial is rinsed with OPGM and added dropwise to the conical tube of cells with swirling, then the volume is adjusted to 20-30 mL with addition of OPGM. The cells are centrifuged at 200×g for 15 minutes at room temperature and all but approximately 3 mL of supernatant is removed to a new conical tube. The cells are suspended in the remaining supernatant and the volume is adjusted to 10-15 mL with OPGM added dropwise with swirling. The cells are centrifuged at 200×g for 15 minutes at room temperature and all but approximately 1 mL of supernatant is removed. The cells are resuspended in the remaining supernatant, counted, and the volume adjusted with an appropriate amount of OPGM to provide approximately $1\times10^5$ cells/mL. A 0.1 mL aliquot of cells is added to each well of a 96-well plate. Compound to be tested is prepared in DMSO for plating at a high concentration of 2.5 mM, with 8 point 1:3 serial dilutions. A 1 µL aliquot of each compound dilution is added to a 96 well v-bottom polypropylene plate and 0.124 mL of OPGM is added to the compound. Then 50 µL of the compound in OPGM is added to the osteoclast precursor cells in 96-well plate (providing highest test concentration of 5 µM). RANKL (2 µg) from the BulletKit is reconstituted in 1 mL of OPGM, then vortexed and centrifuged briefly. A 792 µL aliquot of RANKL is added to 6 mL of OPGM and 50 µL is added to low control wells. Then 76.6 µL M-CSF (10 µg/mL) from the BulletKit is added to the remaining 5.8 mL of OPGM/RANKL solution (4×RANKL/M-CSF/OPGM). A 50 µL aliquot of this is added to the remaining wells, and the remainder is stored at 4° C. for later use. The plate is incubated at 37° C. for 6 days, then the remaining OPGM/RANKL/M-CSF solution is warmed to 37° C. The remaining approximately 198 µL is combined with 6 mL of OPGM. The media is aspirated from the osteoclast wells and 100 µL of RANKL/OPGM is added to the low controls. The remaining RANKL/OPGM is combined with the approximately 18.5 µL of remaining M-CSF. The remaining 4×RANKL/M-CSF/OPGM from day 0 is diluted to 1× and combined with the freshly prepared solution. A 0.1 mL aliquot of this is added to each osteoclast well and incubated for 37° C. for 1 day. The Acid Phosphatase kit (Cayman Chemical catalog #10008051) is warmed to room temperature. The assay buffer is diluted 5 mL with 45 mL of water. For each plate, two substrate tablets are dissolved in 4.5 mL of the assay buffer, mixing by vortex to break up the tablet. Stop solution is diluted 12 mL with 36 mL of water. In a tissue culture hood, 20 µL of each osteoclast well supernatant is transferred to a 96 well plate. A 30 µL aliquot of the substrate solution is added to each well and incubated at 37° C. for 20 minutes, then added 100 µL stop solution to each well. The absorbance of each well is read at 405 nM on Safire plate reader. The absorbance reading is plotted vs. concentration to provide the $IC_{50}$ for each compound.

The Fms and Kit biochemical inhibitory activity and selectivity (Kit $IC_{50}$/Fms$IC_{50}$) and the BCR-FMS/BaF3 and BCR-KIT/BaF3 cell based inhibitory activity selectivity (Kit $IC_{50}$/Fms$IC_{50}$) for exemplary compounds listed in Tables 1 and 3-10 have been described in US patent application publication numbers US 2009/0076046 and US 2011/0112127, which are incorporated by reference.

The Fms and Flt-3 biochemical inhibitory activity and the BCR-FMS/BaF3 and MV-4-11 cell based inhibitory activity for certain compounds listed in Tables 4-6 have been described in US patent application publication No.: US 2011/0112127, which are incorporated by reference. The compounds listed in Tables 1, 3 and 10 as described herein exhibit an $IC_{50}$ less than 0.1 µM in Fms and Flt-3 biochemical assays and BCR-FMS/BaF3 and MV-4-11 cell based assays.

Compounds P-1554, P-2001, P-2003, P-2004, P-2019, P-2028, P-2029, P-2030, P-2031, P-2032, P-2037, P-2038, P-2045, P-2048, P-2049, P-2052, P-2057, P-2061, P-2063, P-2064, P-2070, P-2146, P-2147, P-2157, P-2165, P-2176, P-2193 and those set forth in Tables 1 and 3-10 demonstrated an $IC_{50}$ below 0.1 µM in the osteoclast differentiation assay.

Compounds listed in Tables 1, 3-10 and those that described herein demonstrated an $IC_{50}$ below 1 µM in at least one of the Fms assays described in US Patent Application Publication numbers US 2007/0032519, US 2009/0076046 and US 2011/0112127.

As an indication of relative solubility, the turbidity of compounds in aqueous solutions is assessed. To assess possible compound properties in different physiological compartments, such as stomach, intestine, and blood, a series of aqueous buffers with varying pH is used. Thus each compound is diluted into four different physiologically relevant buffers and solution turbidity is measured by spectrophotometry. The concentration of compound that demonstrates turbidity by forming enough insoluble suspension to raise the average optical density above 0.01 at three wavelengths (490, 535, and 650 nm) is used to define the limit of the compound solubility in that buffer.

Compounds are dissolved at a concentration of 25 mM in dimethyl sulfoxide, then serially diluted 1:1 into a 96 well plate, diluting 10 times in pure dimethyl sulfoxide, with the final well of each row a dimethyl sulfoxide blank. In an assay plate, 99 µL of appropriate buffer is added to each well, and 1 µL of each sample dilution is added to the buffer, achieving a range of final total concentrations in aqueous solutions having different pH. The buffers used are Simulated Gastric Fluid (SGF-pH 1.5) 0.5M NaCl, pH 1.5; Simulated Intestinal fluid (SIF-pH 4.5 and pH 6.8) 0.05M $NaH_2PO_4$, pH 4.5 and 6.8; and Hepes Buffer (HEPES-pH 7.4) 10 mM HEPES, 150 mM NaCl, pH 7.4. Control compounds pyrene, estriol and propranolol HCl are also assessed. Plates are spun and then mixed for 1 minute, and the absorbance is read using a Tecan Safire II to read wavelengths in the visible range (490, 535, and 650 nm) at four locations per well, reflecting the degree of turbidity present. The average optical density for each wavelength in each well is graphed vs. compound concentration, and the concentration at which the curve crosses a threshold O.D. of 0.01 for each wavelength is reported as the endpoint turbidity assay result. The average of the three wavelengths is used to compare turbidity of compounds. Compounds are considered to have low solubility if the threshold concentration is <31.3 µM, moderate solubility if the threshold concentration is 31.3 µM to 250 µM, and high solubility if the threshold concentration is >250 µM.

The relative solubility (L=low, M=moderate, H=high) based on turbidity threshold concentration at each pH for exemplary compounds listed in Tables 3-6 has been described in US patent application publication No.: US 2011/0112127, which are incorporated by reference.

CYP (Cytochrome P450) enzymes are the major drug metabolizing enzymes present in the liver. The inhibition of CYP enzyme activity ($IC_{50}$) for each of CYP1A2, CYP2C19, CYP2C9, CYP2D6, CYP3A4(BFC) and CYP3A4(BQ) is determined for each of the compounds listed in Tables 1, and 3-6, where inhibition of metabolism of a known substrate leads to a decrease in the fluorescence of the metabolized product. The fluorescence of the product is monitored as a function of compound concentration.

Compounds are dissolved in DMSO to a concentration of 100 mM. These are diluted 1 µL into 82 µL of acetonitrile. An 11 µL aliquot of this solution is then added to 204 µL of cofactor mix (1.3% NADPH Regeneration system Solution A, 1.04% NADPH Regeneration system Solution B from BD Biosciences, 5% acetonitrile and 0.05% DMSO). These are then serially diluted 1:1 (160 µL to 160 µL co-factor mix) for a total of 10 points. A 10 µL aliquot of this final mixture is dispensed into 384 well assay plates and incubated for 10 minutes at 37° C. Enzyme and substrate mix (10 µL; 0.5 pmol CYP1A2/5 µM CEC; 1.0 pmol CYP2C9/75 µM MFC; 0.5 pmol CYP2C19/25 µM CEC; 1.5 pmol CYP2D6/1.5 µM AMMC; 1.0 pmol CYP3A4/50 µM BFC; or 1.0 pmol CYP3A4/40 µM BQ) is added to these assay plates. Assay plates are incubated at 37° C. (CYP1A2-15 min; CYP2C9-45 min; CYP2C19, 2D6 and 3A4-30 min) and read in a Tecan Safire 2 plate reader (CYP1A2, 2C19 and 3A4 409 ex/460 em; CYP2C9 and 2D6 409 ex/530 em). The signal versus compound concentration is used to determine the $IC_{50}$. The enzymes and substrates for this assay are obtained from BD Biosciences. While other factors are involved in determining CYP effects in vivo, compounds preferably have $IC_{50}$ values of >5 µM, more preferably $IC_{50}$ values of >10 µM.

The Cyp inhibition for exemplary compounds listed in Tables 3-6 has been described in US patent application publication No.: US 2011/0112127, which is incorporated by reference herein.

Pharmacokinetic properties of compounds (including any solid forms or formulations thereof) are assessed in male Sprague Dawley rats or male Beagle dogs. Rats are dosed daily with compound either by IV injections via surgically implanted jugular catheters or by oral gavage (PO). Each compound is prepared as a 20 mg/mL stock solution in dimethyl sulfoxide, which is further diluted to provide the dosing stock at the desired concentration for the IV or PO formulations. For IV dosing, the dosing stock is diluted into a 1:1:8 mixture of Solutol®:ethanol:water. For PO dosing, the dosing stock is diluted into 1% methylcellulose. In a cassette format (or each compound, solid form thereof or formulation thereof is done individually), compounds are diluted to 0.5 mg/mL each for IV dosing and 0.4 mg/mL each for PO dosing and dosed at 1 mg/kg (2 mL/kg) or 2 mg/kg (5 mL/kg), respectively. For IV dosed animals, tail vein blood samples are collected with lithium heparin anticoagulant at 5, 15, 30, and 60 minutes and 4, 8, and 24 hours post dosing each day. For PO dosed animals, tail vein blood samples are collected with lithium heparin anticoagulant at 30 minutes, 1, 2, 4, 8 and 24 hours post dosing each day. Dogs are dosed daily by oral capsules in a suitable formulation at 50 mg/mL. Cephalic vein blood samples are collected with lithium heparin anticoagulant at 30 minutes, 1, 2, 4, 8 and 24 hours post dosing each day. All samples are processed to plasma and frozen for later analysis of each compound by LC/MS/MS. Plasma levels as a function of time are plotted to assess the AUC (ng*hr/mL). Compounds contemplated for use according to the present disclosure preferably show improved pharmacokinetic properties relative to previously described compounds, i.e. they have substantially higher values for one or more of AUC, Cmax and half-life relative to previously described compounds.

Analysis of penetration of compound into the brain can be assessed similarly. Each compound is prepared as a 100 mg/mL stock solution in dimethyl sulfoxide, as well as control compounds atenolol at 100 mg/mL and antipyrine at 50 mg/mL. In a cassette format, up to three test compounds, along with atenolol and antipyrine, are combined, 180 µL each, and added to 17.1 mL of 1% methylcellulose. The compounds are in a suspension that is administered in a single dose (10 mL per kg body weight) to 2 groups of CD rats (8-9 weeks, n=3 per group) by oral gavage, an additional group of rats dosed with vehicle only. One group of compound treated rats is sacrificed at 2 hours post dosing, the other group at 6 hours. Plasma is collected in Li-heparin and the brains are collected, cut into right and left hemispheres, weighed and flash frozen. Brain homogenate (30%) and plasma samples are assessed by equilibrium dialysis using a 96 well equilibrium dialysis apparatus with a 5K MW cut off membrane (The Nest Group, Inc.) as per the vendor's protocol with the samples on one side of the dialysis membrane and an equal volume of 1×PBS on the other side. The apparatus is incubated overnight at 37° C. on a plate rotator (The Nest Group, Inc.). The compound concentrations on both sides are analyzed by LC/MS/MS to calculate the mass balance recovery. The concentration in the PBS side is calculated using a standard curve generated for each compound. The PBS concentration is the free compound concentration, while the side with the biological sample provides the concentration in plasma or brain.

Additional features of the complex can be used to demonstrate improved properties, such as comparison of the intrinsic dissolution rate of a similarly prepared substantially amorphous citrate complex or formulation thereof as compared to that of a crystalline form of the compound or similar formulation thereof in simulated gastric fluid (SGF) without enzyme and in simulated intestinal fluid (SIF). A pellet of test sample is dissolved in the appropriate fluid, and the UV absorbance as a function of time is measured at 254 nm (SGF) or 310 nm (SIF) and plotted.

Example 4

In Vivo Model System Testing

The protocols for in vivo animal model testing of rheumatoid arthritis (RA) have been described in PCT Publication No. WO 2011/057022, which is hereby incorporated by reference in its entirety. Compounds of Formulas I, I', II, II', IIa, III, and III' and IV and the compounds listed in Tables 1 and 3-10; and the compounds described in the Examples, or compositions thereof, hydrates or solvates thereof, are tested in mice and are found to be effective for treating RA.

Similarly, other model systems can be used to evaluate compounds described herein. Compounds as described herein, including compounds of Formulas I, I', II, II', IIa, III, and III' and IV; the compounds listed in Tables 1 and 3-10; and the compounds described in the Examples, or compositions thereof, hydrates or solvates thereof, are tested in mice for the treatment of various diseases and conditions as described herein.

Treatment of mice with a compound of Formulas I, I', II, II', IIa, III, and III' and IV; the compounds listed in Tables 1 and 3-10; and the compounds described in the Examples, or compositions thereof, hydrates or solvates thereof, results in depletion of TAMs in stroma and significant decrease in tumor mass.

Treatment of Mice with Radiotherapy and CSF-1R Inhibitor

RT-PCR analysis of U251 GBM tumors (glioblastoma multiforme) growing in mice revealed a more than 2.5-fold increase in expression of CSF-1 after treatment with a single dose of 12 Gy ionization radiation (IR). Increased CSF-1 expression in these tumors correlated with increased recruitment of CD11b$^+$ monocytes. Immunohistochemistry (IHC) and fluorescence activated cell sorting (FACS) showed that the number of CD11b$^+$ monocytes in GBM tumors had approximately doubled within 2 weeks of IR treatment. F4/80 staining indicated that the majority of the CD11b$^+$ cells were mature macrophages. Treatment with 40 mg/kg/day of a compound of Table 1, which inhibits the receptor for CSF-1 (CSF-1R), effectively blocked the recruitment of monocytes/macrophages to the irradiated tumors. Bioluminescence imaging (BLI) of intracranial U251-luciferase tumors growing in mice showed that combined treatment with IR and a compound of Table 1 was more effective at inhibiting tumor growth than IR alone. Eighty percent of mice treated with IR and a compound of Table 1 were alive at 50 days post-irradiation whereas there were no survivors among groups receiving monotherapy. These results suggest inhibition of CSF-1R can prevent post-irradiation recurrence of GBM by blocking the recruitment of tumor-infiltrating monocytes/macrophages.

Combination of Radiotherapy and CSF-1R Inhibitor for Mice with Prostate Tumor

Ras+myc-transformed RM-1 prostate tumor bearing mice were treated with control (food chow), radiation (3 Gy×5 days), a compound of Table 1 (food chow) or in combination. Radiation reduced tumor size by 43% at day 10, 1 day after cessation of radiation (p<0.001). The size of irradiated tumors reached nadir for a short duration, and subsequently resumed an aggressive tumor growth rate, whereas the combined radiation therapy (RT) and a compound of Table 1 treated group maintained a much slower rate of tumor regrowth. Both FACS and histologic analysis of tumors revealed a significant reduction of MDSCs and tumor associated macrophages (TAMs) in the compound of Table 1 treated group and in the combined treatment group in tumors as well as in spleens. Interestingly, both subsets of CD11b$^+$ Gr-1$^+$ myeloid-derived suppressive cells (MDSCs) (monocytic and polymorphonuclear) were reduced. At the molecular level, CSF1R blockade treatment significantly reduced RT-induced CSF1, MMP-9 and Arg-1 RNA. The latter 2 genes are known to be involved in cancer progression and metastasis by promoting tissue remodeling, angiogenesis, and immunosuppression. In summary, we observed that prostate tumor-directed RT can potently induce the influx of TIMs, which in turn can thwart efficacy of treatment. The addition of a potent CSF1R inhibitor, such as a compound of Table 1 can prevent the influx of Tumor-infiltrating myeloid cells (TIMs) and halt their protumorigenic functions leading to more effective and durable tumor growth control.

Reduced Macrophages Recruitment and Improved Fracture Healing in Mdx Mice

Mdx mice were fed with a compound of Table 1 one week prior to fracture and until sacrifice. At day 7 post-fracture, cartilage volume was significantly increased in compound of Table 1 treated mdx mice compared to mdx mice fed with normal diet as shown by histomorphometric analyses and Safranin-O (SO) staining. No significant difference was observed between cartilage volume of treated mdx mice and wild type mice, suggesting that the treatment rescues the chondrogenic delay observed in mdx mice. In parallel, we confirmed decreased macrophage recruitment in the fracture callus after a compound of Table 1 treatment by F4/80 immunostaining. Indeed, the number of F4/80+ cells significantly decreased after the treatment, providing strong evidence for a link between the increased inflammatory state of mdx muscle and the delay in bone healing.

Example 5

Efficacy of CSF-1R Inhibitor to Decrease the Severity of PLP139-151-Induced Relapsing-remitting EAE in Specialized Mice Method: CSF-1R inhibitors as described herein were tested in mouse relapsing-remitting multiple sclerosis (MS) model. Compound A is like FTY720 without rebound. Female specialized mice 6 weeks old were purchased from Harlan and maintained for 1 week prior to beginning the experiment. Mice were randomly assigned into groups of 10 animals (plus the additional mice per group to be used for histology), and primed with 50 µg PLP139-151/CFA on Day 0. On Day 16-20 post disease induction (onset of remission), the experimental compounds in dose groups 2 and 3 were administered daily via gavage to the groups for a period of 3 weeks (with the final treatment on ~Day 37-41 post disease induction). On Day 10 post disease induction (disease onset) treatment of group 4 began, and continued to the same day as groups 2 and 3 (~Day 37-41 post disease induction). After administration of the test compounds, the mice were followed until Day 45 to assess clinical disease, delayed type hypersensitivity (DTH), and various in vitro immunological assays. Histological signs of disease at various time points during the disease course were also assessed. Sections were stained for proteolipid protein (PLP) (to determine myelin expression), CD4 (to determine infiltrating T cells), and F4/80 (to determine infiltrating antigen presenting cells (APCs). Spinal cords and brains were harvested on Day 10 post disease induction (disease onset) from 3 mice, Day 12 and 16 post disease induction (peak of acute) from 6 mice on each respective day (3 mice from Vehicle and 3 mice from High Dose Day 10 initiation), Day 37-41 post disease induction (last day of treatment) from 18 mice (3 mice from each group), and Day 45 post disease induction from 18 mice (3 mice from each group).

Results: Compounds as described herein demonstrated robust efficacy in the relapsing-remitting Experimental autoimmune encephalomyelitis (EAE) model, and importantly, appears to promote efficacy equivalent, or better, than that obtained using the developmental compound FTY-720 or anti-CD80 Fab treatment. In addition, discontinuation of therapy leads in contrast to the compound A treated animals to a rapid rebound of clinical scores in the FTY-720 dose group. FIG. 1 demonstrates the efficacy of a c-fms inhibitor, e.g. compound A to decrease the severity of PLP139-151-induced relapsing-remitting EAE in SJL mice.

Experimental Design

EAE Induction: EAE induction was performed according to the following protocol. In brief, 300 μg of myelin oligodendrocyte glycoprotein $(MOG)_{35-55}$ peptide was dissolved in 100 μl of PBS and emulsified in an equal volume of Freund's Complete Adjuvant (CFA) containing 5 mg/ml of *Mycobacterium tuberculosis* H37 RA. The emulsion (200 μl) was be injected subcutaneously into the flank of female C57BL/6 mice on days 0 and 7. Pertussis toxin, 500 ng in 500 μl of PBS (List Biological Labs), was administered intravenously into each tail vein on days 0 and 2.

Experimental Grouping: Evaluation of Compound a in the MOG EAE Mouse Model (n=12 Animals)

| GROUP | TREATMENT | DOSE | ROUTE | REGIMEN | VOLUME | # ANIMALS |
|---|---|---|---|---|---|---|
| 1 | VEHICLE | — | PO | QD × 30+ | 0.1 mL | 12 |
| 2 | Compound A | 50 mg/kg | PO | QD × 30+ | 0.1 mL | 12 |

Example 6

Figure 2A:
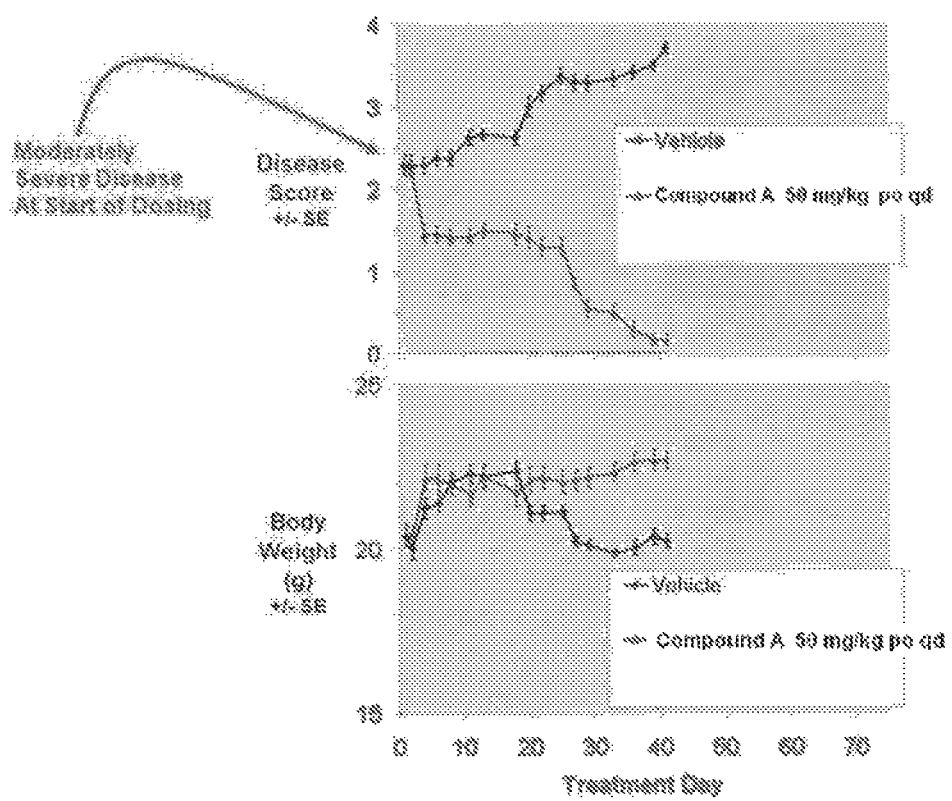
FIGS. 2A and 2B show mouse MOG-EAE model of primary progressive multiple sclerosis (PPMS). A compound as described herein significantly improves disease score compared to vehicle.
Figure 2B:
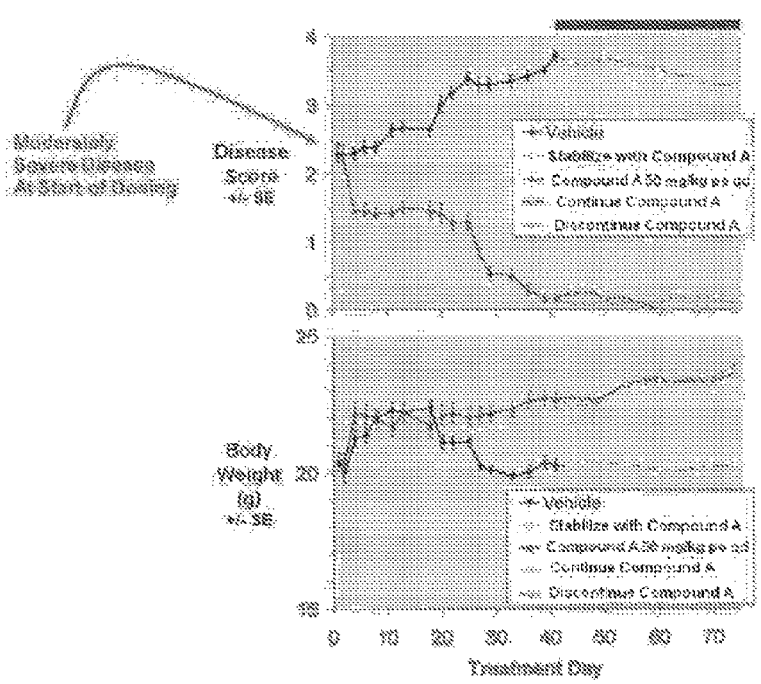
Figure 2C:
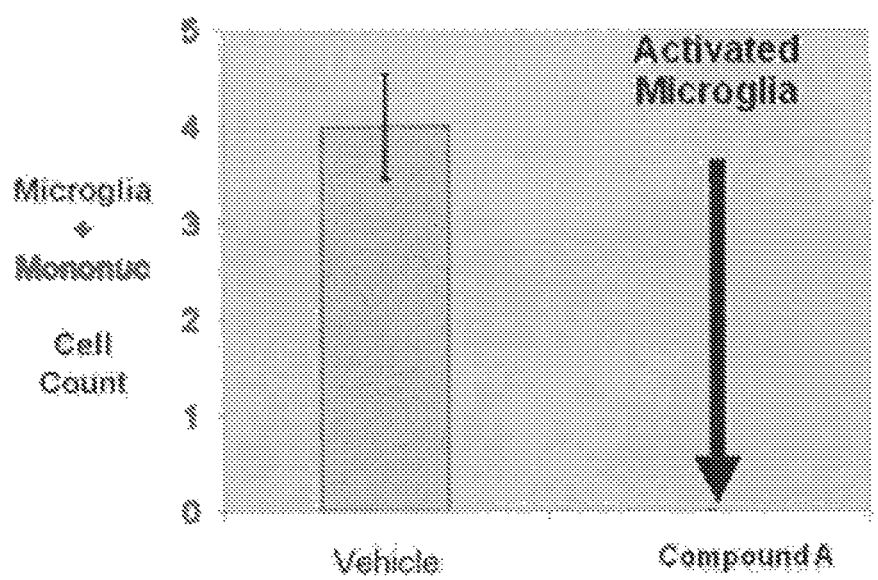
FIG. 2C shows mouse MOG EAE model histology. A compound as described herein abolishes macrophage/microglial infiltration.

Evaluation in the Acute MOG-induced EAE Model in Primary Progressive Multiple Sclerosis As shown in FIGS. 2A-2C, compounds as described herein were evaluated in the myelin oligodendrocyte glycoprotein (MOG) peptide induced experimental autoimmune encephalomyelitis (EAE) model.
Materials and Methods
Test System
Species/strain: C57 Female Mice
Physiological state: Normal
Age/weight range at start of study: 6-9 weeks
Animal supplier: Harlan
Number/sex of animals: 12 mice/group
Identification: Ear punch
Randomization: 2-2.5 EAE Score
EAE Scoring: Score for initiation of treatment of compound A to start after randomization at a clinical score of 2-2.5 at approximately day 17-20 of the challenge
Justification: 12 mice/group requested by Sponsor
Replacement: Animals were not be replaced during the course of the study.
Animal Housing and Environment
Housing: Microisolator cages, 5 animals/cage
Acclimation: 7 days
Environmental conditions: Maintained under pathogen-free conditions
Food/water: Food: Standard fresh Rodent Chow
  Water: Water was available ad-libitum.
Administration of Test Articles
Route and method of administration: PO (oral)
Justification for route of administration: This route has been requested by Sponsor
Frequency and duration of dosing: Q.D×30+(starting on the day of randomization) [qd (once daily) dosing was subsequently extended when compound A-treated animals demonstrated marked improvement in clinical score. Compound A group was split into to two to investigate the effects of 1) stopping and 2) continuing treatment. Vehicle group, which had reached a score of 3.5-4.0, began Compound A treatment.]
Administered doses: 50 mg/kg
Administered volume(s): 0.1 mL (~5 mL/kg)
Justification for dose levels: Requested by Sponsor
Body Weight
  Body weights were recorded twice a week starting on the first day of treatment and including the day of study termination.
EAE Scoring
  EAE clinical score were measured three times a week according to the following scoring scheme:
    0: No clinical disease
    1: Tail flaccidity
    2: Hind limb weakness
    3: Hind limb paralysis
    4: Forelimb paralysis or loss of ability to right from supine
    5: Moribund or death
Animals Found Dead or Moribund
  Percentage of animal mortality and time to death was recorded for every group in the study. Mice may be defined as moribund and sacrificed if one or more of the following criteria are met:
    1) Loss of body weight of 20% or greater in a 1-week period.
    2) EAE scoring of 4.5 or higher
    3) Prolonged, excessive diarrhea leading to excessive weight loss (>20%).
    4) Persistent wheezing and respiratory distress.
  Animals can also be considered moribund if there is prolonged or excessive pain or distress as defined by clinical observations such as: prostration, hunched posture, paralysis/paresis, distended abdomen, ulcerations, abscesses, seizures and/or hemorrhages.

Example 7

Study of CSF1 Receptor Antagonists Reduce Microglia Mediated Neuroinflammation in LPS-Injected and Alzheimer Disease (AD) Mouse Models To evaluate the potential for CSF1 receptor antagonists on brain microglia number and activation LPS (lipopolysaccharide) was administered to 2-month old C57/b6 mice (3 injections over 1 week; I.P.; n=4 per group) alongside chow containing either vehicle, or a CSF-1R inhibitor as described herein, e.g. Compound A (1160 mg/kg chow). Following this treatment, animals were sacrificed, brains extracted with one half fixed in 4% p-formaldehyde (PFA) for immunohistochemistry, and the other homogenised for biochemical analysis.

Figure 3A:
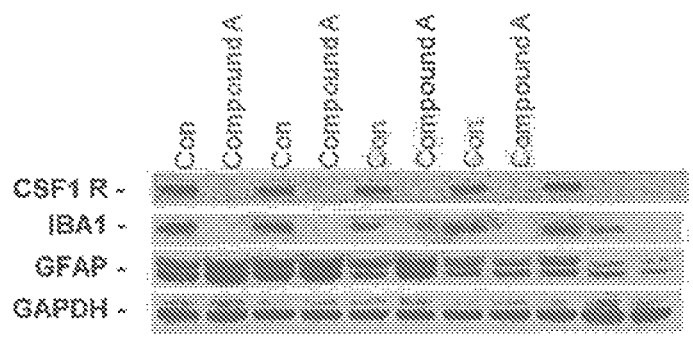
FIG. 3A shows CSF1 receptor antagonists reduce brain microglia and IBA1 levels in LPS treated C57 mice.

As shown in FIG. 3A, steady state levels of the microglia marker IBA1 were significantly increased in the brain homogenate with LPS injection. Mice treated with a compound as described herein showed significantly lower IBA1 levels than either control or LPS injected mice, while mice treated with compound A had significantly lower IBA1 levels than LPS injected mice, but equivalent to control animals.

Figure 3B:
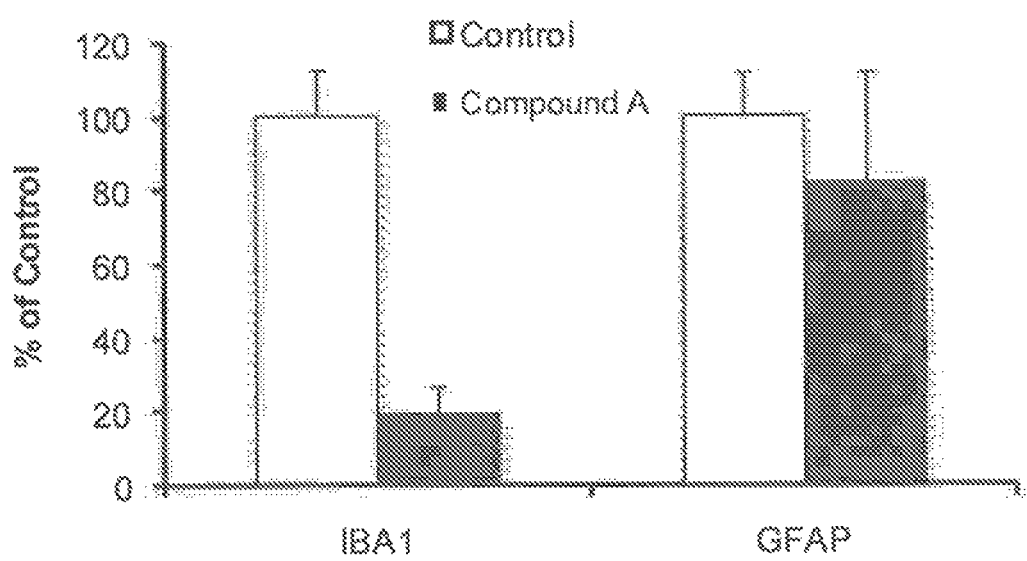
FIG. 3B shows reductions in microglia with CSF1 receptor antagonists in aged 3×Tg-AD mice.

As shown in FIG. 3B, steady state levels of IBA1 are reduced 80% by treatment, but astrocyctic marker GFAP levels are not altered.

Figure 3C:
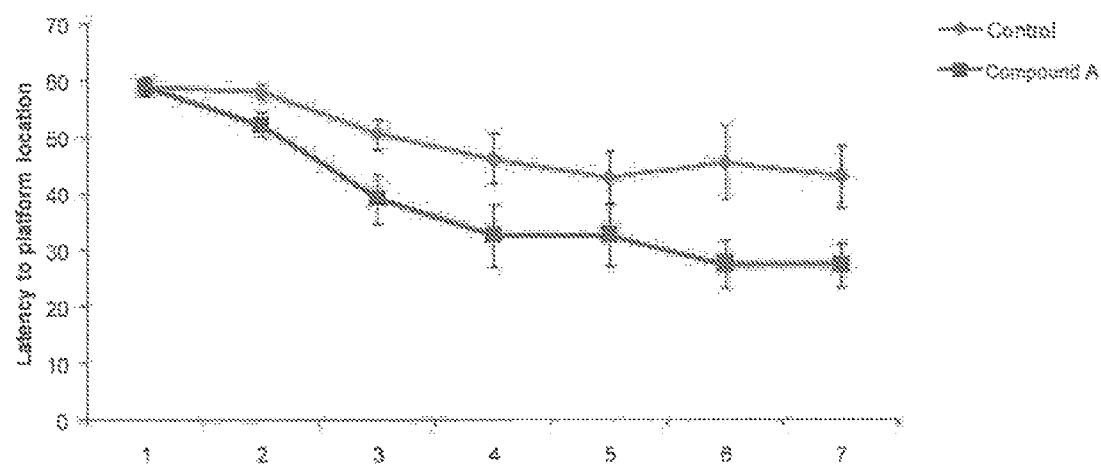
FIG. 3C shows unprecedented improvements in learning and memory performance with compound A treatment in 3×Tg-AD mice with extremely advanced disease.

As shown in FIG. 3C, after 3 months of treatment, learning and memory was assessed using the Morris Water Maze. 3×Tg-AD mice having extremely advanced disease treated with a compound as described herein showed improved acquisition, compared to untreated mice. Probe trials conducted at 24 hours after the last training trial revealed no differences in memory. The study demonstrates that compounds of Formulas I, I', II, II', IIa, III, and III' and IV and the compounds listed in Tables 1 and 3-10; and the compounds described in the Examples are able to reduce neuro-inflammation in CaM/Tet-diphtheria toxin (DT) neuronal loss model.

Figure 3D:
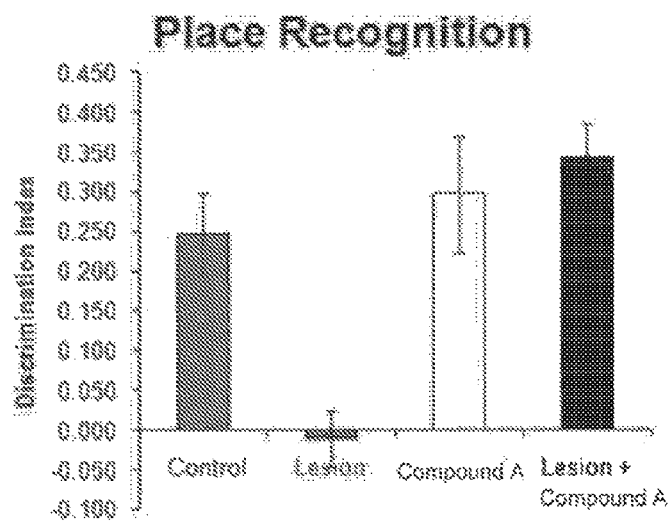
FIG. 3D shows cognitive benefit found in mice with the treatment of a compound as described herein.

As shown in FIG. 3D, a compound as described herein was found to improve recognition learning in CaM/Tet-diphtheria toxin (DT) neuronal loss model. Mice with neutral loss recover normal ability to discriminate new versus prior object placement. Lower latency means faster recall better memory performance. This study demonstrates that the compounds of Formulas I, I', II, II', IIa, III, and III' and IV and the compounds listed in Tables 1 and 3-10; and the compounds described in the Examples are able to improve recognition learning in mice in CaM/Tet-diphtheria toxin (DT) neuronal loss model.

Example 8

Inhibition of Growth and MAPK Signaling in Malignant Peripheral Nerve Sheath Cells (MPNST)

Xenograft models of sarcoma were developed and utilized to test both rapamycin and a compound as described herein, e.g. Compound A single agent and combination effects in vivo. The tumors were followed over time for changes in tumor size and tumors were collected at the predetermined time points and at the end of the study to examine for changes in indices of proliferation and for induction of apoptosis.

Figure 4:
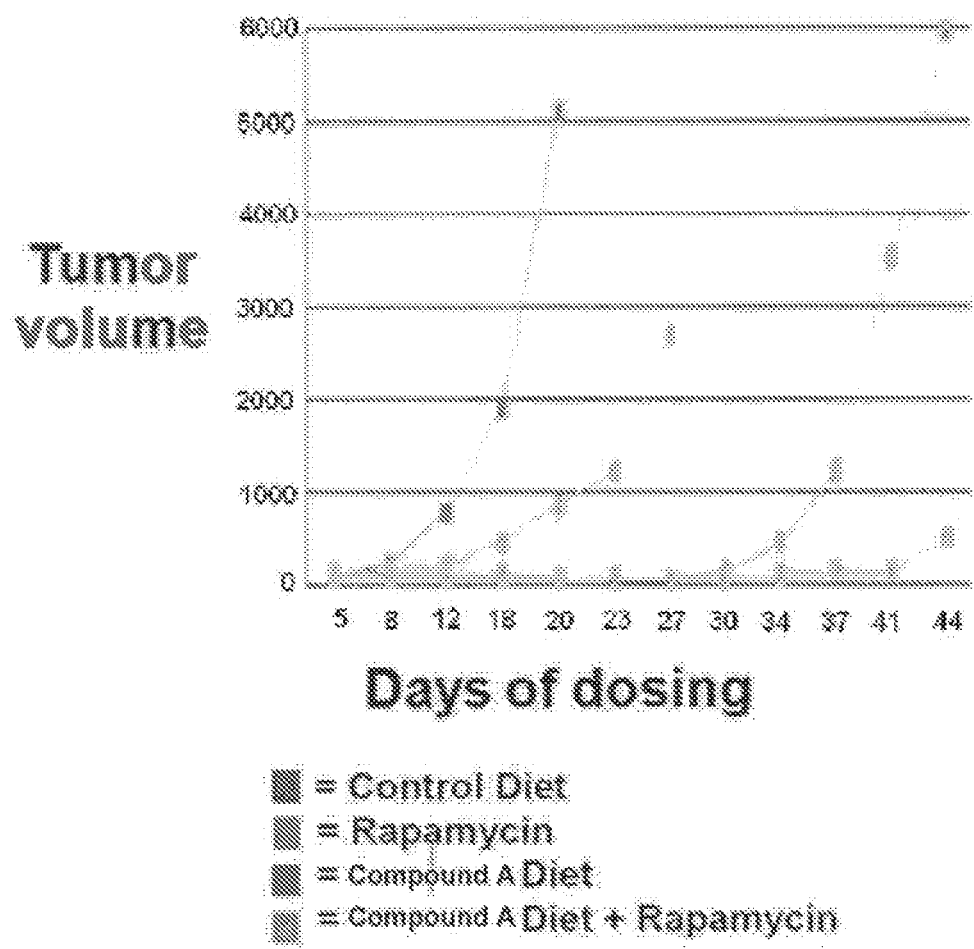
FIG. 4 shows tumor volume changes in MPNST xenografts by administering a compound as described herein together or in the absence of rapamycin combination.

Mice: Severe combined immunodeficiency
(SCID) mice, 8 weeks old, weight ~30 g
Cells: MPNST3 serial transplants, single flank s.c with matrigel
Drugs: Rapamycin 20 mg/kg i.p. Mon-Wed-Fri
Compound chow
Tumor size: 100-150 mm³ when treatment starts
Growth Curve: (48 animals total, tumor size 100-150 mm³)
Treatment groups: (12 mice/group):
1. Control chow
2. rapamycin 20 mg/kg i.p. Mon-Wed-Fri for 3 weeks
3. compound chow×3 weeks
4. rapamycin 20 mg/kg i.p. Mon-Wed-Fri+chow×3 weeks
Tumor Measurements: Twice a Week
Tumor Collection: Collect 2 tumor/group at the end of week 1, week 2 and week 3 of treatment. Fix ½ in formalin and freeze ½ in liquid nitrogen for pharmcodynamics (PD) studies. FIG. 4 demonstrates the change of tumor volume after administering of a compound as described herein. For NF1 patients, stable disease×8 months, improved gait, increased activity.

Example 9

CSF-1R Inhibition Decreases Mesothelioma Tumor Burden

Figure 5:
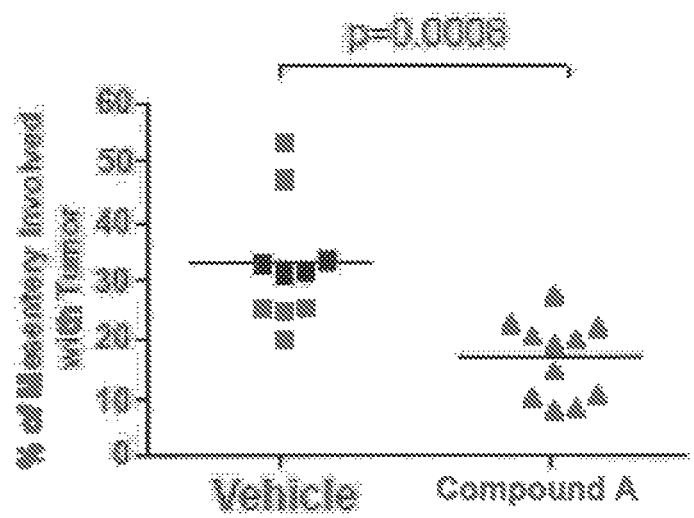
FIG. 5 shows quantitation of mesenteric tumor burden in 3 representative H&Es serial sectioned 90 μm apart (n=10 mice/group, p=0.0008 by two-tailed unpaired T-test) and demonstrates CSF-1R inhibition decreases tumor burden.

Mice were treated with vehicle or a compound as described herein, e.g. Compound A from d14-d35 post-tumor cell implantation. CSF-1R inhibition by a compound described herein, decreases tumor burden in a mouse model of malignant mesothelioma. As demonstrated in FIG. 5, a CSF-1R inhibitor, for example, a compound of Formulas I, I', II, II', IIa, III, and III' and IV and a compound listed in Tables 1 and 3-10; and a compound described in the Examples decreases mesothelioma tumor burden.

Example 10

Tumor Associated Macrophages (TAMs) in Gastrointestinal Stromal Tumor

Figure 6A:
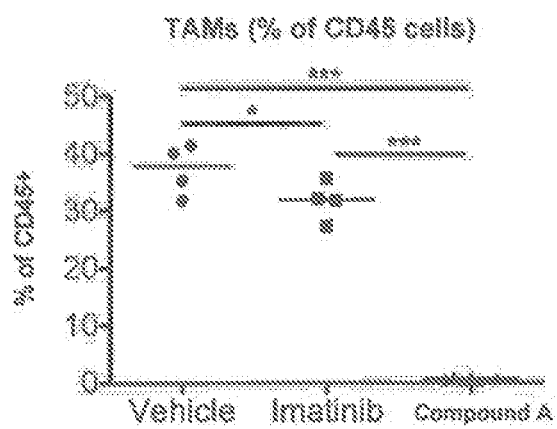
FIGS. 6A-6C demonstrate compounds described herein are highly effective in treating GIST.
Figure 6B:
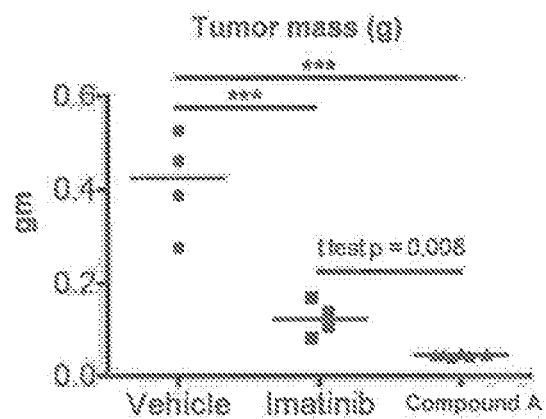
Figure 6C:
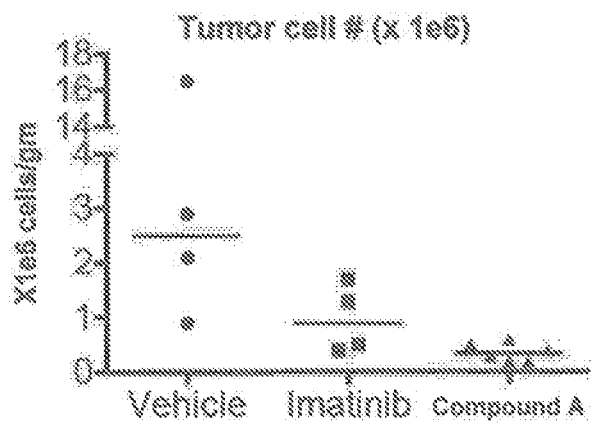

GIST mice were treated with a compound as described herein, e.g. Compound A (290 mg free base/kg of chow) or imatinib (LC labs) for 4 weeks. Tumors harvested, processed using type II collagenase/DNAse I digestion, and analyzed by flow cytometry. Paraffin sections of tumors stained using Masson-Trichrome protocol. FIGS. 6A to 6C have demonstrated that compounds of Formulas I, I', II, II', IIa, III, and III' and IV and the compounds listed in Tables 1 and 3-10; and the compounds described in the Examples are highly effective for treating gastrointestinal stromal tumor (GIST).

Figure 6D:
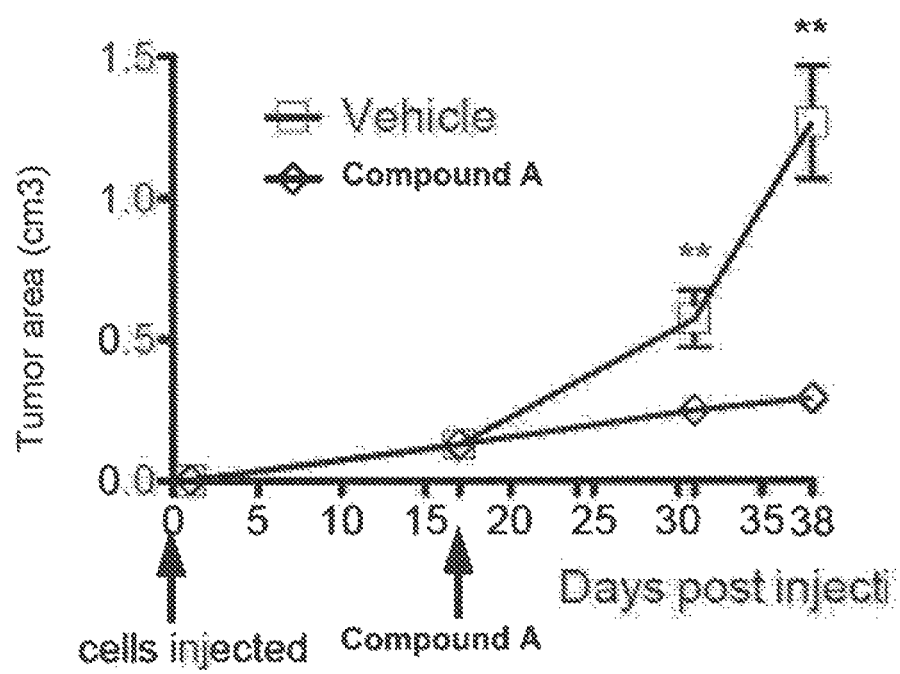
FIGS. 6D-6E demonstrates depletion of TAMs using compounds described herein delays tumor growth.
Figure 6E:
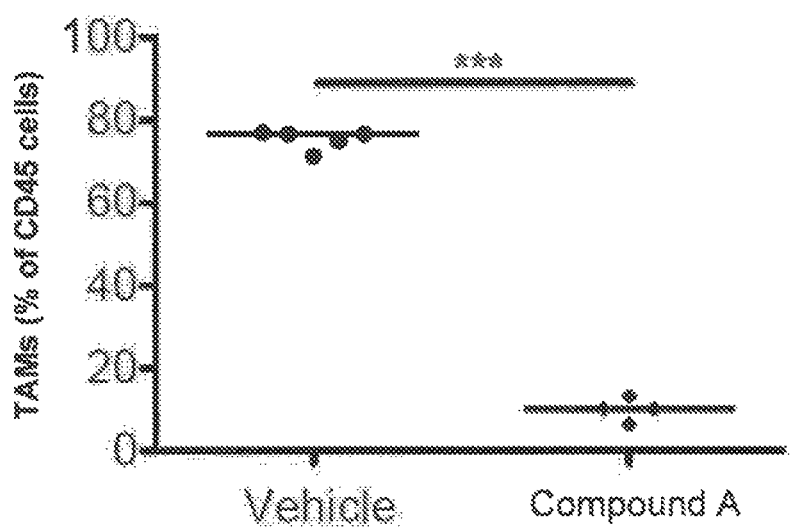

C57Bl/6 mice were implanted with subcutaneous tumors using an aggressive, imatinib-resistant (kit independent) cell line derived from GIST mice (S2 cell line). TAMs in this model were more typical of M2 TAMs, and potently suppress T cell proliferation. FIGS. 6D-6E demonstrate depletion of TAMs from an aggressive implantable tumor with compounds of Formulas I, I', II, II', IIa, III, and III' and IV and the compounds listed in Tables 1 and 3-10; and the compounds described in the Examples, delays tumor growth.

Example 11

Study of C-kit/C-fms Inhibitors in a NF1 Mouse Model of Plexiform Neurofibromas

Figure 7A:
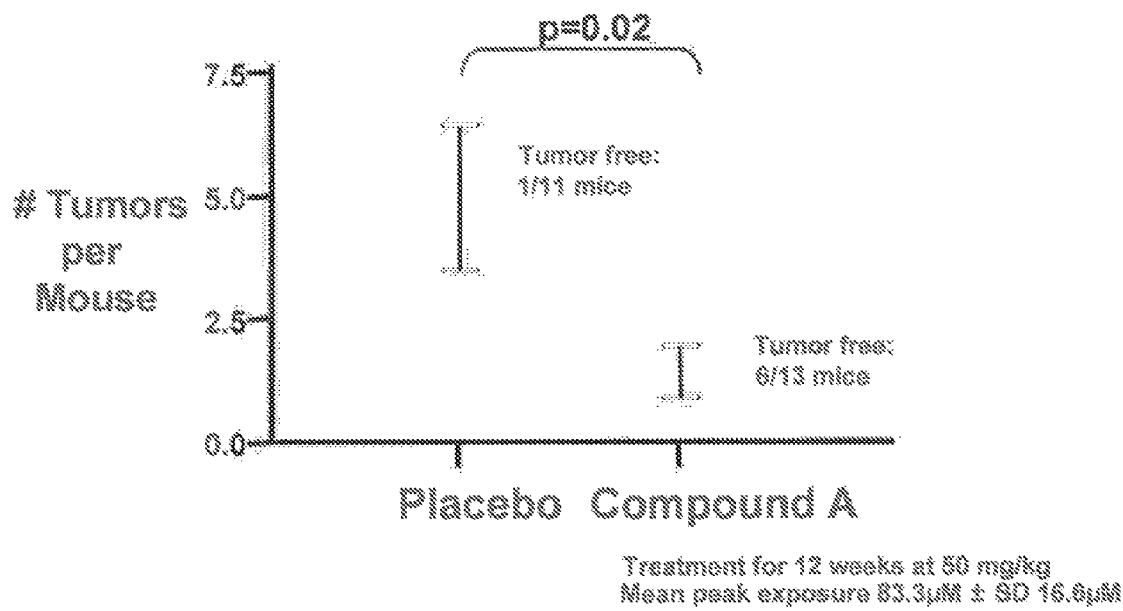
FIG. 7A shows tumor number changes following the treatment of a compound as described herein.

A conditional mouse model, in which Schwann cells were nullizygous at Nf1 and other lineages are heterozygous at Nf1 (haploinsufficient) was treated for 3 months with 50 mg/kg of a compound as described herein, e.g. compound A by oral gavage, and tumor incidence and growth were measured by FDG-PET imaging. FIG. 7A demonstrates that compounds of Formulas I, I', II, II', IIa, III, and III' and IV and the compounds listed in Tables 1 and 3-10; and the compounds described in the Examples significantly inhibit Plexiform tumor development.

Eleven mice were enrolled in the placebo (vehicle treated) group and thirteen mice were enrolled in the inhibitor treatment group. As shown in FIG. 7A, the numbers of tumors in each mouse were measured.

Example 12

Inhibition of M-CSF/C-fms Pathway Increases Bone Mass in NF1 Mutant Mice

Figure 7B:
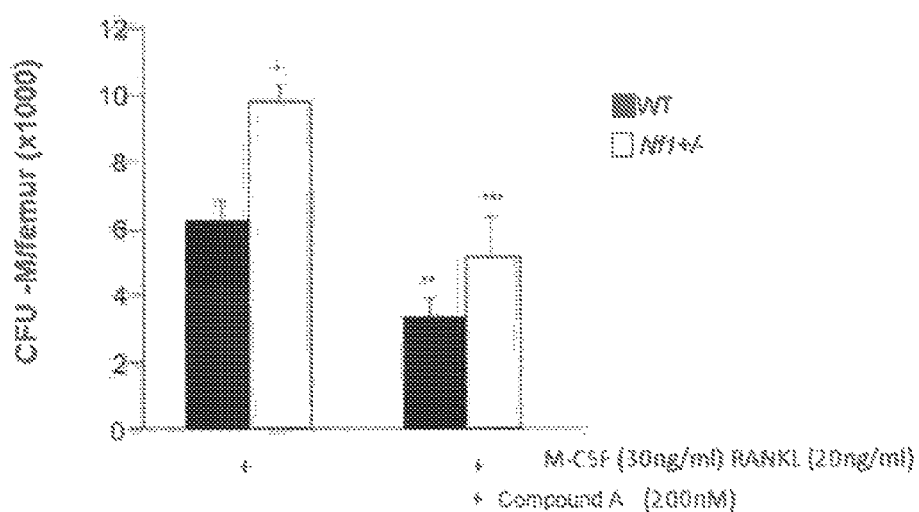
FIGS. 7B-7E demonstrates a c-fms inhibitor as described herein blocks osteoclast function in normal and NF1 cells.

C-kit/C-fms Inhibitor Reduced the Frequency of Osteoclast Progenitors and Reduced Osteoclast Formation CFU-M was examined using the bone marrow mononuclear cells (BMMNCs) of WT or Nf1+/− mice in semisolid methylcellulose culture in the presence of M-CSF with or without a c-kit/c-fms inhibitor as described herein. Seven days after the culture, CFU-M was counted under phase contrast microscope. Consistent with our previous data, Nf1+/− mice had a significantly increased number of CFU-M as compared to wild type (WT) mice (FIG. 7B). Importantly, addition of a c-kit/c-fms inhibitor as described herein dramatically reduced CFU-M formation in both WT and Nf1+/− cultures (FIG. 7B).

Figure 7C:
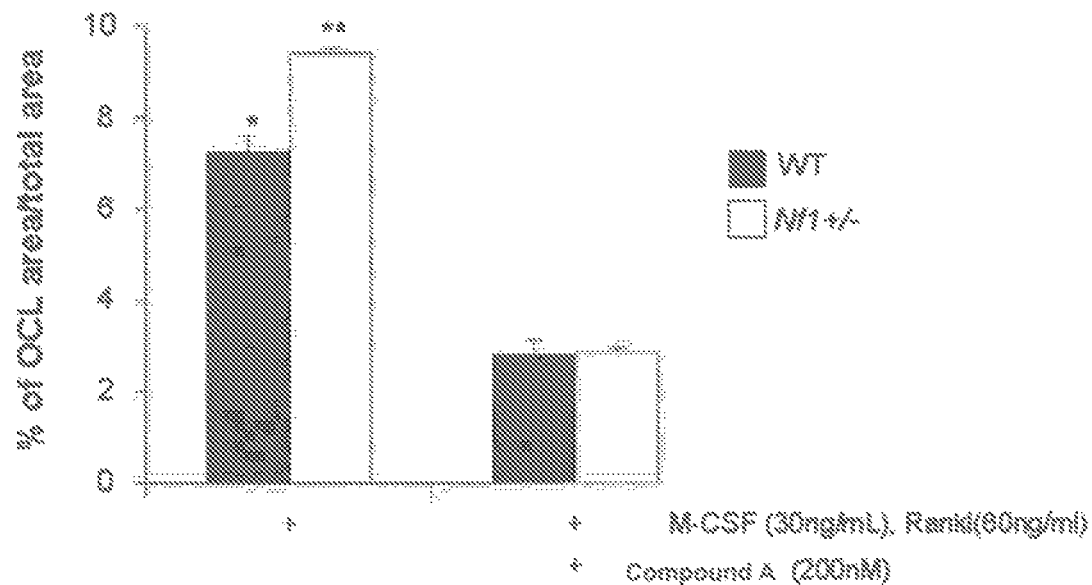

Osteoclast cultures in the presence of M-CSF/RANKL with or without a c-kit/c-fms inhibitor was established. Five days after the culture, the cultures were subjected to tartrate resistant acid phosphatase (TRACP) staining. Osteoclast formation was evaluated by calculating the ratio of TRACP+ area over total cell culture area. Nf1+/− cultures contain significantly increased TRACP+ area as compared to WT cultures (FIG. 7C). Addition of a c-kit/c-fms inhibitor dramatically reduced osteoclast formation in both WT and Nf1+/− cultures.

C-kit/C-fms Inhibitors Restored Nf1+/− Osteoclast Migration

Figure 7D:
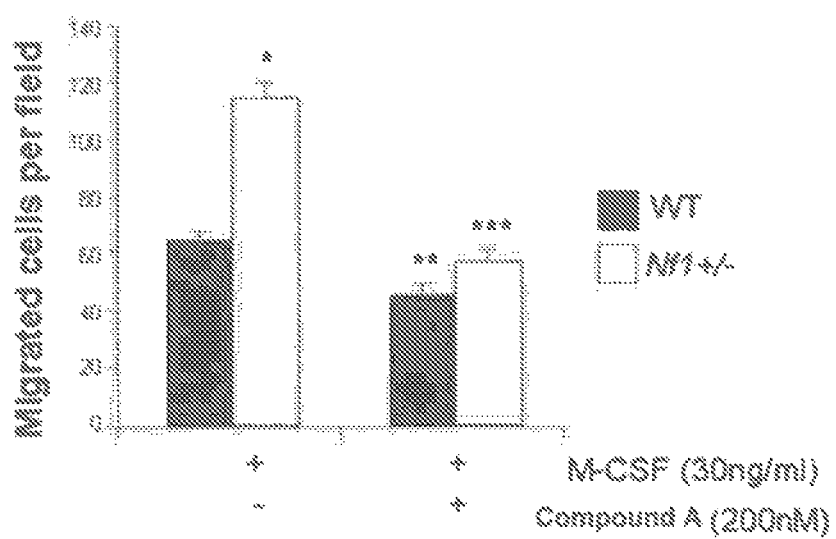

The ability of osteoclasts to migrate across the bone surface is a key cellular function required for bone resorption. Osteoclast migration was assessed by transwell assays. Bottom chambers containing media alone without M-CSF were used as negative controls. After four hours of migration, M-CSF induced a significantly higher level of migration in Nf1+/− cultures than that of WT cultures (FIG. 7D). Furthermore, a c-kit/c-fms inhibitor dramatically reduced Nf1+/− osteoclast migration to that of WT level.

C-kit/C-fms Inhibitors Inhibited Osteoclast Bone Resorption

Figure 7E:
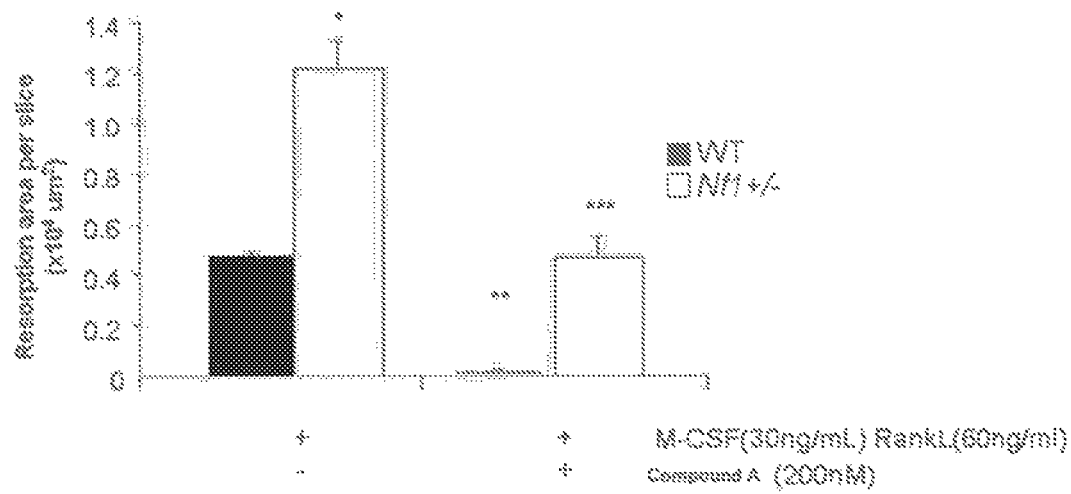

To assess the impact of a c-kit/c-fms inhibitor on osteoclast bone erosive activity, pit formation assays were conducted. M-CSF with or without a c-kit/c-fms inhibitor was added to the culture wells containing dentin slides and pre-osteoclasts. Wells containing media alone without M-CSF were used as negative controls. Three days after the culture, pit forming area in μm2 was calculated using Metamorph software. M-CSF induced a pit formation in the wells containing WT osteoclasts. In contrast, a 2-3 fold larger pit forming area was observed in cultures containing Nf1+/− osteoclasts compared to that of WT osteoclasts (FIG. 7E). The c-kit/c-fms inhibitor dramatically reduced pit forming area in both WT and Nf1+/− cultures. These data indicate that the c-kit/c-fms inhibitors as described herein not only inhibit the osteoclast formation but also osteoclast bone resorptive activity.

Figure 7F:
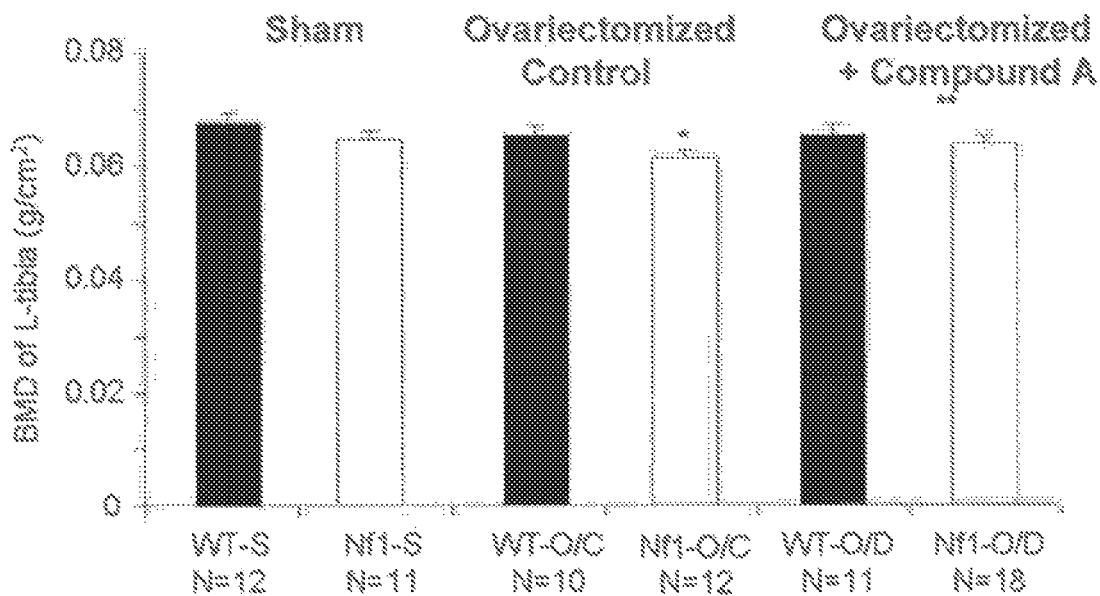
FIGS. 7F-G shows a compound as described herein improves osteoporosis in NF1 mice model.
Figure 7G:
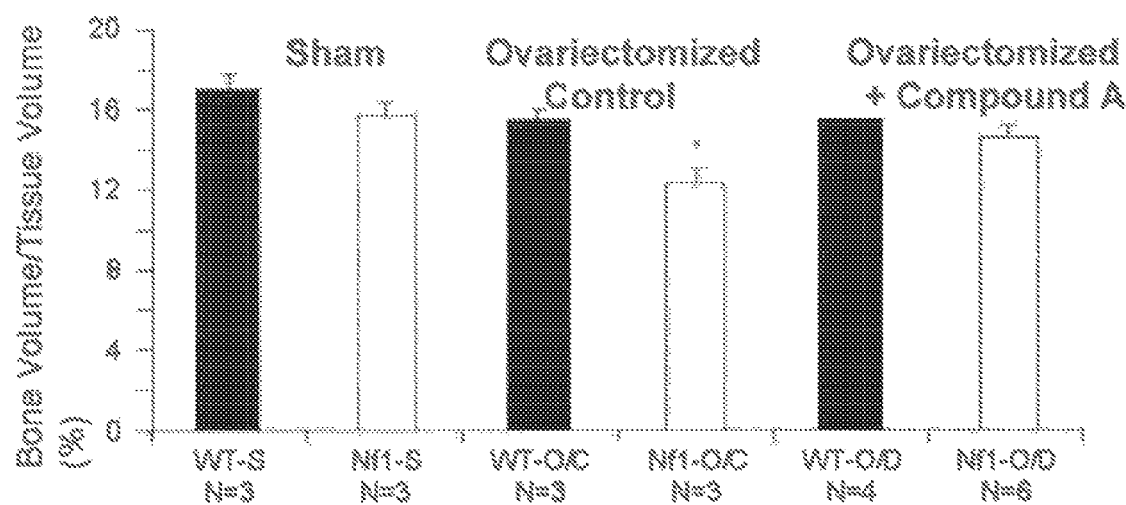

C-kit/C-fms Inhibitors Improves Osteoporosis and Prevent Bone Loss in NF1 Mice Model To evaluate the impact of c-kit/c-fms inhibitors as described herein on bone mass, volumetric bone mineral density (BMD; mg/cm3) was measured in the proximal tibial metaphysis 1 mm distal to the proximal growth plate of mice received placebo or a c-kit/c-fms inhibitor for 12 weeks. The Nf1+/− OVX mice lost significantly more bone mass than the WT OVX mice (FIG. 7F), verifying that a pro-resorptive challenge induces a greater osteoclastic response in Nf1 haploinsufficient mice. Nf1+/− OVX mice feed with a c-kit/c-fms inhibitor revealed a significant increase in BMD in the left tibial diaphysis compared to the mice received placebo treatment. To further investigate the role of the c-kit/c-fms inhibitor on modulating trabecular bone, micro computerized tomography (μCT) was conducted to examine the architecture of trabecular bone. Representative photographs of μCT are shown in FIG. 7G. While Nf1+/− OVX mice displayed dramatically less trabecular bone as determined by bone volume/tissue volume, as compared to WT-OVX mice that received placebo treatment, the c-kit/c-fms inhibitors significantly increased the trabecular bone in Nf1+/− OVX mice. Collectively, these data demonstrate that the c-kit/c-fms inhibitors as described herein are able to prevent bone loss in Nf1+/− osteoporotic model.

Example 13

Figure 8:
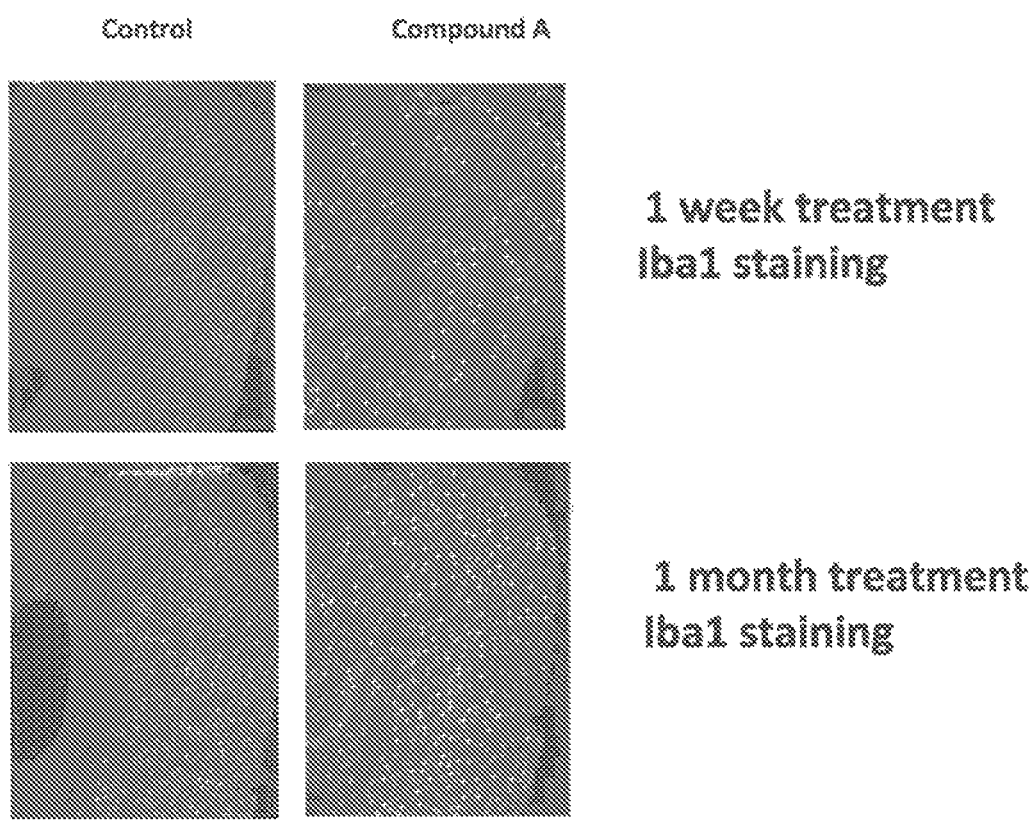
FIG. 8 shows a compound as described herein reduces microglia in 1.5 month old PGRN KO mice in frontotemporal dementia (FTD) model.

Reduction of Inflammatory Responses of PGRN-deficient Microglia and Protect Against Microglia-mediated Neurotoxicity Primary microglial cultures or microglia-neuron cocultures were derived from PGRN null mice. Cells were treated with either a compound as described herein, e.g. Compound A or control compound, then stimulated with either LPS or amyloid beta peptides to induce microglial-mediated toxicity. The effects of the compound measured with levels of proinflammatory mediators, including TNF-α, IL-6, and IL-1β. Neurotoxicity were measured with cell viability assays or MAP2 staining, as described in *J Biol Chem* 280:40364-74 (2005). FIG. 8 demonstrates the c-kit/c-fms inhibitors as described herein reduce microglia in PGRN KO mice.

Example 14

Figure 9A:
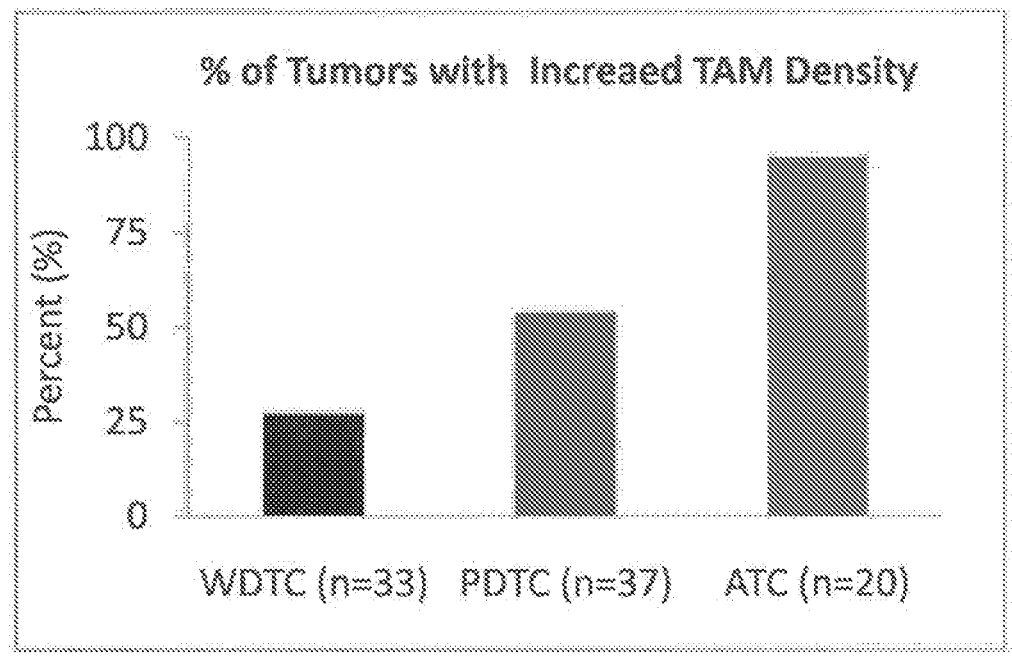
FIG. 9A shows tumor associated macrophages (TAMs) correlate with tumor progression in human thyroid cancers.
Figure 9B:
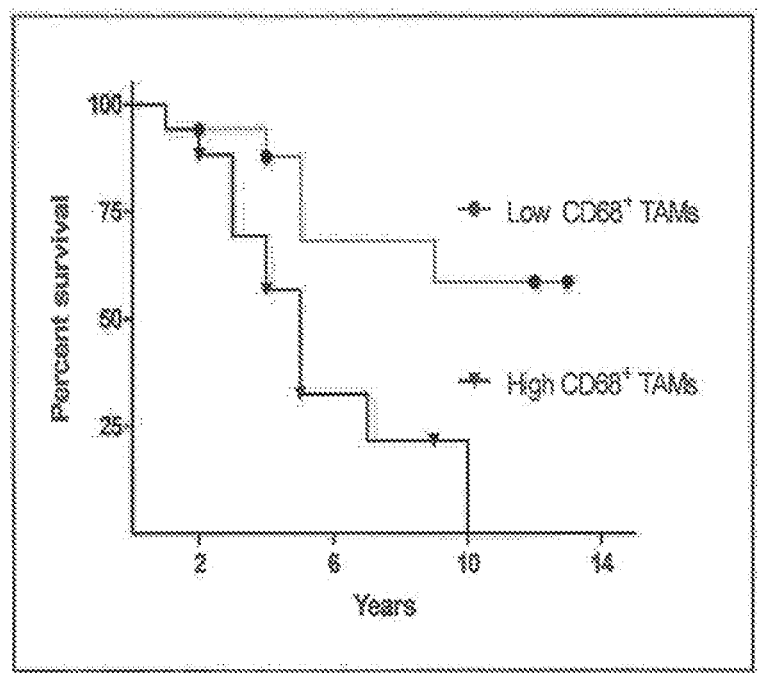
FIG. 9B shows increased TAMs are associated with tumor invasion and decreased survival in poorly differentiated thyroid cancer (PDTC).

Effects of Targeted Inhibition of C-Fms on Papillary Thyroid Cancer (PTC) Progression Using two mouse models of Braf-induced PTC, targeted inhibition of c-Fms impairs PTC initiation and/or progression through inhibition of TAM recruitment and/or proliferation were examined. In the dox-inducible model of PTC initiation, Tg-rTTa/tetO-Braf mice aged 4-6 weeks old received doxycycline 2,500 ppm in the food supply from days 0-7. On days 0, 3 and 6 mice received either vehicle or a csf-1R inhibitor as described herein, e.g. compound A. Mice were sacrificed on day 7. The bone marrow, blood and spleen were collected and processed for flow cytometry using the monocyte/macrophage markers Cd11b, F4/80, Ly6C, Cd115 to characterize the effects of c-kit/fms inhibitors as described herein on precursor, circulating and resident monocyte/macrophage populations, respectively. Thyroids were harvested for histological and immunohistochemical (IHC) analyses to determine the effects of each drug on PTC phenotype (H &E stains), proliferative and apoptotic indices (Ki67 and TUNEL IHC), Brafactivation (p-ERK and p-MEK IHC) and on stromal density (anti-Mac2 & anti-alpha smooth muscle actin IHC). Pooled thyroids (n=4-6) from vehicle and the compound A treated mice were processed into single cell suspensions for FACS analysis of TAM populations. FIG. 9A shows tumor associated macrophages (TAMs) correlate with tumor progression in human thyroid cancers. FIG. 9B shows increased TAMs are associated with tumor invasion and decreased survival in poorly differentiated thyroid cancer (PDTC).

Figure 9C:
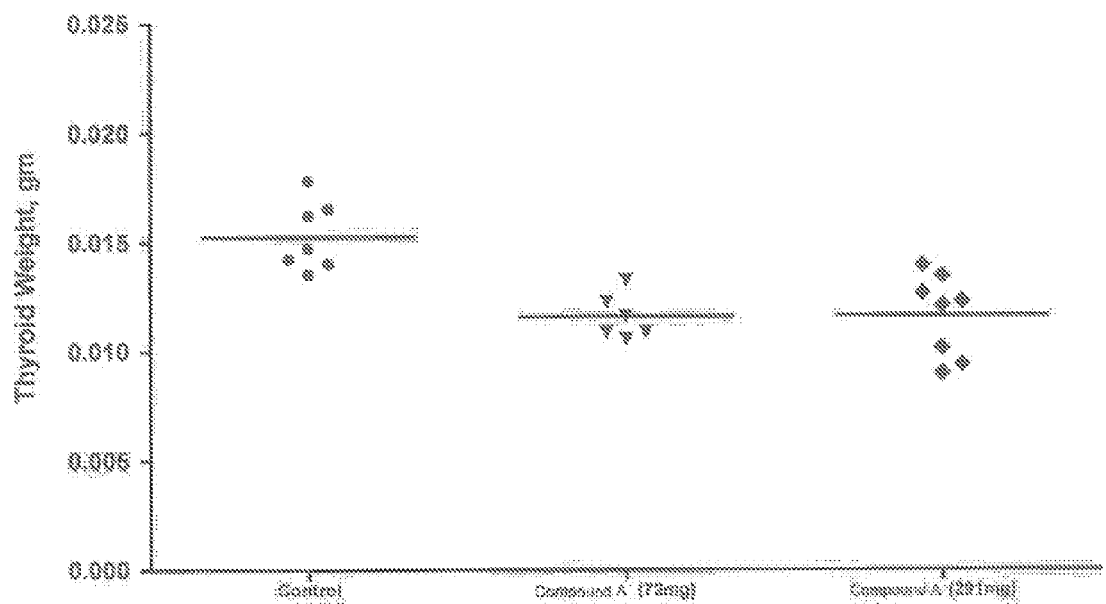
FIG. 9C shows a comparison of thyroid weight after treatment in dox-induced Tg-rTta/TetO-Braf mice.

Effects of c-kit/fms inhibitors on PTC progression using TPO-Cre/LSL-Braf mice were examined. Thyroids from TPO-Cre/LSL-Braf mice develop diffuse PTCs by 5 weeks of age with 100% penetrance, were angioinvasive, had extrathyroidal skeletal muscle invasion and developed foci of poorly-differentiated thyroid cancer. These PTCs were densely infiltrated with TAMs. Mice between the ages of 4-8 weeks of age received vehicle vs. a ckit/c-fms inhibitor as described herein every other day for 1, 2 and 3 weeks. Bone marrow, blood, spleen and thyroids were collected 24 hours after the final dose and examined. FIG. 9C shows the changes of thyroid weight with and without application of the c-kit/fms inhibitor.

Example 15

Efficacy of Combination in the Treatment of A2058 Human Melanoma Xenograft Model Experimental Methods and Procedures
Cell Line The A2058 tumor cell line was maintained in vitro as monolayer culture in DMEM medium supplemented with 10% heat inactivated fetal calf serum, 100 U/ml penicillin and 100 μg/ml streptomycin, and L-glutamine (2 mM) at 37° C. in an atmosphere of 5% $CO_2$ in air. The tumor cells were routinely subcultured twice weekly by trypsin-EDTA treatment. The cells growing in an exponential growth phase were harvested and counted for tumor inoculation.
Tumor Inoculation Each mouse was inoculated subcutaneously with A2058 tumor fragments (2 mm×2 mm×2 mm) on the right flank for tumor development. Drug treatment was started at day 11 after tumor inoculation when the mean tumor size reached approximately 140 $mm^3$. Each group consisted of 10 mice. The test articles administrated to the tumor-bearing mice according to predetermined regimen.
Observations All the procedures related to animal handling, care, and the treatment in this study were performed according to guidelines approved by the Institutional Animal Care and Use Committee (IACUC) of Pharmaron following the guidance of the Association for Assessment and Accreditation of Laboratory Animal Care (AAALAC). At the time of routine monitoring, the animals were checked for any effects of tumor growth on normal behavior such as mobility, food and water consumption (by looking only), body weight gain/loss (body weights were measured twice weekly), eye/hair matting and any other abnormal effect. Death and observed clinical signs were recorded on the basis of the numbers of animals within each subset.
Tumor Measurement and Endpoints The major endpoint was to see if the tumor growth can be delayed or mice can be cured. Tumor size was measured twice weekly in two dimensions using a caliper, and the volume was expressed in $mm^3$ using the formula: $V=0.536 a \times b^2$ where a and b are the long and short diameters of the tumor, respectively. The tumor size is then used for calculations of T/C values. The T/C value (in percent) is an indication of antitumor effectiveness; T and C are the mean volume of the treated and control groups, respectively, on a given day.

The tumor-bearing mice were euthanized when the tumor size reached larger than 2,500 $mm^3$ as "death" to calculate the survival curves. The survival of all animals was followed and median survival time (MST) was calculated for each group. The increase in life-span (ILS) was calculated by dividing the MST of treatment group by the MST of the control group and was expressed as the percent increase over the life-span of the control animals.

Figure 10:
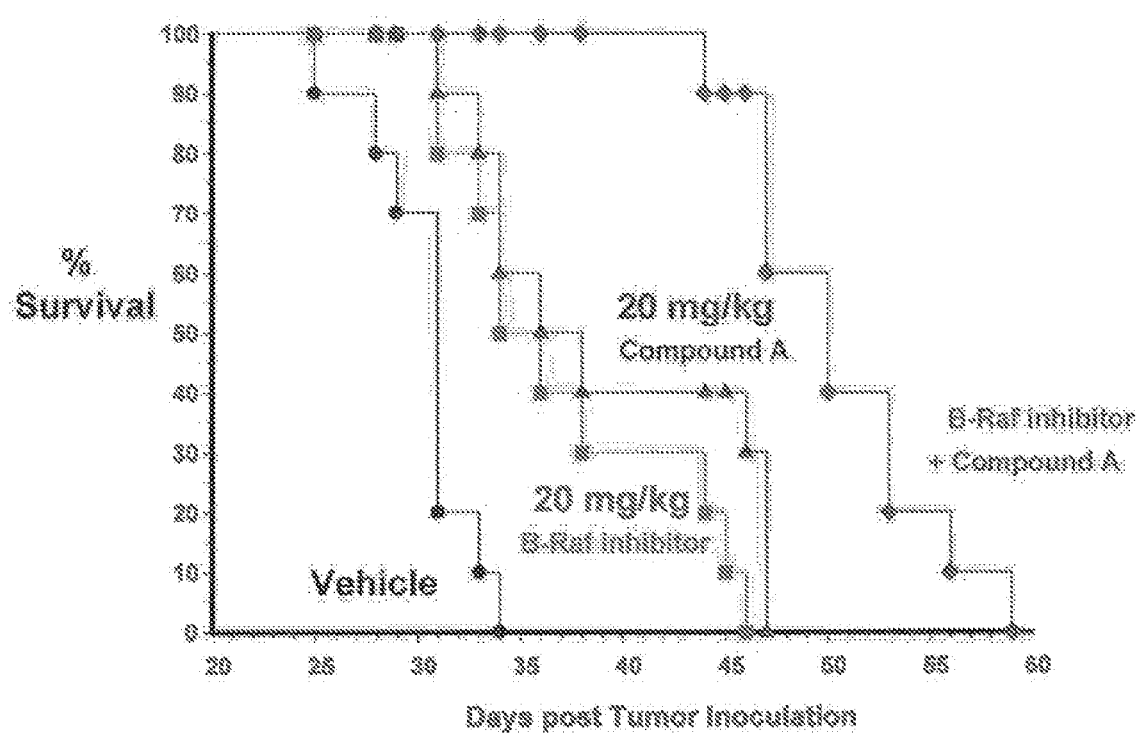
FIG. 10 shows the effects of a combination of B-raf inhibitor and a compound as described herein on survival times of tumor-bearing mice.
Figure 11:
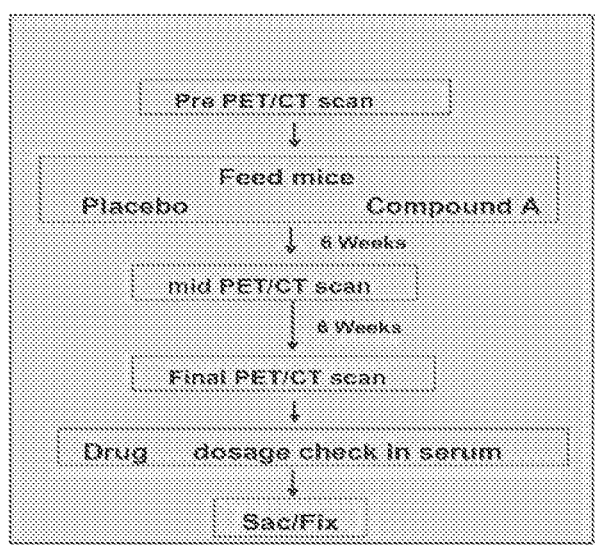
FIG. 11 shows a summary of the protocol described in Example 11.

The bilateral armpit lymph nodes and lungs of the tumor-bearing mice in all of the groups were collected at euthanasia of the animals when their tumor size reached larger than 2,500 $mm^3$; and the paraffin embedded blocks were made for histopathological evaluation. The number of lung metastatic loci were counted.
Statistical Analysis Statistical analysis of difference in tumor volume among the groups was conducted using one-way ANOVA, and the differences in the survivals between the groups were analyzed for significance using the Wilcoxon test, all data were analyzed using software SPSS 16.0; $p<0.05$ was considered to be statistically significant.
Results The survival data and the survival curves of the tumor-bearing mice in all groups are shown in FIG. 10. The median survival time (MST) of the vehicle treated control mice is 31 days. A B-raf-inhibitor and a compound as described herein as a single agent resulted in MSTs of 34 days (ILS=9.7%, p=0.002 compared with control group) and 36 days (ILS=16.1%, p<0.001), respectively. There is not statistically different (p=0.324) in the survival time between these two treatments. The combination therapy of a B-raf inhibitor and a compound as described herein produced an MST of 50 days (ILS=61.3%, p<0.0001) compared to the monotherapy groups.

All patents and other references cited in the specification are indicative of the level of skill of those skilled in the art to which the disclosure pertains, and are incorporated by reference in their entireties, including any tables and figures, to the same extent as if each reference had been incorporated by reference in its entirety individually.

One skilled in the art would readily appreciate that the present disclosure is well adapted to obtain the ends and advantages mentioned, as well as those inherent therein. The methods, variances, and compositions described herein as presently representative of preferred embodiments are exemplary and are not intended as limitations on the scope of the disclosure. Changes therein and other uses will occur to those skilled in the art, which are encompassed within the spirit of the disclosure, are defined by the scope of the claims.

The disclosure illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. Thus, for an embodiment of the disclosure using one of the terms, the disclosure also includes another embodiment wherein one of these terms is replaced with another of these terms. In each embodiment, the terms have their established meaning. Thus, for example, one embodiment may encompass a method "comprising" a series of steps, another embodiment would encompass a method "consisting essentially of" the same steps, and a third embodiment would encompass a method "consisting of" the same steps. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure as defined by the appended claims.

In addition, where features or aspects of the disclosure are described in terms of Markush groups or other grouping of alternatives, those skilled in the art will recognize that the disclosure is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described disclosure.

Thus, additional embodiments are within the scope of the disclosure and within the following claims.

What is claimed is:

1. A method for treating a subject suffering from malignant peripheral nerve sheath tumors (MPNST), said method comprising administering to the subject sirolimus and an effective amount of a compound having the formula:

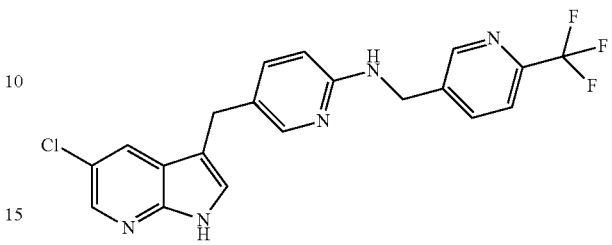

or a pharmaceutically acceptable salt thereof.

2. The method of claim 1, where the administration is oral.

3. The method of claim 1, wherein the effective amount is 0.1 mg/kg to 20 mg/kg.

* * * * *